US012575855B2

(12) United States Patent
Yates et al.

(10) Patent No.: US 12,575,855 B2
(45) Date of Patent: Mar. 17, 2026

(54) SURGICAL SYSTEM DISTRIBUTED PROCESSING

(71) Applicant: Cilag GmbH International, Zug (CH)

(72) Inventors: David C. Yates, Morrow, OH (US);
Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 281 days.

(21) Appl. No.: 17/217,642

(22) Filed: Mar. 30, 2021

(65) Prior Publication Data

US 2021/0212717 A1    Jul. 15, 2021

Related U.S. Application Data

(63) Continuation of application No. 15/940,663, filed on Mar. 29, 2018, now Pat. No. 11,419,630.

(Continued)

(51) Int. Cl.
*A61B 17/3211*    (2006.01)
*A61B 17/00*    (2006.01)
(Continued)

(52) U.S. Cl.
CPC ........ *A61B 17/3211* (2013.01); *A61B 17/068* (2013.01); *G16H 20/40* (2018.01);
(Continued)

(58) Field of Classification Search
CPC .............. A61B 17/3211; A61B 17/068; A61B 2017/00137; A61B 2017/00225;
(Continued)

(56) References Cited

U.S. PATENT DOCUMENTS 1,853,416 A    4/1932  Hall
2,222,125 A    11/1940  Stehlik
(Continued)

FOREIGN PATENT DOCUMENTS

AU    2015201140 A1    3/2015
CA    2709634 A1    7/2009
(Continued)

OTHER PUBLICATIONS

US 10,504,709 B2, 12/2019, Karancsi et al. (withdrawn)
(Continued)

*Primary Examiner* — Rachelle L Reichert
(74) *Attorney, Agent, or Firm* — Condo Roccia Koptiw LLP

(57)    ABSTRACT

Surgical hub systems are disclosed. A surgical hub system comprises a surgical hub configured to communicably couple to a modular device comprising a sensor configured to detect data associated with the modular device and a device processor. The surgical hub comprises a hub processor, a hub memory coupled to the hub processor. The surgical hub system also comprises a distributed control system executable at least in part by each of the device processor and the hub processor. The distributed control system is configured to: receive the data detected by the sensor; determine control adjustments for the modular device according to the data; and control the modular device according to the control adjustments. When in a first mode, the distributed control system is executed by both the hub processor and the device processor. In a second mode, the distributed control system is executed solely by the device processor.

18 Claims, 58 Drawing Sheets

Related U.S. Application Data

(60) Provisional application No. 62/649,300, filed on Mar. 28, 2018, provisional application No. 62/611,339, filed on Dec. 28, 2017, provisional application No. 62/611,340, filed on Dec. 28, 2017, provisional application No. 62/611,341, filed on Dec. 28, 2017.

(51) Int. Cl.

| | |
|---|---|
| *A61B 17/068* | (2006.01) |
| *A61B 18/00* | (2006.01) |
| *G16H 20/40* | (2018.01) |
| *G16H 40/60* | (2018.01) |
| *G16H 40/63* | (2018.01) |
| *G16H 40/67* | (2018.01) |

(52) U.S. Cl.
CPC ............. *G16H 40/60* (2018.01); *G16H 40/63* (2018.01); *G16H 40/67* (2018.01); *A61B 2017/00137* (2013.01); *A61B 2017/00225* (2013.01); *A61B 2018/00702* (2013.01); *H04L 2209/42* (2013.01)

(58) Field of Classification Search
CPC ......... A61B 2018/00702; G16H 20/40; G16H 40/60; G16H 40/63; G16H 40/67; H04L 2209/42

See application file for complete search history.

(56) References Cited

U.S. PATENT DOCUMENTS

| | | | |
|---|---|---|---|
| 3,082,426 | A | 3/1963 | Miles |
| 3,503,396 | A | 3/1970 | Pierie et al. |
| 3,584,628 | A | 6/1971 | Green |
| 3,626,457 | A | 12/1971 | Duerr et al. |
| 3,633,584 | A | 1/1972 | Farrell |
| 3,759,017 | A | 9/1973 | Young |
| 3,863,118 | A | 1/1975 | Lander et al. |
| 3,898,545 | A | 8/1975 | Coppa et al. |
| 3,912,121 | A | 10/1975 | Steffen |
| 3,915,271 | A | 10/1975 | Harper |
| 3,932,812 | A | 1/1976 | Milligan |
| 4,041,362 | A | 8/1977 | Ichiyanagi |
| 4,052,649 | A | 10/1977 | Greenwell et al. |
| 4,087,730 | A | 5/1978 | Goles |
| 4,157,859 | A | 6/1979 | Terry |
| 4,171,700 | A | 10/1979 | Farin |
| 4,202,722 | A | 5/1980 | Paquin |
| 4,412,539 | A | 11/1983 | Jarvik |
| 4,448,193 | A | 5/1984 | Ivanov |
| 4,523,695 | A | 6/1985 | Braun et al. |
| 4,608,160 | A | 8/1986 | Zoch |
| 4,614,366 | A | 9/1986 | North et al. |
| 4,633,874 | A | 1/1987 | Chow et al. |
| 4,701,193 | A | 10/1987 | Robertson et al. |
| 4,735,603 | A | 4/1988 | Goodson et al. |
| 4,779,687 | A | 10/1988 | Schreiber et al. |
| 4,788,977 | A | 12/1988 | Farin et al. |
| 4,827,911 | A | 5/1989 | Broadwin et al. |
| 4,849,752 | A | 7/1989 | Bryant |
| D303,787 | S | 10/1989 | Messenger et al. |
| 4,892,244 | A | 1/1990 | Fox et al. |
| 4,962,681 | A | 10/1990 | Yang |
| 4,976,173 | A | 12/1990 | Yang |
| 5,010,341 | A | 4/1991 | Huntley et al. |
| 5,026,387 | A | 6/1991 | Thomas |
| 5,035,692 | A | 7/1991 | Lyon et al. |
| 5,042,460 | A | 8/1991 | Sakurai et al. |
| 5,047,043 | A | 9/1991 | Kubota et al. |
| 5,084,057 | A | 1/1992 | Green et al. |
| 5,100,402 | A | 3/1992 | Fan |
| D327,061 | S | 6/1992 | Soren et al. |
| 5,129,570 | A | 7/1992 | Schulze et al. |
| 5,151,102 | A | 9/1992 | Kamiyama et al. |
| 5,156,315 | A | 10/1992 | Green et al. |
| 5,158,585 | A | 10/1992 | Saho et al. |
| 5,160,334 | A | 11/1992 | Billings et al. |
| 5,171,247 | A | 12/1992 | Hughett et al. |
| 5,189,277 | A | 2/1993 | Boisvert et al. |
| 5,197,962 | A | 3/1993 | Sansom et al. |
| 5,204,669 | A | 4/1993 | Dorfe et al. |
| 5,217,003 | A | 6/1993 | Wilk |
| 5,242,474 | A | 9/1993 | Herbst et al. |
| 5,253,793 | A | 10/1993 | Green et al. |
| 5,271,543 | A | 12/1993 | Grant et al. |
| RE34,519 | E | 1/1994 | Fox et al. |
| 5,275,323 | A | 1/1994 | Schulze et al. |
| 5,318,516 | A | 6/1994 | Cosmescu |
| 5,318,563 | A | 6/1994 | Malis et al. |
| 5,322,055 | A | 6/1994 | Davison et al. |
| 5,342,349 | A | 8/1994 | Kaufman |
| 5,364,003 | A | 11/1994 | Williamson, IV |
| 5,383,880 | A | 1/1995 | Hooven |
| 5,385,544 | A | 1/1995 | Edwards et al. |
| 5,391,144 | A | 2/1995 | Sakurai et al. |
| 5,396,900 | A | 3/1995 | Slater et al. |
| 5,397,046 | A | 3/1995 | Savage et al. |
| 5,403,312 | A | 4/1995 | Yates et al. |
| 5,403,327 | A | 4/1995 | Thornton et al. |
| 5,413,267 | A | 5/1995 | Solyntjes et al. |
| 5,415,335 | A | 5/1995 | Knodell, Jr. |
| 5,417,699 | A | 5/1995 | Klein et al. |
| 5,439,468 | A | 8/1995 | Schulze et al. |
| 5,445,304 | A | 8/1995 | Plyley et al. |
| 5,462,545 | A | 10/1995 | Wang et al. |
| 5,465,895 | A | 11/1995 | Knodel et al. |
| 5,467,911 | A | 11/1995 | Tsuruta et al. |
| 5,474,566 | A | 12/1995 | Alesi et al. |
| 5,485,947 | A | 1/1996 | Olson et al. |
| 5,496,315 | A | 3/1996 | Weaver et al. |
| 5,496,317 | A | 3/1996 | Goble et al. |
| 5,503,320 | A | 4/1996 | Webster et al. |
| 5,507,773 | A | 4/1996 | Huitema et al. |
| 5,529,235 | A | 6/1996 | Boiarski et al. |
| 5,531,743 | A | 7/1996 | Nettekoven et al. |
| 5,545,148 | A | 8/1996 | Wurster |
| 5,552,685 | A | 9/1996 | Young et al. |
| 5,560,372 | A | 10/1996 | Cory |
| 5,584,425 | A | 12/1996 | Savage et al. |
| 5,607,436 | A | 3/1997 | Pratt et al. |
| 5,610,379 | A | 3/1997 | Muz et al. |
| 5,610,811 | A | 3/1997 | Honda |
| 5,613,966 | A | 3/1997 | Makower et al. |
| 5,619,881 | A | 4/1997 | Morikawa et al. |
| 5,624,452 | A | 4/1997 | Yates |
| D379,346 | S | 5/1997 | Mieki |
| 5,626,587 | A | 5/1997 | Bishop et al. |
| 5,643,291 | A | 7/1997 | Pier et al. |
| 5,654,750 | A | 8/1997 | Weil et al. |
| 5,673,841 | A | 10/1997 | Schulze et al. |
| 5,673,842 | A | 10/1997 | Bittner et al. |
| 5,675,227 | A | 10/1997 | Roos et al. |
| 5,693,042 | A | 12/1997 | Boiarski et al. |
| 5,693,052 | A | 12/1997 | Weaver |
| 5,695,502 | A | 12/1997 | Pier et al. |
| 5,697,926 | A | 12/1997 | Weaver |
| 5,706,998 | A | 1/1998 | Plyley et al. |
| 5,718,359 | A | 2/1998 | Palmer et al. |
| 5,720,287 | A | 2/1998 | Chapelon et al. |
| 5,724,468 | A | 3/1998 | Leone et al. |
| 5,725,536 | A | 3/1998 | Oberlin et al. |
| 5,725,542 | A | 3/1998 | Yoon |
| 5,735,445 | A | 4/1998 | Vidal et al. |
| 5,735,848 | A | 4/1998 | Yates et al. |
| 5,746,209 | A | 5/1998 | Yost et al. |
| 5,749,362 | A | 5/1998 | Funda et al. |
| 5,749,893 | A | 5/1998 | Vidal et al. |
| 5,752,644 | A | 5/1998 | Bolanos et al. |
| 5,762,255 | A | 6/1998 | Chrisman et al. |
| 5,762,458 | A | 6/1998 | Wang et al. |
| 5,766,186 | A | 6/1998 | Faraz et al. |
| 5,769,791 | A | 6/1998 | Benaron et al. |
| 5,775,331 | A | 7/1998 | Raymond et al. |

(56)                References Cited

U.S. PATENT DOCUMENTS

| | | |
|---|---|---|
| 5,796,188 A | 8/1998 | Bays |
| 5,797,537 A | 8/1998 | Oberlin et al. |
| 5,800,350 A | 9/1998 | Coppleson et al. |
| 5,807,393 A | 9/1998 | Williamson, IV et al. |
| D399,561 S | 10/1998 | Ellingson |
| 5,817,093 A | 10/1998 | Williamson, IV et al. |
| 5,820,009 A | 10/1998 | Melling et al. |
| 5,833,690 A | 11/1998 | Yates et al. |
| 5,836,849 A | 11/1998 | Mathiak et al. |
| 5,836,869 A | 11/1998 | Kudo et al. |
| 5,836,909 A | 11/1998 | Cosmescu |
| 5,843,080 A | 12/1998 | Fleenor et al. |
| 5,846,237 A | 12/1998 | Nettekoven |
| 5,849,022 A | 12/1998 | Sakashita et al. |
| 5,873,873 A | 2/1999 | Smith et al. |
| 5,878,938 A | 3/1999 | Bittner et al. |
| 5,893,849 A | 4/1999 | Weaver |
| 5,906,625 A | 5/1999 | Bito et al. |
| 5,942,333 A | 8/1999 | Arnett et al. |
| 5,947,996 A | 9/1999 | Logeman |
| 5,968,032 A | 10/1999 | Sleister |
| 5,980,510 A | 11/1999 | Tsonton et al. |
| 5,987,346 A | 11/1999 | Benaron et al. |
| 5,997,528 A | 12/1999 | Bisch et al. |
| 6,004,269 A | 12/1999 | Crowley et al. |
| 6,010,054 A | 1/2000 | Johnson et al. |
| 6,030,437 A | 2/2000 | Gourrier et al. |
| 6,036,637 A | 3/2000 | Kudo |
| 6,039,734 A | 3/2000 | Goble |
| 6,039,735 A | 3/2000 | Greep |
| 6,059,799 A | 5/2000 | Aranyi et al. |
| 6,066,137 A | 5/2000 | Greep |
| 6,079,606 A | 6/2000 | Milliman et al. |
| 6,090,107 A | 7/2000 | Borgmeier et al. |
| 6,099,537 A | 8/2000 | Sugai et al. |
| 6,102,907 A | 8/2000 | Smethers et al. |
| 6,109,500 A | 8/2000 | Alli et al. |
| 6,113,598 A | 9/2000 | Baker |
| 6,126,592 A | 10/2000 | Proch et al. |
| 6,126,658 A | 10/2000 | Baker |
| 6,131,789 A | 10/2000 | Schulze et al. |
| 6,139,561 A | 10/2000 | Shibata et al. |
| 6,155,473 A | 12/2000 | Tompkins et al. |
| 6,214,000 B1 | 4/2001 | Fleenor et al. |
| 6,258,105 B1 | 7/2001 | Hart et al. |
| 6,269,411 B1 | 7/2001 | Reasoner |
| 6,273,887 B1 | 8/2001 | Yamauchi et al. |
| 6,283,960 B1 | 9/2001 | Ashley |
| 6,301,495 B1 | 10/2001 | Gueziec et al. |
| 6,302,881 B1 | 10/2001 | Farin |
| 6,308,089 B1 | 10/2001 | von der Ruhr et al. |
| 6,325,808 B1 | 12/2001 | Bernard et al. |
| 6,325,811 B1 | 12/2001 | Messerly |
| 6,331,181 B1 | 12/2001 | Tierney et al. |
| 6,341,164 B1 | 1/2002 | Dilkie et al. |
| 6,391,102 B1 | 5/2002 | Bodden et al. |
| 6,423,057 B1 | 7/2002 | He et al. |
| 6,434,416 B1 | 8/2002 | Mizoguchi et al. |
| 6,443,973 B1 | 9/2002 | Whitman |
| 6,451,015 B1 | 9/2002 | Rittman, III et al. |
| 6,454,781 B1 | 9/2002 | Witt et al. |
| 6,457,625 B1 | 10/2002 | Tormala et al. |
| 6,461,352 B2 | 10/2002 | Morgan et al. |
| 6,466,817 B1 | 10/2002 | Kaula et al. |
| 6,480,796 B2 | 11/2002 | Wiener |
| 6,482,217 B1 | 11/2002 | Pintor et al. |
| 6,524,307 B1 | 2/2003 | Palmerton et al. |
| 6,530,933 B1 | 3/2003 | Yeung et al. |
| 6,551,243 B2 | 4/2003 | Bocionek et al. |
| 6,569,109 B2 | 5/2003 | Sakurai et al. |
| 6,582,424 B2 | 6/2003 | Fleenor et al. |
| 6,584,358 B2 | 6/2003 | Carter et al. |
| 6,585,791 B1 | 7/2003 | Garito et al. |
| 6,611,793 B1 | 8/2003 | Burnside et al. |
| 6,618,626 B2 | 9/2003 | West, Jr. et al. |
| 6,628,989 B1 | 9/2003 | Penner et al. |
| 6,633,234 B2 | 10/2003 | Wiener et al. |
| 6,648,223 B2 | 11/2003 | Boukhny et al. |
| 6,678,552 B2 | 1/2004 | Pearlman |
| 6,679,899 B2 | 1/2004 | Wiener et al. |
| 6,685,704 B2 | 2/2004 | Greep |
| 6,695,199 B2 | 2/2004 | Whitman |
| 6,699,187 B2 | 3/2004 | Webb et al. |
| 6,731,514 B2 | 5/2004 | Evans |
| 6,742,895 B2 | 6/2004 | Robir |
| 6,752,816 B2 | 6/2004 | Culp et al. |
| 6,760,616 B2 | 7/2004 | Hoey et al. |
| 6,770,072 B1 | 8/2004 | Truckai et al. |
| 6,773,444 B2 | 8/2004 | Messerly |
| 6,775,575 B2 | 8/2004 | Bommannan et al. |
| 6,778,846 B1 | 8/2004 | Martinez et al. |
| 6,781,683 B2 | 8/2004 | Kacyra et al. |
| 6,783,524 B2 | 8/2004 | Anderson et al. |
| 6,783,525 B2 | 8/2004 | Greep et al. |
| 6,793,652 B1 | 9/2004 | Whitman et al. |
| 6,793,663 B2 | 9/2004 | Kneifel et al. |
| 6,824,539 B2 | 11/2004 | Novak |
| 6,846,308 B2 | 1/2005 | Whitman et al. |
| 6,849,071 B2 | 2/2005 | Whitman et al. |
| 6,849,074 B2 | 2/2005 | Chen et al. |
| 6,852,219 B2 | 2/2005 | Hammond |
| 6,863,650 B1 | 3/2005 | Irion |
| 6,869,430 B2 | 3/2005 | Balbierz et al. |
| 6,869,435 B2 | 3/2005 | Blake, III |
| 6,911,033 B2 | 6/2005 | de Guillebon et al. |
| 6,913,471 B2 | 7/2005 | Smith |
| 6,937,892 B2 | 8/2005 | Leyde et al. |
| 6,945,981 B2 | 9/2005 | Donofrio et al. |
| 6,951,559 B1 | 10/2005 | Greep |
| 6,962,587 B2 | 11/2005 | Johnson et al. |
| 6,978,921 B2 | 12/2005 | Shelton, IV et al. |
| 6,988,649 B2 | 1/2006 | Shelton, IV et al. |
| 7,000,818 B2 | 2/2006 | Shelton, IV et al. |
| 7,009,511 B2 | 3/2006 | Mazar et al. |
| 7,030,146 B2 | 4/2006 | Baynes et al. |
| 7,032,798 B2 | 4/2006 | Whitman et al. |
| 7,041,941 B2 | 5/2006 | Faries, Jr. et al. |
| 7,044,352 B2 | 5/2006 | Shelton, IV et al. |
| 7,044,911 B2 | 5/2006 | Drinan et al. |
| 7,044,949 B2 | 5/2006 | Orszulak et al. |
| 7,048,775 B2 | 5/2006 | Jornitz et al. |
| 7,053,752 B2 | 5/2006 | Wang et al. |
| 7,055,730 B2 | 6/2006 | Ehrenfels et al. |
| 7,073,765 B2 | 7/2006 | Newkirk |
| 7,077,853 B2 | 7/2006 | Kramer et al. |
| 7,077,856 B2 | 7/2006 | Whitman |
| 7,081,096 B2 | 7/2006 | Brister et al. |
| 7,094,231 B1 | 8/2006 | Ellman et al. |
| 7,097,640 B2 | 8/2006 | Wang et al. |
| 7,103,688 B2 | 9/2006 | Strong |
| 7,104,949 B2 | 9/2006 | Anderson et al. |
| 7,118,564 B2 | 10/2006 | Ritchie et al. |
| 7,121,460 B1 | 10/2006 | Parsons et al. |
| 7,137,980 B2 | 11/2006 | Buysse et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,147,139 B2 | 12/2006 | Schwemberger et al. |
| 7,155,316 B2 | 12/2006 | Sutherland et al. |
| 7,164,940 B2 | 1/2007 | Hareyama et al. |
| 7,169,145 B2 | 1/2007 | Isaacson et al. |
| 7,177,533 B2 | 2/2007 | McFarlin et al. |
| 7,182,775 B2 | 2/2007 | de Guillebon et al. |
| 7,207,472 B2 | 4/2007 | Wukusick et al. |
| 7,208,005 B2 | 4/2007 | Frecker et al. |
| 7,217,269 B2 | 5/2007 | El-Galley et al. |
| 7,230,529 B2 | 6/2007 | Ketcherside, Jr. et al. |
| 7,232,447 B2 | 6/2007 | Gellman et al. |
| 7,236,817 B2 | 6/2007 | Papas et al. |
| 7,246,734 B2 | 7/2007 | Shelton, IV |
| 7,252,664 B2 | 8/2007 | Nasab et al. |
| 7,278,563 B1 | 10/2007 | Green |
| 7,294,106 B2 | 11/2007 | Birkenbach et al. |
| 7,294,116 B1 | 11/2007 | Ellman et al. |

(56) References Cited

U.S. PATENT DOCUMENTS

| | | | |
|---|---|---|---|
| 7,296,724 B2 | 11/2007 | Green et al. |
| 7,317,955 B2 | 1/2008 | McGreevy |
| 7,328,828 B2 | 2/2008 | Ortiz et al. |
| 7,334,717 B2 | 2/2008 | Rethy et al. |
| 7,343,565 B2 | 3/2008 | Ying et al. |
| 7,344,532 B2 | 3/2008 | Goble et al. |
| 7,353,068 B2 | 4/2008 | Tanaka et al. |
| 7,362,228 B2 | 4/2008 | Nycz et al. |
| 7,371,227 B2 | 5/2008 | Zeiner |
| 7,380,695 B2 | 6/2008 | Doll et al. |
| 7,383,088 B2 | 6/2008 | Spinelli et al. |
| 7,391,173 B2 | 6/2008 | Schena |
| 7,407,074 B2 | 8/2008 | Ortiz et al. |
| 7,408,439 B2 | 8/2008 | Wang et al. |
| 7,413,541 B2 | 8/2008 | Konishi |
| 7,422,136 B1 | 9/2008 | Marczyk |
| 7,422,139 B2 | 9/2008 | Shelton, IV et al. |
| 7,422,586 B2 | 9/2008 | Morris et al. |
| 7,423,972 B2 | 9/2008 | Shaham et al. |
| D579,876 S | 11/2008 | Novotney et al. |
| 7,445,620 B2 | 11/2008 | Kefer |
| 7,457,804 B2 | 11/2008 | Uber, III et al. |
| D583,328 S | 12/2008 | Chiang |
| 7,464,847 B2 | 12/2008 | Viola et al. |
| 7,464,849 B2 | 12/2008 | Shelton, IV et al. |
| 7,496,418 B2 | 2/2009 | Kim et al. |
| D589,447 S | 3/2009 | Sasada et al. |
| 7,515,961 B2 | 4/2009 | Germanson et al. |
| 7,518,502 B2 | 4/2009 | Austin et al. |
| 7,554,343 B2 | 6/2009 | Bromfield |
| 7,563,259 B2 | 7/2009 | Takahashi |
| 7,568,604 B2 | 8/2009 | Ehrenfels et al. |
| 7,575,144 B2 | 8/2009 | Ortiz et al. |
| 7,597,731 B2 | 10/2009 | Palmerton et al. |
| 7,617,137 B2 | 11/2009 | Kreiner et al. |
| 7,621,192 B2 | 11/2009 | Conti et al. |
| 7,621,898 B2 | 11/2009 | Lalomia et al. |
| 7,631,793 B2 | 12/2009 | Rethy et al. |
| 7,637,410 B2 | 12/2009 | Marczyk |
| 7,637,907 B2 | 12/2009 | Blaha |
| 7,641,092 B2 | 1/2010 | Kruszynski et al. |
| 7,644,848 B2 | 1/2010 | Swayze et al. |
| 7,667,592 B2 | 2/2010 | Ohyama et al. |
| 7,667,839 B2 | 2/2010 | Bates |
| 7,670,334 B2 | 3/2010 | Hueil et al. |
| 7,694,865 B2 | 4/2010 | Scirica |
| 7,699,772 B2 | 4/2010 | Pauker et al. |
| 7,699,860 B2 | 4/2010 | Huitema et al. |
| 7,717,312 B2 | 5/2010 | Beetel |
| 7,720,306 B2 | 5/2010 | Gardiner et al. |
| 7,721,934 B2 | 5/2010 | Shelton, IV et al. |
| 7,721,936 B2 | 5/2010 | Shalton, IV et al. |
| 7,722,603 B2 | 5/2010 | McPherson |
| 7,736,357 B2 | 6/2010 | Lee, Jr. et al. |
| 7,742,176 B2 | 6/2010 | Braunecker et al. |
| 7,743,960 B2 | 6/2010 | Whitman et al. |
| 7,753,245 B2 | 7/2010 | Boudreaux et al. |
| 7,757,028 B2 | 7/2010 | Druke et al. |
| 7,766,207 B2 | 8/2010 | Mather et al. |
| 7,766,905 B2 | 8/2010 | Paterson et al. |
| 7,770,773 B2 | 8/2010 | Whitman et al. |
| 7,771,429 B2 | 8/2010 | Ballard et al. |
| 7,776,037 B2 | 8/2010 | Odom |
| 7,782,789 B2 | 8/2010 | Stultz et al. |
| 7,784,663 B2 | 8/2010 | Shelton, IV |
| 7,803,151 B2 | 9/2010 | Whitman |
| 7,810,692 B2 | 10/2010 | Hall et al. |
| 7,818,041 B2 | 10/2010 | Kim et al. |
| 7,819,298 B2 | 10/2010 | Hall et al. |
| 7,832,612 B2 | 11/2010 | Baxter, III et al. |
| 7,833,219 B2 | 11/2010 | Tashiro et al. |
| 7,836,085 B2 | 11/2010 | Petakov et al. |
| 7,837,079 B2 | 11/2010 | Holsten et al. |
| 7,837,680 B2 | 11/2010 | Isaacson et al. |
| 7,841,980 B2 | 11/2010 | Minosawa et al. |
| 7,845,537 B2 | 12/2010 | Shelton, IV et al. |
| 7,857,185 B2 | 12/2010 | Swayze et al. |
| D631,252 S | 1/2011 | Leslie |
| 7,862,560 B2 | 1/2011 | Marion |
| 7,862,579 B2 | 1/2011 | Ortiz et al. |
| 7,865,236 B2 | 1/2011 | Cory et al. |
| 7,884,735 B2 | 2/2011 | Newkirk |
| 7,887,530 B2 | 2/2011 | Zemlok et al. |
| 7,892,337 B2 | 2/2011 | Palmerton et al. |
| 7,907,166 B2 | 3/2011 | Lamprecht et al. |
| 7,913,891 B2 | 3/2011 | Doll et al. |
| 7,918,230 B2 | 4/2011 | Whitman et al. |
| 7,918,377 B2 | 4/2011 | Measamer et al. |
| 7,920,706 B2 | 4/2011 | Asokan et al. |
| 7,922,063 B2 | 4/2011 | Zemlok et al. |
| 7,927,014 B2 | 4/2011 | Dehler |
| 7,932,826 B2 | 4/2011 | Fritchie et al. |
| 7,942,300 B2 | 5/2011 | Rethy et al. |
| 7,945,065 B2 | 5/2011 | Menzl et al. |
| 7,945,342 B2 | 5/2011 | Tsai et al. |
| 7,950,560 B2 | 5/2011 | Zemlok et al. |
| 7,951,148 B2 | 5/2011 | McClurken |
| 7,954,682 B2 | 6/2011 | Giordano et al. |
| 7,954,687 B2 | 6/2011 | Zemlok et al. |
| 7,955,322 B2 | 6/2011 | Devengenzo et al. |
| 7,956,620 B2 | 6/2011 | Gilbert |
| 7,963,433 B2 | 6/2011 | Whitman et al. |
| 7,966,269 B2 | 6/2011 | Bauer et al. |
| 7,967,180 B2 | 6/2011 | Scirica |
| 7,976,553 B2 | 7/2011 | Shelton, IV et al. |
| 7,979,157 B2 | 7/2011 | Anvari |
| 7,980,443 B2 | 7/2011 | Scheib et al. |
| 7,982,776 B2 | 7/2011 | Dunki-Jacobs et al. |
| 7,988,028 B2 | 8/2011 | Farascioni et al. |
| 7,993,140 B2 | 8/2011 | Sakezles |
| 7,993,354 B1 | 8/2011 | Brecher et al. |
| 7,993,954 B2 | 8/2011 | Wieting |
| 7,995,045 B2 | 8/2011 | Dunki-Jacobs |
| 8,005,947 B2 | 8/2011 | Morris et al. |
| 8,007,494 B1 | 8/2011 | Taylor et al. |
| 8,007,513 B2 | 8/2011 | Nalagatla et al. |
| 8,010,180 B2 | 8/2011 | Quaid et al. |
| 8,012,170 B2 | 9/2011 | Whitman et al. |
| 8,015,976 B2 | 9/2011 | Shah |
| 8,016,855 B2 | 9/2011 | Whitman et al. |
| 8,019,094 B2 | 9/2011 | Hsieh et al. |
| 8,025,199 B2 | 9/2011 | Whitman et al. |
| 8,027,710 B1 | 9/2011 | Dannan |
| 8,035,685 B2 | 10/2011 | Jensen |
| 8,038,686 B2 | 10/2011 | Huitema et al. |
| 8,038,693 B2 | 10/2011 | Allen |
| 8,043,560 B2 | 10/2011 | Okumoto et al. |
| 8,054,184 B2 | 11/2011 | Cline et al. |
| 8,054,752 B2 | 11/2011 | Druke et al. |
| 8,062,306 B2 | 11/2011 | Nobis et al. |
| 8,062,330 B2 | 11/2011 | Prommersberger et al. |
| 8,066,721 B2 | 11/2011 | Kortenbach et al. |
| 8,074,861 B2 | 12/2011 | Ehrenfels et al. |
| 8,075,571 B2 | 12/2011 | Vitali et al. |
| 8,095,327 B2 | 1/2012 | Tahara et al. |
| 8,096,459 B2 | 1/2012 | Ortiz et al. |
| 8,116,848 B2 | 2/2012 | Shahidi |
| 8,118,206 B2 | 2/2012 | Zand et al. |
| 8,120,301 B2 | 2/2012 | Goldberg et al. |
| 8,123,764 B2 | 2/2012 | Meade et al. |
| D655,678 S | 3/2012 | Kobayashi et al. |
| 8,128,625 B2 | 3/2012 | Odom |
| 8,131,565 B2 | 3/2012 | Dicks et al. |
| 8,136,712 B2 | 3/2012 | Zingman |
| 8,146,149 B2 | 3/2012 | Steinkogler et al. |
| D657,368 S | 4/2012 | Magee et al. |
| 8,147,486 B2 | 4/2012 | Honour et al. |
| 8,155,479 B2 | 4/2012 | Hoffman et al. |
| 8,157,145 B2 | 4/2012 | Shelton, IV et al. |
| 8,157,150 B2 | 4/2012 | Viola et al. |
| 8,157,151 B2 | 4/2012 | Ingmanson et al. |
| 8,160,098 B1 | 4/2012 | Yan et al. |
| 8,160,690 B2 | 4/2012 | Wilfley et al. |
| 8,161,977 B2 | 4/2012 | Shelton, IV et al. |

(56) References Cited

U.S. PATENT DOCUMENTS

| | | | |
|---|---|---|---|
| 8,170,396 B2 | 5/2012 | Kuspa et al. |
| 8,172,836 B2 | 5/2012 | Ward |
| 8,181,839 B2 | 5/2012 | Beetel |
| 8,185,409 B2 | 5/2012 | Putnam et al. |
| 8,206,345 B2 | 6/2012 | Abboud et al. |
| 8,208,707 B2 | 6/2012 | Mendonca et al. |
| 8,210,411 B2 | 7/2012 | Yates et al. |
| 8,211,100 B2 | 7/2012 | Podhajsky et al. |
| 8,214,007 B2 | 7/2012 | Baker et al. |
| 8,216,849 B2 | 7/2012 | Petty |
| 8,220,688 B2 | 7/2012 | Laurent et al. |
| 8,225,643 B2 | 7/2012 | Abboud et al. |
| 8,225,979 B2 | 7/2012 | Farascioni et al. |
| 8,229,549 B2 | 7/2012 | Whitman et al. |
| 8,231,042 B2 | 7/2012 | Hessler et al. |
| 8,239,066 B2 | 8/2012 | Jennings et al. |
| 8,241,322 B2 | 8/2012 | Whitman et al. |
| 8,255,045 B2 | 8/2012 | Gharib et al. |
| D667,838 S | 9/2012 | Magee et al. |
| 8,257,387 B2 | 9/2012 | Cunningham |
| 8,260,016 B2 | 9/2012 | Maeda et al. |
| 8,262,560 B2 | 9/2012 | Whitman |
| 8,292,639 B2 | 10/2012 | Achammer et al. |
| 8,292,888 B2 | 10/2012 | Whitman |
| 8,295,902 B2 | 10/2012 | Salahieh et al. |
| 8,308,040 B2 | 11/2012 | Huang et al. |
| 8,321,581 B2 | 11/2012 | Katis et al. |
| 8,322,590 B2 | 12/2012 | Patel et al. |
| 8,328,065 B2 | 12/2012 | Shah |
| 8,335,590 B2 | 12/2012 | Costa et al. |
| D675,164 S | 1/2013 | Kobayashi et al. |
| 8,343,065 B2 | 1/2013 | Bartol et al. |
| 8,346,392 B2 | 1/2013 | Walser et al. |
| 8,360,299 B2 | 1/2013 | Zemlok et al. |
| 8,364,222 B2 | 1/2013 | Cook et al. |
| D676,392 S | 2/2013 | Gassauer |
| 8,365,975 B1 | 2/2013 | Manoux et al. |
| D678,196 S | 3/2013 | Miyauchi et al. |
| D678,304 S | 3/2013 | Yakoub et al. |
| 8,388,652 B2 | 3/2013 | Viola |
| 8,393,514 B2 | 3/2013 | Shelton, IV et al. |
| 8,397,972 B2 | 3/2013 | Kostrzewski |
| 8,398,541 B2 | 3/2013 | DiMaio et al. |
| 8,403,944 B2 | 3/2013 | Pain et al. |
| 8,403,945 B2 | 3/2013 | Whitfield et al. |
| 8,403,946 B2 | 3/2013 | Whitfield et al. |
| 8,406,859 B2 | 3/2013 | Zuzak et al. |
| 8,411,034 B2 | 4/2013 | Boillot et al. |
| 8,413,871 B2 | 4/2013 | Racenet et al. |
| 8,422,035 B2 | 4/2013 | Hinderling et al. |
| 8,423,182 B2 | 4/2013 | Robinson et al. |
| 8,428,722 B2 | 4/2013 | Verhoef et al. |
| 8,429,153 B2 | 4/2013 | Birdwell et al. |
| 8,439,910 B2 | 5/2013 | Greep et al. |
| 8,444,663 B2 | 5/2013 | Houser et al. |
| 8,452,615 B2 | 5/2013 | Abri |
| 8,453,906 B2 | 6/2013 | Huang et al. |
| 8,454,506 B2 | 6/2013 | Rothman et al. |
| 8,461,744 B2 | 6/2013 | Wiener et al. |
| 8,468,030 B2 | 6/2013 | Stroup et al. |
| 8,469,973 B2 | 6/2013 | Meade et al. |
| 8,472,630 B2 | 6/2013 | Konrad et al. |
| 8,473,066 B2 | 6/2013 | Aghassian et al. |
| D687,146 S | 7/2013 | Juzkiw et al. |
| 8,476,227 B2 | 7/2013 | Kaplan et al. |
| 8,478,418 B2 | 7/2013 | Fahey |
| 8,489,235 B2 | 7/2013 | Moll et al. |
| 8,499,992 B2 | 8/2013 | Whitman et al. |
| 8,500,728 B2 | 8/2013 | Newton et al. |
| 8,500,756 B2 | 8/2013 | Papa et al. |
| 8,503,759 B2 | 8/2013 | Greer et al. |
| 8,505,801 B2 | 8/2013 | Ehrenfels et al. |
| 8,506,478 B2 | 8/2013 | Mizuyoshi |
| 8,512,325 B2 | 8/2013 | Mathonnet |
| 8,512,365 B2 | 8/2013 | Wiener et al. |
| 8,515,520 B2 | 8/2013 | Brunnett et al. |
| 8,517,239 B2 | 8/2013 | Scheib et al. |
| 8,521,331 B2 | 8/2013 | Itkowitz |
| 8,523,043 B2 | 9/2013 | Ullrich et al. |
| 8,533,475 B2 | 9/2013 | Frikart et al. |
| 8,535,342 B2 | 9/2013 | Malackowski et al. |
| 8,540,709 B2 | 9/2013 | Allen |
| 8,543,240 B2 | 9/2013 | Itkowitz et al. |
| 8,546,996 B2 | 10/2013 | Messerly et al. |
| 8,554,697 B2 | 10/2013 | Claus et al. |
| 8,560,047 B2 | 10/2013 | Haider et al. |
| 8,561,870 B2 | 10/2013 | Baxter, III et al. |
| 8,562,598 B2 | 10/2013 | Falkenstein et al. |
| 8,566,115 B2 | 10/2013 | Moore |
| 8,567,393 B2 | 10/2013 | Hickle et al. |
| 8,568,411 B2 | 10/2013 | Falkenstein et al. |
| 8,571,598 B2 | 10/2013 | Valavi |
| 8,573,459 B2 | 11/2013 | Smith et al. |
| 8,573,465 B2 | 11/2013 | Shelton, IV |
| 8,574,229 B2 | 11/2013 | Eder et al. |
| 8,585,631 B2 | 11/2013 | Dacquay |
| 8,585,694 B2 | 11/2013 | Amoah et al. |
| 8,590,762 B2 | 11/2013 | Hess et al. |
| 8,591,536 B2 | 11/2013 | Robertson |
| 8,595,607 B2 | 11/2013 | Nekoomaram et al. |
| 8,596,513 B2 | 12/2013 | Olson et al. |
| 8,596,515 B2 | 12/2013 | Okoniewski |
| 8,604,709 B2 | 12/2013 | Jalbout et al. |
| 8,608,044 B2 | 12/2013 | Hueil et al. |
| 8,608,045 B2 | 12/2013 | Smith et al. |
| 8,616,431 B2 | 12/2013 | Timm et al. |
| 8,617,155 B2 | 12/2013 | Johnson et al. |
| 8,620,055 B2 | 12/2013 | Barratt et al. |
| 8,620,473 B2 | 12/2013 | Diolaiti et al. |
| 8,622,275 B2 | 1/2014 | Baxter, III et al. |
| 8,623,027 B2 | 1/2014 | Price et al. |
| 8,627,483 B2 | 1/2014 | Rachlin et al. |
| 8,627,993 B2 | 1/2014 | Smith et al. |
| 8,627,995 B2 | 1/2014 | Smith et al. |
| 8,628,518 B2 | 1/2014 | Blumenkranz et al. |
| 8,628,545 B2 | 1/2014 | Cabrera et al. |
| 8,631,987 B2 | 1/2014 | Shelton, IV et al. |
| 8,632,525 B2 | 1/2014 | Kerr et al. |
| 8,636,190 B2 | 1/2014 | Zemlok et al. |
| 8,636,736 B2 | 1/2014 | Yates et al. |
| 8,641,621 B2 | 2/2014 | Razzaque et al. |
| 8,652,086 B2 | 2/2014 | Gerg et al. |
| 8,652,121 B2 | 2/2014 | Quick et al. |
| 8,652,128 B2 | 2/2014 | Ward |
| 8,657,176 B2 | 2/2014 | Shelton, IV et al. |
| 8,657,177 B2 | 2/2014 | Scirica et al. |
| 8,663,220 B2 | 3/2014 | Wiener et al. |
| 8,663,222 B2 | 3/2014 | Anderson et al. |
| 8,666,544 B2 | 3/2014 | Moll et al. |
| 8,679,114 B2 | 3/2014 | Chapman et al. |
| 8,682,049 B2 | 3/2014 | Zhao et al. |
| 8,682,489 B2 | 3/2014 | Itkowitz et al. |
| 8,685,056 B2 | 4/2014 | Evans et al. |
| 8,688,188 B2 | 4/2014 | Heller et al. |
| 8,690,864 B2 | 4/2014 | Hoarau |
| 8,701,962 B2 | 4/2014 | Kostrzewski |
| 8,708,213 B2 | 4/2014 | Shelton, IV et al. |
| D704,839 S | 5/2014 | Juzkiw et al. |
| 8,719,061 B2 | 5/2014 | Birchall |
| 8,720,766 B2 | 5/2014 | Hess et al. |
| 8,733,613 B2 | 5/2014 | Huitema et al. |
| 8,740,840 B2 | 6/2014 | Foley et al. |
| 8,740,866 B2 | 6/2014 | Reasoner et al. |
| 8,747,238 B2 | 6/2014 | Shelton, IV et al. |
| 8,752,749 B2 | 6/2014 | Moore et al. |
| 8,757,465 B2 | 6/2014 | Woodard, Jr. et al. |
| 8,761,717 B1 | 6/2014 | Buchheit |
| 8,763,879 B2 | 7/2014 | Shelton, IV et al. |
| 8,768,251 B2 | 7/2014 | Claus et al. |
| 8,771,270 B2 | 7/2014 | Burbank |
| 8,775,196 B2 | 7/2014 | Simpson et al. |
| 8,779,648 B2 | 7/2014 | Giordano et al. |
| 8,790,253 B2 | 7/2014 | Sunagawa et al. |
| 8,794,497 B2 | 8/2014 | Zingman |

(56) References Cited

U.S. PATENT DOCUMENTS

| | | | |
|---|---|---|---|
| 8,795,001 B1 | 8/2014 | Lam et al. | |
| 8,799,008 B2 | 8/2014 | Johnson et al. | |
| 8,799,009 B2 | 8/2014 | Mellin et al. | |
| 8,800,838 B2 | 8/2014 | Shelton, IV | |
| 8,801,703 B2 | 8/2014 | Gregg et al. | |
| 8,814,996 B2 | 8/2014 | Giurgiutiu et al. | |
| 8,818,556 B2 | 8/2014 | Sanchez et al. | |
| 8,819,581 B2 | 8/2014 | Nakamura et al. | |
| 8,820,603 B2 | 9/2014 | Shelton, IV et al. | |
| 8,820,607 B2 | 9/2014 | Marczyk | |
| 8,820,608 B2 | 9/2014 | Miyamoto | |
| 8,827,134 B2 | 9/2014 | Viola et al. | |
| 8,827,136 B2 | 9/2014 | Hessler | |
| 8,840,003 B2 | 9/2014 | Morgan et al. | |
| D716,333 S | 10/2014 | Chotin et al. | |
| 8,851,354 B2 | 10/2014 | Swensgard et al. | |
| 8,852,174 B2 | 10/2014 | Burbank | |
| 8,864,747 B2 | 10/2014 | Merchant et al. | |
| 8,875,973 B2 | 11/2014 | Whitman | |
| 8,876,857 B2 | 11/2014 | Burbank | |
| 8,882,662 B2 | 11/2014 | Charles | |
| 8,885,032 B2 | 11/2014 | Igarashi et al. | |
| 8,886,790 B2 | 11/2014 | Harrang et al. | |
| 8,893,946 B2 | 11/2014 | Boudreaux et al. | |
| 8,893,949 B2 | 11/2014 | Shelton, IV et al. | |
| 8,899,479 B2 | 12/2014 | Cappuzzo et al. | |
| 8,905,977 B2 | 12/2014 | Shelton et al. | |
| 8,912,746 B2 | 12/2014 | Reid et al. | |
| 8,914,098 B2 | 12/2014 | Brennan et al. | |
| 8,917,513 B1 | 12/2014 | Hazzard | |
| 8,918,207 B2 | 12/2014 | Prisco | |
| 8,920,186 B2 | 12/2014 | Shishikura | |
| 8,920,414 B2 | 12/2014 | Stone et al. | |
| 8,920,433 B2 | 12/2014 | Barrier et al. | |
| 8,930,203 B2 | 1/2015 | Kiaie et al. | |
| 8,930,214 B2 | 1/2015 | Woolford | |
| 8,931,679 B2 | 1/2015 | Kostrzewski | |
| 8,934,684 B2 | 1/2015 | Mohamed | |
| 8,936,614 B2 | 1/2015 | Allen, IV | |
| 8,945,095 B2 | 2/2015 | Blumenkranz et al. | |
| 8,945,163 B2 | 2/2015 | Voegele et al. | |
| 8,955,732 B2 | 2/2015 | Zemlok et al. | |
| 8,956,581 B2 | 2/2015 | Rosenbaum et al. | |
| 8,960,519 B2 | 2/2015 | Whitman et al. | |
| 8,960,520 B2 | 2/2015 | McCuen | |
| 8,962,062 B2 | 2/2015 | Podhajsky et al. | |
| 8,967,443 B2 | 3/2015 | McCuen | |
| 8,967,455 B2 | 3/2015 | Zhou | |
| 8,968,276 B2 | 3/2015 | Zemlok et al. | |
| 8,968,296 B2 | 3/2015 | McPherson | |
| 8,968,309 B2 | 3/2015 | Roy et al. | |
| 8,968,312 B2 | 3/2015 | Marczyk et al. | |
| 8,968,337 B2 | 3/2015 | Whitfield et al. | |
| 8,968,358 B2 | 3/2015 | Reschke | |
| 8,974,429 B2 | 3/2015 | Gordon et al. | |
| 8,979,890 B2 | 3/2015 | Boudreaux | |
| 8,986,288 B2 | 3/2015 | Konishi | |
| 8,986,302 B2 | 3/2015 | Aldridge et al. | |
| 8,989,903 B2 | 3/2015 | Weir et al. | |
| 8,991,678 B2 | 3/2015 | Wellman et al. | |
| 8,992,565 B2 | 3/2015 | Brisson et al. | |
| 8,998,797 B2 | 4/2015 | Omori | |
| 9,002,518 B2 | 4/2015 | Manzo et al. | |
| 9,005,230 B2 | 4/2015 | Yates et al. | |
| 9,010,608 B2 | 4/2015 | Casasanta, Jr. et al. | |
| 9,010,611 B2 | 4/2015 | Ross et al. | |
| 9,011,366 B2 | 4/2015 | Dean et al. | |
| 9,011,427 B2 | 4/2015 | Price et al. | |
| 9,016,539 B2 | 4/2015 | Kostrzewski et al. | |
| 9,017,326 B2 | 4/2015 | DiNardo et al. | |
| 9,020,240 B2 | 4/2015 | Pettersson et al. | |
| D729,267 S | 5/2015 | Yoo et al. | |
| 9,023,032 B2 | 5/2015 | Robinson | |
| 9,023,071 B2 | 5/2015 | Miller et al. | |
| 9,023,079 B2 | 5/2015 | Boulnois et al. | |
| 9,027,431 B2 | 5/2015 | Tang et al. | |
| 9,028,494 B2 | 5/2015 | Shelton, IV et al. | |
| 9,033,973 B2 | 5/2015 | Krapohl et al. | |
| 9,035,568 B2 | 5/2015 | Ganton et al. | |
| 9,038,882 B2 | 5/2015 | Racenet et al. | |
| 9,043,027 B2 | 5/2015 | Durant et al. | |
| 9,044,227 B2 | 6/2015 | Shelton, IV et al. | |
| 9,044,244 B2 | 6/2015 | Ludwin et al. | |
| 9,044,261 B2 | 6/2015 | Houser | |
| 9,050,063 B2 | 6/2015 | Roe et al. | |
| 9,050,083 B2 | 6/2015 | Yates et al. | |
| 9,050,120 B2 | 6/2015 | Swarup et al. | |
| 9,052,809 B2 | 6/2015 | Vesto | |
| 9,055,035 B2 | 6/2015 | Porsch et al. | |
| 9,055,870 B2 | 6/2015 | Meador et al. | |
| 9,060,770 B2 | 6/2015 | Shelton, IV et al. | |
| 9,060,775 B2 | 6/2015 | Wiener et al. | |
| 9,066,650 B2 | 6/2015 | Sekiguchi | |
| 9,072,523 B2 | 7/2015 | Houser et al. | |
| 9,072,535 B2 | 7/2015 | Shelton, IV et al. | |
| 9,072,536 B2 | 7/2015 | Shelton, IV et al. | |
| 9,078,653 B2 | 7/2015 | Leimbach et al. | |
| 9,078,727 B2 | 7/2015 | Miller | |
| 9,084,606 B2 | 7/2015 | Greep | |
| 9,089,360 B2 | 7/2015 | Messerly et al. | |
| 9,095,362 B2 | 8/2015 | Dachs, II et al. | |
| 9,095,367 B2 | 8/2015 | Olson et al. | |
| 9,099,863 B2 | 8/2015 | Smith et al. | |
| 9,101,358 B2 | 8/2015 | Kerr et al. | |
| 9,101,359 B2 | 8/2015 | Smith et al. | |
| 9,101,374 B1 | 8/2015 | Hoch et al. | |
| 9,106,270 B2 | 8/2015 | Puterbaugh et al. | |
| 9,107,573 B2 | 8/2015 | Birnkrant | |
| 9,107,662 B2 | 8/2015 | Kostrzewski | |
| 9,107,684 B2 | 8/2015 | Ma | |
| 9,107,688 B2 | 8/2015 | Kimball et al. | |
| 9,107,689 B2 | 8/2015 | Robertson et al. | |
| 9,107,694 B2 | 8/2015 | Hendriks et al. | |
| 9,111,548 B2 | 8/2015 | Nandy et al. | |
| 9,113,880 B2 | 8/2015 | Zemlok et al. | |
| 9,114,494 B1 | 8/2015 | Mah | |
| 9,116,597 B1 | 8/2015 | Gulasky | |
| 9,119,617 B2 | 9/2015 | Souls et al. | |
| 9,119,655 B2 | 9/2015 | Bowling et al. | |
| 9,119,657 B2 | 9/2015 | Shelton, IV et al. | |
| 9,123,155 B2 | 9/2015 | Cunningham et al. | |
| 9,125,644 B2 | 9/2015 | Lane et al. | |
| 9,129,054 B2 | 9/2015 | Nawana et al. | |
| 9,131,957 B2 | 9/2015 | Skarbnik et al. | |
| 9,137,254 B2 | 9/2015 | Bilbrey et al. | |
| 9,138,129 B2 | 9/2015 | Diolaiti | |
| 9,138,225 B2 | 9/2015 | Huang et al. | |
| 9,141,758 B2 | 9/2015 | Kress et al. | |
| 9,149,322 B2 | 10/2015 | Knowlton | |
| 9,155,503 B2 | 10/2015 | Cadwell | |
| 9,160,853 B1 | 10/2015 | Daddi et al. | |
| 9,161,803 B2 | 10/2015 | Yates et al. | |
| 9,168,054 B2 | 10/2015 | Turner et al. | |
| 9,168,091 B2 | 10/2015 | Janssen et al. | |
| 9,168,104 B2 | 10/2015 | Dein | |
| 9,179,912 B2 | 11/2015 | Yates et al. | |
| 9,183,723 B2 | 11/2015 | Sherman et al. | |
| 9,186,143 B2 | 11/2015 | Timm et al. | |
| 9,192,375 B2 | 11/2015 | Skinlo et al. | |
| 9,192,447 B2 | 11/2015 | Choi et al. | |
| 9,192,707 B2 | 11/2015 | Gerber et al. | |
| 9,198,711 B2 | 12/2015 | Joseph | |
| 9,198,835 B2 | 12/2015 | Swisher et al. | |
| 9,202,078 B2 | 12/2015 | Abuelsaad et al. | |
| 9,204,830 B2 | 12/2015 | Zand et al. | |
| 9,204,879 B2 | 12/2015 | Shelton, IV | |
| 9,204,995 B2 | 12/2015 | Scheller et al. | |
| 9,211,120 B2 | 12/2015 | Scheib et al. | |
| 9,216,062 B2 | 12/2015 | Duque et al. | |
| 9,218,053 B2 | 12/2015 | Komuro et al. | |
| 9,220,502 B2 | 12/2015 | Zemlok et al. | |
| 9,220,505 B2 | 12/2015 | Vasudevan et al. | |
| 9,226,689 B2 | 1/2016 | Jacobsen et al. | |
| 9,226,751 B2 | 1/2016 | Shelton, IV et al. | |

(56)           References Cited

U.S. PATENT DOCUMENTS

| | | |
|---|---|---|
| 9,226,766 B2 | 1/2016 | Aldridge et al. |
| 9,226,767 B2 | 1/2016 | Stulen et al. |
| 9,226,791 B2 | 1/2016 | McCarthy et al. |
| 9,232,883 B2 | 1/2016 | Ozawa et al. |
| 9,237,891 B2 | 1/2016 | Shelton, IV |
| 9,237,921 B2 | 1/2016 | Messerly et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,247,996 B1 | 2/2016 | Merana et al. |
| 9,250,172 B2 | 2/2016 | Harris et al. |
| 9,255,907 B2 | 2/2016 | Heanue et al. |
| 9,259,282 B2 | 2/2016 | Azizian et al. |
| 9,265,429 B2 | 2/2016 | St. Pierre et al. |
| 9,265,585 B2 | 2/2016 | Wingardner et al. |
| 9,265,959 B2 | 2/2016 | Drew et al. |
| 9,272,406 B2 | 3/2016 | Aronhalt et al. |
| 9,277,956 B2 | 3/2016 | Zhang |
| 9,277,961 B2 | 3/2016 | Panescu et al. |
| 9,277,969 B2 | 3/2016 | Brannan et al. |
| 9,280,884 B1 | 3/2016 | Schultz et al. |
| 9,282,962 B2 | 3/2016 | Schmid et al. |
| 9,282,974 B2 | 3/2016 | Shelton, IV |
| 9,283,045 B2 | 3/2016 | Rhee et al. |
| 9,283,054 B2 | 3/2016 | Morgan et al. |
| 9,289,211 B2 | 3/2016 | Williams et al. |
| 9,289,212 B2 | 3/2016 | Shelton, IV et al. |
| 9,295,514 B2 | 3/2016 | Shelton, IV et al. |
| 9,299,138 B2 | 3/2016 | Zellner et al. |
| 9,301,691 B2 | 4/2016 | Hufnagel et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,301,810 B2 | 4/2016 | Amiri et al. |
| 9,302,213 B2 | 4/2016 | Manahan et al. |
| 9,307,894 B2 | 4/2016 | von Grunberg et al. |
| 9,307,914 B2 | 4/2016 | Fahey |
| 9,307,986 B2 | 4/2016 | Hall et al. |
| 9,314,246 B2 | 4/2016 | Shelton, IV et al. |
| 9,314,308 B2 | 4/2016 | Parihar et al. |
| 9,320,563 B2 | 4/2016 | Brustad et al. |
| 9,325,732 B1 | 4/2016 | Stickle et al. |
| 9,326,767 B2 | 5/2016 | Koch et al. |
| 9,326,770 B2 | 5/2016 | Shelton, IV et al. |
| 9,331,422 B2 | 5/2016 | Nazzaro et al. |
| 9,332,987 B2 | 5/2016 | Leimbach et al. |
| 9,333,042 B2 | 5/2016 | Diolaiti et al. |
| 9,336,385 B1 | 5/2016 | Spencer et al. |
| 9,341,704 B2 | 5/2016 | Picard et al. |
| 9,345,481 B2 | 5/2016 | Hall et al. |
| 9,345,490 B2 | 5/2016 | Ippisch |
| 9,345,544 B2 | 5/2016 | Hourtash et al. |
| 9,345,546 B2 | 5/2016 | Toth et al. |
| 9,345,900 B2 | 5/2016 | Wu et al. |
| 9,351,726 B2 | 5/2016 | Leimbach et al. |
| 9,351,727 B2 | 5/2016 | Leimbach et al. |
| 9,358,003 B2 | 6/2016 | Hall et al. |
| 9,358,685 B2 | 6/2016 | Meier et al. |
| 9,360,449 B2 | 6/2016 | Duric |
| 9,364,200 B2 | 6/2016 | Whitman et al. |
| 9,364,230 B2 | 6/2016 | Shelton, IV et al. |
| 9,364,231 B2 | 6/2016 | Wenchell |
| 9,364,249 B2 | 6/2016 | Kimball et al. |
| 9,364,294 B2 | 6/2016 | Razzaque et al. |
| 9,370,400 B2 | 6/2016 | Parihar |
| 9,375,282 B2 | 6/2016 | Nau, Jr. et al. |
| 9,375,539 B2 | 6/2016 | Stearns et al. |
| 9,381,003 B2 | 7/2016 | Todor et al. |
| 9,381,058 B2 | 7/2016 | Houser et al. |
| 9,386,984 B2 | 7/2016 | Aronhalt et al. |
| 9,386,988 B2 | 7/2016 | Baxter, III et al. |
| 9,387,295 B1 | 7/2016 | Mastri et al. |
| 9,393,017 B2 | 7/2016 | Flanagan et al. |
| 9,393,037 B2 | 7/2016 | Olson et al. |
| 9,398,905 B2 | 7/2016 | Martin |
| 9,398,911 B2 | 7/2016 | Auld |
| 9,402,629 B2 | 8/2016 | Ehrenfels et al. |
| 9,404,868 B2 | 8/2016 | Yamanaka et al. |
| 9,414,776 B2 | 8/2016 | Sillay et al. |
| 9,414,940 B2 | 8/2016 | Stein et al. |
| 9,419,018 B2 | 8/2016 | Sasagawa et al. |
| 9,421,014 B2 | 8/2016 | Ingmanson et al. |
| 9,433,470 B2 | 9/2016 | Choi |
| 9,439,622 B2 | 9/2016 | Case et al. |
| 9,439,668 B2 | 9/2016 | Timm et al. |
| 9,439,736 B2 | 9/2016 | Olson |
| 9,445,764 B2 | 9/2016 | Gross et al. |
| 9,445,813 B2 | 9/2016 | Shelton, IV et al. |
| 9,450,701 B2 | 9/2016 | Do et al. |
| 9,451,949 B2 | 9/2016 | Gorek et al. |
| 9,451,958 B2 | 9/2016 | Shelton, IV et al. |
| 9,463,022 B2 | 10/2016 | Swayze et al. |
| 9,463,646 B2 | 10/2016 | Payne et al. |
| 9,468,438 B2 | 10/2016 | Baber et al. |
| 9,474,565 B2 | 10/2016 | Shikhman et al. |
| D772,252 S | 11/2016 | Myers et al. |
| 9,480,492 B2 | 11/2016 | Aranyi et al. |
| 9,485,475 B2 | 11/2016 | Speier et al. |
| 9,486,271 B2 | 11/2016 | Dunning |
| 9,492,146 B2 | 11/2016 | Kostrzewski et al. |
| 9,492,237 B2 | 11/2016 | Kang et al. |
| 9,493,807 B2 | 11/2016 | Little et al. |
| 9,498,182 B2 | 11/2016 | Case et al. |
| 9,498,215 B2 | 11/2016 | Duque et al. |
| 9,498,219 B2 | 11/2016 | Moore et al. |
| 9,498,231 B2 | 11/2016 | Haider et al. |
| 9,498,279 B2 | 11/2016 | Artale et al. |
| 9,498,291 B2 | 11/2016 | Balaji et al. |
| 9,509,566 B2 | 11/2016 | Chu et al. |
| 9,516,239 B2 | 12/2016 | Blanquart et al. |
| 9,519,753 B1 | 12/2016 | Gerdeman et al. |
| 9,522,003 B2 | 12/2016 | Weir et al. |
| 9,526,407 B2 | 12/2016 | Hoeg et al. |
| 9,526,499 B2 | 12/2016 | Kostrzewski et al. |
| 9,526,580 B2 | 12/2016 | Humayun et al. |
| 9,526,587 B2 | 12/2016 | Zhao et al. |
| 9,532,827 B2 | 1/2017 | Morgan et al. |
| 9,532,845 B1 | 1/2017 | Dossett et al. |
| 9,539,007 B2 | 1/2017 | Dhakad et al. |
| 9,539,020 B2 | 1/2017 | Conlon et al. |
| 9,542,481 B2 | 1/2017 | Halter et al. |
| 9,545,216 B2 | 1/2017 | D'Angelo et al. |
| 9,546,662 B2 | 1/2017 | Shener-Irmakoglu et al. |
| 9,549,781 B2 | 1/2017 | He et al. |
| 9,554,692 B2 | 1/2017 | Levy |
| 9,554,794 B2 | 1/2017 | Baber et al. |
| 9,554,854 B2 | 1/2017 | Yates et al. |
| 9,561,038 B2 | 2/2017 | Shelton, IV et al. |
| 9,561,045 B2 | 2/2017 | Hinman et al. |
| 9,561,082 B2 | 2/2017 | Yen et al. |
| 9,561,982 B2 | 2/2017 | Enicks et al. |
| 9,566,708 B2 | 2/2017 | Kurnianto |
| 9,572,592 B2 | 2/2017 | Price et al. |
| 9,579,099 B2 | 2/2017 | Penna et al. |
| 9,579,503 B2 | 2/2017 | McKinney et al. |
| 9,585,657 B2 | 3/2017 | Shelton, IV et al. |
| 9,585,658 B2 | 3/2017 | Shelton, IV |
| 9,592,095 B2 | 3/2017 | Panescu et al. |
| 9,597,081 B2 | 3/2017 | Swayze et al. |
| 9,600,031 B2 | 3/2017 | Kaneko et al. |
| 9,600,138 B2 | 3/2017 | Thomas et al. |
| 9,603,024 B2 | 3/2017 | Wang et al. |
| 9,603,277 B2 | 3/2017 | Morgan et al. |
| 9,603,609 B2 | 3/2017 | Kawashima et al. |
| D783,675 S | 4/2017 | Yagisawa et al. |
| D784,270 S | 4/2017 | Bhattacharya |
| 9,610,114 B2 | 4/2017 | Baxter, III et al. |
| 9,610,412 B2 | 4/2017 | Zemlok et al. |
| 9,615,877 B2 | 4/2017 | Tyrrell et al. |
| 9,622,684 B2 | 4/2017 | Wybo |
| 9,622,808 B2 | 4/2017 | Beller et al. |
| 9,628,501 B2 | 4/2017 | Datta Ray et al. |
| 9,629,560 B2 | 4/2017 | Joseph |
| 9,629,623 B2 | 4/2017 | Lytle, IV et al. |

(56) References Cited

U.S. PATENT DOCUMENTS

| | | | |
|---|---|---|---|
| 9,629,628 B2 | 4/2017 | Aranyi | |
| 9,629,629 B2 | 4/2017 | Leimbach et al. | |
| 9,630,318 B2 | 4/2017 | Ibarz Gabardos et al. | |
| 9,636,096 B1 | 5/2017 | Heaton, II et al. | |
| 9,636,112 B2 | 5/2017 | Penna et al. | |
| 9,636,188 B2 | 5/2017 | Gattani et al. | |
| 9,636,239 B2 | 5/2017 | Durand et al. | |
| 9,636,825 B2 | 5/2017 | Penn et al. | |
| 9,641,596 B2 | 5/2017 | Unagami et al. | |
| 9,641,815 B2 | 5/2017 | Richardson et al. | |
| 9,642,620 B2 | 5/2017 | Baxter, III et al. | |
| 9,643,022 B2 | 5/2017 | Mashiach et al. | |
| 9,649,089 B2 | 5/2017 | Smith et al. | |
| 9,649,110 B2 | 5/2017 | Parihar et al. | |
| 9,649,111 B2 | 5/2017 | Shelton, IV et al. | |
| 9,649,126 B2 | 5/2017 | Robertson et al. | |
| 9,649,169 B2 | 5/2017 | Cinquin et al. | |
| 9,652,655 B2 | 5/2017 | Satish et al. | |
| 9,655,614 B2 | 5/2017 | Swensgard et al. | |
| 9,655,616 B2 | 5/2017 | Aranyi | |
| 9,656,092 B2 | 5/2017 | Golden | |
| 9,662,104 B1 | 5/2017 | Nobles et al. | |
| 9,662,116 B2 | 5/2017 | Smith et al. | |
| 9,662,177 B2 | 5/2017 | Weir et al. | |
| 9,668,729 B2 | 6/2017 | Williams et al. | |
| 9,668,732 B2 | 6/2017 | Patel et al. | |
| 9,668,765 B2 | 6/2017 | Grace et al. | |
| 9,671,860 B2 | 6/2017 | Ogawa et al. | |
| 9,675,264 B2 | 6/2017 | Acquista et al. | |
| 9,675,354 B2 | 6/2017 | Weir et al. | |
| 9,681,870 B2 | 6/2017 | Baxter, III et al. | |
| 9,686,306 B2 | 6/2017 | Chizeck et al. | |
| 9,687,230 B2 | 6/2017 | Leimbach et al. | |
| 9,690,362 B2 | 6/2017 | Leimbach et al. | |
| 9,700,292 B2 | 7/2017 | Nawana et al. | |
| 9,700,309 B2 | 7/2017 | Jaworek et al. | |
| 9,700,312 B2 | 7/2017 | Kostrzewski et al. | |
| 9,700,320 B2 | 7/2017 | Dinardo et al. | |
| 9,706,993 B2 | 7/2017 | Hessler et al. | |
| 9,710,214 B2 | 7/2017 | Lin et al. | |
| 9,710,644 B2 | 7/2017 | Reybok et al. | |
| 9,713,424 B2 | 7/2017 | Spaide | |
| 9,713,503 B2 | 7/2017 | Goldschmidt | |
| 9,717,141 B1 | 7/2017 | Tegg | |
| 9,717,498 B2 | 8/2017 | Aranyi et al. | |
| 9,717,525 B2 | 8/2017 | Ahluwalia et al. | |
| 9,717,548 B2 | 8/2017 | Couture | |
| 9,724,094 B2 | 8/2017 | Baber et al. | |
| 9,724,100 B2 | 8/2017 | Scheib et al. | |
| 9,724,118 B2 | 8/2017 | Schulte et al. | |
| 9,733,663 B2 | 8/2017 | Leimbach et al. | |
| 9,737,301 B2 | 8/2017 | Baber et al. | |
| 9,737,310 B2 | 8/2017 | Whitfield et al. | |
| 9,737,335 B2 | 8/2017 | Butler et al. | |
| 9,737,355 B2 | 8/2017 | Yates et al. | |
| 9,737,371 B2 | 8/2017 | Romo et al. | |
| 9,740,826 B2 | 8/2017 | Raghavan et al. | |
| 9,743,016 B2 | 8/2017 | Nestares et al. | |
| 9,743,929 B2 | 8/2017 | Leimbach et al. | |
| 9,743,946 B2 | 8/2017 | Faller et al. | |
| 9,743,947 B2 | 8/2017 | Price et al. | |
| 9,750,499 B2 | 9/2017 | Leimbach et al. | |
| 9,750,500 B2 | 9/2017 | Malkowski | |
| 9,750,522 B2 | 9/2017 | Scheib et al. | |
| 9,750,523 B2 | 9/2017 | Tsubuku | |
| 9,750,560 B2 | 9/2017 | Ballakur et al. | |
| 9,750,563 B2 | 9/2017 | Shikhman et al. | |
| 9,753,135 B2 | 9/2017 | Bosch | |
| 9,753,568 B2 | 9/2017 | McMillen | |
| 9,757,126 B2 | 9/2017 | Cappola | |
| 9,757,128 B2 | 9/2017 | Baber et al. | |
| 9,757,142 B2 | 9/2017 | Shimizu | |
| 9,757,152 B2 | 9/2017 | Ogilvie et al. | |
| 9,763,741 B2 | 9/2017 | Alvarez et al. | |
| 9,764,164 B2 | 9/2017 | Wiener et al. | |
| 9,770,541 B2 | 9/2017 | Carr et al. | |
| 9,775,611 B2 | 10/2017 | Kostrzewski | |
| 9,775,623 B2 | 10/2017 | Zammataro et al. | |
| 9,777,913 B2 | 10/2017 | Talbert et al. | |
| 9,782,164 B2 | 10/2017 | Mumaw et al. | |
| 9,782,169 B2 | 10/2017 | Kimsey et al. | |
| 9,782,212 B2 | 10/2017 | Wham et al. | |
| 9,782,214 B2 | 10/2017 | Houser et al. | |
| 9,788,835 B2 | 10/2017 | Morgan et al. | |
| 9,788,836 B2 | 10/2017 | Overmyer et al. | |
| 9,788,851 B2 | 10/2017 | Dannaher et al. | |
| 9,788,902 B2 | 10/2017 | Inoue et al. | |
| 9,788,907 B1 | 10/2017 | Alvi et al. | |
| 9,795,436 B2 | 10/2017 | Yates et al. | |
| 9,797,486 B2 | 10/2017 | Zergiebel et al. | |
| 9,801,531 B2 | 10/2017 | Morita et al. | |
| 9,801,626 B2 | 10/2017 | Parihar et al. | |
| 9,801,627 B2 | 10/2017 | Harris et al. | |
| 9,801,679 B2 | 10/2017 | Trees et al. | |
| 9,802,033 B2 | 10/2017 | Hibner et al. | |
| 9,804,618 B2 | 10/2017 | Leimbach et al. | |
| 9,805,472 B2 | 10/2017 | Chou et al. | |
| 9,808,244 B2 | 11/2017 | Leimbach et al. | |
| 9,808,245 B2 | 11/2017 | Richard et al. | |
| 9,808,246 B2 | 11/2017 | Shelton, IV et al. | |
| 9,808,248 B2 | 11/2017 | Hoffman | |
| 9,808,249 B2 | 11/2017 | Shelton, IV | |
| 9,808,305 B2 | 11/2017 | Hareyama et al. | |
| 9,814,457 B2 | 11/2017 | Martin et al. | |
| 9,814,460 B2 | 11/2017 | Kimsey et al. | |
| 9,814,462 B2 | 11/2017 | Woodard, Jr. et al. | |
| 9,814,463 B2 | 11/2017 | Williams et al. | |
| 9,820,699 B2 | 11/2017 | Bingley et al. | |
| 9,820,738 B2 | 11/2017 | Lytle, IV et al. | |
| 9,820,741 B2 | 11/2017 | Kostrzewski | |
| 9,820,768 B2 | 11/2017 | Gee et al. | |
| 9,826,976 B2 | 11/2017 | Parihar et al. | |
| 9,826,977 B2 | 11/2017 | Leimbach et al. | |
| 9,827,054 B2 | 11/2017 | Richmond et al. | |
| 9,827,059 B2 | 11/2017 | Robinson et al. | |
| 9,830,424 B2 | 11/2017 | Dixon et al. | |
| 9,833,241 B2 | 12/2017 | Huitema et al. | |
| 9,833,254 B1 | 12/2017 | Barral et al. | |
| 9,839,419 B2 | 12/2017 | Deck et al. | |
| 9,839,424 B2 | 12/2017 | Zergiebel et al. | |
| 9,839,428 B2 | 12/2017 | Baxter, III et al. | |
| 9,839,467 B2 | 12/2017 | Harper et al. | |
| 9,839,470 B2 | 12/2017 | Gilbert et al. | |
| 9,839,487 B2 | 12/2017 | Dachs, II | |
| 9,844,321 B1 | 12/2017 | Ekvall et al. | |
| 9,844,368 B2 | 12/2017 | Boudreaux et al. | |
| 9,844,369 B2 | 12/2017 | Huitema et al. | |
| 9,844,374 B2 | 12/2017 | Lytle, IV et al. | |
| 9,844,375 B2 | 12/2017 | Overmyer et al. | |
| 9,844,376 B2 | 12/2017 | Baxter, III et al. | |
| 9,844,379 B2 | 12/2017 | Shelton, IV et al. | |
| 9,848,058 B2 | 12/2017 | Johnson et al. | |
| 9,848,877 B2 | 12/2017 | Shelton, IV et al. | |
| 9,861,354 B2 | 1/2018 | Saliman et al. | |
| 9,861,363 B2 | 1/2018 | Chen et al. | |
| 9,861,428 B2 | 1/2018 | Trees et al. | |
| 9,864,839 B2 | 1/2018 | Baym et al. | |
| 9,867,612 B2 | 1/2018 | Parihar et al. | |
| 9,867,651 B2 | 1/2018 | Wham | |
| 9,867,670 B2 | 1/2018 | Brannan et al. | |
| 9,867,914 B2 | 1/2018 | Bonano et al. | |
| 9,872,609 B2 | 1/2018 | Levy | |
| 9,872,683 B2 | 1/2018 | Hopkins et al. | |
| 9,877,718 B2 | 1/2018 | Weir et al. | |
| 9,877,721 B2 | 1/2018 | Schellin et al. | |
| 9,883,860 B2 | 2/2018 | Leimbach | |
| 9,888,864 B2 | 2/2018 | Rondoni et al. | |
| 9,888,914 B2 | 2/2018 | Martin et al. | |
| 9,888,919 B2 | 2/2018 | Leimbach et al. | |
| 9,888,921 B2 | 2/2018 | Williams et al. | |
| 9,888,975 B2 | 2/2018 | Auld | |
| 9,895,148 B2 | 2/2018 | Shelton, IV et al. | |
| 9,900,787 B2 | 2/2018 | Ou | |
| 9,901,342 B2 | 2/2018 | Shelton, IV et al. | |

(56)      References Cited

U.S. PATENT DOCUMENTS

| 9,901,406 B2 | 2/2018 | State et al. |
| 9,901,411 B2 | 2/2018 | Gombert et al. |
| 9,905,000 B2 | 2/2018 | Chou et al. |
| 9,907,196 B2 | 2/2018 | Susini et al. |
| 9,907,550 B2 | 3/2018 | Sniffin et al. |
| 9,913,642 B2 | 3/2018 | Leimbach et al. |
| 9,913,645 B2 | 3/2018 | Zerkle et al. |
| 9,918,326 B2 | 3/2018 | Gilson et al. |
| 9,918,730 B2 | 3/2018 | Trees et al. |
| 9,918,778 B2 | 3/2018 | Walberg et al. |
| 9,918,788 B2 | 3/2018 | Paul et al. |
| 9,922,304 B2 | 3/2018 | DeBusk et al. |
| 9,924,941 B2 | 3/2018 | Burbank |
| 9,924,944 B2 | 3/2018 | Shelton, IV et al. |
| 9,924,961 B2 | 3/2018 | Shelton, IV et al. |
| 9,931,040 B2 | 4/2018 | Homyk et al. |
| 9,931,118 B2 | 4/2018 | Shelton, IV et al. |
| 9,931,124 B2 | 4/2018 | Gokharu |
| 9,936,863 B2 | 4/2018 | Tesar |
| 9,936,942 B2 | 4/2018 | Chin et al. |
| 9,936,955 B2 | 4/2018 | Miller et al. |
| 9,936,961 B2 | 4/2018 | Chien et al. |
| 9,937,012 B2 | 4/2018 | Hares et al. |
| 9,937,014 B2 | 4/2018 | Bowling et al. |
| 9,937,626 B2 | 4/2018 | Rockrohr |
| 9,938,972 B2 | 4/2018 | Walley |
| 9,943,230 B2 | 4/2018 | Kaku et al. |
| 9,943,309 B2 | 4/2018 | Shelton, IV et al. |
| 9,943,312 B2 | 4/2018 | Posada et al. |
| 9,943,377 B2 | 4/2018 | Yates et al. |
| 9,943,379 B2 | 4/2018 | Gregg, II et al. |
| 9,943,918 B2 | 4/2018 | Grogan et al. |
| 9,943,964 B2 | 4/2018 | Hares |
| 9,949,785 B2 | 4/2018 | Price et al. |
| 9,962,157 B2 | 5/2018 | Sapre |
| 9,968,355 B2 | 5/2018 | Shelton, IV et al. |
| 9,974,595 B2 | 5/2018 | Anderson et al. |
| 9,976,259 B2 | 5/2018 | Tan et al. |
| 9,980,140 B1 | 5/2018 | Spencer et al. |
| 9,980,769 B2 | 5/2018 | Trees et al. |
| 9,980,778 B2 | 5/2018 | Ohline et al. |
| 9,987,000 B2 | 6/2018 | Shelton, IV et al. |
| 9,987,068 B2 | 6/2018 | Anderson et al. |
| 9,987,072 B2 | 6/2018 | McPherson |
| 9,990,856 B2 | 6/2018 | Kuchenbecker et al. |
| 9,993,248 B2 | 6/2018 | Shelton, IV et al. |
| 9,993,258 B2 | 6/2018 | Shelton, IV et al. |
| 9,993,305 B2 | 6/2018 | Andersson |
| 10,004,491 B2 | 6/2018 | Martin et al. |
| 10,004,497 B2 | 6/2018 | Overmyer et al. |
| 10,004,500 B2 | 6/2018 | Shelton, IV et al. |
| 10,004,501 B2 | 6/2018 | Shelton, IV et al. |
| 10,004,527 B2 | 6/2018 | Gee et al. |
| 10,004,557 B2 | 6/2018 | Gross |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,016,538 B2 | 7/2018 | Locke et al. |
| 10,021,318 B2 | 7/2018 | Hugosson et al. |
| 10,022,090 B2 | 7/2018 | Whitman |
| 10,022,120 B2 | 7/2018 | Martin et al. |
| 10,022,391 B2 | 7/2018 | Ruderman Chen et al. |
| 10,022,568 B2 | 7/2018 | Messerly et al. |
| 10,028,402 B1 | 7/2018 | Walker |
| 10,028,744 B2 | 7/2018 | Shelton, IV et al. |
| 10,028,761 B2 | 7/2018 | Leimbach et al. |
| 10,028,788 B2 | 7/2018 | Kang |
| 10,034,704 B2 | 7/2018 | Asher et al. |
| 10,037,641 B2 | 7/2018 | Hyde et al. |
| 10,037,715 B2 | 7/2018 | Toly et al. |
| D826,405 S | 8/2018 | Shelton, IV et al. |
| 10,039,546 B2 | 8/2018 | Williams et al. |
| 10,039,564 B2 | 8/2018 | Hibner et al. |
| 10,039,565 B2 | 8/2018 | Vezzu |
| 10,039,589 B2 | 8/2018 | Virshek et al. |
| 10,041,822 B2 | 8/2018 | Zemlok |
| 10,044,791 B2 | 8/2018 | Kamen et al. |
| 10,045,704 B2 | 8/2018 | Fagin et al. |
| 10,045,776 B2 | 8/2018 | Shelton, IV et al. |
| 10,045,779 B2 | 8/2018 | Savage et al. |
| 10,045,781 B2 | 8/2018 | Cropper et al. |
| 10,045,782 B2 | 8/2018 | Murthy Aravalli |
| 10,045,813 B2 | 8/2018 | Mueller |
| 10,048,379 B2 | 8/2018 | Markendorf et al. |
| 10,052,044 B2 | 8/2018 | Shelton, IV et al. |
| 10,052,102 B2 | 8/2018 | Baxter, III et al. |
| 10,052,104 B2 | 8/2018 | Shelton, IV et al. |
| 10,052,147 B2 | 8/2018 | Merschon et al. |
| 10,054,441 B2 | 8/2018 | Schorr et al. |
| 10,058,393 B2 | 8/2018 | Bonutti et al. |
| 10,069,633 B2 | 9/2018 | Gulati et al. |
| 10,076,326 B2 | 9/2018 | Yates et al. |
| 10,080,618 B2 | 9/2018 | Marshall et al. |
| 10,084,833 B2 | 9/2018 | McDonnell et al. |
| D831,209 S | 10/2018 | Huitema et al. |
| 10,085,748 B2 | 10/2018 | Morgan et al. |
| 10,085,749 B2 | 10/2018 | Cappola et al. |
| 10,092,355 B1 | 10/2018 | Hannaford et al. |
| 10,095,942 B2 | 10/2018 | Mentese et al. |
| 10,097,578 B2 | 10/2018 | Baldonado et al. |
| 10,098,527 B2 | 10/2018 | Weisenburgh, II et al. |
| 10,098,635 B2 | 10/2018 | Burbank |
| 10,098,642 B2 | 10/2018 | Baxter, III et al. |
| 10,098,705 B2 | 10/2018 | Brisson et al. |
| 10,102,926 B1 | 10/2018 | Leonardi |
| 10,105,140 B2 | 10/2018 | Malinouskas et al. |
| 10,105,142 B2 | 10/2018 | Baxter, III et al. |
| 10,105,470 B2 | 10/2018 | Reasoner et al. |
| 10,111,658 B2 | 10/2018 | Chowaniec et al. |
| 10,111,665 B2 | 10/2018 | Aranyi et al. |
| 10,111,679 B2 | 10/2018 | Baber et al. |
| 10,111,703 B2 | 10/2018 | Cosman, Jr. et al. |
| D834,541 S | 11/2018 | You et al. |
| 10,117,649 B2 | 11/2018 | Baxter et al. |
| 10,117,651 B2 | 11/2018 | Whitman et al. |
| 10,117,702 B2 | 11/2018 | Danziger et al. |
| 10,118,119 B2 | 11/2018 | Sappok et al. |
| 10,130,359 B2 | 11/2018 | Hess et al. |
| 10,130,360 B2 | 11/2018 | Olson et al. |
| 10,130,361 B2 | 11/2018 | Yates et al. |
| 10,130,367 B2 | 11/2018 | Cappola et al. |
| 10,130,373 B2 | 11/2018 | Castro et al. |
| 10,130,432 B2 | 11/2018 | Auld et al. |
| 10,133,248 B2 | 11/2018 | Fitzsimmons et al. |
| 10,135,242 B2 | 11/2018 | Baber et al. |
| 10,136,246 B2 | 11/2018 | Yamada |
| 10,136,887 B2 | 11/2018 | Shelton, IV et al. |
| 10,136,891 B2 | 11/2018 | Shelton, IV et al. |
| 10,136,949 B2 | 11/2018 | Felder et al. |
| 10,136,954 B2 | 11/2018 | Johnson et al. |
| 10,137,245 B2 | 11/2018 | Melker et al. |
| 10,143,526 B2 | 12/2018 | Walker et al. |
| 10,143,948 B2 | 12/2018 | Bonifas et al. |
| 10,147,148 B2 | 12/2018 | Wu et al. |
| 10,149,680 B2 | 12/2018 | Parihar et al. |
| 10,152,789 B2 | 12/2018 | Carnes et al. |
| 10,154,841 B2 | 12/2018 | Weaner et al. |
| 10,159,044 B2 | 12/2018 | Hrabak |
| 10,159,481 B2 | 12/2018 | Whitman et al. |
| 10,159,483 B2 | 12/2018 | Beckman et al. |
| 10,164,466 B2 | 12/2018 | Calderoni |
| 10,166,025 B2 | 1/2019 | Leimbach et al. |
| 10,166,061 B2 | 1/2019 | Berry et al. |
| 10,169,862 B2 | 1/2019 | Andre et al. |
| 10,172,618 B2 | 1/2019 | Shelton, IV et al. |
| 10,172,687 B2 | 1/2019 | Garbus et al. |
| 10,175,096 B2 | 1/2019 | Dickerson |
| 10,175,127 B2 | 1/2019 | Collins et al. |
| 10,178,992 B2 | 1/2019 | Wise et al. |
| 10,179,413 B2 | 1/2019 | Rockrohr |
| 10,180,463 B2 | 1/2019 | Beckman et al. |
| 10,182,814 B2 | 1/2019 | Okoniewski |

(56)         References Cited

U.S. PATENT DOCUMENTS

| | | | |
|---|---|---|---|
| 10,182,816 | B2 | 1/2019 | Shelton, IV et al. |
| 10,182,818 | B2 | 1/2019 | Hensel et al. |
| 10,187,742 | B2 | 1/2019 | Dor et al. |
| 10,188,385 | B2 | 1/2019 | Kerr et al. |
| 10,189,157 | B2 | 1/2019 | Schlegel et al. |
| 10,190,888 | B2 | 1/2019 | Hryb et al. |
| 10,194,891 | B2 | 2/2019 | Jeong et al. |
| 10,194,907 | B2 | 2/2019 | Marczyk et al. |
| 10,194,913 | B2 | 2/2019 | Nalagatla et al. |
| 10,194,972 | B2 | 2/2019 | Yates et al. |
| 10,197,803 | B2 | 2/2019 | Badiali et al. |
| 10,198,965 | B2 | 2/2019 | Hart |
| 10,201,311 | B2 | 2/2019 | Chou et al. |
| 10,201,349 | B2 | 2/2019 | Leimbach et al. |
| 10,201,364 | B2 | 2/2019 | Leimbach et al. |
| 10,201,365 | B2 | 2/2019 | Boudreaux et al. |
| 10,205,708 | B1 | 2/2019 | Fletcher et al. |
| 10,206,605 | B2 | 2/2019 | Shelton, IV et al. |
| 10,206,752 | B2 | 2/2019 | Hares et al. |
| 10,213,201 | B2 | 2/2019 | Shelton, IV et al. |
| 10,213,203 | B2 | 2/2019 | Swayze et al. |
| 10,213,266 | B2 | 2/2019 | Zemlok et al. |
| 10,213,268 | B2 | 2/2019 | Dachs, II |
| 10,219,491 | B2 | 3/2019 | Stiles, Jr. et al. |
| 10,220,522 | B2 | 3/2019 | Rockrohr |
| 10,222,750 | B2 | 3/2019 | Bang et al. |
| 10,226,249 | B2 | 3/2019 | Jaworek et al. |
| 10,226,250 | B2 | 3/2019 | Beckman et al. |
| 10,226,254 | B2 | 3/2019 | Cabrera et al. |
| 10,226,302 | B2 | 3/2019 | Lacal et al. |
| 10,231,634 | B2 | 3/2019 | Zand et al. |
| 10,231,733 | B2 | 3/2019 | Ehrenfels et al. |
| 10,231,775 | B2 | 3/2019 | Shelton, IV et al. |
| 10,238,413 | B2 | 3/2019 | Hibner et al. |
| 10,245,027 | B2 | 4/2019 | Shelton, IV et al. |
| 10,245,028 | B2 | 4/2019 | Shelton, IV et al. |
| 10,245,029 | B2 | 4/2019 | Hunter et al. |
| 10,245,030 | B2 | 4/2019 | Hunter et al. |
| 10,245,033 | B2 | 4/2019 | Overmyer et al. |
| 10,245,037 | B2 | 4/2019 | Conklin et al. |
| 10,245,038 | B2 | 4/2019 | Hopkins et al. |
| 10,245,040 | B2 | 4/2019 | Milliman |
| 10,251,661 | B2 | 4/2019 | Collings et al. |
| 10,251,725 | B2 | 4/2019 | Valentine et al. |
| 10,255,995 | B2 | 4/2019 | Ingmanson |
| 10,258,331 | B2 | 4/2019 | Shelton, IV et al. |
| 10,258,359 | B2 | 4/2019 | Kapadia |
| 10,258,362 | B2 | 4/2019 | Conlon |
| 10,258,363 | B2 | 4/2019 | Worrell et al. |
| 10,258,415 | B2 | 4/2019 | Harrah et al. |
| 10,258,418 | B2 | 4/2019 | Shelton, IV et al. |
| 10,258,425 | B2 | 4/2019 | Mustufa et al. |
| 10,263,171 | B2 | 4/2019 | Wiener et al. |
| 10,265,004 | B2 | 4/2019 | Yamaguchi et al. |
| 10,265,035 | B2 | 4/2019 | Fehre et al. |
| 10,265,066 | B2 | 4/2019 | Measamer et al. |
| 10,265,068 | B2 | 4/2019 | Harris et al. |
| 10,265,072 | B2 | 4/2019 | Shelton, IV et al. |
| 10,265,090 | B2 | 4/2019 | Ingmanson et al. |
| 10,265,130 | B2 | 4/2019 | Hess et al. |
| 10,271,840 | B2 | 4/2019 | Sapre |
| 10,271,844 | B2 | 4/2019 | Valentine et al. |
| 10,271,846 | B2 | 4/2019 | Shelton, IV et al. |
| 10,271,850 | B2 | 4/2019 | Williams |
| 10,271,851 | B2 | 4/2019 | Shelton, IV et al. |
| D847,989 | S | 5/2019 | Shelton, IV et al. |
| 10,278,698 | B2 | 5/2019 | Racenet |
| 10,278,778 | B2 | 5/2019 | State et al. |
| 10,282,963 | B2 | 5/2019 | Fahey |
| 10,283,220 | B2 | 5/2019 | Azizian et al. |
| 10,285,694 | B2 | 5/2019 | Viola et al. |
| 10,285,698 | B2 | 5/2019 | Cappola et al. |
| 10,285,700 | B2 | 5/2019 | Scheib |
| 10,285,705 | B2 | 5/2019 | Shelton, IV et al. |
| 10,292,610 | B2 | 5/2019 | Srivastava |
| 10,292,704 | B2 | 5/2019 | Harris et al. |
| 10,292,707 | B2 | 5/2019 | Shelton, IV et al. |
| 10,292,758 | B2 | 5/2019 | Boudreaux et al. |
| 10,292,769 | B1 | 5/2019 | Yu |
| 10,292,771 | B2 | 5/2019 | Wood et al. |
| 10,293,129 | B2 | 5/2019 | Fox et al. |
| 10,299,792 | B2 | 5/2019 | Huitema et al. |
| 10,299,868 | B2 | 5/2019 | Tsuboi et al. |
| 10,299,870 | B2 | 5/2019 | Connolly et al. |
| 10,305,926 | B2 | 5/2019 | Mihan et al. |
| D850,617 | S | 6/2019 | Shelton, IV et al. |
| 10,307,159 | B2 | 6/2019 | Harris et al. |
| 10,307,170 | B2 | 6/2019 | Parfett et al. |
| 10,307,199 | B2 | 6/2019 | Farritor et al. |
| 10,311,036 | B1 | 6/2019 | Hussam et al. |
| 10,313,137 | B2 | 6/2019 | Aarnio et al. |
| 10,314,577 | B2 | 6/2019 | Laurent et al. |
| 10,314,582 | B2 | 6/2019 | Shelton, IV et al. |
| 10,318,928 | B1 | 6/2019 | Kestone et al. |
| 10,321,907 | B2 | 6/2019 | Shelton, IV et al. |
| 10,321,964 | B2 | 6/2019 | Grover et al. |
| 10,327,764 | B2 | 6/2019 | Harris et al. |
| 10,327,779 | B2 | 6/2019 | Richard et al. |
| 10,335,042 | B2 | 7/2019 | Schoenle et al. |
| 10,335,147 | B2 | 7/2019 | Rector et al. |
| 10,335,149 | B2 | 7/2019 | Baxter, III et al. |
| 10,335,180 | B2 | 7/2019 | Johnson et al. |
| 10,335,227 | B2 | 7/2019 | Heard |
| 10,339,496 | B2 | 7/2019 | Matson et al. |
| 10,342,543 | B2 | 7/2019 | Shelton, IV et al. |
| 10,342,602 | B2 | 7/2019 | Strobl et al. |
| 10,342,623 | B2 | 7/2019 | Huelman et al. |
| 10,343,102 | B2 | 7/2019 | Reasoner et al. |
| 10,349,824 | B2 | 7/2019 | Claude et al. |
| 10,349,939 | B2 | 7/2019 | Shelton, IV et al. |
| 10,349,941 | B2 | 7/2019 | Marczyk et al. |
| 10,350,016 | B2 | 7/2019 | Burbank et al. |
| 10,357,184 | B2 | 7/2019 | Crawford et al. |
| 10,357,246 | B2 | 7/2019 | Shelton, IV et al. |
| 10,357,247 | B2 | 7/2019 | Shelton, IV et al. |
| 10,362,179 | B2 | 7/2019 | Harris |
| 10,363,032 | B2 | 7/2019 | Scheib et al. |
| 10,363,037 | B2 | 7/2019 | Aronhalt et al. |
| 10,368,861 | B2 | 8/2019 | Baxter, III et al. |
| 10,368,865 | B2 | 8/2019 | Harris et al. |
| 10,368,867 | B2 | 8/2019 | Harris et al. |
| 10,368,876 | B2 | 8/2019 | Bhatnagar et al. |
| 10,368,894 | B2 | 8/2019 | Madan et al. |
| 10,368,903 | B2 | 8/2019 | Morales et al. |
| 10,376,263 | B2 | 8/2019 | Morgan et al. |
| 10,376,305 | B2 | 8/2019 | Yates et al. |
| 10,376,337 | B2 | 8/2019 | Kilroy et al. |
| 10,376,338 | B2 | 8/2019 | Taylor et al. |
| 10,378,893 | B2 | 8/2019 | Mankovskii |
| 10,383,518 | B2 | 8/2019 | Abu-Tarif et al. |
| 10,383,699 | B2 | 8/2019 | Kilroy et al. |
| 10,384,021 | B2 | 8/2019 | Koeth et al. |
| 10,386,990 | B2 | 8/2019 | Shikhman et al. |
| 10,390,718 | B2 | 8/2019 | Chen et al. |
| 10,390,794 | B2 | 8/2019 | Kuroiwa et al. |
| 10,390,825 | B2 | 8/2019 | Shelton, IV et al. |
| 10,390,831 | B2 | 8/2019 | Holsten et al. |
| 10,390,895 | B2 | 8/2019 | Henderson et al. |
| 10,398,348 | B2 | 9/2019 | Osadchy et al. |
| 10,398,434 | B2 | 9/2019 | Shelton, IV et al. |
| 10,398,517 | B2 | 9/2019 | Eckert et al. |
| 10,398,521 | B2 | 9/2019 | Itkowitz et al. |
| 10,404,521 | B2 | 9/2019 | McChord et al. |
| 10,404,801 | B2 | 9/2019 | Martch |
| 10,405,857 | B2 | 9/2019 | Shelton, IV et al. |
| 10,405,859 | B2 | 9/2019 | Harris et al. |
| 10,405,863 | B2 | 9/2019 | Wise et al. |
| 10,413,291 | B2 | 9/2019 | Worthington et al. |
| 10,413,293 | B2 | 9/2019 | Shelton, IV et al. |
| 10,413,297 | B2 | 9/2019 | Harris et al. |
| 10,417,446 | B2 | 9/2019 | Takeyama |
| 10,420,552 | B2 | 9/2019 | Shelton, IV et al. |
| 10,420,558 | B2 | 9/2019 | Nalagatla et al. |
| 10,420,559 | B2 | 9/2019 | Marczyk et al. |

(56) References Cited

U.S. PATENT DOCUMENTS

| | | | |
|---|---|---|---|
| 10,420,620 B2 | 9/2019 | Rockrohr |
| 10,420,865 B2 | 9/2019 | Reasoner et al. |
| 10,422,727 B2 | 9/2019 | Pliskin |
| 10,426,466 B2 | 10/2019 | Contini et al. |
| 10,426,467 B2 | 10/2019 | Miller et al. |
| 10,426,468 B2 | 10/2019 | Contini et al. |
| 10,426,471 B2 | 10/2019 | Shelton, IV et al. |
| 10,426,481 B2 | 10/2019 | Aronhalt et al. |
| 10,433,837 B2 | 10/2019 | Worthington et al. |
| 10,433,844 B2 | 10/2019 | Shelton, IV et al. |
| 10,433,849 B2 | 10/2019 | Shelton, IV et al. |
| 10,433,918 B2 | 10/2019 | Shelton, IV et al. |
| 10,441,279 B2 | 10/2019 | Shelton, IV et al. |
| 10,441,281 B2 | 10/2019 | Shelton, IV et al. |
| 10,441,344 B2 | 10/2019 | Notz et al. |
| 10,441,345 B2 | 10/2019 | Aldridge et al. |
| 10,448,948 B2 | 10/2019 | Shelton, IV et al. |
| 10,448,950 B2 | 10/2019 | Shelton, IV et al. |
| 10,456,137 B2 | 10/2019 | Vendely et al. |
| 10,456,140 B2 | 10/2019 | Shelton, IV et al. |
| 10,456,193 B2 | 10/2019 | Yates et al. |
| 10,463,365 B2 | 11/2019 | Williams |
| 10,463,367 B2 | 11/2019 | Kostrzewski et al. |
| 10,463,371 B2 | 11/2019 | Kostrzewski |
| 10,463,436 B2 | 11/2019 | Jackson et al. |
| 10,470,684 B2 | 11/2019 | Toth et al. |
| 10,470,762 B2 | 11/2019 | Leimbach et al. |
| 10,470,764 B2 | 11/2019 | Baxter, III et al. |
| 10,470,768 B2 | 11/2019 | Harris et al. |
| 10,470,791 B2 | 11/2019 | Houser |
| 10,471,254 B2 | 11/2019 | Sano et al. |
| 10,478,181 B2 | 11/2019 | Shelton, IV et al. |
| 10,478,182 B2 | 11/2019 | Taylor |
| 10,478,185 B2 | 11/2019 | Nicholas |
| 10,478,189 B2 | 11/2019 | Bear et al. |
| 10,478,190 B2 | 11/2019 | Miller et al. |
| 10,478,544 B2 | 11/2019 | Friederichs et al. |
| 10,485,450 B2 | 11/2019 | Gupta et al. |
| 10,485,542 B2 | 11/2019 | Shelton, IV et al. |
| 10,485,543 B2 | 11/2019 | Shelton, IV et al. |
| 10,492,783 B2 | 12/2019 | Shelton, IV et al. |
| 10,492,784 B2 | 12/2019 | Beardsley et al. |
| 10,492,785 B2 | 12/2019 | Overmyer et al. |
| 10,496,788 B2 | 12/2019 | Amarasingham et al. |
| 10,498,269 B2 | 12/2019 | Zemlok et al. |
| 10,499,847 B2 | 12/2019 | Latimer et al. |
| 10,499,891 B2 | 12/2019 | Chaplin et al. |
| 10,499,914 B2 | 12/2019 | Huang et al. |
| 10,499,915 B2 | 12/2019 | Aranyi |
| 10,499,994 B2 | 12/2019 | Luks et al. |
| 10,507,068 B2 | 12/2019 | Kopp et al. |
| 10,507,278 B2 | 12/2019 | Gao et al. |
| 10,510,267 B2 | 12/2019 | Jarc et al. |
| 10,512,413 B2 | 12/2019 | Schepis et al. |
| 10,512,461 B2 | 12/2019 | Gupta et al. |
| 10,512,499 B2 | 12/2019 | McHenry et al. |
| 10,512,509 B2 | 12/2019 | Bowling et al. |
| 10,512,514 B2 | 12/2019 | Nowlin et al. |
| 10,517,588 B2 | 12/2019 | Gupta et al. |
| 10,517,595 B2 | 12/2019 | Hunter et al. |
| 10,517,596 B2 | 12/2019 | Hunter et al. |
| 10,517,686 B2 | 12/2019 | Vokrot et al. |
| 10,524,789 B2 | 1/2020 | Swayze et al. |
| 10,531,579 B2 | 1/2020 | Hsiao et al. |
| 10,531,874 B2 | 1/2020 | Morgan et al. |
| 10,531,929 B2 | 1/2020 | Widenhouse et al. |
| 10,532,330 B2 | 1/2020 | Diallo et al. |
| 10,536,617 B2 | 1/2020 | Liang et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,537,396 B2 | 1/2020 | Zingaretti et al. |
| 10,537,667 B2 | 1/2020 | Anim |
| 10,542,978 B2 | 1/2020 | Chowaniec et al. |
| 10,542,979 B2 | 1/2020 | Shelton, IV et al. |
| 10,542,982 B2 | 1/2020 | Beckman et al. |
| 10,542,991 B2 | 1/2020 | Shelton, IV et al. |
| D876,466 S | 2/2020 | Kobayashi et al. |
| 10,548,504 B2 | 2/2020 | Shelton, IV et al. |
| 10,548,612 B2 | 2/2020 | Martinez et al. |
| 10,548,673 B2 | 2/2020 | Harris et al. |
| 10,552,574 B2 | 2/2020 | Sweeney |
| 10,555,675 B2 | 2/2020 | Satish et al. |
| 10,555,748 B2 | 2/2020 | Yates et al. |
| 10,555,750 B2 | 2/2020 | Conlon et al. |
| 10,555,769 B2 | 2/2020 | Worrell et al. |
| 10,561,349 B2 | 2/2020 | Wedekind et al. |
| 10,561,422 B2 | 2/2020 | Schellin et al. |
| 10,561,470 B2 | 2/2020 | Hourtash et al. |
| 10,561,471 B2 | 2/2020 | Nichogi |
| 10,561,560 B2 | 2/2020 | Boutoussov et al. |
| 10,561,753 B2 | 2/2020 | Thompson et al. |
| 10,565,170 B2 | 2/2020 | Walling et al. |
| 10,568,625 B2 | 2/2020 | Harris et al. |
| 10,568,626 B2 | 2/2020 | Shelton, IV et al. |
| 10,568,632 B2 | 2/2020 | Miller et al. |
| 10,568,704 B2 | 2/2020 | Savall et al. |
| 10,575,868 B2 | 3/2020 | Hall et al. |
| 10,582,928 B2 | 3/2020 | Hunter et al. |
| 10,582,931 B2 | 3/2020 | Mujawar |
| 10,582,962 B2 | 3/2020 | Friedrichs et al. |
| 10,582,964 B2 | 3/2020 | Weinberg et al. |
| 10,586,074 B2 | 3/2020 | Rose et al. |
| 10,588,623 B2 | 3/2020 | Schmid et al. |
| 10,588,625 B2 | 3/2020 | Weaner et al. |
| 10,588,629 B2 | 3/2020 | Malinouskas et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,711 B2 | 3/2020 | DiCarlo et al. |
| 10,592,067 B2 | 3/2020 | Merdan et al. |
| 10,595,844 B2 | 3/2020 | Nawana et al. |
| 10,595,882 B2 | 3/2020 | Parfett et al. |
| 10,595,887 B2 | 3/2020 | Shelton, IV et al. |
| 10,595,930 B2 | 3/2020 | Scheib et al. |
| 10,595,952 B2 | 3/2020 | Forrest et al. |
| 10,602,007 B2 | 3/2020 | Takano |
| 10,602,848 B2 | 3/2020 | Magana |
| 10,603,036 B2 | 3/2020 | Hunter et al. |
| 10,603,128 B2 | 3/2020 | Zergiebel et al. |
| 10,610,223 B2 | 4/2020 | Wellman et al. |
| 10,610,224 B2 | 4/2020 | Shelton, IV et al. |
| 10,610,286 B2 | 4/2020 | Wiener et al. |
| 10,610,313 B2 | 4/2020 | Bailey et al. |
| 10,617,412 B2 | 4/2020 | Shelton, IV et al. |
| 10,617,413 B2 | 4/2020 | Shelton, IV et al. |
| 10,617,414 B2 | 4/2020 | Shelton, IV et al. |
| 10,617,482 B2 | 4/2020 | Houser et al. |
| 10,617,484 B2 | 4/2020 | Kilroy et al. |
| 10,624,635 B2 | 4/2020 | Harris et al. |
| 10,624,667 B2 | 4/2020 | Faller et al. |
| 10,624,691 B2 | 4/2020 | Wiener et al. |
| 10,631,423 B2 | 4/2020 | Collins et al. |
| 10,631,858 B2 | 4/2020 | Burbank |
| 10,631,912 B2 | 4/2020 | McFarlin et al. |
| 10,631,916 B2 | 4/2020 | Horner et al. |
| 10,631,917 B2 | 4/2020 | Ineson |
| 10,631,939 B2 | 4/2020 | Dachs, II et al. |
| 10,639,027 B2 | 5/2020 | Shelton, IV et al. |
| 10,639,034 B2 | 5/2020 | Harris et al. |
| 10,639,035 B2 | 5/2020 | Shelton, IV et al. |
| 10,639,036 B2 | 5/2020 | Yates et al. |
| 10,639,037 B2 | 5/2020 | Shelton, IV et al. |
| 10,639,039 B2 | 5/2020 | Vendely et al. |
| 10,639,098 B2 | 5/2020 | Cosman et al. |
| 10,639,111 B2 | 5/2020 | Kopp |
| 10,639,185 B2 | 5/2020 | Agrawal et al. |
| 10,653,413 B2 | 5/2020 | Worthington et al. |
| 10,653,476 B2 | 5/2020 | Ross |
| 10,653,489 B2 | 5/2020 | Kopp |
| 10,656,720 B1 | 5/2020 | Holz |
| 10,660,705 B2 | 5/2020 | Piron et al. |
| 10,667,809 B2 | 6/2020 | Bakos et al. |
| 10,667,810 B2 | 6/2020 | Shelton, IV et al. |

(56) References Cited

U.S. PATENT DOCUMENTS

| | | | |
|---|---|---|---|
| 10,667,811 | B2 | 6/2020 | Harris et al. |
| 10,667,877 | B2 | 6/2020 | Kapadia |
| 10,674,897 | B2 | 6/2020 | Levy |
| 10,675,021 | B2 | 6/2020 | Harris et al. |
| 10,675,023 | B2 | 6/2020 | Cappola |
| 10,675,024 | B2 | 6/2020 | Shelton, IV et al. |
| 10,675,025 | B2 | 6/2020 | Swayze et al. |
| 10,675,026 | B2 | 6/2020 | Harris et al. |
| 10,675,035 | B2 | 6/2020 | Zingman |
| 10,675,100 | B2 | 6/2020 | Frushour |
| 10,675,104 | B2 | 6/2020 | Kapadia |
| 10,677,764 | B2 | 6/2020 | Ross et al. |
| 10,679,758 | B2 | 6/2020 | Fox et al. |
| 10,682,136 | B2 | 6/2020 | Harris et al. |
| 10,682,138 | B2 | 6/2020 | Shelton, IV et al. |
| 10,686,805 | B2 | 6/2020 | Reybok, Jr. et al. |
| 10,687,806 | B2 | 6/2020 | Shelton, IV et al. |
| 10,687,809 | B2 | 6/2020 | Shelton, IV et al. |
| 10,687,810 | B2 | 6/2020 | Shelton, IV et al. |
| 10,687,884 | B2 | 6/2020 | Wiener et al. |
| 10,687,905 | B2 | 6/2020 | Kostrzewski |
| 10,695,055 | B2 | 6/2020 | Shelton, IV et al. |
| 10,695,081 | B2 | 6/2020 | Shelton, IV et al. |
| 10,695,134 | B2 | 6/2020 | Barral et al. |
| 10,702,270 | B2 | 7/2020 | Shelton, IV et al. |
| 10,702,271 | B2 | 7/2020 | Aranyi et al. |
| 10,709,446 | B2 | 7/2020 | Harris et al. |
| 10,716,473 | B2 | 7/2020 | Greiner |
| 10,716,489 | B2 | 7/2020 | Kalvoy et al. |
| 10,716,583 | B2 | 7/2020 | Look et al. |
| 10,716,615 | B2 | 7/2020 | Shelton, IV et al. |
| 10,716,639 | B2 | 7/2020 | Kapadia et al. |
| 10,717,194 | B2 | 7/2020 | Griffiths et al. |
| 10,722,222 | B2 | 7/2020 | Aranyi |
| 10,722,233 | B2 | 7/2020 | Wellman |
| 10,722,292 | B2 | 7/2020 | Arya et al. |
| D893,717 | S | 8/2020 | Messerly et al. |
| 10,729,458 | B2 | 8/2020 | Stoddard et al. |
| 10,729,509 | B2 | 8/2020 | Shelton, IV et al. |
| 10,733,267 | B2 | 8/2020 | Pedersen |
| 10,736,219 | B2 | 8/2020 | Seow et al. |
| 10,736,498 | B2 | 8/2020 | Watanabe et al. |
| 10,736,616 | B2 | 8/2020 | Scheib et al. |
| 10,736,628 | B2 | 8/2020 | Yates et al. |
| 10,736,629 | B2 | 8/2020 | Shelton, IV et al. |
| 10,736,636 | B2 | 8/2020 | Baxter, III et al. |
| 10,736,705 | B2 | 8/2020 | Scheib et al. |
| 10,743,872 | B2 | 8/2020 | Leimbach et al. |
| 10,748,115 | B2 | 8/2020 | Laster et al. |
| 10,751,052 | B2 | 8/2020 | Stokes et al. |
| 10,751,136 | B2 | 8/2020 | Farritor et al. |
| 10,751,239 | B2 | 8/2020 | Volek et al. |
| 10,751,768 | B2 | 8/2020 | Hersey et al. |
| 10,755,813 | B2 | 8/2020 | Shelton, IV et al. |
| D896,379 | S | 9/2020 | Shelton, IV et al. |
| 10,758,229 | B2 | 9/2020 | Shelton, IV et al. |
| 10,758,230 | B2 | 9/2020 | Shelton, IV et al. |
| 10,758,294 | B2 | 9/2020 | Jones |
| 10,758,310 | B2 | 9/2020 | Shelton, IV et al. |
| 10,765,376 | B2 | 9/2020 | Brown, III et al. |
| 10,765,424 | B2 | 9/2020 | Baxter, III et al. |
| 10,765,427 | B2 | 9/2020 | Shelton, IV et al. |
| 10,765,470 | B2 | 9/2020 | Yates et al. |
| 10,772,630 | B2 | 9/2020 | Wixey |
| 10,772,651 | B2 | 9/2020 | Shelton, IV et al. |
| 10,772,673 | B2 | 9/2020 | Allen, IV et al. |
| 10,772,688 | B2 | 9/2020 | Peine et al. |
| 10,779,818 | B2 | 9/2020 | Zemlok et al. |
| 10,779,821 | B2 | 9/2020 | Harris et al. |
| 10,779,823 | B2 | 9/2020 | Shelton, IV et al. |
| 10,779,897 | B2 | 9/2020 | Rockrohr |
| 10,779,900 | B2 | 9/2020 | Pedros et al. |
| 10,783,634 | B2 | 9/2020 | Nye et al. |
| 10,786,298 | B2 | 9/2020 | Johnson |
| 10,786,317 | B2 | 9/2020 | Zhou et al. |
| 10,786,327 | B2 | 9/2020 | Anderson et al. |
| 10,792,038 | B2 | 10/2020 | Becerra et al. |
| 10,792,118 | B2 | 10/2020 | Prpa et al. |
| 10,792,422 | B2 | 10/2020 | Douglas et al. |
| 10,799,304 | B2 | 10/2020 | Kapadia et al. |
| 10,803,977 | B2 | 10/2020 | Sanmugalingham |
| 10,806,445 | B2 | 10/2020 | Penna et al. |
| 10,806,453 | B2 | 10/2020 | Chen et al. |
| 10,806,454 | B2 | 10/2020 | Kopp |
| 10,806,499 | B2 | 10/2020 | Castaneda et al. |
| 10,806,506 | B2 | 10/2020 | Gaspredes et al. |
| 10,806,532 | B2 | 10/2020 | Grubbs et al. |
| 10,811,131 | B2 | 10/2020 | Schneider et al. |
| 10,813,638 | B2 | 10/2020 | Shelton, IV et al. |
| 10,813,703 | B2 | 10/2020 | Swayze et al. |
| 10,818,383 | B2 | 10/2020 | Sharifi Sedeh et al. |
| 10,828,028 | B2 | 11/2020 | Harris et al. |
| 10,828,030 | B2 | 11/2020 | Weir et al. |
| 10,835,206 | B2 | 11/2020 | Bell et al. |
| 10,835,245 | B2 | 11/2020 | Swayze et al. |
| 10,835,246 | B2 | 11/2020 | Shelton, IV et al. |
| 10,835,247 | B2 | 11/2020 | Shelton, IV et al. |
| 10,842,473 | B2 | 11/2020 | Scheib et al. |
| 10,842,490 | B2 | 11/2020 | DiNardo et al. |
| 10,842,492 | B2 | 11/2020 | Shelton, IV et al. |
| 10,842,522 | B2 | 11/2020 | Messerly et al. |
| 10,842,523 | B2 | 11/2020 | Shelton, IV et al. |
| 10,842,575 | B2 | 11/2020 | Panescu et al. |
| 10,842,897 | B2 | 11/2020 | Schwartz et al. |
| D904,612 | S | 12/2020 | Wynn et al. |
| 10,849,697 | B2 | 12/2020 | Yates et al. |
| 10,849,700 | B2 | 12/2020 | Kopp et al. |
| 10,856,768 | B2 | 12/2020 | Osadchy et al. |
| 10,856,867 | B2 | 12/2020 | Shelton, IV et al. |
| 10,856,868 | B2 | 12/2020 | Shelton, IV et al. |
| 10,856,870 | B2 | 12/2020 | Harris et al. |
| 10,863,984 | B2 | 12/2020 | Shelton, IV et al. |
| 10,864,037 | B2 | 12/2020 | Mun et al. |
| 10,864,050 | B2 | 12/2020 | Tabandeh et al. |
| 10,872,684 | B2 | 12/2020 | McNutt et al. |
| 10,874,396 | B2 | 12/2020 | Moore et al. |
| 10,881,399 | B2 | 1/2021 | Shelton, IV et al. |
| 10,881,401 | B2 | 1/2021 | Baber et al. |
| 10,881,446 | B2 | 1/2021 | Strobl |
| 10,881,464 | B2 | 1/2021 | Odermatt et al. |
| 10,888,321 | B2 | 1/2021 | Shelton, IV et al. |
| 10,888,322 | B2 | 1/2021 | Morgan et al. |
| 10,892,899 | B2 | 1/2021 | Shelton, IV et al. |
| 10,892,995 | B2 | 1/2021 | Shelton, IV et al. |
| 10,893,863 | B2 | 1/2021 | Shelton, IV et al. |
| 10,893,864 | B2 | 1/2021 | Harris et al. |
| 10,893,884 | B2 | 1/2021 | Stoddard et al. |
| 10,898,105 | B2 | 1/2021 | Weprin et al. |
| 10,898,183 | B2 | 1/2021 | Shelton, IV et al. |
| 10,898,186 | B2 | 1/2021 | Bakos et al. |
| 10,898,189 | B2 | 1/2021 | McDonald, II |
| 10,898,256 | B2 | 1/2021 | Yates et al. |
| 10,898,280 | B2 | 1/2021 | Kopp |
| 10,898,622 | B2 | 1/2021 | Shelton, IV et al. |
| 10,902,944 | B1 | 1/2021 | Casey et al. |
| 10,903,685 | B2 | 1/2021 | Yates et al. |
| 10,905,415 | B2 | 2/2021 | DiNardo et al. |
| 10,905,418 | B2 | 2/2021 | Shelton, IV et al. |
| 10,905,420 | B2 | 2/2021 | Jasemian et al. |
| 10,912,559 | B2 | 2/2021 | Harris et al. |
| 10,912,567 | B2 | 2/2021 | Shelton, IV et al. |
| 10,912,580 | B2 | 2/2021 | Green et al. |
| 10,912,619 | B2 | 2/2021 | Jarc et al. |
| 10,916,415 | B2 | 2/2021 | Karancsi et al. |
| 10,918,385 | B2 | 2/2021 | Overmyer et al. |
| 10,930,400 | B2 | 2/2021 | Robbins et al. |
| D914,878 | S | 3/2021 | Shelton, IV et al. |
| 10,932,705 | B2 | 3/2021 | Muhsin et al. |
| 10,932,772 | B2 | 3/2021 | Shelton, IV et al. |
| 10,932,784 | B2 | 3/2021 | Mozdzierz et al. |
| 10,932,804 | B2 | 3/2021 | Scheib et al. |
| 10,932,806 | B2 | 3/2021 | Shelton, IV et al. |
| 10,932,872 | B2 | 3/2021 | Shelton, IV et al. |
| 10,939,313 | B2 | 3/2021 | Eom et al. |

(56)  References Cited

U.S. PATENT DOCUMENTS

| | | | |
|---|---|---|---|
| 10,943,454 | B2 | 3/2021 | Shelton, IV et al. |
| 10,944,728 | B2 | 3/2021 | Wiener et al. |
| 10,945,727 | B2 | 3/2021 | Shelton, IV et al. |
| 10,950,982 | B2 | 3/2021 | Regnier et al. |
| 10,952,708 | B2 | 3/2021 | Scheib et al. |
| 10,952,732 | B2 | 3/2021 | Binmoeller et al. |
| 10,954,935 | B2 | 3/2021 | O'Shea et al. |
| 10,959,727 | B2 | 3/2021 | Hunter et al. |
| 10,959,729 | B2 | 3/2021 | Ehrenfels et al. |
| 10,959,744 | B2 | 3/2021 | Shelton, IV et al. |
| 10,959,788 | B2 | 3/2021 | Grover et al. |
| 10,960,150 | B2 | 3/2021 | Zergiebel et al. |
| 10,962,449 | B2 | 3/2021 | Unuma et al. |
| 10,966,590 | B2 | 4/2021 | Takahashi et al. |
| 10,966,791 | B2 | 4/2021 | Harris et al. |
| 10,966,798 | B2 | 4/2021 | Tesar et al. |
| 10,973,516 | B2 | 4/2021 | Shelton, IV et al. |
| 10,973,517 | B2 | 4/2021 | Wixey |
| 10,973,520 | B2 | 4/2021 | Shelton, IV et al. |
| 10,973,682 | B2 | 4/2021 | Vezzu et al. |
| 10,980,536 | B2 | 4/2021 | Weaner et al. |
| 10,980,537 | B2 | 4/2021 | Shelton, IV et al. |
| 10,980,560 | B2 | 4/2021 | Shelton, IV et al. |
| 10,980,595 | B2 | 4/2021 | Wham |
| 10,980,610 | B2 | 4/2021 | Rosenberg et al. |
| 10,987,102 | B2 | 4/2021 | Gonzalez et al. |
| 10,987,178 | B2 | 4/2021 | Shelton, IV et al. |
| 10,992,698 | B2 | 4/2021 | Patel et al. |
| 10,993,715 | B2 | 5/2021 | Shelton, IV et al. |
| 10,998,098 | B2 | 5/2021 | Greene et al. |
| 11,000,276 | B2 | 5/2021 | Shelton, IV et al. |
| 11,000,278 | B2 | 5/2021 | Shelton, IV et al. |
| 11,007,004 | B2 | 5/2021 | Shelton, IV et al. |
| 11,007,022 | B2 | 5/2021 | Shelton, IV et al. |
| 11,013,563 | B2 | 5/2021 | Shelton, IV et al. |
| 11,020,115 | B2 | 6/2021 | Scheib et al. |
| 11,026,687 | B2 | 6/2021 | Shelton, IV et al. |
| 11,026,712 | B2 | 6/2021 | Shelton, IV et al. |
| 11,026,713 | B2 | 6/2021 | Stokes et al. |
| 11,026,751 | B2 | 6/2021 | Shelton, IV et al. |
| 11,051,817 | B2 | 7/2021 | Shelton, IV et al. |
| 11,051,902 | B2 | 7/2021 | Kruecker et al. |
| 11,058,501 | B2 | 7/2021 | Tokarchuk et al. |
| 11,071,595 | B2 | 7/2021 | Johnson et al. |
| 11,103,246 | B2 | 8/2021 | Marczyk et al. |
| 11,141,213 | B2 | 10/2021 | Yates et al. |
| 11,183,293 | B2 | 11/2021 | Lu et al. |
| 11,185,325 | B2 | 11/2021 | Shelton, IV et al. |
| 11,197,731 | B2 | 12/2021 | Hoffman et al. |
| 11,273,290 | B2 | 3/2022 | Kowshik |
| 11,289,188 | B2 | 3/2022 | Mabotuwana et al. |
| D950,728 | S | 5/2022 | Bakos et al. |
| D952,144 | S | 5/2022 | Boudreaux |
| 11,322,248 | B2 | 5/2022 | Grantcharov et al. |
| 11,350,932 | B2 | 6/2022 | Shelton, IV et al. |
| 11,373,755 | B2 | 6/2022 | Shelton, IV et al. |
| 11,376,098 | B2 | 7/2022 | Shelton, IV et al. |
| 11,382,715 | B2 | 7/2022 | Arai et al. |
| D964,564 | S | 9/2022 | Boudreaux |
| 11,464,514 | B2 | 10/2022 | Yates et al. |
| 11,464,971 | B2 | 10/2022 | Schepis et al. |
| 11,504,191 | B2 | 11/2022 | Mccloud et al. |
| 11,571,212 | B2 | 2/2023 | Yates et al. |
| 11,602,612 | B2 | 3/2023 | Hara et al. |
| 11,701,139 | B2 | 7/2023 | Nott et al. |
| 11,701,185 | B2 | 7/2023 | Shelton, IV et al. |
| 11,737,668 | B2 | 8/2023 | Shelton, IV et al. |
| 11,786,251 | B2 | 10/2023 | Shelton, IV et al. |
| 11,818,052 | B2 | 11/2023 | Shelton, IV et al. |
| 2001/0056237 | A1 | 12/2001 | Cane et al. |
| 2002/0049551 | A1 | 4/2002 | Friedman et al. |
| 2002/0052616 | A1 | 5/2002 | Wiener et al. |
| 2002/0072746 | A1 | 6/2002 | Lingenfelder et al. |
| 2002/0138642 | A1 | 9/2002 | Miyazawa et al. |
| 2002/0144147 | A1 | 10/2002 | Basson et al. |
| 2002/0169584 | A1 | 11/2002 | Fu et al. |
| 2002/0194023 | A1 | 12/2002 | Turley et al. |
| 2003/0009111 | A1 | 1/2003 | Cory et al. |
| 2003/0009154 | A1 | 1/2003 | Whitman |
| 2003/0018329 | A1 | 1/2003 | Hooven |
| 2003/0028183 | A1 | 2/2003 | Sanchez et al. |
| 2003/0046109 | A1 | 3/2003 | Uchikubo |
| 2003/0050654 | A1 | 3/2003 | Whitman et al. |
| 2003/0069573 | A1 | 4/2003 | Kadhiresan et al. |
| 2003/0093503 | A1 | 5/2003 | Yamaki et al. |
| 2003/0114851 | A1 | 6/2003 | Truckai et al. |
| 2003/0120284 | A1 | 6/2003 | Palacios et al. |
| 2003/0130711 | A1 | 7/2003 | Pearson et al. |
| 2003/0195662 | A1 | 10/2003 | Wang et al. |
| 2003/0208465 | A1 | 11/2003 | Yurko et al. |
| 2003/0210812 | A1 | 11/2003 | Khamene et al. |
| 2003/0223877 | A1 | 12/2003 | Anstine et al. |
| 2004/0015053 | A1 | 1/2004 | Bieger et al. |
| 2004/0044546 | A1 | 3/2004 | Moore |
| 2004/0078236 | A1 | 4/2004 | Stoodley et al. |
| 2004/0082850 | A1 | 4/2004 | Bonner et al. |
| 2004/0092992 | A1 | 5/2004 | Adams et al. |
| 2004/0097913 | A1 | 5/2004 | Refior et al. |
| 2004/0108825 | A1 | 6/2004 | Lee et al. |
| 2004/0199180 | A1 | 10/2004 | Knodel et al. |
| 2004/0199659 | A1 | 10/2004 | Ishikawa et al. |
| 2004/0206365 | A1 | 10/2004 | Knowlton |
| 2004/0215131 | A1 | 10/2004 | Sakurai |
| 2004/0229496 | A1 | 11/2004 | Robinson et al. |
| 2004/0243147 | A1 | 12/2004 | Lipow |
| 2004/0243148 | A1 | 12/2004 | Wasielewski |
| 2004/0243435 | A1 | 12/2004 | Williams |
| 2005/0020909 | A1 | 1/2005 | Moctezuma de la Barrera et al. |
| 2005/0020918 | A1 | 1/2005 | Wilk et al. |
| 2005/0021027 | A1 | 1/2005 | Shields et al. |
| 2005/0023324 | A1 | 2/2005 | Doll et al. |
| 2005/0033108 | A1 | 2/2005 | Sawyer |
| 2005/0063575 | A1 | 3/2005 | Ma et al. |
| 2005/0065438 | A1 | 3/2005 | Miller |
| 2005/0070800 | A1 | 3/2005 | Takahashi |
| 2005/0100867 | A1 | 5/2005 | Hilscher et al. |
| 2005/0131390 | A1 | 6/2005 | Heinrich et al. |
| 2005/0139629 | A1 | 6/2005 | Schwemberger et al. |
| 2005/0143759 | A1 | 6/2005 | Kelly |
| 2005/0148854 | A1 | 7/2005 | Ito et al. |
| 2005/0149001 | A1 | 7/2005 | Uchikubo et al. |
| 2005/0149356 | A1 | 7/2005 | Cyr et al. |
| 2005/0165390 | A1 | 7/2005 | Mauti et al. |
| 2005/0182655 | A1 | 8/2005 | Merzlak et al. |
| 2005/0192633 | A1 | 9/2005 | Montpetit |
| 2005/0203380 | A1 | 9/2005 | Sauer et al. |
| 2005/0203384 | A1 | 9/2005 | Sati et al. |
| 2005/0203504 | A1 | 9/2005 | Wham et al. |
| 2005/0213832 | A1 | 9/2005 | Schofield et al. |
| 2005/0222631 | A1 | 10/2005 | Dalal et al. |
| 2005/0228246 | A1 | 10/2005 | Lee et al. |
| 2005/0228425 | A1 | 10/2005 | Boukhny et al. |
| 2005/0236474 | A1 | 10/2005 | Onuma et al. |
| 2005/0251233 | A1 | 11/2005 | Kanzius |
| 2005/0277913 | A1 | 12/2005 | McCary |
| 2005/0288425 | A1 | 12/2005 | Lee et al. |
| 2006/0020272 | A1 | 1/2006 | Gildenberg |
| 2006/0025816 | A1 | 2/2006 | Shelton |
| 2006/0039105 | A1 | 2/2006 | Smith et al. |
| 2006/0059018 | A1 | 3/2006 | Shiobara et al. |
| 2006/0069388 | A1 | 3/2006 | Truckai et al. |
| 2006/0079872 | A1 | 4/2006 | Eggleston |
| 2006/0079874 | A1 | 4/2006 | Faller et al. |
| 2006/0116908 | A1 | 6/2006 | Dew et al. |
| 2006/0122558 | A1 | 6/2006 | Sherman et al. |
| 2006/0136622 | A1 | 6/2006 | Rouvelin et al. |
| 2006/0142739 | A1 | 6/2006 | DiSilestro et al. |
| 2006/0184160 | A1 | 8/2006 | Ozaki et al. |
| 2006/0241399 | A1 | 10/2006 | Fabian |
| 2006/0282009 | A1 | 12/2006 | Oberg et al. |
| 2006/0287645 | A1 | 12/2006 | Tashiro et al. |
| 2007/0005002 | A1 | 1/2007 | Millman et al. |
| 2007/0010838 | A1 | 1/2007 | Shelton et al. |
| 2007/0016235 | A1 | 1/2007 | Tanaka et al. |

(56) References Cited

U.S. PATENT DOCUMENTS

| | | |
|---|---|---|
| 2007/0016979 A1 | 1/2007 | Damaj et al. |
| 2007/0027459 A1 | 2/2007 | Horvath et al. |
| 2007/0038080 A1 | 2/2007 | Salisbury et al. |
| 2007/0049947 A1 | 3/2007 | Menn et al. |
| 2007/0066970 A1 | 3/2007 | Ineson |
| 2007/0073389 A1 | 3/2007 | Bolduc et al. |
| 2007/0078678 A1 | 4/2007 | DiSilvestro et al. |
| 2007/0084896 A1 | 4/2007 | Doll et al. |
| 2007/0085528 A1 | 4/2007 | Govari et al. |
| 2007/0156019 A1 | 7/2007 | Larkin et al. |
| 2007/0156139 A1 | 7/2007 | Schechter et al. |
| 2007/0161979 A1 | 7/2007 | McPherson |
| 2007/0167702 A1 | 7/2007 | Hasser et al. |
| 2007/0168461 A1 | 7/2007 | Moore |
| 2007/0173803 A1 | 7/2007 | Wham et al. |
| 2007/0173811 A1 | 7/2007 | Couture et al. |
| 2007/0175951 A1 | 8/2007 | Shelton et al. |
| 2007/0175955 A1 | 8/2007 | Shelton et al. |
| 2007/0179482 A1 | 8/2007 | Anderson |
| 2007/0179508 A1 | 8/2007 | Arndt |
| 2007/0191713 A1 | 8/2007 | Eichmann et al. |
| 2007/0192139 A1 | 8/2007 | Cookson et al. |
| 2007/0203744 A1 | 8/2007 | Scholl |
| 2007/0225556 A1 | 9/2007 | Ortiz et al. |
| 2007/0225690 A1 | 9/2007 | Sekiguchi et al. |
| 2007/0239028 A1 | 10/2007 | Houser et al. |
| 2007/0244478 A1 | 10/2007 | Bahney |
| 2007/0249990 A1 | 10/2007 | Cosmescu |
| 2007/0270660 A1 | 11/2007 | Caylor et al. |
| 2007/0270688 A1 | 11/2007 | Gelbart et al. |
| 2007/0282195 A1 | 12/2007 | Masini et al. |
| 2007/0282321 A1 | 12/2007 | Shah et al. |
| 2007/0282333 A1 | 12/2007 | Fortson et al. |
| 2007/0293218 A1 | 12/2007 | Meylan et al. |
| 2008/0013460 A1 | 1/2008 | Allen et al. |
| 2008/0015664 A1 | 1/2008 | Podhajsky |
| 2008/0015912 A1 | 1/2008 | Rosenthal et al. |
| 2008/0019393 A1 | 1/2008 | Yamaki |
| 2008/0033404 A1 | 2/2008 | Romoda et al. |
| 2008/0039742 A1 | 2/2008 | Hashimshony et al. |
| 2008/0040151 A1 | 2/2008 | Moore |
| 2008/0058593 A1 | 3/2008 | Gu et al. |
| 2008/0059658 A1 | 3/2008 | Williams |
| 2008/0077158 A1 | 3/2008 | Haider et al. |
| 2008/0083414 A1 | 4/2008 | Messerges |
| 2008/0091071 A1 | 4/2008 | Kumar et al. |
| 2008/0114212 A1 | 5/2008 | Messerges |
| 2008/0114350 A1 | 5/2008 | Park et al. |
| 2008/0129465 A1 | 6/2008 | Rao |
| 2008/0140090 A1 | 6/2008 | Aranyi et al. |
| 2008/0164296 A1 | 7/2008 | Shelton et al. |
| 2008/0167644 A1 | 7/2008 | Shelton et al. |
| 2008/0177258 A1 | 7/2008 | Govari et al. |
| 2008/0177362 A1 | 7/2008 | Phillips et al. |
| 2008/0200940 A1 | 8/2008 | Eichmann et al. |
| 2008/0223904 A1 | 9/2008 | Marczyk |
| 2008/0234708 A1 | 9/2008 | Houser et al. |
| 2008/0235052 A1 | 9/2008 | Node-Langlois et al. |
| 2008/0245841 A1 | 10/2008 | Smith et al. |
| 2008/0255413 A1 | 10/2008 | Zemlok et al. |
| 2008/0262654 A1 | 10/2008 | Omori et al. |
| 2008/0272172 A1 | 11/2008 | Zemlok et al. |
| 2008/0281301 A1 | 11/2008 | DeBoer et al. |
| 2008/0281678 A1 | 11/2008 | Keuls et al. |
| 2008/0296346 A1 | 12/2008 | Shelton, IV et al. |
| 2008/0306759 A1 | 12/2008 | Ilkin et al. |
| 2008/0312953 A1 | 12/2008 | Claus |
| 2009/0017910 A1 | 1/2009 | Rofougaran et al. |
| 2009/0030437 A1 | 1/2009 | Houser et al. |
| 2009/0036750 A1 | 2/2009 | Weinstein et al. |
| 2009/0036794 A1 | 2/2009 | Stubhaug et al. |
| 2009/0043253 A1 | 2/2009 | Podaima |
| 2009/0046146 A1 | 2/2009 | Hoyt |
| 2009/0048589 A1 | 2/2009 | Takashino et al. |
| 2009/0048595 A1 | 2/2009 | Mihori et al. |
| 2009/0048611 A1 | 2/2009 | Funda et al. |
| 2009/0076409 A1 | 3/2009 | Wu et al. |
| 2009/0090763 A1 | 4/2009 | Zemlok et al. |
| 2009/0099866 A1 | 4/2009 | Newman |
| 2009/0114699 A1 | 5/2009 | Viola |
| 2009/0128084 A1 | 5/2009 | Johnson et al. |
| 2009/0138095 A1 | 5/2009 | Giordano |
| 2009/0157072 A1 | 6/2009 | Wham et al. |
| 2009/0157695 A1 | 6/2009 | Roberts |
| 2009/0182577 A1 | 7/2009 | Squilla et al. |
| 2009/0188094 A1 | 7/2009 | Cunningham et al. |
| 2009/0192591 A1 | 7/2009 | Ryan et al. |
| 2009/0206131 A1 | 8/2009 | Weisenburgh, II et al. |
| 2009/0217932 A1 | 9/2009 | Voegele |
| 2009/0234352 A1 | 9/2009 | Behnke et al. |
| 2009/0259149 A1 | 10/2009 | Tahara et al. |
| 2009/0259221 A1 | 10/2009 | Tahara et al. |
| 2009/0259489 A1 | 10/2009 | Kimura et al. |
| 2009/0270678 A1 | 10/2009 | Scott et al. |
| 2009/0281541 A1 | 11/2009 | Ibrahim et al. |
| 2009/0299214 A1 | 12/2009 | Wu et al. |
| 2009/0306581 A1 | 12/2009 | Claus |
| 2009/0307681 A1 | 12/2009 | Armado et al. |
| 2009/0326321 A1 | 12/2009 | Jacobsen et al. |
| 2009/0326336 A1 | 12/2009 | Lemke et al. |
| 2010/0036374 A1 | 2/2010 | Ward |
| 2010/0036405 A1 | 2/2010 | Giordano et al. |
| 2010/0038403 A1 | 2/2010 | D'Arcangelo |
| 2010/0057106 A1 | 3/2010 | Sorrentino et al. |
| 2010/0065604 A1 | 3/2010 | Weng |
| 2010/0069939 A1 | 3/2010 | Konishi |
| 2010/0069942 A1 | 3/2010 | Shelton, IV |
| 2010/0070417 A1 | 3/2010 | Flynn et al. |
| 2010/0120266 A1 | 5/2010 | Rimborg |
| 2010/0132334 A1 | 6/2010 | Duclos et al. |
| 2010/0137845 A1 | 6/2010 | Ramstein et al. |
| 2010/0137886 A1 | 6/2010 | Zergiebel et al. |
| 2010/0168561 A1 | 7/2010 | Anderson |
| 2010/0179831 A1 | 7/2010 | Brown et al. |
| 2010/0191100 A1 | 7/2010 | Anderson et al. |
| 2010/0194574 A1 | 8/2010 | Monk et al. |
| 2010/0198200 A1 | 8/2010 | Horvath |
| 2010/0198220 A1 | 8/2010 | Boudreaux et al. |
| 2010/0198248 A1 | 8/2010 | Vakharia |
| 2010/0204717 A1 | 8/2010 | Knodel |
| 2010/0217991 A1 | 8/2010 | Choi |
| 2010/0234996 A1 | 9/2010 | Schreiber et al. |
| 2010/0235689 A1 | 9/2010 | Tian et al. |
| 2010/0250571 A1 | 9/2010 | Pierce et al. |
| 2010/0258327 A1 | 10/2010 | Esenwein et al. |
| 2010/0280247 A1 | 11/2010 | Mutti et al. |
| 2010/0292535 A1 | 11/2010 | Paskar |
| 2010/0292684 A1 | 11/2010 | Cybulski et al. |
| 2010/0301095 A1 | 12/2010 | Shelton, IV et al. |
| 2011/0006876 A1 | 1/2011 | Moberg et al. |
| 2011/0015649 A1 | 1/2011 | Anvari et al. |
| 2011/0022032 A1 | 1/2011 | Zemlok et al. |
| 2011/0036890 A1 | 2/2011 | Ma |
| 2011/0043612 A1 | 2/2011 | Keller et al. |
| 2011/0046618 A1 | 2/2011 | Minar et al. |
| 2011/0071530 A1 | 3/2011 | Carson |
| 2011/0077512 A1 | 3/2011 | Boswell |
| 2011/0087238 A1 | 4/2011 | Wang et al. |
| 2011/0087502 A1 | 4/2011 | Yelton et al. |
| 2011/0105277 A1 | 5/2011 | Shauli |
| 2011/0105895 A1 | 5/2011 | Kornblau et al. |
| 2011/0112569 A1 | 5/2011 | Friedman et al. |
| 2011/0118708 A1 | 5/2011 | Burbank et al. |
| 2011/0119075 A1 | 5/2011 | Dhoble |
| 2011/0125149 A1 | 5/2011 | El-Galley et al. |
| 2011/0152712 A1 | 6/2011 | Cao et al. |
| 2011/0163147 A1 | 7/2011 | Laurent et al. |
| 2011/0166883 A1 | 7/2011 | Palmer et al. |
| 2011/0196398 A1 | 8/2011 | Robertson et al. |
| 2011/0209128 A1 | 8/2011 | Nikara et al. |
| 2011/0218526 A1 | 9/2011 | Mathur |
| 2011/0222746 A1 | 9/2011 | Kotula et al. |
| 2011/0237883 A1 | 9/2011 | Chun |
| 2011/0238079 A1 | 9/2011 | Hannaford et al. |

(56) References Cited

U.S. PATENT DOCUMENTS

| | | |
|---|---|---|
| 2011/0251612 A1 | 10/2011 | Faller et al. |
| 2011/0264000 A1 | 10/2011 | Paul et al. |
| 2011/0264078 A1 | 10/2011 | Lipow et al. |
| 2011/0264086 A1 | 10/2011 | Ingle |
| 2011/0265311 A1 | 11/2011 | Kondo et al. |
| 2011/0273465 A1 | 11/2011 | Konishi et al. |
| 2011/0278343 A1 | 11/2011 | Knodel et al. |
| 2011/0290024 A1 | 12/2011 | Lefler |
| 2011/0295270 A1 | 12/2011 | Giordano et al. |
| 2011/0306840 A1 | 12/2011 | Allen et al. |
| 2011/0307284 A1 | 12/2011 | Thompson et al. |
| 2012/0012638 A1 | 1/2012 | Huang et al. |
| 2012/0021684 A1 | 1/2012 | Schultz et al. |
| 2012/0022519 A1 | 1/2012 | Huang et al. |
| 2012/0029354 A1 | 2/2012 | Mark et al. |
| 2012/0046662 A1 | 2/2012 | Gilbert |
| 2012/0059684 A1 | 3/2012 | Hampapur et al. |
| 2012/0078247 A1 | 3/2012 | Worrell et al. |
| 2012/0080336 A1 | 4/2012 | Shelton, IV et al. |
| 2012/0080498 A1 | 4/2012 | Shelton, IV et al. |
| 2012/0083786 A1 | 4/2012 | Artale et al. |
| 2012/0100517 A1 | 4/2012 | Bowditch et al. |
| 2012/0101488 A1 | 4/2012 | Aldridge et al. |
| 2012/0116265 A1 | 5/2012 | Houser et al. |
| 2012/0116381 A1 | 5/2012 | Houser et al. |
| 2012/0116394 A1 | 5/2012 | Timm et al. |
| 2012/0130217 A1 | 5/2012 | Kauphusman et al. |
| 2012/0145714 A1 | 6/2012 | Farascioni et al. |
| 2012/0172696 A1 | 7/2012 | Kallback et al. |
| 2012/0190981 A1 | 7/2012 | Harris et al. |
| 2012/0191091 A1 | 7/2012 | Allen |
| 2012/0191162 A1 | 7/2012 | Villa |
| 2012/0197619 A1 | 8/2012 | Namer Yelin et al. |
| 2012/0203067 A1 | 8/2012 | Higgins et al. |
| 2012/0203143 A1 | 8/2012 | Sanai et al. |
| 2012/0203785 A1 | 8/2012 | Awada |
| 2012/0211542 A1 | 8/2012 | Racenet |
| 2012/0226150 A1 | 9/2012 | Balicki et al. |
| 2012/0232549 A1 | 9/2012 | Willyard et al. |
| 2012/0245958 A1 | 9/2012 | Lawrence et al. |
| 2012/0253329 A1 | 10/2012 | Zemlok et al. |
| 2012/0253847 A1 | 10/2012 | Dell'Anno et al. |
| 2012/0265555 A1 | 10/2012 | Cappuzzo et al. |
| 2012/0292367 A1 | 11/2012 | Morgan et al. |
| 2012/0319859 A1 | 12/2012 | Taub et al. |
| 2013/0001121 A1 | 1/2013 | Metzger |
| 2013/0006241 A1 | 1/2013 | Takashino |
| 2013/0008677 A1 | 1/2013 | Huifu |
| 2013/0024213 A1 | 1/2013 | Poon |
| 2013/0046182 A1 | 2/2013 | Hegg et al. |
| 2013/0046279 A1 | 2/2013 | Niklewski et al. |
| 2013/0046295 A1 | 2/2013 | Kerr et al. |
| 2013/0066647 A1 | 3/2013 | Andrie et al. |
| 2013/0085413 A1 | 4/2013 | Tsamir et al. |
| 2013/0090526 A1 | 4/2013 | Suzuki et al. |
| 2013/0090755 A1 | 4/2013 | Kiryu et al. |
| 2013/0093829 A1 | 4/2013 | Rosenblatt et al. |
| 2013/0096597 A1 | 4/2013 | Anand et al. |
| 2013/0116218 A1 | 5/2013 | Kaplan et al. |
| 2013/0131845 A1 | 5/2013 | Guilleminot |
| 2013/0144284 A1 | 6/2013 | Behnke, II et al. |
| 2013/0153635 A1 | 6/2013 | Hodgkinson |
| 2013/0165776 A1 | 6/2013 | Blomqvist |
| 2013/0168435 A1 | 7/2013 | Huang et al. |
| 2013/0178853 A1 | 7/2013 | Hyink et al. |
| 2013/0190755 A1 | 7/2013 | Deborski et al. |
| 2013/0191154 A1 | 7/2013 | William et al. |
| 2013/0191647 A1 | 7/2013 | Ferrara, Jr. et al. |
| 2013/0193188 A1 | 8/2013 | Shelton, IV et al. |
| 2013/0196703 A1 | 8/2013 | Masoud et al. |
| 2013/0197531 A1 | 8/2013 | Boukhny et al. |
| 2013/0201356 A1 | 8/2013 | Kennedy et al. |
| 2013/0206813 A1 | 8/2013 | Nalagatla |
| 2013/0214025 A1 | 8/2013 | Zemlok et al. |
| 2013/0253480 A1 | 9/2013 | Kimball et al. |
| 2013/0256373 A1 | 10/2013 | Schmid et al. |
| 2013/0261503 A1 | 10/2013 | Sherman et al. |
| 2013/0267874 A1 | 10/2013 | Marcotte et al. |
| 2013/0268283 A1 | 10/2013 | Vann et al. |
| 2013/0277410 A1 | 10/2013 | Fernandez et al. |
| 2013/0317837 A1 | 11/2013 | Ballantyne et al. |
| 2013/0321425 A1 | 12/2013 | Greene et al. |
| 2013/0325809 A1 | 12/2013 | Kim et al. |
| 2013/0331873 A1 | 12/2013 | Ross et al. |
| 2013/0331875 A1 | 12/2013 | Ross et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0006132 A1 | 1/2014 | Barker |
| 2014/0009894 A1 | 1/2014 | Yu |
| 2014/0013565 A1 | 1/2014 | MacDonald et al. |
| 2014/0018788 A1 | 1/2014 | Engelman et al. |
| 2014/0029411 A1 | 1/2014 | Nayak et al. |
| 2014/0033926 A1 | 2/2014 | Fassel et al. |
| 2014/0035762 A1 | 2/2014 | Shelton, IV et al. |
| 2014/0039491 A1 | 2/2014 | Bakos et al. |
| 2014/0058407 A1 | 2/2014 | Tsekos et al. |
| 2014/0066700 A1 | 3/2014 | Wilson et al. |
| 2014/0073893 A1 | 3/2014 | Bencini |
| 2014/0074076 A1 | 3/2014 | Gertner |
| 2014/0081255 A1 | 3/2014 | Johnson et al. |
| 2014/0081659 A1 | 3/2014 | Nawana et al. |
| 2014/0084949 A1 | 3/2014 | Smith et al. |
| 2014/0087999 A1 | 3/2014 | Kaplan et al. |
| 2014/0092089 A1 | 4/2014 | Kasuya et al. |
| 2014/0107697 A1 | 4/2014 | Patani et al. |
| 2014/0108035 A1 | 4/2014 | Akbay et al. |
| 2014/0108983 A1 | 4/2014 | William et al. |
| 2014/0117256 A1 | 5/2014 | Mueller et al. |
| 2014/0121669 A1 | 5/2014 | Claus |
| 2014/0142963 A1 | 5/2014 | Hill et al. |
| 2014/0148729 A1 | 5/2014 | Schmitz et al. |
| 2014/0148803 A1 | 5/2014 | Taylor |
| 2014/0163359 A1 | 6/2014 | Sholev et al. |
| 2014/0166724 A1 | 6/2014 | Schellin et al. |
| 2014/0171778 A1 | 6/2014 | Tsusaka et al. |
| 2014/0171787 A1 | 6/2014 | Garbey et al. |
| 2014/0176576 A1 | 6/2014 | Spencer |
| 2014/0187856 A1 | 7/2014 | Holoien et al. |
| 2014/0188440 A1 | 7/2014 | Donhowe et al. |
| 2014/0194864 A1 | 7/2014 | Martin et al. |
| 2014/0195052 A1 | 7/2014 | Tsusaka et al. |
| 2014/0204190 A1 | 7/2014 | Rosenblatt, III et al. |
| 2014/0207124 A1 | 7/2014 | Aldridge et al. |
| 2014/0226572 A1 | 8/2014 | Thota et al. |
| 2014/0243799 A1 | 8/2014 | Parihar |
| 2014/0243809 A1 | 8/2014 | Gelfand et al. |
| 2014/0243811 A1 | 8/2014 | Reschke et al. |
| 2014/0246475 A1 | 9/2014 | Hall et al. |
| 2014/0249557 A1 | 9/2014 | Koch et al. |
| 2014/0252064 A1 | 9/2014 | Mozdzierz et al. |
| 2014/0263541 A1 | 9/2014 | Leimbach et al. |
| 2014/0263552 A1 | 9/2014 | Hall et al. |
| 2014/0275760 A1 | 9/2014 | Lee et al. |
| 2014/0276748 A1 | 9/2014 | Ku et al. |
| 2014/0276749 A1 | 9/2014 | Johnson |
| 2014/0278219 A1 | 9/2014 | Canavan et al. |
| 2014/0287393 A1 | 9/2014 | Kumar et al. |
| 2014/0296694 A1 | 10/2014 | Jaworski |
| 2014/0303660 A1 | 10/2014 | Boyden et al. |
| 2014/0303990 A1 | 10/2014 | Schoenefeld et al. |
| 2014/0336943 A1 | 11/2014 | Pellini et al. |
| 2014/0337052 A1 | 11/2014 | Pellini et al. |
| 2014/0364691 A1 | 12/2014 | Krivopisk et al. |
| 2015/0006201 A1 | 1/2015 | Pait et al. |
| 2015/0012010 A1 | 1/2015 | Adler et al. |
| 2015/0025549 A1 | 1/2015 | Kilroy et al. |
| 2015/0032150 A1 | 1/2015 | Ishida et al. |
| 2015/0033128 A1 | 1/2015 | Curd et al. |
| 2015/0051452 A1 | 2/2015 | Ciaccio |
| 2015/0051598 A1 | 2/2015 | Orszulak et al. |
| 2015/0051617 A1 | 2/2015 | Takemura et al. |
| 2015/0053737 A1 | 2/2015 | Leimbach et al. |
| 2015/0053743 A1 | 2/2015 | Yates et al. |

(56) References Cited

U.S. PATENT DOCUMENTS

| | | |
|---|---|---|
| 2015/0053746 A1 | 2/2015 | Shelton, IV et al. |
| 2015/0053749 A1 | 2/2015 | Shelton, IV et al. |
| 2015/0057675 A1 | 2/2015 | Akeel et al. |
| 2015/0062316 A1 | 3/2015 | Haraguchi et al. |
| 2015/0066000 A1 | 3/2015 | An et al. |
| 2015/0070187 A1 | 3/2015 | Wiesner et al. |
| 2015/0073400 A1 | 3/2015 | Sverdlik et al. |
| 2015/0077528 A1 | 3/2015 | Awdeh |
| 2015/0083774 A1 | 3/2015 | Measamer et al. |
| 2015/0099458 A1 | 4/2015 | Weisner et al. |
| 2015/0108198 A1 | 4/2015 | Estrella |
| 2015/0133945 A1 | 5/2015 | Dushyant et al. |
| 2015/0136833 A1 | 5/2015 | Shelton, IV et al. |
| 2015/0140982 A1 | 5/2015 | Postrel |
| 2015/0141980 A1 | 5/2015 | Jadhav et al. |
| 2015/0142016 A1 | 5/2015 | Bolduc et al. |
| 2015/0145682 A1 | 5/2015 | Harris |
| 2015/0148830 A1 | 5/2015 | Stulen et al. |
| 2015/0157354 A1 | 6/2015 | Bales, Jr. et al. |
| 2015/0168126 A1 | 6/2015 | Nevet et al. |
| 2015/0173673 A1 | 6/2015 | Toth et al. |
| 2015/0173756 A1 | 6/2015 | Baxter, III et al. |
| 2015/0182220 A1 | 7/2015 | Yates et al. |
| 2015/0196295 A1 | 7/2015 | Shelton, IV et al. |
| 2015/0199109 A1 | 7/2015 | Lee |
| 2015/0201918 A1 | 7/2015 | Kumar et al. |
| 2015/0202014 A1 | 7/2015 | Kim et al. |
| 2015/0208934 A1 | 7/2015 | Sztrubel et al. |
| 2015/0223725 A1 | 8/2015 | Engel et al. |
| 2015/0223868 A1 | 8/2015 | Brandt et al. |
| 2015/0237502 A1 | 8/2015 | Schmidt et al. |
| 2015/0238118 A1 | 8/2015 | Legassey et al. |
| 2015/0257783 A1 | 9/2015 | Levine et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0272694 A1 | 10/2015 | Charles |
| 2015/0282733 A1 | 10/2015 | Fielden et al. |
| 2015/0282796 A1 | 10/2015 | Nawana et al. |
| 2015/0282821 A1 | 10/2015 | Look et al. |
| 2015/0286787 A1 | 10/2015 | Chen et al. |
| 2015/0289820 A1 | 10/2015 | Miller et al. |
| 2015/0289925 A1 | 10/2015 | Voegele et al. |
| 2015/0296042 A1 | 10/2015 | Aoyama |
| 2015/0297200 A1 | 10/2015 | Fitzsimmons et al. |
| 2015/0297222 A1 | 10/2015 | Huitema et al. |
| 2015/0297228 A1 | 10/2015 | Huitema et al. |
| 2015/0297233 A1 | 10/2015 | Huitema et al. |
| 2015/0297311 A1 | 10/2015 | Tesar |
| 2015/0302157 A1 | 10/2015 | Collar et al. |
| 2015/0305828 A1 | 10/2015 | Park et al. |
| 2015/0310174 A1 | 10/2015 | Coudert et al. |
| 2015/0313538 A1 | 11/2015 | Bechtel et al. |
| 2015/0317899 A1 | 11/2015 | Dumbauld et al. |
| 2015/0320423 A1 | 11/2015 | Aranyi |
| 2015/0324114 A1 | 11/2015 | Hurley et al. |
| 2015/0328474 A1 | 11/2015 | Flyash et al. |
| 2015/0331995 A1 | 11/2015 | Zhao et al. |
| 2015/0332003 A1 | 11/2015 | Stamm et al. |
| 2015/0332196 A1 | 11/2015 | Stiller et al. |
| 2015/0335344 A1 | 11/2015 | Aljuri et al. |
| 2015/0374259 A1 | 12/2015 | Garbey et al. |
| 2016/0000437 A1 | 1/2016 | Giordano et al. |
| 2016/0001411 A1 | 1/2016 | Alberti |
| 2016/0005169 A1 | 1/2016 | Sela et al. |
| 2016/0015471 A1 | 1/2016 | Piron et al. |
| 2016/0019346 A1 | 1/2016 | Boston et al. |
| 2016/0022374 A1 | 1/2016 | Haider et al. |
| 2016/0034648 A1 | 2/2016 | Mohlenbrock et al. |
| 2016/0038224 A1 | 2/2016 | Couture et al. |
| 2016/0038253 A1 | 2/2016 | Piron et al. |
| 2016/0048780 A1 | 2/2016 | Sethumadhavan et al. |
| 2016/0051315 A1 | 2/2016 | Boudreaux |
| 2016/0058439 A1 | 3/2016 | Shelton, IV et al. |
| 2016/0066913 A1 | 3/2016 | Swayze et al. |
| 2016/0100837 A1 | 4/2016 | Huang et al. |
| 2016/0103810 A1 | 4/2016 | Hanning |
| 2016/0106516 A1 | 4/2016 | Mesallum |
| 2016/0106934 A1 | 4/2016 | Hiraga et al. |
| 2016/0121143 A1 | 5/2016 | Mumaw et al. |
| 2016/0143659 A1 | 5/2016 | Glutz et al. |
| 2016/0147954 A1* | 5/2016 | Ng Tari ................. G16H 40/20 705/3 |
| 2016/0157717 A1 | 6/2016 | Gaster |
| 2016/0158468 A1 | 6/2016 | Tang et al. |
| 2016/0166336 A1 | 6/2016 | Razzaque et al. |
| 2016/0174998 A1 | 6/2016 | Lal et al. |
| 2016/0175025 A1 | 6/2016 | Strobl |
| 2016/0180045 A1 | 6/2016 | Syed |
| 2016/0182637 A1 | 6/2016 | Adriaens et al. |
| 2016/0184054 A1 | 6/2016 | Lowe |
| 2016/0192960 A1 | 7/2016 | Bueno et al. |
| 2016/0203599 A1 | 7/2016 | Gillies et al. |
| 2016/0206202 A1 | 7/2016 | Frangioni |
| 2016/0206362 A1 | 7/2016 | Mehta et al. |
| 2016/0224760 A1 | 8/2016 | Petak et al. |
| 2016/0225551 A1 | 8/2016 | Shedletsky |
| 2016/0228061 A1 | 8/2016 | Kallback et al. |
| 2016/0228204 A1 | 8/2016 | Quaid et al. |
| 2016/0235303 A1 | 8/2016 | Fleming et al. |
| 2016/0242836 A1 | 8/2016 | Eggers et al. |
| 2016/0249910 A1 | 9/2016 | Shelton, IV et al. |
| 2016/0249916 A1* | 9/2016 | Shelton, IV ........... G16H 40/20 705/2 |
| 2016/0249920 A1 | 9/2016 | Gupta et al. |
| 2016/0270732 A1 | 9/2016 | Källbäck et al. |
| 2016/0270842 A1 | 9/2016 | Strobl et al. |
| 2016/0270861 A1 | 9/2016 | Guru et al. |
| 2016/0275259 A1 | 9/2016 | Nolan et al. |
| 2016/0278841 A1 | 9/2016 | Panescu et al. |
| 2016/0287312 A1 | 10/2016 | Tegg et al. |
| 2016/0287316 A1 | 10/2016 | Worrell et al. |
| 2016/0287337 A1 | 10/2016 | Aram et al. |
| 2016/0287912 A1 | 10/2016 | Warnking |
| 2016/0292456 A1 | 10/2016 | Dubey et al. |
| 2016/0296246 A1 | 10/2016 | Schaller |
| 2016/0302210 A1 | 10/2016 | Thornton et al. |
| 2016/0310055 A1 | 10/2016 | Zand et al. |
| 2016/0310204 A1 | 10/2016 | Mchenry et al. |
| 2016/0314716 A1 | 10/2016 | Grubbs |
| 2016/0314717 A1 | 10/2016 | Grubbs |
| 2016/0317172 A1 | 11/2016 | Kumada et al. |
| 2016/0321400 A1 | 11/2016 | Durrant et al. |
| 2016/0323283 A1 | 11/2016 | Kang et al. |
| 2016/0331460 A1 | 11/2016 | Cheatham, III et al. |
| 2016/0331473 A1 | 11/2016 | Yamamura |
| 2016/0338685 A1 | 11/2016 | Nawana et al. |
| 2016/0342753 A1 | 11/2016 | Feazell |
| 2016/0342916 A1 | 11/2016 | Arceneaux et al. |
| 2016/0345857 A1 | 12/2016 | Jensrud et al. |
| 2016/0350490 A1 | 12/2016 | Martinez et al. |
| 2016/0354155 A1 | 12/2016 | Hodges et al. |
| 2016/0354160 A1 | 12/2016 | Crowley et al. |
| 2016/0354162 A1 | 12/2016 | Yen et al. |
| 2016/0356852 A1 | 12/2016 | Lee |
| 2016/0361070 A1 | 12/2016 | Ardel et al. |
| 2016/0367305 A1 | 12/2016 | Hareland |
| 2016/0367401 A1 | 12/2016 | Claus |
| 2016/0374710 A1 | 12/2016 | Sinelnikov et al. |
| 2016/0374723 A1 | 12/2016 | Frankhouser et al. |
| 2016/0374762 A1 | 12/2016 | Case et al. |
| 2016/0379504 A1 | 12/2016 | Bailey et al. |
| 2017/0000516 A1 | 1/2017 | Stulen et al. |
| 2017/0000553 A1 | 1/2017 | Wiener et al. |
| 2017/0005911 A1 | 1/2017 | Kasargod et al. |
| 2017/0007247 A1 | 1/2017 | Shelton, IV et al. |
| 2017/0027603 A1 | 2/2017 | Pandey |
| 2017/0042604 A1 | 2/2017 | McFarland et al. |
| 2017/0049522 A1 | 2/2017 | Kapadia |
| 2017/0056038 A1 | 3/2017 | Hess et al. |
| 2017/0068792 A1 | 3/2017 | Reiner |
| 2017/0079530 A1 | 3/2017 | DiMaio et al. |
| 2017/0079730 A1 | 3/2017 | Azizian et al. |

(56)  References Cited

U.S. PATENT DOCUMENTS

| | | |
|---|---|---|
| 2017/0086829 A1 | 3/2017 | Vendely et al. |
| 2017/0086906 A1 | 3/2017 | Tsuruta |
| 2017/0086930 A1 | 3/2017 | Thompson et al. |
| 2017/0105754 A1 | 4/2017 | Boudreaux et al. |
| 2017/0105787 A1 | 4/2017 | Witt et al. |
| 2017/0116873 A1 | 4/2017 | Lendvay et al. |
| 2017/0119477 A1 | 5/2017 | Amiot et al. |
| 2017/0127499 A1 | 5/2017 | Unoson et al. |
| 2017/0132374 A1 | 5/2017 | Lee et al. |
| 2017/0132385 A1 | 5/2017 | Hunter et al. |
| 2017/0132785 A1 | 5/2017 | Wshah et al. |
| 2017/0143284 A1 | 5/2017 | Sehnert et al. |
| 2017/0143366 A1 | 5/2017 | Groene et al. |
| 2017/0147759 A1 | 5/2017 | Iyer et al. |
| 2017/0154156 A1 | 6/2017 | Sevenster et al. |
| 2017/0161443 A1 | 6/2017 | Bassham et al. |
| 2017/0164996 A1 | 6/2017 | Honda et al. |
| 2017/0164997 A1 | 6/2017 | Johnson et al. |
| 2017/0165008 A1 | 6/2017 | Finley |
| 2017/0165012 A1 | 6/2017 | Chaplin et al. |
| 2017/0172550 A1 | 6/2017 | Mukherjee et al. |
| 2017/0172565 A1 | 6/2017 | Heneveld |
| 2017/0172614 A1 | 6/2017 | Scheib et al. |
| 2017/0172674 A1 | 6/2017 | Hanuschik et al. |
| 2017/0172676 A1 | 6/2017 | Itkowitz et al. |
| 2017/0173262 A1 | 6/2017 | Veltz |
| 2017/0177807 A1 | 6/2017 | Fabian |
| 2017/0178069 A1 | 6/2017 | Paterra et al. |
| 2017/0185732 A1 | 6/2017 | Niklewski et al. |
| 2017/0196583 A1 | 7/2017 | Sugiyama |
| 2017/0202305 A1 | 7/2017 | Huard et al. |
| 2017/0202591 A1 | 7/2017 | Shelton, IV et al. |
| 2017/0202595 A1 | 7/2017 | Shelton, IV |
| 2017/0202607 A1 | 7/2017 | Shelton, IV et al. |
| 2017/0202608 A1 | 7/2017 | Shelton, IV et al. |
| 2017/0209145 A1 | 7/2017 | Swayze et al. |
| 2017/0215944 A1 | 8/2017 | Keffeler |
| 2017/0224332 A1 | 8/2017 | Hunter et al. |
| 2017/0224334 A1 | 8/2017 | Worthington et al. |
| 2017/0224428 A1 | 8/2017 | Kopp |
| 2017/0231553 A1 | 8/2017 | Igarashi et al. |
| 2017/0231627 A1 | 8/2017 | Shelton, IV et al. |
| 2017/0231628 A1 | 8/2017 | Shelton, IV et al. |
| 2017/0235897 A1 | 8/2017 | Henderson et al. |
| 2017/0245809 A1 | 8/2017 | Ma et al. |
| 2017/0249431 A1 | 8/2017 | Shelton, IV et al. |
| 2017/0249432 A1* | 8/2017 | Grantcharov ............. G06F 1/12 |
| 2017/0252095 A1* | 9/2017 | Johnson ............. A61B 18/1445 |
| 2017/0254013 A1 | 9/2017 | Pratt et al. |
| 2017/0262604 A1 | 9/2017 | Francois |
| 2017/0265864 A1 | 9/2017 | Hessler et al. |
| 2017/0265943 A1 | 9/2017 | Sela et al. |
| 2017/0270323 A1 | 9/2017 | Butler et al. |
| 2017/0273715 A1 | 9/2017 | Piron et al. |
| 2017/0281171 A1 | 10/2017 | Shelton, IV et al. |
| 2017/0281173 A1 | 10/2017 | Shelton, IV et al. |
| 2017/0281186 A1 | 10/2017 | Shelton, IV et al. |
| 2017/0281189 A1 | 10/2017 | Nalagatla et al. |
| 2017/0289617 A1 | 10/2017 | Song et al. |
| 2017/0290585 A1 | 10/2017 | Shelton, IV et al. |
| 2017/0296169 A1 | 10/2017 | Yates et al. |
| 2017/0296173 A1 | 10/2017 | Shelton, IV et al. |
| 2017/0296185 A1 | 10/2017 | Swensgard et al. |
| 2017/0296213 A1 | 10/2017 | Swensgard et al. |
| 2017/0296301 A1 | 10/2017 | Dor et al. |
| 2017/0303984 A1 | 10/2017 | Malackowski |
| 2017/0304007 A1 | 10/2017 | Piron et al. |
| 2017/0304020 A1 | 10/2017 | Ng et al. |
| 2017/0311777 A1 | 11/2017 | Hirayama et al. |
| 2017/0312456 A1 | 11/2017 | Phillips |
| 2017/0319268 A1 | 11/2017 | Akagane |
| 2017/0325876 A1 | 11/2017 | Nakadate et al. |
| 2017/0325878 A1 | 11/2017 | Messerly et al. |
| 2017/0333147 A1 | 11/2017 | Bernstein |
| 2017/0333152 A1 | 11/2017 | Wade |
| 2017/0337043 A1 | 11/2017 | Brincat et al. |
| 2017/0337493 A1 | 11/2017 | Paramasivan et al. |
| 2017/0348047 A1 | 12/2017 | Reiter et al. |
| 2017/0360358 A1 | 12/2017 | Amiot et al. |
| 2017/0360499 A1 | 12/2017 | Greep et al. |
| 2017/0367583 A1 | 12/2017 | Black et al. |
| 2017/0367754 A1 | 12/2017 | Narisawa |
| 2017/0367771 A1 | 12/2017 | Tako et al. |
| 2017/0367772 A1 | 12/2017 | Gunn et al. |
| 2017/0370710 A1 | 12/2017 | Chen et al. |
| 2018/0008359 A1 | 1/2018 | Randle |
| 2018/0011983 A1 | 1/2018 | Zuhars et al. |
| 2018/0014764 A1 | 1/2018 | Bechtel et al. |
| 2018/0021058 A1 | 1/2018 | Meglan |
| 2018/0028088 A1 | 2/2018 | Garbey et al. |
| 2018/0042659 A1 | 2/2018 | Rupp et al. |
| 2018/0050196 A1 | 2/2018 | Pawsey et al. |
| 2018/0052971 A1 | 2/2018 | Hanina et al. |
| 2018/0055529 A1 | 3/2018 | Messerly et al. |
| 2018/0056496 A1 | 3/2018 | Rubens et al. |
| 2018/0065248 A1 | 3/2018 | Barral et al. |
| 2018/0078170 A1 | 3/2018 | Panescu et al. |
| 2018/0082480 A1 | 3/2018 | White et al. |
| 2018/0085102 A1 | 3/2018 | Kikuchi |
| 2018/0098049 A1 | 4/2018 | Sugano et al. |
| 2018/0098816 A1 | 4/2018 | Govari et al. |
| 2018/0108438 A1 | 4/2018 | Ryan et al. |
| 2018/0110398 A1 | 4/2018 | Schwartz et al. |
| 2018/0110523 A1 | 4/2018 | Shelton, IV |
| 2018/0116662 A1 | 5/2018 | Shelton, IV et al. |
| 2018/0116735 A1 | 5/2018 | Tierney et al. |
| 2018/0122506 A1 | 5/2018 | Grantcharov et al. |
| 2018/0125590 A1 | 5/2018 | Giordano et al. |
| 2018/0132895 A1 | 5/2018 | Silver |
| 2018/0144243 A1 | 5/2018 | Hsieh et al. |
| 2018/0144314 A1 | 5/2018 | Miller |
| 2018/0153436 A1 | 6/2018 | Olson |
| 2018/0153574 A1 | 6/2018 | Faller et al. |
| 2018/0153632 A1 | 6/2018 | Tokarchuk et al. |
| 2018/0154297 A1 | 6/2018 | Maletich et al. |
| 2018/0161062 A1 | 6/2018 | Kaga et al. |
| 2018/0161716 A1 | 6/2018 | Li et al. |
| 2018/0165780 A1 | 6/2018 | Romeo |
| 2018/0168574 A1 | 6/2018 | Robinson et al. |
| 2018/0168575 A1 | 6/2018 | Simms et al. |
| 2018/0168577 A1 | 6/2018 | Aronhalt et al. |
| 2018/0168578 A1 | 6/2018 | Aronhalt et al. |
| 2018/0168579 A1 | 6/2018 | Aronhalt et al. |
| 2018/0168584 A1 | 6/2018 | Harris et al. |
| 2018/0168590 A1 | 6/2018 | Overmyer et al. |
| 2018/0168592 A1 | 6/2018 | Overmyer et al. |
| 2018/0168597 A1 | 6/2018 | Fanelli et al. |
| 2018/0168598 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168614 A1 | 6/2018 | Shelton, IV et al. |
| 2018/0168615 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168625 A1 | 6/2018 | Posada et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0168739 A1 | 6/2018 | Alikhani et al. |
| 2018/0172420 A1 | 6/2018 | Hein et al. |
| 2018/0177383 A1 | 6/2018 | Noonan et al. |
| 2018/0182475 A1 | 6/2018 | Cossler et al. |
| 2018/0183684 A1 | 6/2018 | Jacobson et al. |
| 2018/0193579 A1 | 7/2018 | Hanrahan et al. |
| 2018/0206884 A1 | 7/2018 | Beaupre |
| 2018/0206905 A1 | 7/2018 | Batchelor et al. |
| 2018/0211726 A1 | 7/2018 | Courtemanche et al. |
| 2018/0214025 A1 | 8/2018 | Homyk et al. |
| 2018/0221005 A1 | 8/2018 | Hamel et al. |
| 2018/0221598 A1 | 8/2018 | Silver |

(56)                References Cited

U.S. PATENT DOCUMENTS

| | | |
|---|---|---|
| 2018/0228557 A1 | 8/2018 | Darisse et al. |
| 2018/0233222 A1 | 8/2018 | Daley et al. |
| 2018/0233235 A1 | 8/2018 | Angelides |
| 2018/0235719 A1 | 8/2018 | Jarc |
| 2018/0235722 A1 | 8/2018 | Baghdadi et al. |
| 2018/0242967 A1 | 8/2018 | Meade |
| 2018/0247128 A1 | 8/2018 | Alvi et al. |
| 2018/0247711 A1 | 8/2018 | Terry |
| 2018/0250086 A1 | 9/2018 | Grubbs |
| 2018/0250825 A1 | 9/2018 | Hashimoto et al. |
| 2018/0263699 A1 | 9/2018 | Murphy et al. |
| 2018/0263710 A1 | 9/2018 | Sakaguchi et al. |
| 2018/0268320 A1 | 9/2018 | Shekhar |
| 2018/0271520 A1 | 9/2018 | Shelton, IV et al. |
| 2018/0271603 A1 | 9/2018 | Nir et al. |
| 2018/0289427 A1 | 10/2018 | Griffiths et al. |
| 2018/0294060 A1 | 10/2018 | Kassab |
| 2018/0296286 A1 | 10/2018 | Peine et al. |
| 2018/0296289 A1 | 10/2018 | Rodriguez-Navarro et al. |
| 2018/0300506 A1 | 10/2018 | Kawakami et al. |
| 2018/0303552 A1 | 10/2018 | Ryan et al. |
| 2018/0304471 A1 | 10/2018 | Tokuchi |
| 2018/0310986 A1 | 11/2018 | Batchelor et al. |
| 2018/0315492 A1 | 11/2018 | Bishop et al. |
| 2018/0317916 A1 | 11/2018 | Wixey |
| 2018/0325619 A1 | 11/2018 | Rauniyar et al. |
| 2018/0333188 A1 | 11/2018 | Nott et al. |
| 2018/0333207 A1 | 11/2018 | Moctezuma De la Barrera |
| 2018/0333209 A1 | 11/2018 | Frushour et al. |
| 2018/0345501 A1 | 12/2018 | Jumis et al. |
| 2018/0349721 A1 | 12/2018 | Agrawal et al. |
| 2018/0353186 A1 | 12/2018 | Mozdzierz et al. |
| 2018/0357383 A1 | 12/2018 | Allen et al. |
| 2018/0360456 A1 | 12/2018 | Shelton, IV et al. |
| 2018/0366213 A1 | 12/2018 | Fidone et al. |
| 2018/0368930 A1 | 12/2018 | Esterberg et al. |
| 2019/0000478 A1 | 1/2019 | Messerly et al. |
| 2019/0000569 A1 | 1/2019 | Crawford et al. |
| 2019/0001079 A1 | 1/2019 | Zergiebel et al. |
| 2019/0005641 A1 | 1/2019 | Yamamoto |
| 2019/0006047 A1 | 1/2019 | Gorek et al. |
| 2019/0025040 A1 | 1/2019 | Andreason et al. |
| 2019/0036688 A1 | 1/2019 | Wasily et al. |
| 2019/0038335 A1 | 2/2019 | Mohr et al. |
| 2019/0038364 A1 | 2/2019 | Enoki |
| 2019/0045515 A1 | 2/2019 | Kwasnick et al. |
| 2019/0046198 A1 | 2/2019 | Stokes et al. |
| 2019/0053801 A1 | 2/2019 | Wixey et al. |
| 2019/0053866 A1 | 2/2019 | Seow et al. |
| 2019/0059986 A1 | 2/2019 | Shelton, IV et al. |
| 2019/0059997 A1 | 2/2019 | Frushour |
| 2019/0069949 A1 | 3/2019 | Vrba et al. |
| 2019/0069964 A1 | 3/2019 | Hagn |
| 2019/0069966 A1 | 3/2019 | Petersen et al. |
| 2019/0070550 A1 | 3/2019 | Lalomia et al. |
| 2019/0070731 A1 | 3/2019 | Bowling et al. |
| 2019/0083190 A1 | 3/2019 | Graves et al. |
| 2019/0083809 A1 | 3/2019 | Zhang |
| 2019/0087544 A1 | 3/2019 | Peterson |
| 2019/0099221 A1 | 4/2019 | Schmidt et al. |
| 2019/0099226 A1 | 4/2019 | Hallen |
| 2019/0104919 A1 | 4/2019 | Shelton, IV et al. |
| 2019/0105468 A1 | 4/2019 | Kato et al. |
| 2019/0110828 A1 | 4/2019 | Despatie |
| 2019/0110855 A1 | 4/2019 | Barral et al. |
| 2019/0110856 A1 | 4/2019 | Barral et al. |
| 2019/0115108 A1 | 4/2019 | Hegedus et al. |
| 2019/0122330 A1 | 4/2019 | Saget et al. |
| 2019/0125320 A1 | 5/2019 | Shelton, IV et al. |
| 2019/0125321 A1 | 5/2019 | Shelton, IV et al. |
| 2019/0125324 A1 | 5/2019 | Scheib et al. |
| 2019/0125335 A1 | 5/2019 | Shelton, IV et al. |
| 2019/0125336 A1 | 5/2019 | Deck et al. |
| 2019/0125338 A1 | 5/2019 | Shelton, IV et al. |
| 2019/0125348 A1 | 5/2019 | Shelton, IV et al. |
| 2019/0125352 A1 | 5/2019 | Shelton, IV et al. |
| 2019/0125353 A1 | 5/2019 | Shelton, IV et al. |
| 2019/0125354 A1 | 5/2019 | Deck et al. |
| 2019/0125355 A1 | 5/2019 | Shelton, IV et al. |
| 2019/0125356 A1 | 5/2019 | Shelton, IV et al. |
| 2019/0125357 A1 | 5/2019 | Shelton, IV et al. |
| 2019/0125358 A1 | 5/2019 | Shelton, IV et al. |
| 2019/0125359 A1 | 5/2019 | Shelton, IV et al. |
| 2019/0125360 A1 | 5/2019 | Shelton, IV et al. |
| 2019/0125361 A1 | 5/2019 | Shelton, IV et al. |
| 2019/0125377 A1 | 5/2019 | Shelton, IV |
| 2019/0125378 A1 | 5/2019 | Shelton, IV et al. |
| 2019/0125379 A1 | 5/2019 | Shelton, IV et al. |
| 2019/0125380 A1 | 5/2019 | Hunter et al. |
| 2019/0125384 A1 | 5/2019 | Scheib et al. |
| 2019/0125387 A1 | 5/2019 | Parihar et al. |
| 2019/0125388 A1 | 5/2019 | Shelton, IV et al. |
| 2019/0125430 A1 | 5/2019 | Shelton, IV et al. |
| 2019/0125431 A1 | 5/2019 | Shelton, IV et al. |
| 2019/0125432 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125456 A1 | 5/2019 | Shelton, IV et al. |
| 2019/0125457 A1 | 5/2019 | Parihar et al. |
| 2019/0125458 A1 | 5/2019 | Shelton, IV et al. |
| 2019/0125459 A1 | 5/2019 | Shelton, IV et al. |
| 2019/0125476 A1 | 5/2019 | Shelton, IV et al. |
| 2019/0133703 A1 | 5/2019 | Seow et al. |
| 2019/0142535 A1 | 5/2019 | Seow et al. |
| 2019/0145942 A1 | 5/2019 | Dutriez et al. |
| 2019/0150975 A1 | 5/2019 | Kawasaki et al. |
| 2019/0159778 A1 | 5/2019 | Shelton, IV et al. |
| 2019/0163875 A1 | 5/2019 | Allen et al. |
| 2019/0167296 A1 | 6/2019 | Tsubuku et al. |
| 2019/0192044 A1 | 6/2019 | Ravi et al. |
| 2019/0192157 A1 | 6/2019 | Scott et al. |
| 2019/0192236 A1 | 6/2019 | Shelton, IV et al. |
| 2019/0200844 A1 | 7/2019 | Shelton, IV et al. |
| 2019/0200863 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200977 A1 | 7/2019 | Shelton, IV et al. |
| 2019/0200980 A1 | 7/2019 | Shelton, IV et al. |
| 2019/0200981 A1 | 7/2019 | Harris et al. |
| 2019/0200984 A1 | 7/2019 | Shelton, IV et al. |
| 2019/0200985 A1 | 7/2019 | Shelton, IV et al. |
| 2019/0200986 A1 | 7/2019 | Shelton, IV et al. |
| 2019/0200987 A1 | 7/2019 | Shelton, IV et al. |
| 2019/0200988 A1 | 7/2019 | Shelton, IV |
| 2019/0200996 A1 | 7/2019 | Shelton, IV et al. |
| 2019/0200997 A1 | 7/2019 | Shelton, IV et al. |
| 2019/0200998 A1 | 7/2019 | Shelton, IV et al. |
| 2019/0201020 A1 | 7/2019 | Shelton, IV et al. |
| 2019/0201021 A1 | 7/2019 | Shelton, IV et al. |
| 2019/0201023 A1 | 7/2019 | Shelton, IV et al. |
| 2019/0201024 A1 | 7/2019 | Shelton, IV et al. |
| 2019/0201025 A1 | 7/2019 | Shelton, IV et al. |
| 2019/0201026 A1 | 7/2019 | Shelton, IV et al. |
| 2019/0201027 A1 | 7/2019 | Shelton, IV et al. |
| 2019/0201028 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201033 A1 | 7/2019 | Yates et al. |
| 2019/0201034 A1 | 7/2019 | Shelton, IV et al. |
| 2019/0201036 A1 | 7/2019 | Nott et al. |
| 2019/0201037 A1 | 7/2019 | Houser et al. |
| 2019/0201038 A1 | 7/2019 | Yates et al. |
| 2019/0201039 A1 | 7/2019 | Widenhouse et al. |
| 2019/0201040 A1 | 7/2019 | Messerly et al. |
| 2019/0201041 A1 | 7/2019 | Kimball et al. |
| 2019/0201042 A1 | 7/2019 | Nott et al. |
| 2019/0201043 A1 | 7/2019 | Shelton, IV et al. |
| 2019/0201044 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201073 A1 | 7/2019 | Nott et al. |
| 2019/0201074 A1 | 7/2019 | Yates et al. |
| 2019/0201075 A1 | 7/2019 | Shelton, IV et al. |

(56) References Cited

U.S. PATENT DOCUMENTS

| | | |
|---|---|---|
| 2019/0201076 A1 | 7/2019 | Honda et al. |
| 2019/0201077 A1 | 7/2019 | Yates et al. |
| 2019/0201079 A1 | 7/2019 | Shelton, IV et al. |
| 2019/0201080 A1 | 7/2019 | Messerly et al. |
| 2019/0201081 A1 | 7/2019 | Shelton, IV et al. |
| 2019/0201082 A1 | 7/2019 | Shelton, IV et al. |
| 2019/0201083 A1 | 7/2019 | Shelton, IV et al. |
| 2019/0201084 A1 | 7/2019 | Shelton, IV et al. |
| 2019/0201085 A1 | 7/2019 | Shelton, IV et al. |
| 2019/0201086 A1 | 7/2019 | Shelton, IV et al. |
| 2019/0201087 A1 | 7/2019 | Shelton, IV et al. |
| 2019/0201090 A1 | 7/2019 | Shelton, IV et al. |
| 2019/0201091 A1 | 7/2019 | Yates et al. |
| 2019/0201092 A1 | 7/2019 | Yates et al. |
| 2019/0201102 A1 | 7/2019 | Shelton, IV et al. |
| 2019/0201104 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201114 A1 | 7/2019 | Shelton, IV et al. |
| 2019/0201115 A1 | 7/2019 | Shelton, IV et al. |
| 2019/0201116 A1 | 7/2019 | Shelton, IV et al. |
| 2019/0201118 A1 | 7/2019 | Shelton, IV et al. |
| 2019/0201120 A1 | 7/2019 | Shelton, IV et al. |
| 2019/0201123 A1 | 7/2019 | Shelton, IV et al. |
| 2019/0201124 A1 | 7/2019 | Shelton, IV et al. |
| 2019/0201125 A1 | 7/2019 | Shelton, IV et al. |
| 2019/0201126 A1 | 7/2019 | Shelton, IV et al. |
| 2019/0201127 A1 | 7/2019 | Shelton, IV et al. |
| 2019/0201128 A1 | 7/2019 | Yates et al. |
| 2019/0201129 A1 | 7/2019 | Shelton, IV et al. |
| 2019/0201130 A1 | 7/2019 | Shelton, IV et al. |
| 2019/0201135 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201138 A1 | 7/2019 | Yates et al. |
| 2019/0201139 A1 | 7/2019 | Shelton, IV et al. |
| 2019/0201140 A1 | 7/2019 | Yates et al. |
| 2019/0201141 A1 | 7/2019 | Shelton, IV et al. |
| 2019/0201142 A1 | 7/2019 | Shelton, IV et al. |
| 2019/0201145 A1 | 7/2019 | Shelton, IV et al. |
| 2019/0201146 A1 | 7/2019 | Shelton, IV et al. |
| 2019/0201158 A1 | 7/2019 | Shelton, IV et al. |
| 2019/0201159 A1 | 7/2019 | Shelton, IV et al. |
| 2019/0201594 A1 | 7/2019 | Shelton, IV et al. |
| 2019/0201597 A1 | 7/2019 | Shelton, IV et al. |
| 2019/0204201 A1 | 7/2019 | Shelton, IV et al. |
| 2019/0205001 A1 | 7/2019 | Messerly et al. |
| 2019/0205441 A1 | 7/2019 | Shelton, IV et al. |
| 2019/0205566 A1 | 7/2019 | Shelton, IV et al. |
| 2019/0205567 A1 | 7/2019 | Shelton, IV et al. |
| 2019/0206003 A1 | 7/2019 | Harris et al. |
| 2019/0206004 A1 | 7/2019 | Shelton, IV et al. |
| 2019/0206050 A1 | 7/2019 | Yates et al. |
| 2019/0206542 A1 | 7/2019 | Shelton, IV et al. |
| 2019/0206551 A1 | 7/2019 | Yates et al. |
| 2019/0206555 A1 | 7/2019 | Morgan et al. |
| 2019/0206556 A1 | 7/2019 | Shelton, IV et al. |
| 2019/0206561 A1 | 7/2019 | Shelton, IV et al. |
| 2019/0206562 A1 | 7/2019 | Shelton, IV et al. |
| 2019/0206563 A1 | 7/2019 | Shelton, IV et al. |
| 2019/0206564 A1 | 7/2019 | Shelton, IV et al. |
| 2019/0206565 A1 | 7/2019 | Shelton, IV |
| 2019/0206569 A1 | 7/2019 | Shelton, IV et al. |
| 2019/0206576 A1 | 7/2019 | Shelton, IV et al. |
| 2019/0208641 A1 | 7/2019 | Yates et al. |
| 2019/0216452 A1 | 7/2019 | Nawana et al. |
| 2019/0224434 A1 | 7/2019 | Silver et al. |
| 2019/0254759 A1 | 8/2019 | Azizian |
| 2019/0261984 A1 | 8/2019 | Nelson et al. |
| 2019/0269476 A1 | 9/2019 | Bowling et al. |
| 2019/0272917 A1 | 9/2019 | Couture et al. |
| 2019/0274662 A1 | 9/2019 | Rockman et al. |
| 2019/0274705 A1 | 9/2019 | Sawhney et al. |
| 2019/0274706 A1 | 9/2019 | Nott et al. |
| 2019/0274707 A1 | 9/2019 | Sawhney et al. |
| 2019/0274708 A1 | 9/2019 | Boudreaux |
| 2019/0274709 A1 | 9/2019 | Scoggins |
| 2019/0274710 A1 | 9/2019 | Black |
| 2019/0274711 A1 | 9/2019 | Scoggins et al. |
| 2019/0274712 A1 | 9/2019 | Faller et al. |
| 2019/0274713 A1 | 9/2019 | Scoggins et al. |
| 2019/0274714 A1 | 9/2019 | Cuti et al. |
| 2019/0274716 A1 | 9/2019 | Nott et al. |
| 2019/0274717 A1 | 9/2019 | Nott et al. |
| 2019/0274718 A1 | 9/2019 | Denzinger et al. |
| 2019/0274719 A1 | 9/2019 | Stulen |
| 2019/0274720 A1 | 9/2019 | Gee et al. |
| 2019/0274749 A1 | 9/2019 | Brady et al. |
| 2019/0274750 A1 | 9/2019 | Jayme et al. |
| 2019/0274752 A1 | 9/2019 | Denzinger et al. |
| 2019/0278262 A1 | 9/2019 | Taylor et al. |
| 2019/0282311 A1 | 9/2019 | Nowlin et al. |
| 2019/0290389 A1 | 9/2019 | Kopp |
| 2019/0298340 A1 | 10/2019 | Shelton, IV et al. |
| 2019/0298341 A1 | 10/2019 | Shelton, IV et al. |
| 2019/0298342 A1 | 10/2019 | Shelton, IV et al. |
| 2019/0298343 A1 | 10/2019 | Shelton, IV et al. |
| 2019/0298346 A1 | 10/2019 | Shelton, IV et al. |
| 2019/0298347 A1 | 10/2019 | Shelton, IV et al. |
| 2019/0298350 A1 | 10/2019 | Shelton, IV et al. |
| 2019/0298352 A1 | 10/2019 | Shelton, IV et al. |
| 2019/0298353 A1 | 10/2019 | Shelton, IV et al. |
| 2019/0298354 A1 | 10/2019 | Shelton, IV et al. |
| 2019/0298355 A1 | 10/2019 | Shelton, IV et al. |
| 2019/0298356 A1 | 10/2019 | Shelton, IV et al. |
| 2019/0298357 A1 | 10/2019 | Shelton, IV et al. |
| 2019/0298464 A1 | 10/2019 | Abbott |
| 2019/0307520 A1 | 10/2019 | Peine et al. |
| 2019/0311802 A1 | 10/2019 | Kokubo et al. |
| 2019/0314015 A1 | 10/2019 | Shelton, IV et al. |
| 2019/0314016 A1 | 10/2019 | Huitema et al. |
| 2019/0314081 A1 | 10/2019 | Brogna |
| 2019/0320929 A1 | 10/2019 | Spencer et al. |
| 2019/0321117 A1 | 10/2019 | Itkowitz et al. |
| 2019/0325386 A1 | 10/2019 | Laster et al. |
| 2019/0333626 A1 | 10/2019 | Mansi et al. |
| 2019/0343594 A1 | 11/2019 | Garcia Kilroy et al. |
| 2019/0365569 A1 | 12/2019 | Skovgaard et al. |
| 2019/0374140 A1 | 12/2019 | Tucker et al. |
| 2019/0374292 A1 | 12/2019 | Barral et al. |
| 2019/0378610 A1 | 12/2019 | Barral et al. |
| 2020/0000470 A1 | 1/2020 | Du et al. |
| 2020/0000509 A1 | 1/2020 | Hayashida et al. |
| 2020/0022687 A1 | 1/2020 | Takemoto et al. |
| 2020/0038120 A1 | 2/2020 | Ziraknejad et al. |
| 2020/0046353 A1 | 2/2020 | Deck et al. |
| 2020/0054317 A1 | 2/2020 | Pisarnwongs et al. |
| 2020/0054320 A1 | 2/2020 | Harris et al. |
| 2020/0054321 A1 | 2/2020 | Harris et al. |
| 2020/0054322 A1 | 2/2020 | Harris et al. |
| 2020/0054323 A1 | 2/2020 | Harris et al. |
| 2020/0054326 A1 | 2/2020 | Harris et al. |
| 2020/0054328 A1 | 2/2020 | Harris et al. |
| 2020/0054330 A1 | 2/2020 | Harris et al. |
| 2020/0078070 A1 | 3/2020 | Henderson et al. |
| 2020/0078071 A1 | 3/2020 | Asher |
| 2020/0078076 A1 | 3/2020 | Henderson et al. |
| 2020/0078077 A1 | 3/2020 | Henderson et al. |
| 2020/0078078 A1 | 3/2020 | Henderson et al. |
| 2020/0078079 A1 | 3/2020 | Morgan et al. |
| 2020/0078080 A1 | 3/2020 | Henderson et al. |
| 2020/0078081 A1 | 3/2020 | Jayme et al. |
| 2020/0078082 A1 | 3/2020 | Henderson et al. |
| 2020/0078089 A1 | 3/2020 | Henderson et al. |
| 2020/0078096 A1 | 3/2020 | Barbagli et al. |
| 2020/0078106 A1 | 3/2020 | Henderson et al. |
| 2020/0078110 A1 | 3/2020 | Henderson et al. |
| 2020/0078111 A1 | 3/2020 | Oberkircher et al. |
| 2020/0078112 A1 | 3/2020 | Henderson et al. |
| 2020/0078113 A1 | 3/2020 | Sawhney et al. |
| 2020/0078114 A1 | 3/2020 | Asher et al. |
| 2020/0078115 A1 | 3/2020 | Asher et al. |
| 2020/0078116 A1 | 3/2020 | Oberkircher et al. |
| 2020/0078117 A1 | 3/2020 | Henderson et al. |

(56) References Cited

U.S. PATENT DOCUMENTS

| | | |
|---|---|---|
| 2020/0078118 A1 | 3/2020 | Henderson et al. |
| 2020/0078119 A1 | 3/2020 | Henderson et al. |
| 2020/0078120 A1 | 3/2020 | Aldridge et al. |
| 2020/0081585 A1 | 3/2020 | Petre et al. |
| 2020/0090808 A1 | 3/2020 | Carroll et al. |
| 2020/0100825 A1 | 4/2020 | Henderson et al. |
| 2020/0100830 A1 | 4/2020 | Henderson et al. |
| 2020/0106220 A1 | 4/2020 | Henderson et al. |
| 2020/0162896 A1 | 5/2020 | Su et al. |
| 2020/0168323 A1 | 5/2020 | Bullington et al. |
| 2020/0178760 A1 | 6/2020 | Kashima et al. |
| 2020/0178971 A1 | 6/2020 | Harris et al. |
| 2020/0193600 A1 | 6/2020 | Shameli et al. |
| 2020/0197027 A1 | 6/2020 | Hershberger et al. |
| 2020/0203004 A1 | 6/2020 | Shanbhag et al. |
| 2020/0214699 A1 | 7/2020 | Shelton, IV et al. |
| 2020/0222079 A1 | 7/2020 | Swaney et al. |
| 2020/0222149 A1 | 7/2020 | Valentine et al. |
| 2020/0226751 A1 | 7/2020 | Jin et al. |
| 2020/0230803 A1 | 7/2020 | Yamashita et al. |
| 2020/0237372 A1 | 7/2020 | Park |
| 2020/0237452 A1 | 7/2020 | Wolf et al. |
| 2020/0261075 A1 | 8/2020 | Boudreaux et al. |
| 2020/0261076 A1 | 8/2020 | Boudreaux et al. |
| 2020/0261077 A1 | 8/2020 | Shelton, IV et al. |
| 2020/0261078 A1 | 8/2020 | Bakos et al. |
| 2020/0261080 A1 | 8/2020 | Bakos et al. |
| 2020/0261081 A1 | 8/2020 | Boudreaux et al. |
| 2020/0261082 A1 | 8/2020 | Boudreaux et al. |
| 2020/0261083 A1 | 8/2020 | Bakos et al. |
| 2020/0261084 A1 | 8/2020 | Bakos et al. |
| 2020/0261085 A1 | 8/2020 | Boudreaux et al. |
| 2020/0261086 A1 | 8/2020 | Zeiner et al. |
| 2020/0261087 A1 | 8/2020 | Timm et al. |
| 2020/0261088 A1 | 8/2020 | Harris et al. |
| 2020/0261089 A1 | 8/2020 | Shelton, IV et al. |
| 2020/0273581 A1 | 8/2020 | Wolf et al. |
| 2020/0275928 A1 | 9/2020 | Shelton, IV et al. |
| 2020/0275930 A1 | 9/2020 | Harris et al. |
| 2020/0281665 A1 | 9/2020 | Kopp |
| 2020/0305924 A1 | 10/2020 | Carroll |
| 2020/0305945 A1 | 10/2020 | Morgan et al. |
| 2020/0314569 A1 | 10/2020 | Morgan et al. |
| 2020/0348662 A1 | 11/2020 | Cella et al. |
| 2020/0352664 A1 | 11/2020 | King et al. |
| 2020/0388385 A1 | 12/2020 | De Los Reyes et al. |
| 2020/0405304 A1 | 12/2020 | Mozdzierz et al. |
| 2020/0405375 A1 | 12/2020 | Shelton, IV et al. |
| 2021/0000555 A1 | 1/2021 | Shelton, IV et al. |
| 2021/0007760 A1 | 1/2021 | Reisin |
| 2021/0015568 A1 | 1/2021 | Liao et al. |
| 2021/0022731 A1 | 1/2021 | Eisinger |
| 2021/0022738 A1 | 1/2021 | Weir et al. |
| 2021/0022809 A1 | 1/2021 | Crawford et al. |
| 2021/0059674 A1 | 3/2021 | Shelton, IV et al. |
| 2021/0068834 A1 | 3/2021 | Shelton, IV et al. |
| 2021/0076966 A1 | 3/2021 | Grantcharov et al. |
| 2021/0128149 A1 | 5/2021 | Whitfield et al. |
| 2021/0153889 A1 | 5/2021 | Nott et al. |
| 2021/0169516 A1 | 6/2021 | Houser et al. |
| 2021/0176179 A1 | 6/2021 | Shelton, IV |
| 2021/0177452 A1 | 6/2021 | Nott et al. |
| 2021/0177489 A1 | 6/2021 | Yates et al. |
| 2021/0186454 A1 | 6/2021 | Behzadi et al. |
| 2021/0192914 A1 | 6/2021 | Shelton, IV et al. |
| 2021/0201646 A1 | 7/2021 | Shelton, IV et al. |
| 2021/0205020 A1 | 7/2021 | Shelton, IV et al. |
| 2021/0205021 A1 | 7/2021 | Shelton, IV et al. |
| 2021/0205028 A1 | 7/2021 | Shelton, IV et al. |
| 2021/0205029 A1 | 7/2021 | Wiener et al. |
| 2021/0205030 A1 | 7/2021 | Shelton, IV et al. |
| 2021/0205031 A1 | 7/2021 | Shelton, IV et al. |
| 2021/0212602 A1 | 7/2021 | Shelton, IV et al. |
| 2021/0212694 A1 | 7/2021 | Shelton, IV et al. |
| 2021/0212719 A1 | 7/2021 | Houser et al. |
| 2021/0212770 A1 | 7/2021 | Messerly et al. |
| 2021/0212771 A1 | 7/2021 | Shelton, IV et al. |
| 2021/0212774 A1 | 7/2021 | Shelton, IV et al. |
| 2021/0212775 A1 | 7/2021 | Shelton, IV et al. |
| 2021/0212782 A1 | 7/2021 | Shelton, IV et al. |
| 2021/0219976 A1 | 7/2021 | DiNardo et al. |
| 2021/0220058 A1 | 7/2021 | Messerly et al. |
| 2021/0240852 A1 | 8/2021 | Shelton, IV et al. |
| 2021/0241898 A1 | 8/2021 | Shelton, IV et al. |
| 2021/0249125 A1 | 8/2021 | Morgan et al. |
| 2021/0259687 A1 | 8/2021 | Gonzalez et al. |
| 2021/0259697 A1 | 8/2021 | Shelton, IV et al. |
| 2021/0259698 A1 | 8/2021 | Shelton, IV et al. |
| 2021/0282780 A1 | 9/2021 | Shelton, IV et al. |
| 2021/0282781 A1 | 9/2021 | Shelton, IV et al. |
| 2021/0306176 A1 | 9/2021 | Park et al. |
| 2021/0315579 A1 | 10/2021 | Shelton, IV et al. |
| 2021/0315580 A1 | 10/2021 | Shelton, IV et al. |
| 2021/0315581 A1 | 10/2021 | Shelton, IV et al. |
| 2021/0315582 A1 | 10/2021 | Shelton, IV et al. |
| 2021/0322014 A1 | 10/2021 | Shelton, IV et al. |
| 2021/0322015 A1 | 10/2021 | Shelton, IV et al. |
| 2021/0322017 A1 | 10/2021 | Shelton, IV et al. |
| 2021/0322018 A1 | 10/2021 | Shelton, IV et al. |
| 2021/0322019 A1 | 10/2021 | Shelton, IV et al. |
| 2021/0322020 A1 | 10/2021 | Shelton, IV et al. |
| 2021/0336939 A1 | 10/2021 | Wiener et al. |
| 2021/0353287 A1 | 11/2021 | Shelton, IV et al. |
| 2021/0353288 A1 | 11/2021 | Shelton, IV et al. |
| 2021/0358599 A1 | 11/2021 | Alvi et al. |
| 2021/0361284 A1 | 11/2021 | Shelton, IV et al. |
| 2022/0000484 A1 | 1/2022 | Shelton, IV et al. |
| 2022/0054158 A1 | 2/2022 | Shelton, IV et al. |
| 2022/0061836 A1 | 3/2022 | Parihar et al. |
| 2022/0079591 A1 | 3/2022 | Bakos et al. |
| 2022/0104880 A1 | 4/2022 | Frushour |
| 2022/0157306 A1 | 5/2022 | Albrecht et al. |
| 2022/0175374 A1 | 6/2022 | Shelton, IV et al. |
| 2022/0230738 A1 | 7/2022 | Shelton, IV et al. |
| 2022/0241027 A1 | 8/2022 | Shelton, IV et al. |
| 2022/0323092 A1 | 10/2022 | Shelton, IV et al. |
| 2022/0323150 A1 | 10/2022 | Yates et al. |
| 2022/0331011 A1 | 10/2022 | Shelton, IV et al. |
| 2022/0331018 A1 | 10/2022 | Parihar et al. |
| 2022/0346792 A1 | 11/2022 | Shelton, IV et al. |
| 2022/0370117 A1 | 11/2022 | Messerly et al. |
| 2022/0370126 A1 | 11/2022 | Shelton, IV et al. |
| 2022/0374414 A1 | 11/2022 | Shelton, IV et al. |
| 2022/0395276 A1 | 12/2022 | Yates et al. |
| 2022/0401099 A1 | 12/2022 | Shelton, IV et al. |
| 2022/0406452 A1 | 12/2022 | Shelton, IV |
| 2022/0409302 A1 | 12/2022 | Shelton, IV et al. |
| 2023/0000518 A1 | 1/2023 | Nott et al. |
| 2023/0037577 A1 | 2/2023 | Kimball et al. |
| 2023/0064821 A1 | 3/2023 | Shelton, IV |
| 2023/0092371 A1 | 3/2023 | Yates et al. |
| 2023/0098870 A1 | 3/2023 | Harris et al. |
| 2023/0116571 A1 | 4/2023 | Shelton, IV et al. |
| 2023/0146947 A1 | 5/2023 | Shelton, IV et al. |
| 2023/0165642 A1 | 6/2023 | Shelton, IV et al. |
| 2023/0171266 A1 | 6/2023 | Brunner et al. |
| 2023/0171304 A1 | 6/2023 | Shelton, IV et al. |
| 2023/0187060 A1 | 6/2023 | Morgan et al. |
| 2023/0190390 A1 | 6/2023 | Shelton, IV et al. |
| 2023/0200889 A1 | 6/2023 | Shelton, IV et al. |
| 2023/0210611 A1 | 7/2023 | Shelton, IV et al. |
| 2023/0233245 A1 | 7/2023 | Nott et al. |
| 2023/0263548 A1 | 8/2023 | Shelton, IV et al. |
| 2023/0320792 A1 | 10/2023 | Shelton, IV et al. |
| 2023/0355265 A1 | 11/2023 | Nott et al. |

FOREIGN PATENT DOCUMENTS

| | | | |
|---|---|---|---|
| CA | 2795323 A1 | 5/2014 |
| CN | 101617950 A | 1/2010 |
| CN | 106027664 A | 10/2016 |
| CN | 106413578 A | 2/2017 |
| CN | 106456169 A | 2/2017 |
| CN | 104490448 B | 3/2017 |

(56)          References Cited

FOREIGN PATENT DOCUMENTS

| | | | |
|---|---|---|---|
| CN | 206097107 | U | 4/2017 |
| CN | 106777916 | A | 5/2017 |
| CN | 107811710 | A | 3/2018 |
| CN | 108652695 | A | 10/2018 |
| DE | 3016131 | A1 | 10/1981 |
| DE | 3824913 | A1 | 2/1990 |
| DE | 4002843 | C1 | 4/1991 |
| DE | 102005051367 | A1 | 4/2007 |
| DE | 102016207666 | A1 | 11/2017 |
| EP | 0000756 | B1 | 10/1981 |
| EP | 0408160 | A1 | 1/1991 |
| EP | 0473987 | A1 | 3/1992 |
| EP | 0929263 | B1 | 7/1999 |
| EP | 1214913 | A2 | 6/2002 |
| EP | 2730209 | A1 | 5/2014 |
| EP | 2732772 | A1 | 5/2014 |
| EP | 2942023 | A2 | 11/2015 |
| EP | 3047806 | A1 | 7/2016 |
| EP | 3056923 | A1 | 8/2016 |
| EP | 3095399 | A2 | 11/2016 |
| EP | 3120781 | A2 | 1/2017 |
| EP | 3135225 | A2 | 3/2017 |
| EP | 3141181 | A1 | 3/2017 |
| FR | 2838234 | A1 | 10/2003 |
| GB | 2037167 | A1 | 7/1980 |
| GB | 2509523 | A | 7/2014 |
| JP | S5191993 | U | 7/1976 |
| JP | S5373315 | A | 6/1978 |
| JP | S57185848 | A | 11/1982 |
| JP | S58207752 | A | 12/1983 |
| JP | S63315049 | A | 12/1988 |
| JP | H06142113 | A | 5/1994 |
| JP | H06178780 | A | 6/1994 |
| JP | H06209902 | A | 8/1994 |
| JP | H07132122 | A | 5/1995 |
| JP | H08071072 | A | 3/1996 |
| JP | H08332169 | A | 12/1996 |
| JP | H0928663 | A | 2/1997 |
| JP | H09154850 | A | 6/1997 |
| JP | H11151247 | A | 6/1999 |
| JP | H11197159 | A | 7/1999 |
| JP | H11309156 | A | 11/1999 |
| JP | 2000058355 | A | 2/2000 |
| JP | 2001029353 | A | 2/2001 |
| JP | 2001195686 | A | 7/2001 |
| JP | 2001314411 | A | 11/2001 |
| JP | 2001340350 | A | 12/2001 |
| JP | 2002272758 | A | 9/2002 |
| JP | 2003061975 | A | 3/2003 |
| JP | 2003070921 | A | 3/2003 |
| JP | 2003153918 | A | 5/2003 |
| JP | 2004118664 | A | 4/2004 |
| JP | 2005111080 | A | 4/2005 |
| JP | 2005309702 | A | 11/2005 |
| JP | 2005348797 | A | 12/2005 |
| JP | 2006077626 | A | 3/2006 |
| JP | 2006117143 | A | 5/2006 |
| JP | 2006164251 | A | 6/2006 |
| JP | 2006280804 | A | 10/2006 |
| JP | 2006288431 | A | 10/2006 |
| JP | 2007123394 | A | 5/2007 |
| JP | 2007139822 | A | 6/2007 |
| JP | 2007300312 | A | 11/2007 |
| JP | 2009039515 | A | 2/2009 |
| JP | 2010057642 | A | 3/2010 |
| JP | 2010131265 | A | 6/2010 |
| JP | 2010269067 | A | 12/2010 |
| JP | 2012065698 | A | 4/2012 |
| JP | 2012239669 | A | 12/2012 |
| JP | 2012240158 | A | 12/2012 |
| JP | 2012533346 | A | 12/2012 |
| JP | 2013044303 | A | 3/2013 |
| JP | 2013081282 | A | 5/2013 |
| JP | 2013135738 | A | 7/2013 |
| JP | 2013144057 | A | 7/2013 |
| JP | 2014155207 | A | 8/2014 |
| JP | 2015085454 | A | 5/2015 |
| JP | 2016514017 | A | 5/2016 |
| JP | 2016528010 | A | 9/2016 |
| JP | 2016174836 | A | 10/2016 |
| JP | 2016214553 | A | 12/2016 |
| JP | 2017047022 | A | 3/2017 |
| JP | 2017096359 | A | 6/2017 |
| JP | 2017513561 | A | 6/2017 |
| JP | 2017526510 | A | 9/2017 |
| JP | 2017532168 | A | 11/2017 |
| KR | 20140104587 | A | 8/2014 |
| KR | 101587721 | B1 | 1/2016 |
| RU | 2020860 | C1 | 10/1994 |
| WO | WO-9734533 | A1 | 9/1997 |
| WO | WO-9808449 | A1 | 3/1998 |
| WO | WO-0024322 | A1 | 5/2000 |
| WO | WO-0108578 | A1 | 2/2001 |
| WO | WO-0112089 | A1 | 2/2001 |
| WO | WO-0120892 | A2 | 3/2001 |
| WO | WO-03079909 | A2 | 10/2003 |
| WO | WO-2006001264 | A1 | 1/2006 |
| WO | WO-2007137304 | A2 | 11/2007 |
| WO | WO-2008053485 | A1 | 5/2008 |
| WO | WO-2008056618 | A2 | 5/2008 |
| WO | WO-2008069816 | A1 | 6/2008 |
| WO | WO-2008076079 | A1 | 6/2008 |
| WO | WO-2008147555 | A2 | 12/2008 |
| WO | WO-2011112931 | A1 | 9/2011 |
| WO | WO-2013143573 | A1 | 10/2013 |
| WO | WO-2014031800 | A1 | 2/2014 |
| WO | WO-2014071184 | A1 | 5/2014 |
| WO | WO-2014116961 | A1 | 7/2014 |
| WO | WO-2014134196 | A1 | 9/2014 |
| WO | WO-2015030157 | A1 | 3/2015 |
| WO | WO-2015054665 | A1 | 4/2015 |
| WO | WO-2015129395 | A1 | 9/2015 |
| WO | WO-2016093049 | A1 | 6/2016 |
| WO | WO-2016100719 | A1 | 6/2016 |
| WO | WO-2016118752 | A1 | 7/2016 |
| WO | WO-2016206015 | A1 | 12/2016 |
| WO | WO-2017011382 | A1 | 1/2017 |
| WO | WO-2017011646 | A1 | 1/2017 |
| WO | WO-2017058617 | | 4/2017 |
| WO | WO-2017058695 | A1 | 4/2017 |
| WO | WO-2017151996 | A1 | 9/2017 |
| WO | WO-2017183353 | A1 | 10/2017 |
| WO | WO-2017189317 | A1 | 11/2017 |
| WO | WO-2017205308 | A1 | 11/2017 |
| WO | WO-2017210499 | A1 | 12/2017 |
| WO | WO-2017210501 | A1 | 12/2017 |
| WO | WO-2018116247 | A1 | 6/2018 |
| WO | WO-2018152141 | A1 | 8/2018 |
| WO | WO-2018176414 | A1 | 10/2018 |

OTHER PUBLICATIONS

Sorrells, P., "Application Note AN680. Passive RFID Basics," retrieved from http://ww1.microchip.com/downloads/en/AppNotes/00680b.pdf on Feb. 26, 2020, Dec. 31, 1998, pp. 1-7.

IEEE Std 802.3-2012 (Revision of IEEE Std 802.3-2008, published Dec. 28, 2012.

"ATM-MPLS Network Interworking Version 2.0, af-aic-0178.001" ATM Standard, The ATM Forum Technical Committe, published Aug. 2003.

Flores et al., "Large-scale Offloading in the Internet of Things," 2017 IEEE International Conference on Pervasive Computing and Communications Workshops (PERCOM Workshops), IEEE, pp. 479-484, Mar. 13, 2017.

Kalantarian et al., "Computation Offloading for Real-Time Health-Monitoring Devices," 2016 38th Annual International Conference of the IEEE Engineering in Medicine and Biology Society (EBMC), IEEE, pp. 4971-4974, Aug. 16, 2016.

Yuyi Mao et al., "A Survey on Mobile Edge Computing: The Communication Perspective," IEEE Communications Surveys & Tutorials, pp. 2322-2358, Jun. 13, 2017.

(56)        References Cited

OTHER PUBLICATIONS

Khazaei et al., "Health Informatics for Neonatal Intensive Care Units: An Analytical Modeling Perspective," IEEE Journal of Translational Engineering in Health and Medicine, vol. 3, pp. 1-9, Oct. 21, 2015.

Benkmann et al., "Concept of iterative optimization of minimally invasive surgery," 2017 22nd International Conference on Methods and Models in Automation and Robotics (MMAR), IEEE pp. 443-446, Aug. 28, 2017.

Trautman, Peter, "Breaking the Human-Robot Deadlock: Surpassing Shared Control Performance Limits with Sparse Human-Robot Interaction," Robotics: Science and Systems XIIII, pp. 1-10, Jul. 12, 2017.

Yang et al., "A dynamic stategy for packet scheduling and bandwidth allocation based on channel quality in IEEE 802.16e OFDMA system," Journal of Network and Computer Applications, vol. 39, pp. 52-60, May 2, 2013.

Takahashi et al., "Automatic smoke evacuation in laparoscopic surgery: a simplified method for objective evaluation," Surgical Endoscopy, vol. 27, No. 8, pp. 2980-2987, Feb. 23, 2013.

Miksch et al., "Utilizing temporal data abstraction for data validation and therapy planning for artificially ventilated newborn infants," Artificial Intelligence in Medicine, vol. 8, No. 6, pp. 543-576 (1996).

Horn et al., "Effective data validation of high-frequency data: Time-point-time-interval-, and trend-based methods," Computers in Biology and Medic, New York, NY, vol. 27, No. 5, pp. 389-409 (1997).

Stacey et al., "Temporal abstraction in intelligent clinical data analysis: A survey," Artificial Intelligence in Medicine, vol. 39, No. 1, pp. 1-24 (2006).

Zoccali, Bruno, "A Method for Approximating Component Temperatures at Altitude Conditions Based on CFD Analysis at Sea Level Conditions," (white paper), www.tdmginc.com, Dec. 6, 2018 (9 pages).

Slocinski et al., "Distance measure for impedance spectra for quantified evaluations," Lecture Notes on Impedance Spectroscopy, vol. 3, Taylor and Francis Group (Jul. 2012)—Book Not Attached.

Engel et al. "A safe robot system for craniofacial surgery", 2013 IEEE International Conference on Robotics and Automation (ICRA); May 6-10, 2013; Karlsruhe, Germany, vol. 2, Jan. 1, 2001, pp. 2020-2024.

Bonaci et al., "To Make a Robot Secure: An Experimental Analysis of Cyber Security Threats Against Teleoperated Surgical Robots," May 13, 2015. Retrieved from the Internet: URL:https://arxiv.org/pdf/1504.04339v2.pdf [retrieved on Aug. 24, 2019].

Homa Alemzadeh et al., "Targeted Attacks on Teleoperated Surgical Robots: Dynamic Model-Based Detection and Mitigation," 2016 46th Annual IEEE/IFIP International Conference on Dependable Systems and Networks (DSN), IEEE, Jun. 28, 2016, pp. 395-406.

Phumzile Malindi, "5. QoS in Telemedicine," "Telemedicine," Jun. 20, 2011, IntechOpen, pp. 119-138.

Staub et al., "Contour-based Surgical Instrument Tracking Supported by Kinematic Prediction," Proceedings of the 2010 3rd IEEE RAS & EMBS International Conference on Biomedical Robotics and Biomechatronics, Sep. 1, 2010, pp. 746-752.

Allan et al., "3-D Pose Estimation of Articulated Instruments in Robotic Minimally Invasive Surgery," IEEE Transactions on Medical Imaging, vol. 37, No. 5, May 1, 2018, pp. 1204-1213.

Kassahun et al., "Surgical Robotics Beyond Enhanced Dexterity Instrumentation: A Survey of the Machine Learning Techniques and their Role in Intelligent and Autonomous Surgical Actions." International Journal of Computer Assisted Radiology and Surgery, vol. 11, No. 4, Oct. 8, 2015, pp. 553-568.

Weede et al. "An Intelligent and Autonomous Endoscopic Guidance System for Minimally Invasive Surgery," 2013 IEEE International Conference on Robotics ad Automation (ICRA), May 6-10, 2013. Karlsruhe, Germany, May 1, 2011, pp. 5762-5768.

Altenberg et al., "Genes of Glycolysis are Ubiquitously Overexpressed in 24 Cancer Classes," Genomics, vol. 84, pp. 1014-1020 (2004).

Harold I. Brandon and V. Leroy Young, Mar. 1997, Surgical Services Management vol. 3 No. 3. retrieved from the internet <https://www.surgimedics.com/Research%20Articles/Electrosurgical%20Plume/Characterization%20And%20Removal%20Of%20Electrosurgical%20Smoke.pdf> (Year: 1997).

Marshall Brain, How Microcontrollers Work, 2006, retrieved from the internet <https://web.archive.org/web/20060221235221/http://electronics.howstuffworks.com/microcontroller.htm/printable> (Year: 2006).

CRC Press, "The Measurement, Instrumentation and Sensors Handbook," 1999, Section VII, Chapter 41, Peter O'Shea, "Phase Measurement," pp. 1303-1321, ISBN 0-8493-2145-X.

Jiang, "'Sound of Silence': a secure indoor wireless ultrasonic communication system," Article, 2014, pp. 46-50, Snapshots of Doctoral Research at University College Cork, School of Engineering—Electrical & Electronic Engineering, UCC, Cork, Ireland.

Li, et al., "Short-range ultrasonic communications in air using quadrature modulation," Journal, Oct. 30, 2009, pp. 2060-2072, IEEE Transactions on Ultrasonics, Ferroelectrics, and Frequency Control, vol. 56, No. 10, IEEE.

Salamon, "AI Detects Polyps Better Than Colonoscopists" Online Article, Jun. 3, 2018, Medscape Medical News, Digestive Disease Week (DDW) 2018: Presentation 133.

Misawa, et al. "Artificial Intelligence-Assisted Polyp Detection for Colonoscopy: Initial Experience," Article, Jun. 2018, pp. 2027-2029, vol. 154, Issue 8, American Gastroenterolgy Association.

Dottorato, "Analysis and Design of the Rectangular Microstrip Patch Antennas for TM0n0 operating mode," Article, Oct. 8, 2010, pp. 1-9, Microwave Journal.

Miller, et al., "Impact of Powered and Tissue-Specific Endoscopic Stapling Technology on Clinical and Economic Outcomes of Video-Assisted Thoracic Surgery Lobectomy Procedures: A Retrospective, Observational Study," Article, Apr. 2018, pp. 707-723, vol. 35 (Issue 5), Advances in Therapy.

Hsiao-Wei Tang, "ARCM", Video, Sep. 2012, YouTube, 5 screenshots, Retrieved from internet: <https://www.youtube.com/watch?v=UIdQaxb3fRw&feature=youtu.be>.

Giannios, et al., "Visible to near-infrared refractive properties of freshly-excised human-liver tissues: marking hepatic malignancies," Article, Jun. 14, 2016, pp. 1-10, Scientific Reports 6, Article No. 27910, Nature.

Vander Heiden, et al., "Understanding the Warburg effect: the metabolic requirements of cell proliferation," Article, May 22, 2009, pp. 1-12, vol. 324, Issue 5930, Science.

Hirayama et al., "Quantitative Metabolome Profiling of Colon and Stomach Cancer Microenvironment by Capillary Electrophoresis Time-of-Flight Mass Spectrometry," Article, Jun. 2009, pp. 4918-4925, vol. 69, Issue 11, Cancer Research.

Cengiz, et al., "A Tale of Two Compartments: Interstitial Versus Blood Glucose Monitoring," Article, Jun. 2009, pp. S11-S16, vol. 11, Supplement 1, Diabetes Technology & Therapeutics.

Shen, et al., "An iridium nanoparticles dispersed carbon based thick film electrochemical biosensor and its application for a single use, disposable glucose biosensor," Article, Feb. 3, 2007, pp. 106-113, vol. 125, Issue 1, Sensors and Actuators B: Chemical, Science Direct.

"ATM-MPLS Network Interworking Version 2.0, af-aic-0178.001" ATM Standard, The ATM Forum Technical Committee, published Aug. 2003.

IEEE Std No. 177, "Standard Definitions and Methods of Measurement for Piezoelectric Vibrators," published May 1966, The Institute of Electrical and Electronics Engineers, Inc., New York, N.Y.

Shi et al., An intuitive control console for robotic syrgery system, 2014, IEEE, p. 404-407 (Year: 2014).

Choi et al., A haptic augmented reality surgeon console for a laparoscopic surgery robot system, 2013, IEEE, p. 355-357 (Year: 2013).

Xie et al., Development of stereo vision and master-slave controller for a compact surgical robot system, 2015, IEEE, p. 403-407 (Year: 2015).

Sun et al., Innovative effector design for simulation training in robotic surgery, 2010, IEEE, p. 1735-1759 (Year: 2010).

(56) References Cited

OTHER PUBLICATIONS

Anonymous, "Internet of Things Powers Connected Surgical Device Infrastructure Case Study", Dec. 31, 2016 (Dec. 31, 2016), Retrieved from the Internet: URL:https://www.cognizant.com/services-resources/150110_IoT_connected_surgical_devices.pdf.

Draijer, Matthijs et al., "Review of laser speckle contrast techniques for visualizing tissue perfusion," Lasers in Medical Science, Springer-Verlag, LO, vol. 24, No. 4, Dec. 3, 2008, pp. 639-651.

Roy D Cullum, "Handbook of Engineering Design", ISBN: 9780408005586, Jan. 1, 1988 (Jan. 1, 1988), XP055578597, ISBN: 9780408005586, 10-20, Chapter 6, p. 138, right-hand column, paragraph 3.

"Surgical instrumentation: the true cost of instrument trays and a potential strategy for optimization"; Mhlaba et al.; Sep. 23, 2015 (Year: 2015).

Nabil Simaan et al, "Intelligent Surgical Robots with Situational Awareness: From Good to Great Surgeons", DOI: 10.1115/1 .Sep. 6, 2015 external link, Sep. 2015 (Sep. 2015), p. 3-6, Retrieved from the Internet: URL:http://memagazineselect.asmedigitalcollection.asme.org/data/journals/meena/936888/me-2015-sep6.pdf XP055530863.

Anonymous: "Titanium Key Chain Tool 1.1, Ultralight Multipurpose Key Chain Tool, Forward Cutting Can Opener—Vargo Titanium," vargooutdoors.com, Jul. 5, 2014 (Jul. 5, 2014), retrieved from the internet: https://vargooutdoors.com/titanium-key-chain-tool-1-1.html.

Anonymous: "Screwdriver—Wikipedia", en.wikipedia.org, Jun. 23, 2019, XP055725151, Retrieved from the Internet: URL:https://en.wikipedia.org/w/index.php?title=Screwdriver&oldid=903111203 [retrieved on Mar. 20, 2021].

Nordlinger, Christopher, "The Internet of Things and the Operating Room of the Future," May 4, 2015, https://medium.com/@chrisnordlinger/the-internet-of-things-and-the-operating-room-of-the-future-8999a143d7b1, retrieved from the internet on Apr. 27, 2021, 9 pages.

Screen captures from YouTube video clip entitled "Four ways to use the Lego Brick Separator Tool," 2 pages, uploaded on May 29, 2014 by user "Sarah Lewis". Retrieved from internet: https://www.youtube.com/watch?v=ucKiRD6U1LU (Year: 2014).

Anonymous: "Cloud computing—Wikipedia", Dec. 19, 2017, Retrieved from the Internet: URL:https://en.wikipedia.org/w/index.php?title=Cloud_computing&oldid=816206558 [retrieved Feb. 14, 2023], pp. 1-21.

Anonymous: "Differentiated services—Wikipedia", Dec. 14, 2017, Retrieved from the Internet: URL:https://en.wikipedia.org/w/index.php?title=Differentiated_services&oldid=815415620 [retrieved on Feb. 14, 2023], pp. 1-7.

Anonymous: "Quality of service—Wikipedia", Dec. 7, 2017, Retrieved from the Internet: URL:https://en.wikipedia.org/w/index.php?title=Quality_of_service&oldid=814298744#Applications [retrieved on Feb. 14, 2023], pp. 1-12.

Hu, Jinwen, Stimulations of adaptive temperature control with self-focused hyperthermia system for tumor treatment, Jan. 9, 2012, Ultrasonics 53, pp. 171-177, (Year: 2012).

Hussain et al., "A survey on resource allocation in high performance distributed computing systems", Parallel Computing, vol. 39, No. 11, pp. 709-736 (2013).

Lalys, et al., "Automatic knowledge-based recognition of low-level tasks in ophthalmological procedures", Int J CARS, vol. 8, No. 1, pp. 1-49, Apr. 19, 2012.

* cited by examiner

5000a

5004a

Receive data from data sources

5006a

Derive contextual information

5008a

Determine control adjustments for the modular device(s)

5010a

Control the modular device(s) according to the control adjustments

5000b

Receive perioperative data from a first modular device — 5004b

Derive contextual information — 5006b

Determine control adjustments for a second modular device — 5008b

Control the second modular device accordingly — 5010b

5179

5181

Segmentectomy procedure

Receive stapler perioperative data

5183

5187

Surgical procedure on step of ligating arteries and veins

No

Stapler previously utilized?

5185

Yes

Surgical procedure on step of transecting parenchyma

5189

SURGICAL SYSTEM DISTRIBUTED PROCESSING

CROSS-REFERENCE TO RELATED APPLICATIONS

This application is a continuation patent application claiming priority under 35 U.S.C. § 120 to U.S. patent application Ser. No. 15/940,663, titled SURGICAL SYSTEM DISTRIBUTED PROCESSING, filed Mar. 29, 2018, now U.S. Patent Application Publication No. 2019/0201033, which claims the benefit of priority under 35 U.S.C. § 119(e) to U.S. Provisional Patent Application Ser. No. 62/649,300, titled SURGICAL HUB SITUATIONAL AWARENESS, filed Mar. 28, 2018, the disclosure of each of which is hereby incorporated by reference in its entirety.

This application is a continuation patent application claiming priority under 35 U.S.C. § 120 to U.S. patent application Ser. No. 15/940,663, titled SURGICAL SYSTEM DISTRIBUTED PROCESSING, filed Mar. 29, 2018, now U.S. Patent Application Publication No. 2019/0201033, which also claims the benefit of priority under 35 U.S.C. § 119(e) to U.S. Provisional Patent Application Ser. No. 62/611,341, titled INTERACTIVE SURGICAL PLATFORM, filed Dec. 28, 2017, of U.S. Provisional Patent Application Ser. No. 62/611,340, titled CLOUD-BASED MEDICAL ANALYTICS, filed Dec. 28, 2017, of U.S. Provisional Patent Application Ser. No. 62/611,339, titled ROBOT ASSISTED SURGICAL PLATFORM, filed Dec. 28, 2017, the disclosure of each of which is herein incorporated by reference in its entirety.

BACKGROUND

The present disclosure relates to various surgical systems. Surgical procedures are typically performed in surgical operating theaters or rooms in a healthcare facility such as, for example, a hospital. A sterile field is typically created around the patient. The sterile field may include the scrubbed team members, who are properly attired, and all furniture and fixtures in the area. Various surgical devices and systems are utilized in performance of a surgical procedure.

SUMMARY

In one general aspect, a system is provided. The system comprises a surgical hub configured to communicably couple to a modular device. The modular device comprises a sensor configured to detect data associated with the modular device and a device processor. The surgical hub comprises a hub processor, a hub memory coupled to the hub processor. In addition to the surgical hub, the system also comprises a distributed control system executable at least in part by each of the device processor and the hub processor. The distributed control system is configured to: receive the data detected by the sensor; determine control adjustments for the modular device according to the data; and control the modular device according to the control adjustments. When in a first mode, the distributed control system is executed by both the hub processor and the device processor. When in a second mode, the distributed control system is executed solely by the device processor.

In another general aspect, another system is provided. The system comprises a modular device configured to communicably couple to a surgical hub made up of a hub processor. The modular device comprises a sensor configured to detect data associated with the modular device; a device memory; and a device processor coupled to the device memory and the sensor. In addition to the modular device, the system also comprises a distributed control system executable at least in part by each of the device processor and the hub processor. The distributed control system is configured to receive the data detected by the sensor; determine control adjustments for the modular device according to the data; and control the modular device according to the control adjustments. In a first mode, the distributed control system is executed by both the hub processor and the device processor. In a second mode, the distributed control system is executed solely by the device processor.

In yet another general aspect, another system is provided. The system is configured to control a modular device comprising a sensor configured to detect data associated with the modular device. The system comprises a first surgical hub configured to communicably couple to the modular device and to a second surgical hub comprising a second processor. The first surgical hub comprises a memory and a first processor coupled to the memory. The system also comprises a distributed control system executable at least in part by each of the first processor and the second processor. The distributed control system is configured to receive the data detected by the sensor; determine control adjustments for the modular device according to the data; and control the modular device according to the control adjustments.

FIGURES

The features of various aspects are set forth with particularity in the appended claims. The various aspects, however, both as to organization and methods of operation, together with further objects and advantages thereof, may best be understood by reference to the following description, taken in conjunction with the accompanying drawings as follows.

DESCRIPTION

Figure 1:
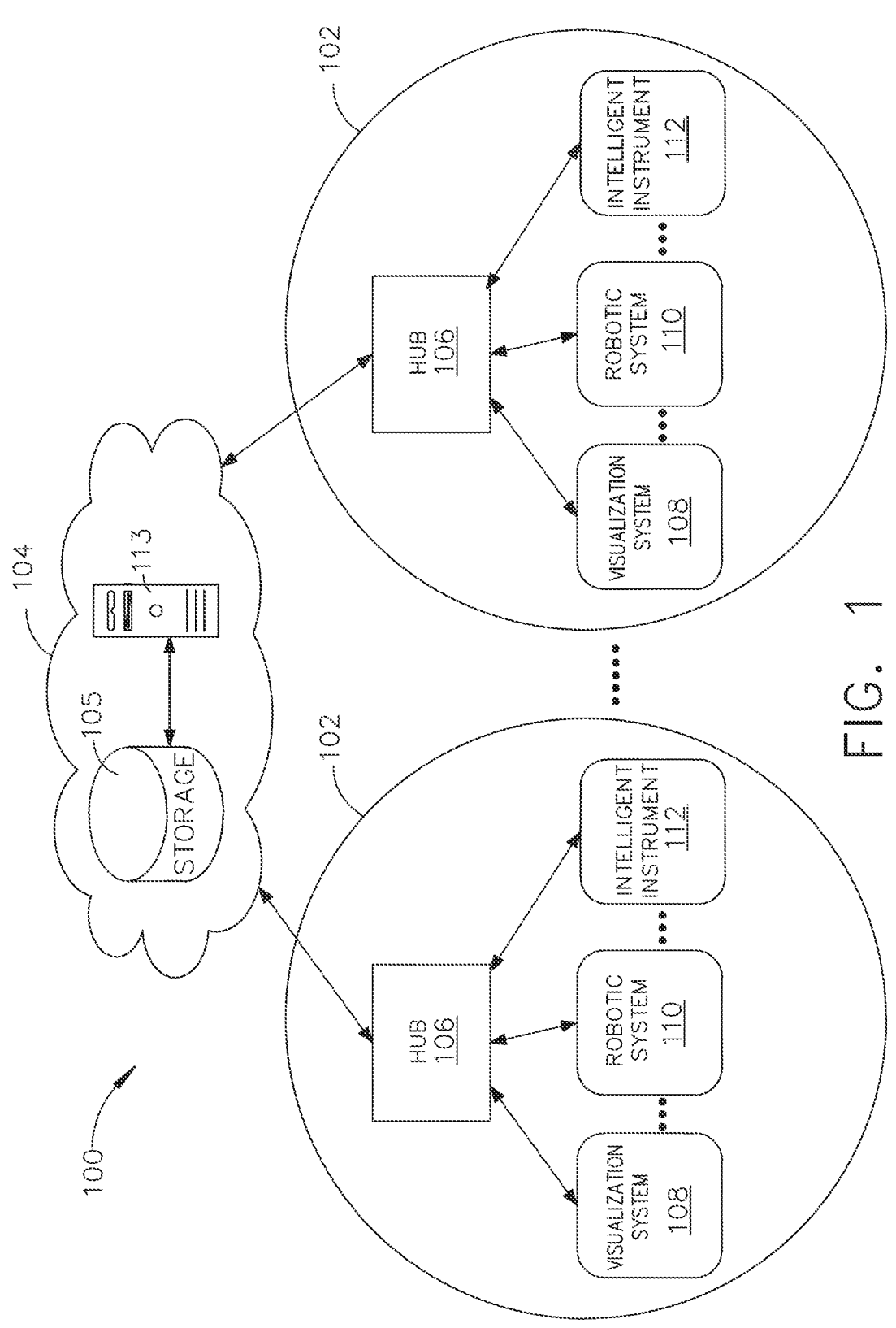
FIG. 1 is a block diagram of a computer-implemented interactive surgical system, in accordance with at least one aspect of the present disclosure.

Applicant of the present application owns the following U.S. Provisional Patent Applications, filed on Mar. 28, 2018, each of which is herein incorporated by reference in its entirety:

U.S. Provisional Patent Application Ser. No. 62/649,302, titled INTERACTIVE SURGICAL SYSTEMS WITH ENCRYPTED COMMUNICATION CAPABILITIES;

U.S. Provisional Patent Application Ser. No. 62/649,294, titled DATA STRIPPING METHOD TO INTERROGATE PATIENT RECORDS AND CREATE ANONYMIZED RECORD;

U.S. Provisional Patent Application Ser. No. 62/649,300, titled SURGICAL HUB SITUATIONAL AWARENESS;

U.S. Provisional Patent Application Ser. No. 62/649,309, titled SURGICAL HUB SPATIAL AWARENESS TO DETERMINE DEVICES IN OPERATING THEATER;

U.S. Provisional Patent Application Ser. No. 62/649,310, titled COMPUTER IMPLEMENTED INTERACTIVE SURGICAL SYSTEMS;

U.S. Provisional Patent Application Ser. No. 62/649,291, titled USE OF LASER LIGHT AND RED-GREEN-BLUE COLORATION TO DETERMINE PROPERTIES OF BACK SCATTERED LIGHT;

U.S. Provisional Patent Application Ser. No. 62/649,296, titled ADAPTIVE CONTROL PROGRAM UPDATES FOR SURGICAL DEVICES;

U.S. Provisional Patent Application Ser. No. 62/649,333, titled CLOUD-BASED MEDICAL ANALYTICS FOR CUSTOMIZATION AND RECOMMENDATIONS TO A USER;

U.S. Provisional Patent Application Ser. No. 62/649,327, titled CLOUD-BASED MEDICAL ANALYTICS FOR SECURITY AND AUTHENTICATION TRENDS AND REACTIVE MEASURES;

U.S. Provisional Patent Application Ser. No. 62/649,315, titled DATA HANDLING AND PRIORITIZATION IN A CLOUD ANALYTICS NETWORK;

U.S. Provisional Patent Application Ser. No. 62/649,313, titled CLOUD INTERFACE FOR COUPLED SURGICAL DEVICES;

U.S. Provisional Patent Application Ser. No. 62/649,320, titled DRIVE ARRANGEMENTS FOR ROBOT-ASSISTED SURGICAL PLATFORMS;

U.S. Provisional Patent Application Ser. No. 62/649,307, titled AUTOMATIC TOOL ADJUSTMENTS FOR ROBOT-ASSISTED SURGICAL PLATFORMS; and U.S. Provisional Patent Application Ser. No. 62/649,323, titled SENSING ARRANGEMENTS FOR ROBOT-ASSISTED SURGICAL PLATFORMS.

Applicant of the present application owns the following U.S. Patent Applications, filed on Mar. 29, 2018, each of which is herein incorporated by reference in its entirety:

U.S. patent application Ser. No. 15/940,641, titled INTERACTIVE SURGICAL SYSTEMS WITH encrypted COMMUNICATION CAPABILITIES, now U.S. Patent Application Publication No. 2019/0207911;

U.S. patent application Ser. No. 15/940,648, titled INTERACTIVE SURGICAL SYSTEMS WITH CONDITION HANDLING OF DEVICES AND DATA CAPABILITIES, now U.S. Patent Application Publication No. 2019/0206004;

U.S. patent application Ser. No. 15/940,656, titled SURGICAL HUB COORDINATION OF CONTROL AND COMMUNICATION OF OPERATING ROOM DEVICES, now U.S. Patent Application Publication No. 2019/0201141;

U.S. patent application Ser. No. 15/940,666, titled SPATIAL AWARENESS OF SURGICAL HUBS IN

US 12,575,855 B2

7

OPERATING ROOMS, now U.S. Patent Application Publication No. 2019/0206551;

U.S. patent application Ser. No. 15/940,670, titled COOPERATIVE UTILIZATION OF DATA DERIVED FROM SECONDARY SOURCES BY INTELLIGENT SURGICAL HUBS, now U.S. Patent Application Publication No. 2019/0201116;

U.S. patent application Ser. No. 15/940,677, titled SURGICAL HUB CONTROL ARRANGEMENTS, now U.S. Patent Application Publication No. 2019/0201143;

U.S. patent application Ser. No. 15/940,632, titled DATA STRIPPING METHOD TO INTERROGATE PATIENT RECORDS AND CREATE ANONYMIZED RECORD; now U.S. Patent Application Publication No. 2019/0205566;

U.S. patent application Ser. No. 15/940,640, titled COMMUNICATION HUB AND STORAGE DEVICE FOR STORING PARAMETERS AND STATUS OF A SURGICAL DEVICE TO BE SHARED WITH CLOUD BASED ANALYTICS SYSTEMS, now U.S. Patent Application Publication No. 2019/0200863;

U.S. patent application Ser. No. 15/940,645, titled SELF DESCRIBING DATA PACKETS GENERATED AT AN ISSUING INSTRUMENT, now U.S. Pat. No. 10,892,899;

U.S. patent application Ser. No. 15/940,649, titled DATA PAIRING TO INTERCONNECT A DEVICE MEASURED PARAMETER WITH AN OUTCOME, now U.S. Patent Application Publication No. 2019/0205567;

U.S. patent application Ser. No. 15/940,654, titled SURGICAL HUB SITUATIONAL AWARENESS, now U.S. Patent Application Publication No. 2019/0201140;

U.S. patent application Ser. No. 15/940,668, titled AGGREGATION AND REPORTING OF SURGICAL HUB DATA, now U.S. Patent Application Publication No. 2019/0201115;

U.S. patent application Ser. No. 15/940,671, titled SURGICAL HUB SPATIAL AWARENESS TO DETERMINE DEVICES IN OPERATING THEATER, now U.S. Patent Application Publication No. 2019/0201104;

U.S. patent application Ser. No. 15/940,686, titled DISPLAY OF ALIGNMENT OF STAPLE CARTRIDGE TO PRIOR LINEAR STAPLE LINE, now U.S. Patent Application Publication No. 2019/0201105;

U.S. patent application Ser. No. 15/940,700, titled STERILE FIELD INTERACTIVE CONTROL DISPLAYS, now U.S. Patent Application Publication No. 2019/0205001;

U.S. patent application Ser. No. 15/940,629, titled COMPUTER IMPLEMENTED INTERACTIVE SURGICAL SYSTEMS, now U.S. Patent Application Publication No. 2019/0201112;

U.S. patent application Ser. No. 15/940,704, titled USE OF LASER LIGHT AND RED-GREEN-BLUE COLORATION TO DETERMINE PROPERTIES OF BACK SCATTERED LIGHT, now U.S. Patent Application Publication No. 2019/0206050;

U.S. patent application Ser. No. 15/940,722, titled CHARACTERIZATION OF TISSUE IRREGULARITIES THROUGH THE USE OF MONO-CHROMATIC LIGHT REFRACTIVITY; now U.S. Patent Application Publication No. 2019/0200905; and U.S. patent application Ser. No. 15/940,742, titled DUAL CMOS ARRAY IMAGING, now U.S. Patent Application Publication No. 2019/0200906.

Applicant of the present application owns the following U.S. Patent Applications, filed on Mar. 29, 2018, each of which is herein incorporated by reference in its entirety:

U.S. patent application Ser. No. 15/940,636, titled ADAPTIVE CONTROL PROGRAM UPDATES FOR SURGICAL DEVICES, now U.S. Patent Application Publication No. 2019/0206003;

U.S. patent application Ser. No. 15/940,653, titled ADAPTIVE CONTROL PROGRAM UPDATES FOR SURGICAL DEVICES; now U.S. Patent Application Publication No. 2019/0201114;

U.S. patent application Ser. No. 15/940,660, titled CLOUD-BASED MEDICAL ANALYTICS FOR CUSTOMIZATION AND RECOMMENDATIONS TO A USER; now U.S. Patent Application Publication No. 2019/0206555;

U.S. patent application Ser. No. 15/940,679, titled CLOUD-BASED MEDICAL ANALYTICS FOR LINKING OF LOCAL USAGE TRENDS WITH THE RESOURCE ACQUISITION BEHAVIORS OF LARGER DATA SET, now U.S. Patent Application Publication No. 2019/0201144;

U.S. patent application Ser. No. 15/940,694, titled CLOUD-BASED MEDICAL ANALYTICS FOR MEDICAL FACILITY SEGMENTED INDIVIDUALIZATION OF INSTRUMENT FUNCTION, now U.S. Patent Application Publication No. 2019/0201119;

U.S. patent application Ser. No. 15/940,634, titled CLOUD-BASED MEDICAL ANALYTICS FOR SECURITY AND AUTHENTICATION TRENDS AND REACTIVE MEASURES, now U.S. Patent Application Publication No. 2019/0201138;

U.S. patent application Ser. No. 15/940,706, titled DATA HANDLING AND PRIORITIZATION IN A CLOUD ANALYTICS NETWORK, now U.S. Patent Application Publication No. 2019/0206561; and U.S. patent application Ser. No. 15/940,675, titled CLOUD INTERFACE FOR COUPLED SURGICAL DEVICES, now U.S. Pat. No. 10,849,697.

Applicant of the present application owns the following U.S. Patent Applications, filed on Mar. 29, 2018, each of which is herein incorporated by reference in its entirety:

U.S. patent application Ser. No. 15/940,627, titled DRIVE ARRANGEMENTS FOR ROBOT-ASSISTED SURGICAL PLATFORMS; now U.S. Patent Application Publication No. 2019/0201111;

U.S. patent application Ser. No. 15/940,637, titled COMMUNICATION ARRANGEMENTS FOR ROBOT-ASSISTED SURGICAL PLATFORMS; now U.S. Patent Application Publication No. 2019/0201139;

U.S. patent application Ser. No. 15/940,642, titled CONTROLS FOR ROBOT-ASSISTED SURGICAL PLATFORMS; now U.S. Patent Application Publication No. 2019/0201113;

U.S. patent application Ser. No. 15/940,676, titled AUTOMATIC TOOL ADJUSTMENTS FOR ROBOT-ASSISTED SURGICAL PLATFORMS; now U.S. Patent Application Publication No. 2019/0201142;

U.S. patent application Ser. No. 15/940,680, titled CONTROLLERS FOR ROBOT-ASSISTED SURGICAL PLATFORMS, now U.S. Patent Application Publication No. 2019/0201135;

U.S. patent application Ser. No. 15/940,683, titled COOPERATIVE SURGICAL ACTIONS FOR ROBOT-ASSISTED SURGICAL PLATFORMS; now U.S. Patent Application Publication No. 2019/0201145;

U.S. patent application Ser. No. 15/940,690, titled DIS-
PLAY ARRANGEMENTS FOR ROBOT-ASSISTED
SURGICAL PLATFORMS, now U.S. Patent Applica-
tion Publication No. 2019/0201118; and U.S. patent application Ser. No. 15/940,711, titled SENS-
ING ARRANGEMENTS FOR ROBOT-ASSISTED
SURGICAL PLATFORMS, now U.S. Patent Applica-
tion Publication No. 2019/0201120.

Before explaining various aspects of surgical devices and
generators in detail, it should be noted that the illustrative
examples are not limited in application or use to the details
of construction and arrangement of parts illustrated in the
accompanying drawings and description. The illustrative
examples may be implemented or incorporated in other
aspects, variations and modifications, and may be practiced
or carried out in various ways. Further, unless otherwise
indicated, the terms and expressions employed herein have
been chosen for the purpose of describing the illustrative
examples for the convenience of the reader and are not for
the purpose of limitation thereof. Also, it will be appreciated
that one or more of the following-described aspects, expres-
sions of aspects, and/or examples, can be combined with any
one or more of the other following-described aspects,
expressions of aspects and/or examples.

Referring to FIG. 1, a computer-implemented interactive
surgical system 100 includes one or more surgical systems
102 and a cloud-based system (e.g., the cloud 104 that may
include a remote server 113 coupled to a storage device
105). Each surgical system 102 includes at least one surgical
hub 106 in communication with the cloud 104 that may
include a remote server 113. In one example, as illustrated
in FIG. 1, the surgical system 102 includes a visualization
system 108, a robotic system 110, and a handheld intelligent
surgical instrument 112, which are configured to communi-
cate with one another and/or the hub 106. In some aspects,
a surgical system 102 may include an M number of hubs
106, an N number of visualization systems 108, an O
number of robotic systems 110, and a P number of handheld
intelligent surgical instruments 112, where M, N, O, and P
are integers greater than or equal to one.

Figure 3:
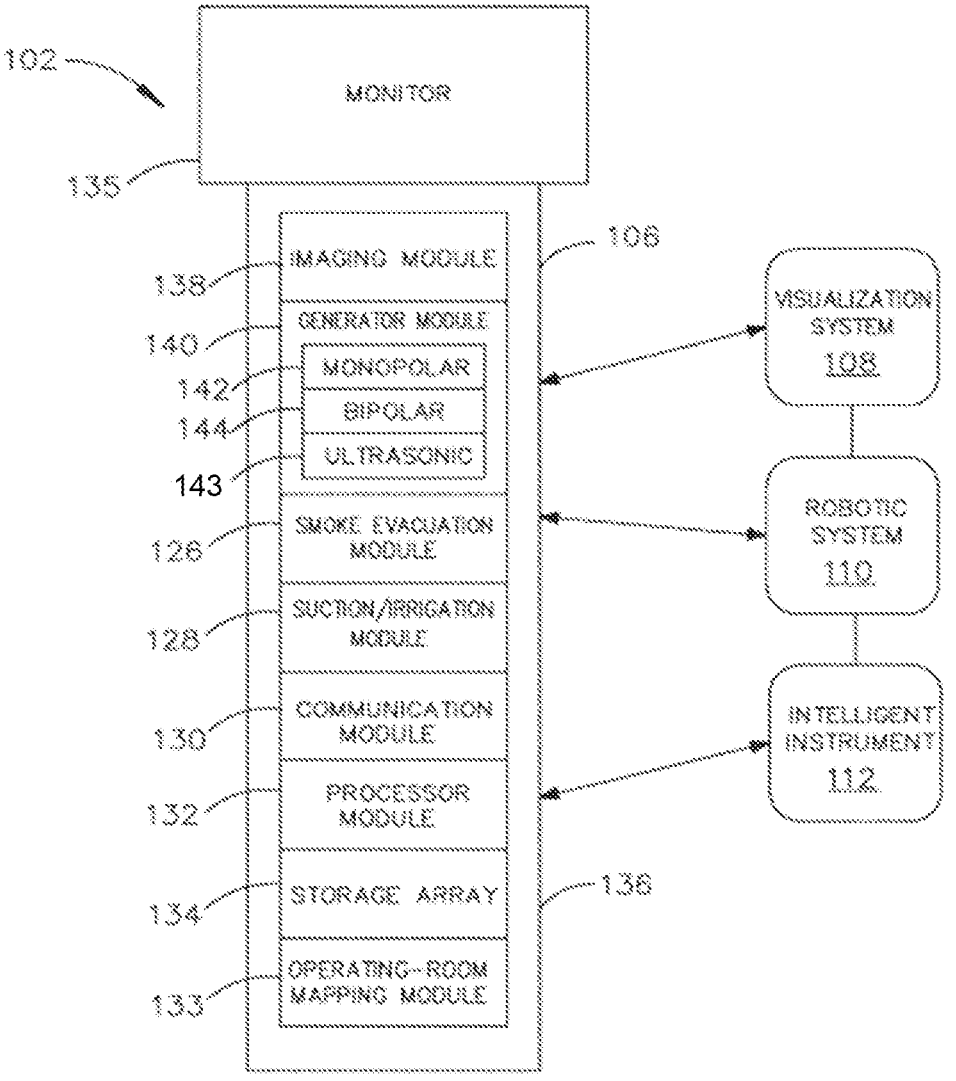
FIG. 3 is a surgical hub paired with a visualization system, a robotic system, and an intelligent instrument, in accordance with at least one aspect of the present disclosure.

FIG. 3 depicts an example of a surgical system 102 being
used to perform a surgical procedure on a patient who is
lying down on an operating table 114 in a surgical operating
room 116. A robotic system 110 is used in the surgical
procedure as a part of the surgical system 102. The robotic
system 110 includes a surgeon's console 118, a patient side
cart 120 (surgical robot), and a surgical robotic hub 122. The
patient side cart 120 can manipulate at least one removably
coupled surgical tool 117 through a minimally invasive
incision in the body of the patient while the surgeon views
the surgical site through the surgeon's console 118. An
image of the surgical site can be obtained by a medical
imaging device 124, which can be manipulated by the
patient side cart 120 to orient the imaging device 124. The
robotic hub 122 can be used to process the images of the
surgical site for subsequent display to the surgeon through
the surgeon's console 118.

Other types of robotic systems can be readily adapted for
use with the surgical system 102. Various examples of
robotic systems and surgical tools that are suitable for use
with the present disclosure are described in U.S. Provisional
Patent Application Ser. No. 62/611,339, titled ROBOT
ASSISTED SURGICAL PLATFORM, filed Dec. 28, 2017,
the disclosure of which is herein incorporated by reference
in its entirety.

Various examples of cloud-based analytics that are per-
formed by the cloud 104, and are suitable for use with the present disclosure, are described in U.S. Provisional Patent
Application Ser. No. 62/611,340, titled CLOUD-BASED
MEDICAL ANALYTICS, filed Dec. 28, 2017, the disclo-
sure of which is herein incorporated by reference in its
entirety.

In various aspects, the imaging device 124 includes at
least one image sensor and one or more optical components.
Suitable image sensors include, but are not limited to,
Charge-Coupled Device (CCD) sensors and Complementary
Metal-Oxide Semiconductor (CMOS) sensors.

The optical components of the imaging device 124 may
include one or more illumination sources and/or one or more
lenses. The one or more illumination sources may be
directed to illuminate portions of the surgical field. The one
or more image sensors may receive light reflected or
refracted from the surgical field, including light reflected or
refracted from tissue and/or surgical instruments.

The one or more illumination sources may be configured
to radiate electromagnetic energy in the visible spectrum as
well as the invisible spectrum. The visible spectrum, some-
times referred to as the optical spectrum or luminous spec-
trum, is that portion of the electromagnetic spectrum that is
visible to (i.e., can be detected by) the human eye and may
be referred to as visible light or simply light. A typical
human eye will respond to wavelengths in air that are from
about 380 nm to about 750 nm.

The invisible spectrum (i.e., the non-luminous spectrum)
is that portion of the electromagnetic spectrum that lies
below and above the visible spectrum (i.e., wavelengths
below about 380 nm and above about 750 nm). The invisible
spectrum is not detectable by the human eye. Wavelengths
greater than about 750 nm are longer than the red visible
spectrum, and they become invisible infrared (IR), micro-
wave, and radio electromagnetic radiation. Wavelengths less
than about 380 nm are shorter than the violet spectrum, and
they become invisible ultraviolet, x-ray, and gamma ray
electromagnetic radiation.

In various aspects, the imaging device 124 is configured
for use in a minimally invasive procedure. Examples of
imaging devices suitable for use with the present disclosure
include, but not limited to, an arthroscope, angioscope,
bronchoscope, choledochoscope, colonoscope, cytoscope,
duodenoscope, enteroscope, esophagogastro-duodenoscope
(gastroscope), endoscope, laryngoscope, nasopharyngo-
neproscope, sigmoidoscope, thoracoscope, and uretero-
scope.

In one aspect, the imaging device employs multi-spec-
trum monitoring to discriminate topography and underlying
structures. A multi-spectral image is one that captures image
data within specific wavelength ranges across the electro-
magnetic spectrum. The wavelengths may be separated by
filters or by the use of instruments that are sensitive to
particular wavelengths, including light from frequencies
beyond the visible light range, e.g., IR and ultraviolet.
Spectral imaging can allow extraction of additional infor-
mation the human eye fails to capture with its receptors for
red, green, and blue. The use of multi-spectral imaging is
described in greater detail under the heading "Advanced
Imaging Acquisition Module" in U.S. Provisional Patent
Application Ser. No. 62/611,341, titled INTERACTIVE
SURGICAL PLATFORM, filed Dec. 28, 2017, the disclo-
sure of which is herein incorporated by reference in its
entirety. Multi-spectrum monitoring can be a useful tool in
relocating a surgical field after a surgical task is completed
to perform one or more of the previously described tests on
the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Figure 2:
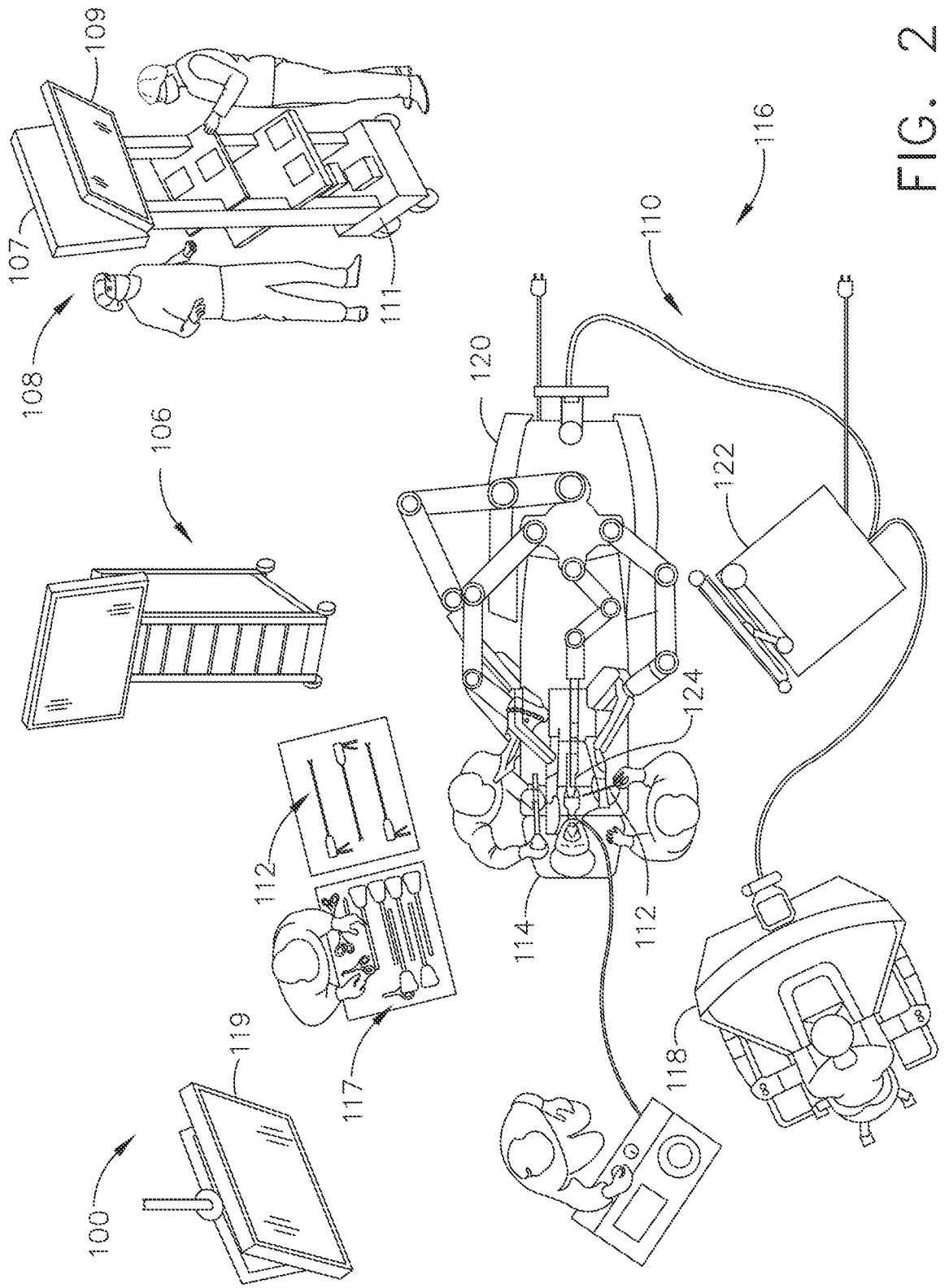
FIG. 2 is a surgical system being used to perform a surgical procedure in an operating room, in accordance with at least one aspect of the present disclosure.

In various aspects, the visualization system 108 includes one or more imaging sensors, one or more image processing units, one or more storage arrays, and one or more displays that are strategically arranged with respect to the sterile field, as illustrated in FIG. 2. In one aspect, the visualization system 108 includes an interface for HL7, PACS, and EMR. Various components of the visualization system 108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 includes a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snap-shot of a surgical site, as recorded by an imaging device 124, on a non-sterile display 107 or 109, while maintaining a live feed of the surgical site on the primary display 119. The snap-shot on the non-sterile display 107 or 109 can permit a non-sterile operator to perform a diagnostic step relevant to the surgical procedure, for example.

In one aspect, the hub 106 is also configured to route a diagnostic input or feedback entered by a non-sterile operator at the visualization tower 111 to the primary display 119 within the sterile field, where it can be viewed by a sterile operator at the operating table. In one example, the input can be in the form of a modification to the snap-shot displayed on the non-sterile display 107 or 109, which can be routed to the primary display 119 by the hub 106.

Referring to FIG. 2, a surgical instrument 112 is being used in the surgical procedure as part of the surgical system 102. The hub 106 is also configured to coordinate information flow to a display of the surgical instrument 112. For example, in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading "Surgical Instrument Hardware" and in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Referring now to FIG. 3, a hub 106 is depicted in communication with a visualization system 108, a robotic system 110, and a handheld intelligent surgical instrument 112. The hub 106 includes a hub display 135, an imaging module 138, a generator module 140, a communication module 130, a processor module 132, an operating-room mapping module 133, and a storage array 134. In certain aspects, as illustrated in FIG. 3, the hub 106 further includes a smoke evacuation module 126 and/or a suction/irrigation module 128.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts.

Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts.

In addition, the modular surgical enclosure also includes a communication bus between the first docking port and the second docking port, configured to facilitate communication between the first energy-generator module and the second energy-generator module.

Figure 5:
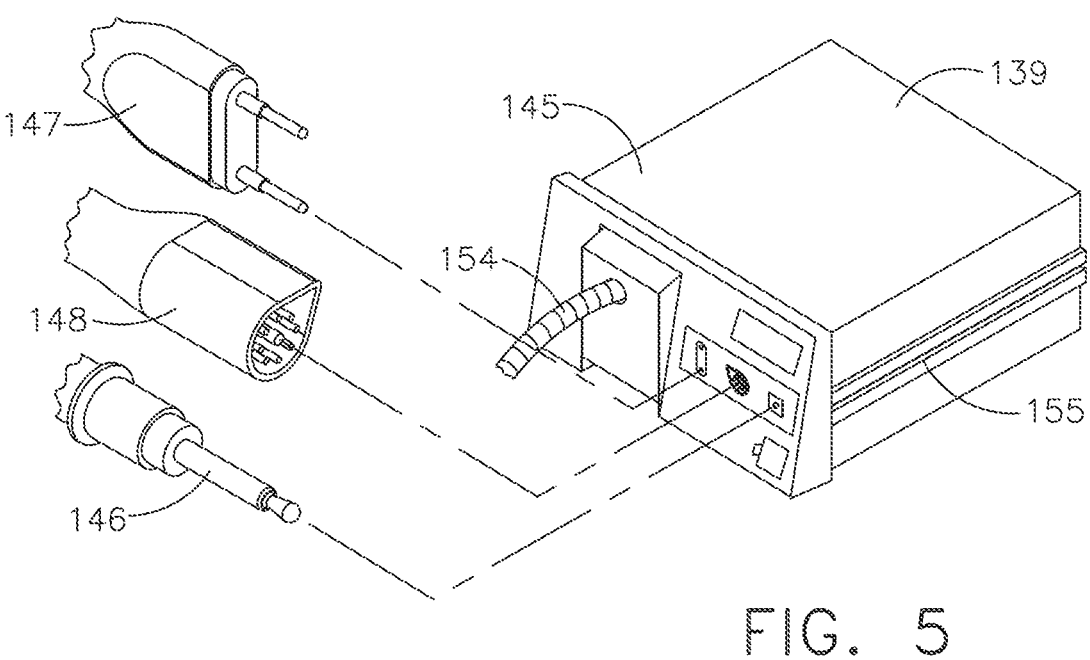
FIG. 5 is a perspective view of a combo generator module with bipolar, ultrasonic, and monopolar contacts and a smoke evacuation component, in accordance with at least one aspect of the present disclosure.

Referring to FIGS. 3-7, aspects of the present disclosure are presented for a hub modular enclosure 136 that allows the modular integration of a generator module 140, a smoke evacuation module 126, and a suction/irrigation module 128. The hub modular enclosure 136 further facilitates interactive communication between the modules 140, 126, 128. As illustrated in FIG. 5, the generator module 140 can be a generator module with integrated monopolar, bipolar, and ultrasonic components supported in a single housing unit 139 slidably insertable into the hub modular enclosure 136. As illustrated in FIG. 5, the generator module 140 can be configured to connect to a monopolar device 146, a bipolar device 147, and an ultrasonic device 148. Alternatively, the generator module 140 may comprise a series of monopolar module 142, bipolar module 144, and/or ultrasonic generator module 143 that interact through the hub modular enclosure 136. The hub modular enclosure 136 can be configured to facilitate the insertion of multiple generators and interactive communication between the generators docked into the hub modular enclosure 136 so that the generators would act as a single generator.

In one aspect, the hub modular enclosure 136 comprises a modular power and communication backplane 149 with external and wireless communication headers to enable the removable attachment of the modules 140, 126, 128 and interactive communication therebetween.

Figure 4:
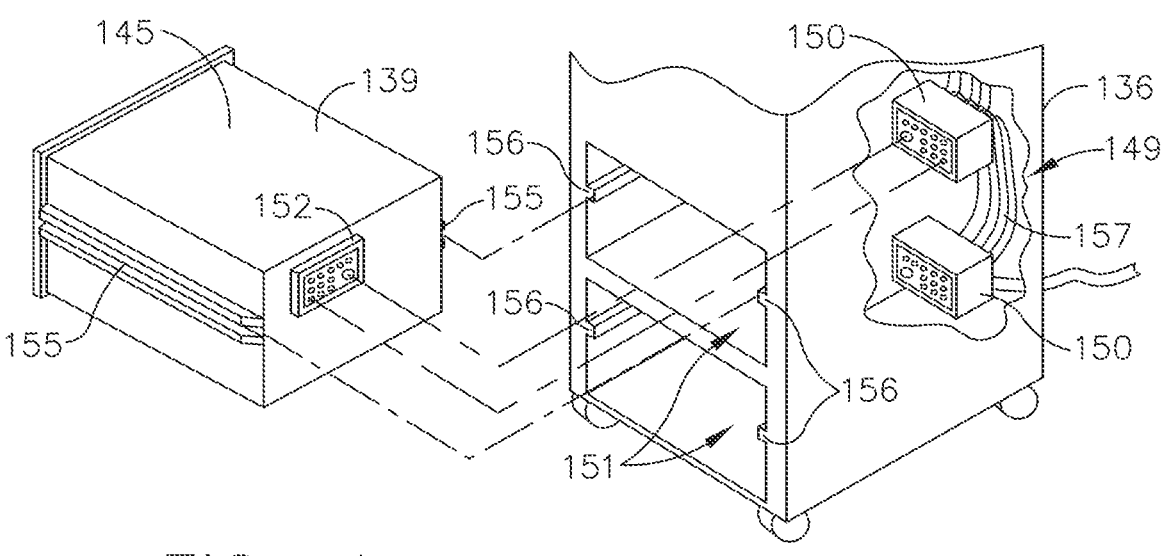
FIG. 4 is a partial perspective view of a surgical hub enclosure, and of a combo generator module slidably receivable in a drawer of the surgical hub enclosure, in accordance with at least one aspect of the present disclosure.

In one aspect, the hub modular enclosure 136 includes docking stations, or drawers, 151, herein also referred to as drawers, which are configured to slidably receive the modules 140, 126, 128. FIG. 4 illustrates a partial perspective view of a surgical hub enclosure 136, and a combo generator module 145 slidably receivable in a docking station 151 of the surgical hub enclosure 136. A docking port 152 with power and data contacts on a rear side of the combo generator module 145 is configured to engage a corresponding docking port 150 with power and data contacts of a corresponding docking station 151 of the hub modular enclosure 136 as the combo generator module 145 is slid into position within the corresponding docking station 151 of the hub module enclosure 136. In one aspect, the combo generator module 145 includes a bipolar, ultrasonic, and monopolar module and a smoke evacuation module integrated together into a single housing unit 139, as illustrated in FIG. 5.

In various aspects, the smoke evacuation module 126 includes a fluid line 154 that conveys captured/collected smoke and/or fluid away from a surgical site and to, for example, the smoke evacuation module 126. Vacuum suction originating from the smoke evacuation module 126 can draw the smoke into an opening of a utility conduit at the surgical site. The utility conduit, coupled to the fluid line, can be in the form of a flexible tube terminating at the smoke evacuation module 126. The utility conduit and the fluid line define a fluid path extending toward the smoke evacuation module 126 that is received in the hub enclosure 136.

In various aspects, the suction/irrigation module 128 is coupled to a surgical tool comprising an aspiration fluid line and a suction fluid line. In one example, the aspiration and suction fluid lines are in the form of flexible tubes extending from the surgical site toward the suction/irrigation module 128. One or more drive systems can be configured to cause irrigation and aspiration of fluids to and from the surgical site.

In one aspect, the surgical tool includes a shaft having an end effector at a distal end thereof and at least one energy treatment associated with the end effector, an aspiration tube, and an irrigation tube. The aspiration tube can have an inlet port at a distal end thereof and the aspiration tube extends through the shaft. Similarly, an irrigation tube can extend through the shaft and can have an inlet port in proximity to the energy deliver implement. The energy deliver implement is configured to deliver ultrasonic and/or RF energy to the surgical site and is coupled to the generator module 140 by a cable extending initially through the shaft.

The irrigation tube can be in fluid communication with a fluid source, and the aspiration tube can be in fluid communication with a vacuum source. The fluid source and/or the vacuum source can be housed in the suction/irrigation module 128. In one example, the fluid source and/or the vacuum source can be housed in the hub enclosure 136 separately from the suction/irrigation module 128. In such example, a fluid interface can be configured to connect the suction/irrigation module 128 to the fluid source and/or the vacuum source.

In one aspect, the modules 140, 126, 128 and/or their corresponding docking stations on the hub modular enclosure 136 may include alignment features that are configured to align the docking ports of the modules into engagement with their counterparts in the docking stations of the hub modular enclosure 136. For example, as illustrated in FIG. 4, the combo generator module 145 includes side brackets 155 that are configured to slidably engage with corresponding brackets 156 of the corresponding docking station 151 of the hub modular enclosure 136. The brackets cooperate to guide the docking port contacts of the combo generator module 145 into an electrical engagement with the docking port contacts of the hub modular enclosure 136.

In some aspects, the drawers 151 of the hub modular enclosure 136 are the same, or substantially the same size, and the modules are adjusted in size to be received in the drawers 151. For example, the side brackets 155 and/or 156 can be larger or smaller depending on the size of the module. In other aspects, the drawers 151 are different in size and are each designed to accommodate a particular module.

Furthermore, the contacts of a particular module can be keyed for engagement with the contacts of a particular drawer to avoid inserting a module into a drawer with mismatching contacts.

As illustrated in FIG. 4, the docking port 150 of one drawer 151 can be coupled to the docking port 150 of another drawer 151 through a communications link 157 to facilitate an interactive communication between the modules housed in the hub modular enclosure 136. The docking ports 150 of the hub modular enclosure 136 may alternatively, or additionally, facilitate a wireless interactive communication between the modules housed in the hub modular enclosure 136. Any suitable wireless communication can be employed, such as for example Air Titan-Bluetooth.

Figure 6:
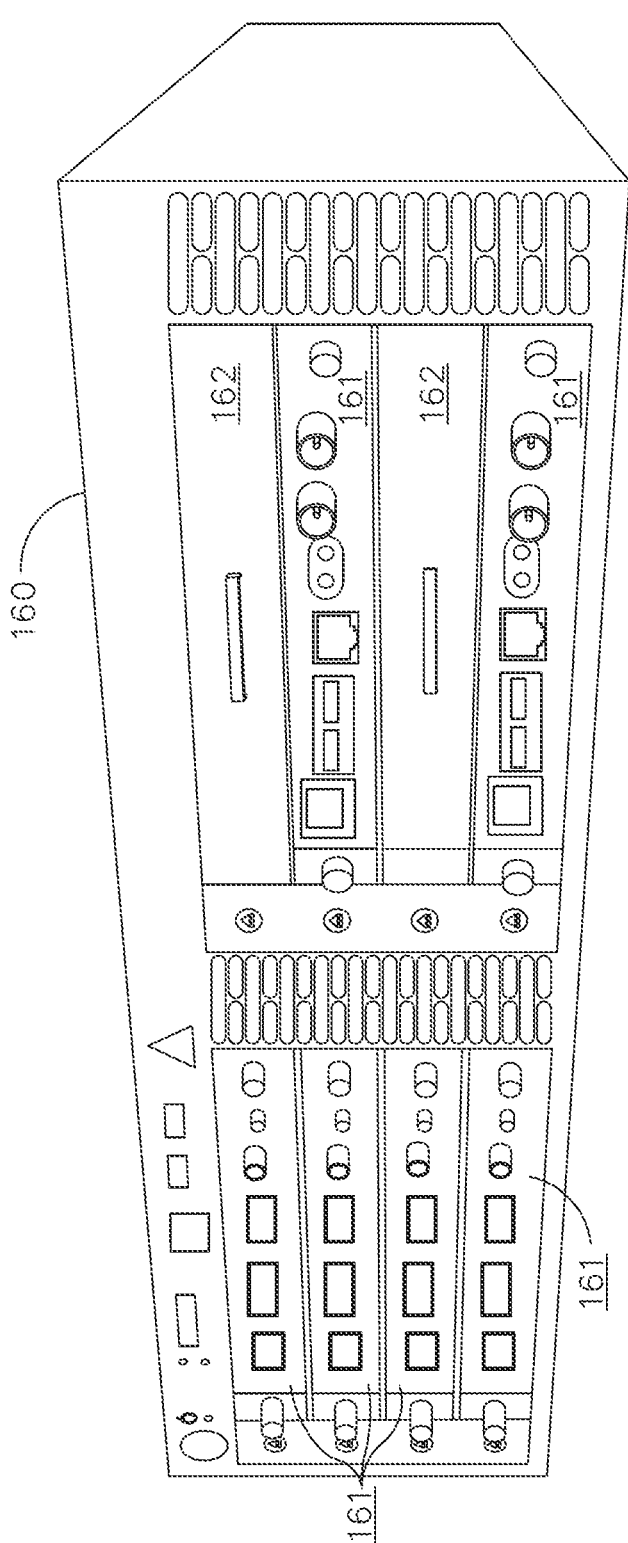
FIG. 6 illustrates individual power bus attachments for a plurality of lateral docking ports of a lateral modular housing configured to receive a plurality of modules, in accordance with at least one aspect of the present disclosure.

FIG. 6 illustrates individual power bus attachments for a plurality of lateral docking ports of a lateral modular housing 160 configured to receive a plurality of modules of a surgical hub 206. The lateral modular housing 160 is configured to laterally receive and interconnect the modules 161. The modules 161 are slidably inserted into docking stations 162 of lateral modular housing 160, which includes a backplane for interconnecting the modules 161. As illustrated in FIG. 6, the modules 161 are arranged laterally in the lateral modular housing 160. Alternatively, the modules 161 may be arranged vertically in a lateral modular housing.

Figure 7:
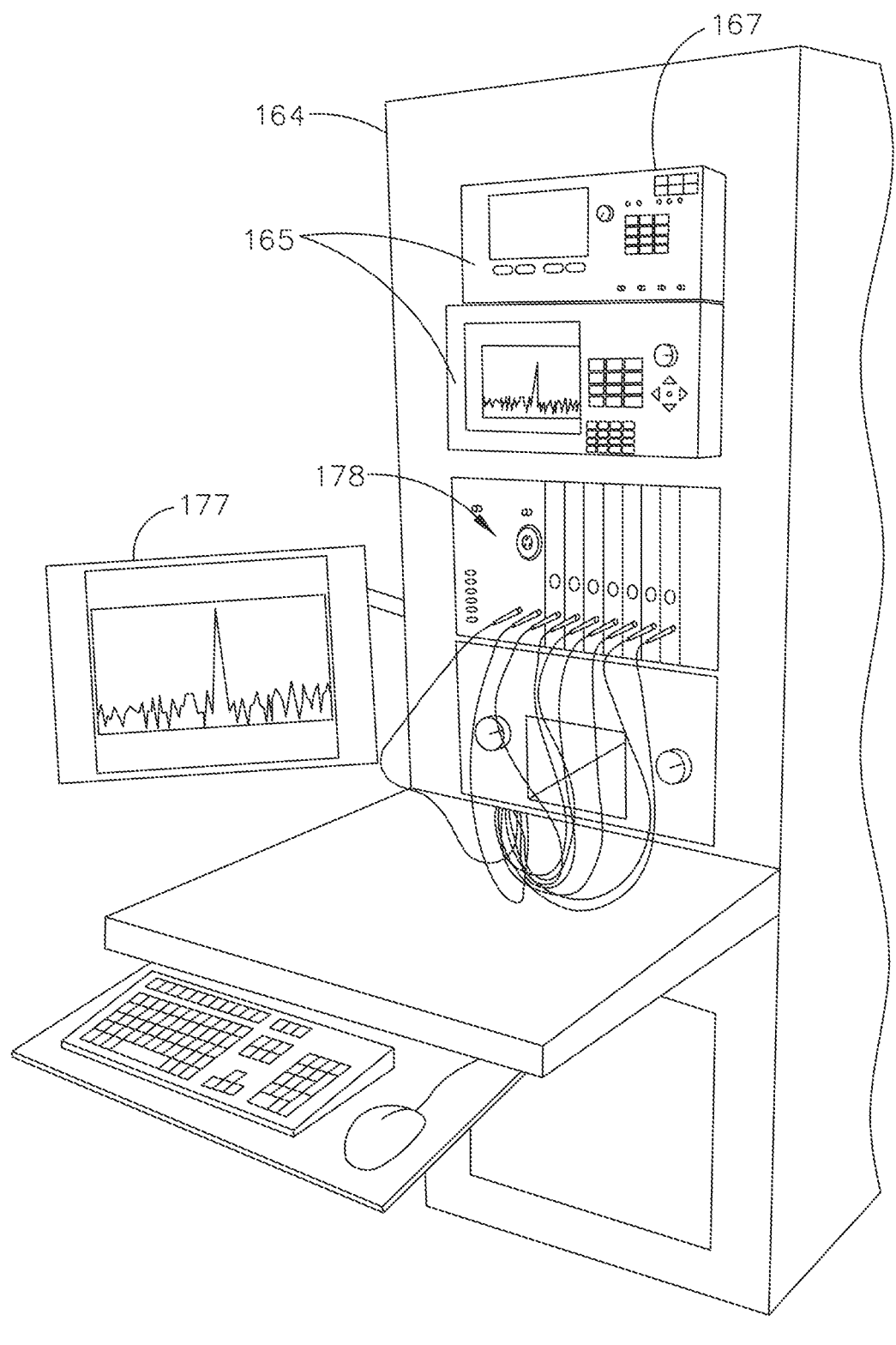
FIG. 7 illustrates a vertical modular housing configured to receive a plurality of modules, in accordance with at least one aspect of the present disclosure.

FIG. 7 illustrates a vertical modular housing 164 configured to receive a plurality of modules 165 of the surgical hub 106. The modules 165 are slidably inserted into docking stations, or drawers, 167 of vertical modular housing 164, which includes a backplane for interconnecting the modules 165. Although the drawers 167 of the vertical modular housing 164 are arranged vertically, in certain instances, a vertical modular housing 164 may include drawers that are arranged laterally. Furthermore, the modules 165 may interact with one another through the docking ports of the vertical modular housing 164. In the example of FIG. 7, a display 177 is provided for displaying data relevant to the operation of the modules 165. In addition, the vertical modular housing 164 includes a master module 178 housing a plurality of sub-modules that are slidably received in the master module 178.

In various aspects, the imaging module 138 comprises an integrated video processor and a modular light source and is adapted for use with various imaging devices. In one aspect, the imaging device is comprised of a modular housing that can be assembled with a light source module and a camera module. The housing can be a disposable housing. In at least one example, the disposable housing is removably coupled to a reusable controller, a light source module, and a camera module. The light source module and/or the camera module can be selectively chosen depending on the type of surgical procedure. In one aspect, the camera module comprises a CCD sensor. In another aspect, the camera module comprises a CMOS sensor. In another aspect, the camera module is configured for scanned beam imaging. Likewise, the light source module can be configured to deliver a white light or a different light, depending on the surgical procedure.

During a surgical procedure, removing a surgical device from the surgical field and replacing it with another surgical device that includes a different camera or a different light source can be inefficient. Temporarily losing sight of the surgical field may lead to undesirable consequences. The module imaging device of the present disclosure is configured to permit the replacement of a light source module or a camera module midstream during a surgical procedure, without having to remove the imaging device from the surgical field.

In one aspect, the imaging device comprises a tubular housing that includes a plurality of channels. A first channel is configured to slidably receive the camera module, which can be configured for a snap-fit engagement with the first channel. A second channel is configured to slidably receive the light source module, which can be configured for a snap-fit engagement with the second channel. In another example, the camera module and/or the light source module can be rotated into a final position within their respective channels. A threaded engagement can be employed in lieu of the snap-fit engagement.

In various examples, multiple imaging devices are placed at different positions in the surgical field to provide multiple views. The imaging module 138 can be configured to switch between the imaging devices to provide an optimal view. In various aspects, the imaging module 138 can be configured to integrate the images from the different imaging device.

Various image processors and imaging devices suitable for use with the present disclosure are described in U.S. Pat. No. 7,995,045, titled COMBINED SBI AND CONVENTIONAL IMAGE PROCESSOR, which issued on Aug. 9, 2011, which is herein incorporated by reference in its entirety. In addition, U.S. Pat. No. 7,982,776, titled SBI MOTION ARTIFACT REMOVAL APPARATUS AND METHOD, which issued on Jul. 19, 2011, which is herein incorporated by reference in its entirety, describes various systems for removing motion artifacts from image data. Such systems can be integrated with the imaging module 138. Furthermore, U.S. Patent Application Publication No. 2011/0306840, titled CONTROLLABLE MAGNETIC SOURCE TO FIXTURE INTRACORPOREAL APPARATUS, which published on Dec. 15, 2011, and U.S. Patent Application Publication No. 2014/0243597, titled SYSTEM FOR PERFORMING A MINIMALLY INVASIVE SURGICAL PROCEDURE, which published on Aug. 28, 2014, now U.S. Pat. No. 10,098,527, each of which is herein incorporated by reference in its entirety.

Figure 8:
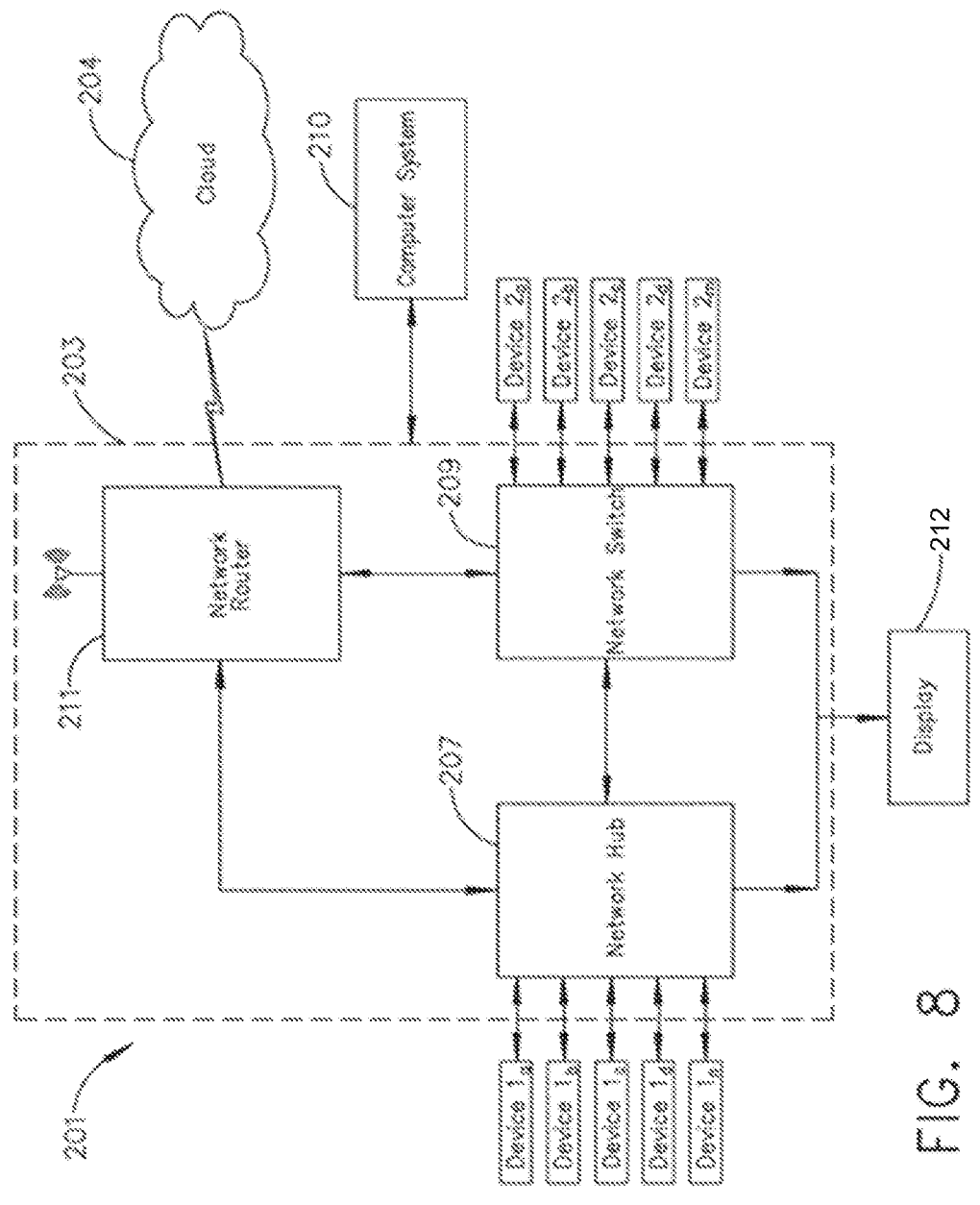
FIG. 8 illustrates a surgical data network comprising a modular communication hub configured to connect modular devices located in one or more operating theaters of a healthcare facility, or any room in a healthcare facility specially equipped for surgical operations, to the cloud, in accordance with at least one aspect of the present disclosure.

FIG. 8 illustrates a surgical data network 201 comprising a modular communication hub 203 configured to connect modular devices located in one or more operating theaters of a healthcare facility, or any room in a healthcare facility specially equipped for surgical operations, to a cloud-based system (e.g., the cloud 204 that may include a remote server 213 coupled to a storage device 205). In one aspect, the modular communication hub 203 comprises a network hub 207 and/or a network switch 209 in communication with a network router. The modular communication hub 203 also can be coupled to a local computer system 210 to provide local computer processing and data manipulation. The surgical data network 201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An intelligent surgical data network may be referred to as a manageable hub or switch. A switching hub reads the destination address of each packet and then forwards the packet to the correct port.

Modular devices 1a-1n located in the operating theater may be coupled to the modular communication hub 203. The network hub 207 and/or the network switch 209 may be coupled to a network router 211 to connect the devices 1a-1n to the cloud 204 or the local computer system 210. Data associated with the devices 1a-1n may be transferred to cloud-based computers via the router for remote data processing and manipulation. Data associated with the devices 1a-1n may also be transferred to the local computer system 210 for local data processing and manipulation. Modular devices 2a-2m located in the same operating theater also may be coupled to a network switch 209. The network switch 209 may be coupled to the network hub 207 and/or the network router 211 to connect to the devices 2a-2m to the cloud 204. Data associated with the devices 2a-2n may be transferred to the cloud 204 via the network router 211 for data processing and manipulation. Data associated with the devices 2a-2m may also be transferred to the local computer system 210 for local data processing and manipulation.

It will be appreciated that the surgical data network 201 may be expanded by interconnecting multiple network hubs 207 and/or multiple network switches 209 with multiple network routers 211. The modular communication hub 203 may be contained in a modular control tower configured to receive multiple devices 1a-1n/2a-2m. The local computer system 210 also may be contained in a modular control tower. The modular communication hub 203 is connected to a display 212 to display images obtained by some of the devices 1a-1n/2a-2m, for example during surgical procedures. In various aspects, the devices 1a-1n/2a-2m may include, for example, various modules such as an imaging module 138 coupled to an endoscope, a generator module 140 coupled to an energy-based surgical device, a smoke evacuation module 126, a suction/irrigation module 128, a communication module 130, a processor module 132, a storage array 134, a surgical device coupled to a display, and/or a non-contact sensor module, among other modular devices that may be connected to the modular communication hub 203 of the surgical data network 201.

In one aspect, the surgical data network 201 may comprise a combination of network hub(s), network switch(es), and network router(s) connecting the devices 1a-1n/2a-2m to the cloud. Any one of or all of the devices 1a-1n/2a-2m coupled to the network hub or network switch may collect data in real time and transfer the data to cloud computers for data processing and manipulation. It will be appreciated that cloud computing relies on sharing computing resources rather than having local servers or personal devices to handle software applications.

The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 203 and/or computer system 210 located in the surgical theater (e.g., a fixed, mobile, temporary, or field operating room or space) and to devices connected to the modular communication hub 203 and/or computer system 210 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1a-1n/2a-2m, the surgical data network provides improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This includes localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud 204 or the local computer system 210 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

In one implementation, the operating theater devices 1a-1n may be connected to the modular communication hub 203 over a wired channel or a wireless channel depending on the configuration of the devices 1a-1n to a network hub. The network hub 207 may be implemented, in one aspect, as a local network broadcast device that works on the physical layer of the Open System Interconnection (OSI) model. The network hub provides connectivity to the devices 1a-1n located in the same operating theater network. The network hub 207 collects data in the form of packets and sends them to the router in half duplex mode. The network hub 207 does not store any media access control/internet protocol (MAC/IP) to transfer the device data. Only one of the devices 1a-1n can send data at a time through the network hub 207. The network hub 207 has no routing tables or intelligence regarding where to send information and broadcasts all network data across each connection and to a remote server 213 (FIG. 9) over the cloud 204. The network hub 207 can detect basic network errors such as collisions, but having all information broadcast to multiple ports can be a security risk and cause bottlenecks.

In another implementation, the operating theater devices 2a-2m may be connected to a network switch 209 over a wired channel or a wireless channel. The network switch 209 works in the data link layer of the OSI model. The network switch 209 is a multicast device for connecting the devices 2a-2m located in the same operating theater to the network. The network switch 209 sends data in the form of frames to the network router 211 and works in full duplex mode. Multiple devices 2a-2m can send data at the same time through the network switch 209. The network switch 209 stores and uses MAC addresses of the devices 2a-2m to transfer data.

The network hub 207 and/or the network switch 209 are coupled to the network router 211 for connection to the cloud 204. The network router 211 works in the network layer of the OSI model. The network router 211 creates a route for transmitting data packets received from the network hub 207 and/or network switch 211 to cloud-based computer resources for further processing and manipulation of the data collected by any one of or all the devices 1a-1n/2a-2m. The network router 211 may be employed to connect two or more different networks located in different locations, such as, for example, different operating theaters of the same healthcare facility or different networks located in different operating theaters of different healthcare facilities. The network router 211 sends data in the form of packets to the cloud 204 and works in full duplex mode. Multiple devices can send data at the same time. The network router 211 uses IP addresses to transfer data.

In one example, the network hub 207 may be implemented as a USB hub, which allows multiple USB devices to be connected to a host computer. The USB hub may expand a single USB port into several tiers so that there are more ports available to connect devices to the host system computer. The network hub 207 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In other examples, the operating theater devices 1a-1n/2a-2m may communicate to the modular communication hub 203 via Bluetooth wireless technology standard for exchanging data over short distances (using short-wavelength UHF radio waves in the ISM band from 2.4 to 2.485 GHZ) from fixed and mobile devices and building personal area networks (PANs). In other aspects, the operating theater devices 1a-1n/2a-2m may communicate to the modular communication hub 203 via a number of wireless or wired communication standards or protocols, including but not limited to Wi-Fi (IEEE 802.11 family), WiMAX (IEEE 802.16 family), IEEE 802.20, long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth, and a second communication module may be dedicated to longer-range wireless communications such as GPS, EDGE, GPRS, CDMA, WIMAX, LTE, Ev-DO, and others.

The modular communication hub 203 may serve as a central connection for one or all of the operating theater devices 1a-1n/2a-2m and handles a data type known as frames. Frames carry the data generated by the devices 1a-1n/2a-2m. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 is generally easy to install, configure, and maintain, making it a good option for networking the operating theater devices 1a-1n/2a-2m.

Figure 9:
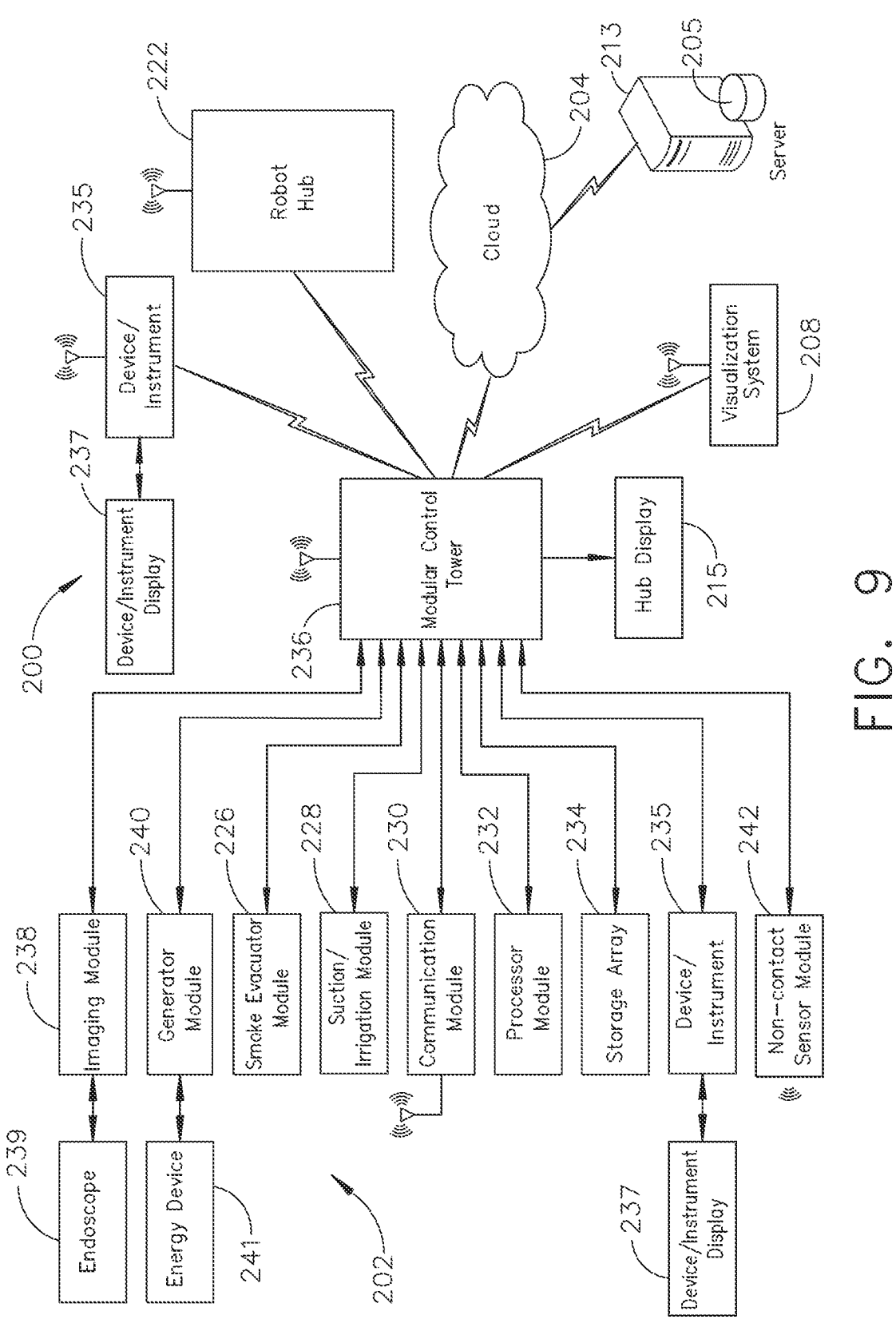
FIG. 9 illustrates a computer-implemented interactive surgical system, in accordance with at least one aspect of the present disclosure.

FIG. 9 illustrates a computer-implemented interactive surgical system 200. The computer-implemented interactive surgical system 200 is similar in many respects to the computer-implemented interactive surgical system 100. For example, the computer-implemented interactive surgical system 200 includes one or more surgical systems 202, which are similar in many respects to the surgical systems 102. Each surgical system 202 includes at least one surgical hub 206 in communication with a cloud 204 that may include a remote server 213. In one aspect, the computer-implemented interactive surgical system 200 comprises a modular control tower 236 connected to multiple operating theater devices such as, for example, intelligent surgical

Figure 10:
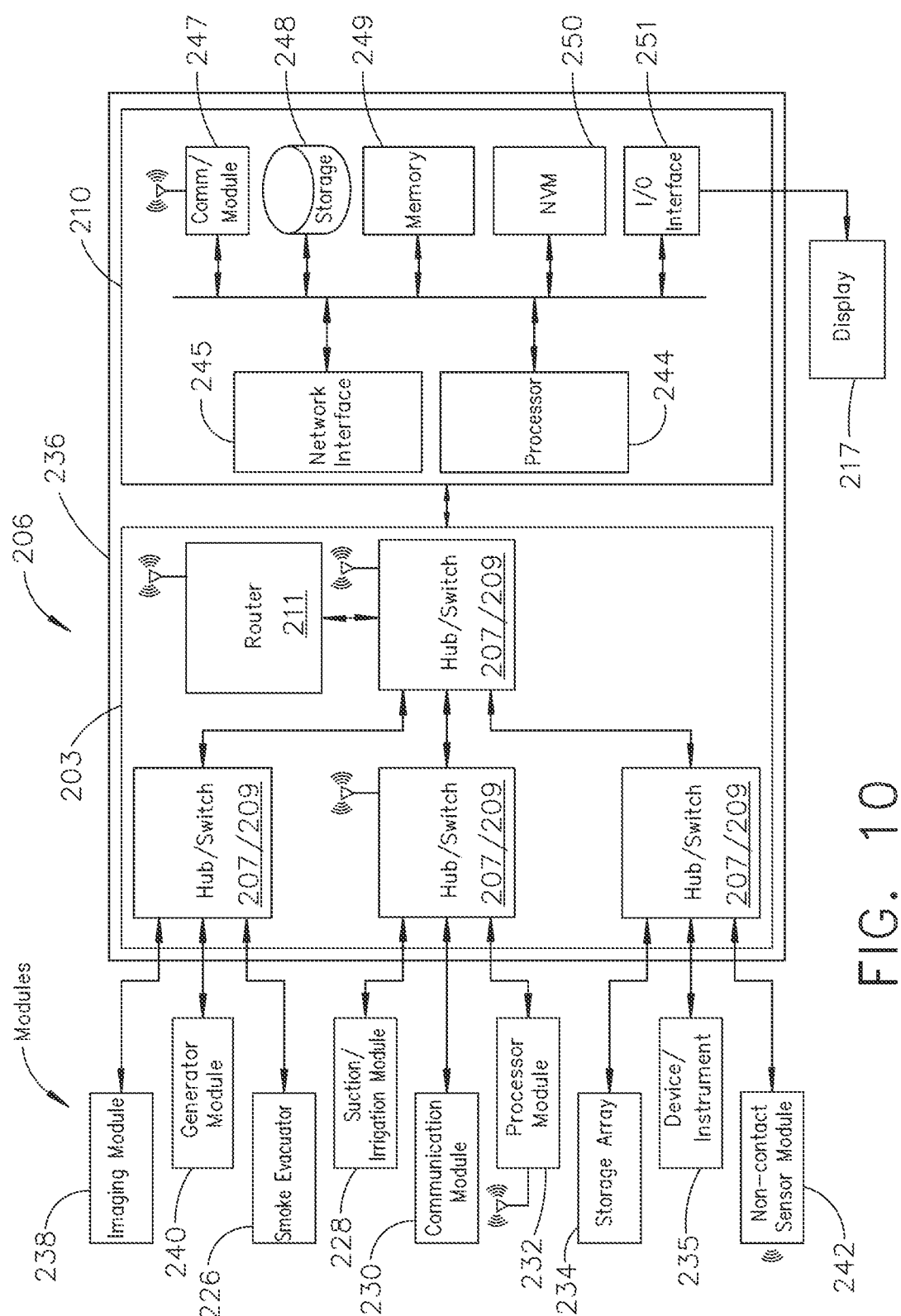
FIG. 10 illustrates a surgical hub comprising a plurality of modules coupled to the modular control tower, in accordance with at least one aspect of the present disclosure.

20 instruments, robots, and other computerized devices located in the operating theater. As shown in FIG. 10, the modular control tower 236 comprises a modular communication hub 203 coupled to a computer system 210. As illustrated in the example of FIG. 9, the modular control tower 236 is coupled to an imaging module 238 that is coupled to an endoscope 239, a generator module 240 that is coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242. The operating theater devices are coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208. The hub display also may display data received from devices connected to the modular control tower in conjunction with images and overlaid images.

FIG. 10 illustrates a surgical hub 206 comprising a plurality of modules coupled to the modular control tower 236. The modular control tower 236 comprises a modular communication hub 203, e.g., a network connectivity device, and a computer system 210 to provide local processing, visualization, and imaging, for example. As shown in FIG. 10, the modular communication hub 203 may be connected in a tiered configuration to expand the number of modules (e.g., devices) that may be connected to the modular communication hub 203 and transfer data associated with the modules to the computer system 210, cloud computing resources, or both. As shown in FIG. 10, each of the network hubs/switches in the modular communication hub 203 includes three downstream ports and one upstream port. The upstream network hub/switch is connected to a processor to provide a communication connection to the cloud computing resources and a local display 217. Communication to the cloud 204 may be made either through a wired or a wireless communication channel.

The surgical hub 206 employs a non-contact sensor module 242 to measure the dimensions of the operating theater and generate a map of the surgical theater using either ultrasonic or laser-type non-contact measurement devices. An ultrasound-based non-contact sensor module scans the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety, in which the sensor module is configured to determine the size of the operating theater and to adjust Bluetooth-pairing distance limits. A laser-based non-contact sensor module scans the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 210 comprises a processor 244 and a network interface 245. The processor 244 is coupled to a communication module 247, storage 248, memory 249, non-volatile memory 250, and input/output interface 251 via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHZ, a prefetch buffer to improve performance above 40 MHz, a 32 KB single-cycle serial random access memory (SRAM), an internal read-only memory (ROM) loaded with Stellar-isWare® software, a 2 KB electrically erasable program-mable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes ran-dom-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SL-DRAM), and direct Rambus RAM (DRRAM).

The computer system 210 also includes removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 210 includes software that acts as an intermediary between users and the basic computer resources described in a suitable operating environment. Such software includes an operating system. The operating system, which can be stored on the disk storage, acts to control and allocate resources of the computer system. System applications take advantage of the management of resources by the operating system through program modules and program data stored either in the system memory or on the disk storage. It is to be appreciated that various components described herein can be imple-mented with various operating systems or combinations of operating systems.

A user enters commands or information into the computer system 210 through input device(s) coupled to the I/O interface 251. The input devices include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output infor-mation from the computer system to an output device. An output adapter is provided to illustrate that there are some output devices like monitors, displays, speakers, and print-ers, among other output devices that require special adapt-ers. The output adapters include, by way of illustration and not limitation, video and sound cards that provide a means of connection between the output device and the system bus. It should be noted that other devices and/or systems of devices, such as remote computer(s), provide both input and output capabilities.

The computer system 210 can operate in a networked environment using logical connections to one or more remote computers, such as cloud computer(s), or local computers. The remote cloud computer(s) can be a personal computer, server, router, network PC, workstation, micro-processor-based appliance, peer device, or other common network node, and the like, and typically includes many or all of the elements described relative to the computer system. For purposes of brevity, only a memory storage device is illustrated with the remote computer(s). The remote computer(s) is logically connected to the computer system through a network interface and then physically connected via a communication connection. The network interface encompasses communication networks such as local area networks (LANs) and wide area networks (WANs). LAN technologies include Fiber Distributed Data Interface (FDDI), Copper Distributed Data Interface (CDDI), Ethernet/IEEE 802.3, Token Ring/IEEE 802.5 and the like. WAN technologies include, but are not limited to, point-to-point links, circuit-switching networks like Inte-grated Services Digital Networks (ISDN) and variations thereon, packet-switching networks, and Digital Subscriber Lines (DSL).

In various aspects, the computer system 210 of FIG. 10, the imaging module 238 and/or visualization system 208, and/or the processor module 232 of FIGS. 9-10, may com-prise an image processor, image processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image processing engine can perform a range of tasks. The image processor may be a system on a chip with multicore processor architecture.

The communication connection(s) refers to the hardware/ software employed to connect the network interface to the bus. While the communication connection is shown for illustrative clarity inside the computer system, it can also be external to the computer system 210. The hardware/software necessary for connection to the network interface includes, for illustrative purposes only, internal and external technologies such as modems, including regular telephone-grade modems, cable modems, and DSL modems, ISDN adapters, and Ethernet cards.

Figure 11:
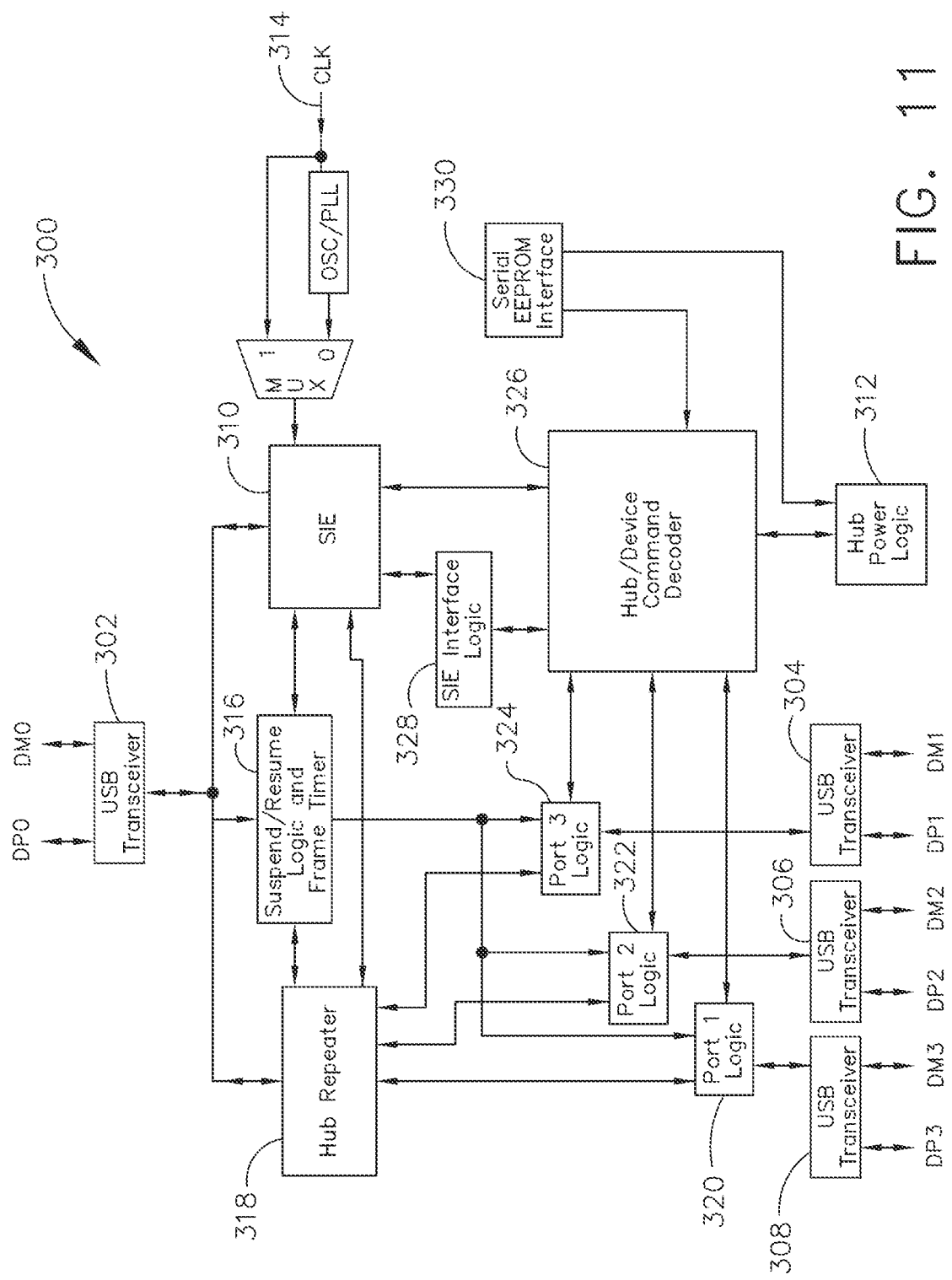
FIG. 11 illustrates one aspect of a Universal Serial Bus (USB) network hub device, in accordance with at least one aspect of the present disclosure.

FIG. 11 illustrates a functional block diagram of one aspect of a USB network hub 300 device, according to one aspect of the present disclosure. In the illustrated aspect, the USB network hub device 300 employs a TUSB2036 integrated circuit hub by Texas Instruments. The USB network hub 300 is a CMOS device that provides an upstream USB transceiver port 302 and up to three downstream USB transceiver ports 304, 306, 308 in compliance with the USB 2.0 specification. The upstream USB transceiver port 302 is a differential root data port comprising a differential data minus (DM0) input paired with a differential data plus (DP0) input. The three downstream USB transceiver ports 304, 306, 308 are differential data ports where each port includes differential data plus (DP1-DP3) outputs paired with differential data minus (DM1-DM3) outputs.

The USB network hub 300 device is implemented with a digital state machine instead of a microcontroller, and no firmware programming is required. Fully compliant USB transceivers are integrated into the circuit for the upstream USB transceiver port 302 and all downstream USB transceiver ports 304, 306, 308. The downstream USB transceiver ports 304, 306, 308 support both full-speed and low-speed devices by automatically setting the slew rate according to the speed of the device attached to the ports. The USB network hub 300 device may be configured either in bus-powered or self-powered mode and includes a hub power logic 312 to manage power.

The USB network hub 300 device includes a serial interface engine 310 (SIE). The SIE 310 is the front end of the USB network hub 300 hardware and handles most of the protocol described in chapter 8 of the USB specification. The SIE 310 typically comprehends signaling up to the transaction level. The functions that it handles could include: packet recognition, transaction sequencing, SOP, EOP, RESET, and RESUME signal detection/generation, clock/ data separation, non-return-to-zero invert (NRZI) data encoding/decoding and bit-stuffing, CRC generation and checking (token and data), packet ID (PID) generation and checking/decoding, and/or serial-parallel/parallel-serial conversion. The 310 receives a clock input 314 and is coupled to a suspend/resume logic and frame timer 316 circuit and a hub repeater circuit 318 to control communication between the upstream USB transceiver port 302 and the downstream USB transceiver ports 304, 306, 308 through port logic circuits 320, 322, 324. The SIE 310 is coupled to a command decoder 326 via interface logic 328 to control commands from a serial EEPROM via a serial EEPROM interface 330.

In various aspects, the USB network hub 300 can connect 127 functions configured in up to six logical layers (tiers) to a single computer. Further, the USB network hub 300 can connect to all peripherals using a standardized four-wire cable that provides both communication and power distribution. The power configurations are bus-powered and self-powered modes. The USB network hub 300 may be configured to support four modes of power management: a bus-powered hub, with either individual-port power management or ganged-port power management, and the self-powered hub, with either individual-port power management or ganged-port power management. In one aspect, using a USB cable, the USB network hub 300, the upstream USB transceiver port 302 is plugged into a USB host controller, and the downstream USB transceiver ports 304, 306, 308 are exposed for connecting USB compatible devices, and so forth.

Surgical Instrument Hardware

Figure 12:
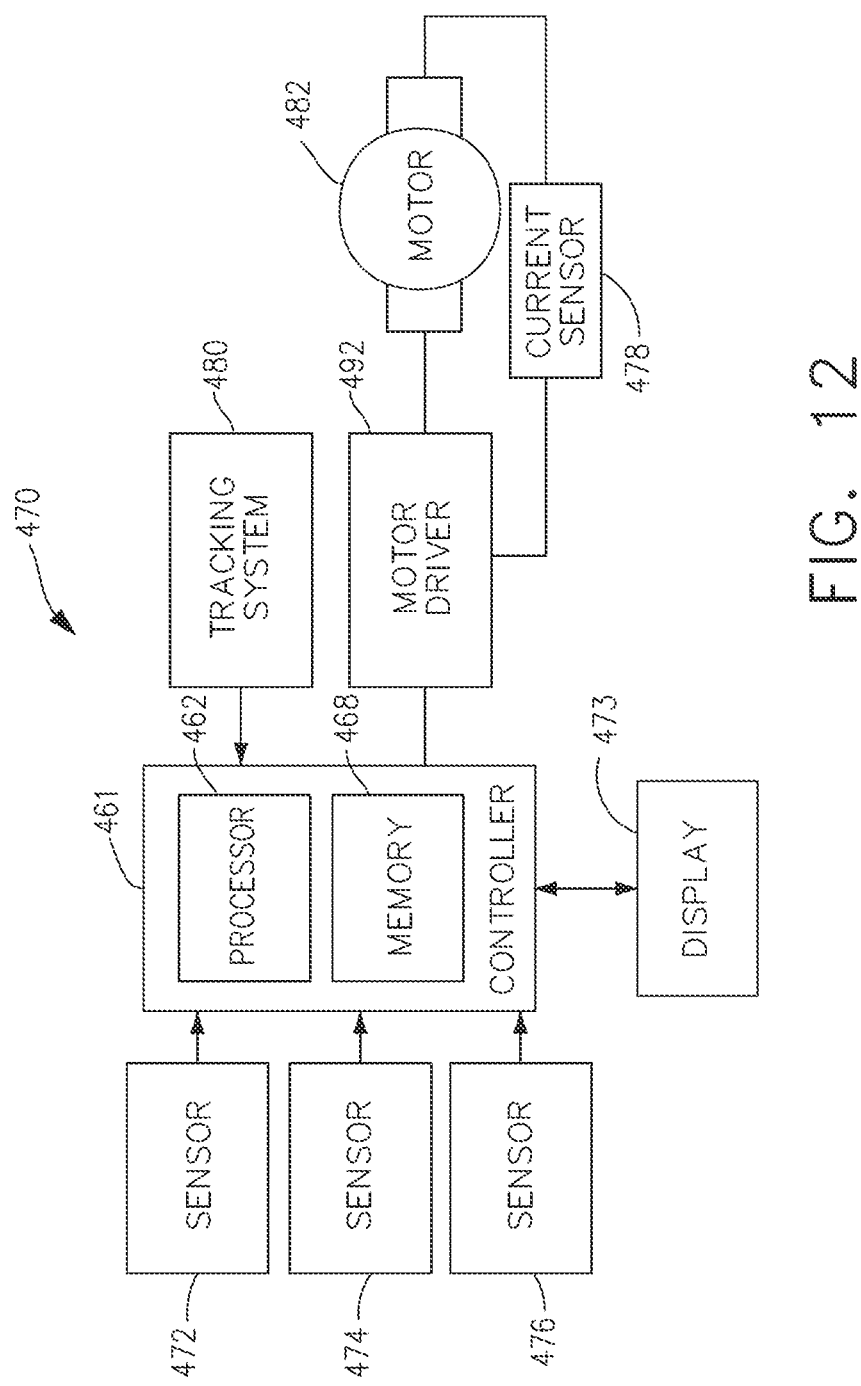
FIG. 12 illustrates a logic diagram of a control system of a surgical instrument or tool, in accordance with at least one aspect of the present disclosure.

FIG. 12 illustrates a logic diagram of a control system 470 of a surgical instrument or tool in accordance with one or more aspects of the present disclosure. The system 470 comprises a control circuit. The control circuit includes a microcontroller 461 comprising a processor 462 and a memory 468. One or more of sensors 472, 474, 476, for example, provide real-time feedback to the processor 462. A motor 482, driven by a motor driver 492, operably couples a longitudinally movable displacement member to drive the I-beam knife element. A tracking system 480 is configured to determine the position of the longitudinally movable displacement member. The position information is provided to the processor 462, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 473 displays a variety of operating conditions of the instruments and may include touch screen functionality for data input. Information displayed on the display 473 may be overlaid with images acquired via endoscopic imaging modules.

In one aspect, the microcontroller 461 may be any single-core or multicore processor such as those known under the trade name ARM Cortex by Texas Instruments. In one aspect, the main microcontroller 461 may be an LM4F230H5QR ARM Cortex-M4F Processor Core, available from Texas Instruments, for example, comprising an on-chip memory of 256 KB single-cycle flash memory, or other non-volatile memory, up to 40 MHZ, a prefetch buffer to improve performance above 40 MHZ, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

In one aspect, the microcontroller 461 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 461 may be programmed to perform various functions such as precise control over the speed and position of the knife and articulation systems. In one aspect, the microcontroller 461 includes a processor 462 and a memory 468. The electric motor 482 may be a brushed direct current (DC) motor with a gearbox and mechanical links to an articulation or knife system. In one aspect, a motor driver 492 may be an A3941 available from Allegro Microsystems, Inc. Other motor drivers may be readily substituted for use in the tracking system 480 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, now U.S. Pat. No. 9,958,764, which is herein incorporated by reference in its entirety.

The microcontroller 461 may be programmed to provide precise control over the speed and position of displacement members and articulation systems. The microcontroller 461 may be configured to compute a response in the software of the microcontroller 461. The computed response is compared to a measured response of the actual system to obtain an "observed" response, which is used for actual feedback decisions. The observed response is a favorable, tuned value that balances the smooth, continuous nature of the simulated response with the measured response, which can detect outside influences on the system.

In one aspect, the motor 482 may be controlled by the motor driver 492 and can be employed by the firing system of the surgical instrument or tool. In various forms, the motor 482 may be a brushed DC driving motor having a maximum rotational speed of approximately 25,000 RPM. In other arrangements, the motor 482 may include a brushless motor, a cordless motor, a synchronous motor, a stepper motor, or any other suitable electric motor. The motor driver 492 may comprise an H-bridge driver comprising field-effect transistors (FETs), for example. The motor 482 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 492 may be an A3941 available from Allegro Microsystems, Inc. The A3941 492 is a full-bridge controller for use with external N-channel power metal-oxide semiconductor field-effect transistors (MOSFETs) specifically designed for inductive loads, such as brush DC motors. The driver 492 comprises a unique charge pump regulator that provides full (>10 V) gate drive for battery voltages down to 7 V and allows the A3941 to operate with a reduced gate drive, down to 5.5 V. A bootstrap capacitor may be employed to provide the above battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the lowside FETs. The power FETs are protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 480 comprising an absolute positioning system.

The tracking system 480 comprises a controlled motor drive circuit arrangement comprising a position sensor 472 according to one aspect of this disclosure. The position sensor 472 for an absolute positioning system provides a unique position signal corresponding to the location of a displacement member. In one aspect, the displacement member represents a longitudinally movable drive member comprising a rack of drive teeth for meshing engagement with a corresponding drive gear of a gear reducer assembly. In other aspects, the displacement member represents the firing member, which could be adapted and configured to include a rack of drive teeth. In yet another aspect, the displacement member represents a firing bar or the I-beam, each of which can be adapted and configured to include a rack of drive teeth. Accordingly, as used herein, the term displacement member is used generically to refer to any movable member of the surgical instrument or tool such as the drive member, the firing member, the firing bar, the I-beam, or any element that can be displaced. In one aspect, the longitudinally movable drive member is coupled to the firing member, the firing bar, and the I-beam. Accordingly, the absolute positioning system can, in effect, track the linear displacement of the I-beam by tracking the linear displacement of the longitudinally movable drive member. In various other aspects, the displacement member may be coupled to any position sensor 472 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photo diodes or photo detectors, or any combination thereof.

The electric motor 482 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 472 element corresponds to some linear longitudinal translation of the displacement member. An arrangement of gearing and sensors can be connected to the linear actuator, via a rack and pinion arrangement, or a rotary actuator, via a spur gear or other connection. A power source supplies power to the absolute positioning system and an output indicator may display the output of the absolute positioning system. The displacement member represents the longitudinally movable drive member comprising a rack of drive teeth formed thereon for meshing engagement with a corresponding drive gear of the gear reducer assembly. The displacement member represents the longitudinally movable firing member, firing bar, I-beam, or combinations thereof.

A single revolution of the sensor element associated with the position sensor 472 is equivalent to a longitudinal linear displacement d1 of the of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 472 completing one or more revolutions for the full stroke of the displacement member. The position sensor 472 may complete multiple revolutions for the full stroke of the displacement member.

A series of switches, where n is an integer greater than one, may be employed alone or in combination with a gear reduction to provide a unique position signal for more than one revolution of the position sensor 472. The state of the switches are fed back to the microcontroller 461 that applies logic to determine a unique position signal corresponding to the longitudinal linear displacement d1+d2+ . . . dn of the displacement member. The output of the position sensor 472 is provided to the microcontroller 461. The position sensor 472 of the sensor arrangement may comprise a magnetic sensor, an analog rotary sensor like a potentiometer, or an array of analog Hall-effect elements, which output a unique combination of position signals or values.

The position sensor 472 may comprise any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

In one aspect, the position sensor 472 for the tracking system 480 comprising an absolute positioning system comprises a magnetic rotary absolute positioning system. The position sensor 472 may be implemented as an AS5055EQFT single-chip magnetic rotary position sensor available from Austria Microsystems, AG. The position sensor 472 is interfaced with the microcontroller 461 to provide an absolute positioning system. The position sensor 472 is a low-voltage and low-power component and includes four Hall-effect elements in an area of the position sensor 472 that is located above a magnet. A high-resolution ADC and a smart power management controller are also provided on the chip. A coordinate rotation digital computer (CORDIC) processor, also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface, such as a serial peripheral interface (SPI) interface, to the microcontroller 461. The position sensor 472 provides 12 or 14 bits of resolution. The position sensor 472 may be an AS5055 chip provided in a small QFN 16-pin 4×4×0.85 mm package.

The tracking system 480 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 472. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, now U.S. Pat. No. 10,881,399, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system takes into account properties like mass, inertial, viscous friction, inductance resistance, etc., to predict what the states and outputs of the physical system will be by knowing the input.

The absolute positioning system provides an absolute position of the displacement member upon power-up of the instrument, without retracting or advancing the displacement member to a reset (zero or home) position as may be required with conventional rotary encoders that merely count the number of steps forwards or backwards that the motor 482 has taken to infer the position of a device actuator, drive bar, knife, or the like.

A sensor 474, such as, for example, a strain gauge or a micro-strain gauge, is configured to measure one or more parameters of the end effector, such as, for example, the amplitude of the strain exerted on the anvil during a clamping operation, which can be indicative of the closure forces applied to the anvil. The measured strain is converted to a digital signal and provided to the processor 462. Alternatively, or in addition to the sensor 474, a sensor 476, such as, for example, a load sensor, can measure the closure force applied by the closure drive system to the anvil. The sensor 476, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also includes a sharpened cutting edge that can be used to sever tissue as the I-beam is advanced distally by the firing bar. Alternatively, a current sensor 478 can be employed to measure the current drawn by the motor 482. The force required to advance the firing member can correspond to the current drawn by the motor 482, for example. The measured force is converted to a digital signal and provided to the processor 462.

In one form, the strain gauge sensor 474 can be used to measure the force applied to the tissue by the end effector. A strain gauge can be coupled to the end effector to measure the force on the tissue being treated by the end effector. A system for measuring forces applied to the tissue grasped by the end effector comprises a strain gauge sensor 474, such as, for example, a micro-strain gauge, that is configured to measure one or more parameters of the end effector, for example. In one aspect, the strain gauge sensor 474 can measure the amplitude or magnitude of the strain exerted on a jaw member of an end effector during a clamping operation, which can be indicative of the tissue compression. The measured strain is converted to a digital signal and provided to a processor 462 of the microcontroller 461. A load sensor 476 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 462.

The measurements of the tissue compression, the tissue thickness, and/or the force required to close the end effector on the tissue, as respectively measured by the sensors 474, 476, can be used by the microcontroller 461 to characterize the selected position of the firing member and/or the corresponding value of the speed of the firing member. In one instance, a memory 468 may store a technique, an equation, and/or a lookup table which can be employed by the microcontroller 461 in the assessment.

The control system 470 of the surgical instrument or tool also may comprise wired or wireless communication circuits to communicate with the modular communication hub as shown in FIGS. 8-11.

Figure 13:
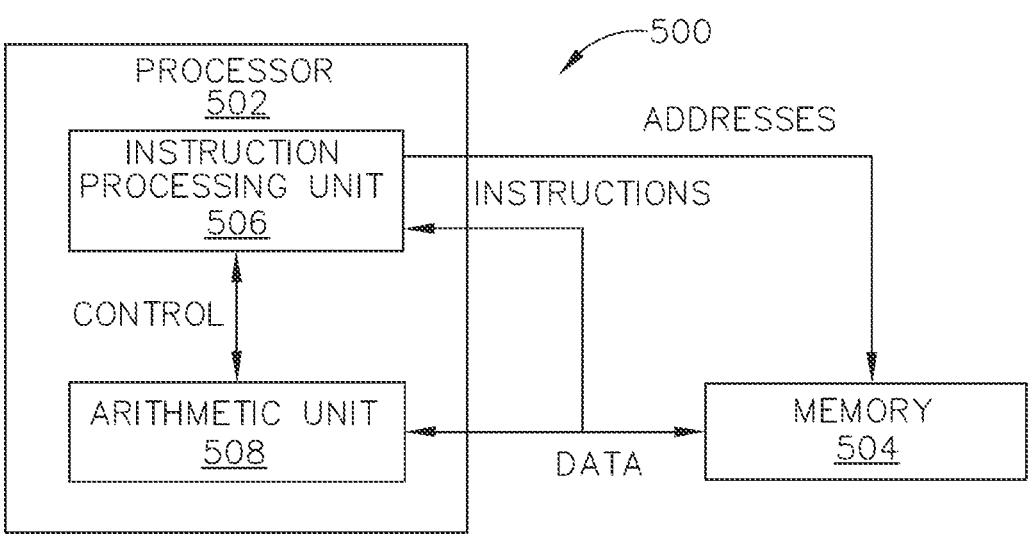
FIG. 13 illustrates a control circuit configured to control aspects of the surgical instrument or tool, in accordance with at least one aspect of the present disclosure.

FIG. 13 illustrates a control circuit 500 configured to control aspects of the surgical instrument or tool according to one aspect of this disclosure. The control circuit 500 can be configured to implement various processes described herein. The control circuit 500 may comprise a microcontroller comprising one or more processors 502 (e.g., microprocessor, microcontroller) coupled to at least one memory circuit 504. The memory circuit 504 stores machine-executable instructions that, when executed by the processor 502, cause the processor 502 to execute machine instructions to implement various processes described herein. The processor 502 may be any one of a number of single-core or multicore processors known in the art. The memory circuit 504 may comprise volatile and non-volatile storage media. The processor 502 may include an instruction processing unit 506 and an arithmetic unit 508. The instruction processing unit may be configured to receive instructions from the memory circuit 504 of this disclosure.

Figure 14:
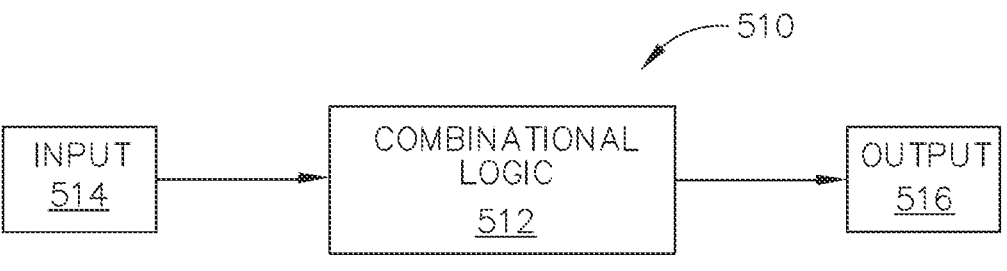
FIG. 14 illustrates a combinational logic circuit configured to control aspects of the surgical instrument or tool, in accordance with at least one aspect of the present disclosure.

FIG. 14 illustrates a combinational logic circuit 510 configured to control aspects of the surgical instrument or tool according to one aspect of this disclosure. The combinational logic circuit 510 can be configured to implement various processes described herein. The combinational logic circuit 510 may comprise a finite state machine comprising a combinational logic 512 configured to receive data associated with the surgical instrument or tool at an input 514, process the data by the combinational logic 512, and provide an output 516.

Figure 15:
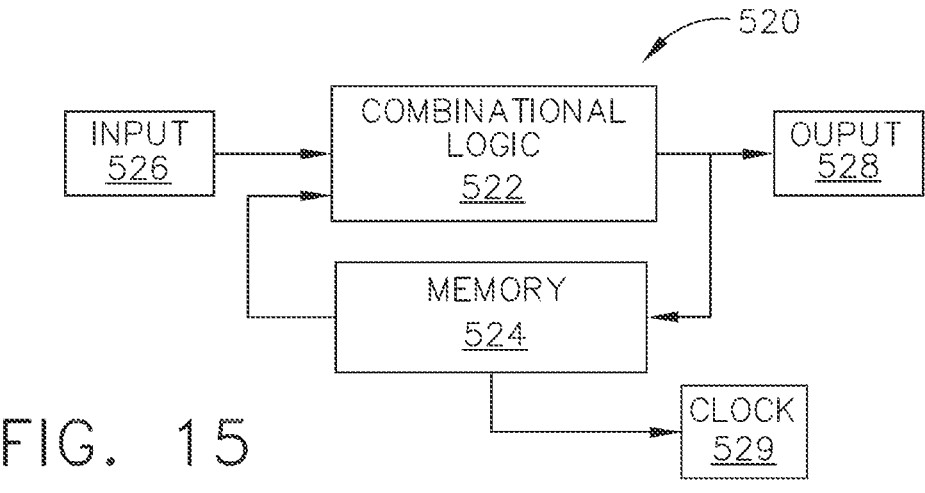
FIG. 15 illustrates a sequential logic circuit configured to control aspects of the surgical instrument or tool, in accordance with at least one aspect of the present disclosure.

FIG. 15 illustrates a sequential logic circuit 520 configured to control aspects of the surgical instrument or tool according to one aspect of this disclosure. The sequential logic circuit 520 or the combinational logic 522 can be configured to implement various processes described herein. The sequential logic circuit 520 may comprise a finite state machine. The sequential logic circuit 520 may comprise a combinational logic 522, at least one memory circuit 524, and a clock 529, for example. The at least one memory circuit 524 can store a current state of the finite state machine. In certain instances, the sequential logic circuit 520 may be synchronous or asynchronous. The combinational logic 522 is configured to receive data associated with the surgical instrument or tool from an input 526, process the data by the combinational logic 522, and provide an output 528. In other aspects, the circuit may comprise a combination of a processor (e.g., processor 502, FIG. 13) and a finite state machine to implement various processes herein. In other aspects, the finite state machine may comprise a combination of a combinational logic circuit (e.g., combinational logic circuit 510, FIG. 14) and the sequential logic circuit 520.

Figure 16:
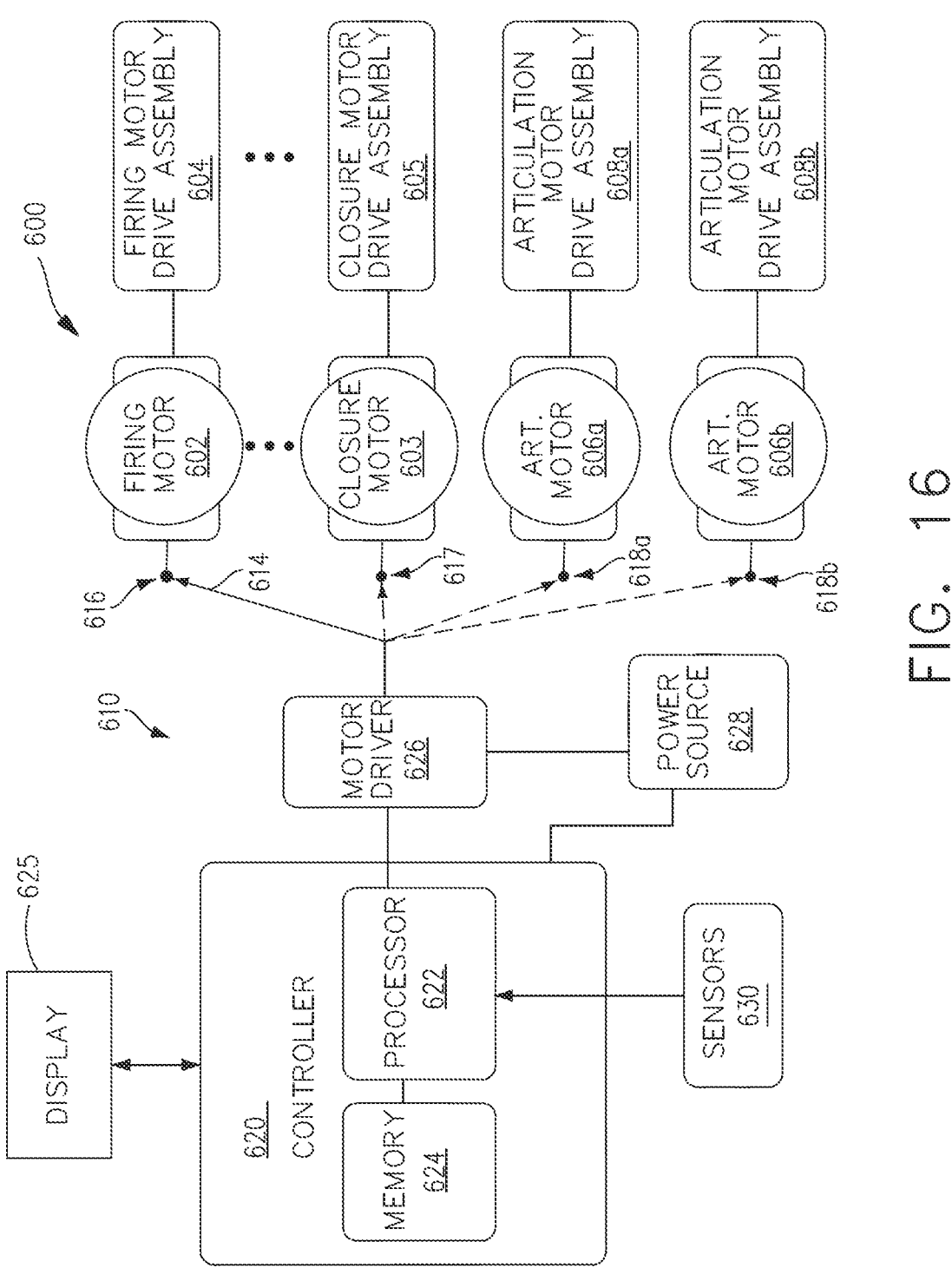
FIG. 16 illustrates a surgical instrument or tool comprising a plurality of motors which can be activated to perform various functions, in accordance with at least one aspect of the present disclosure.

FIG. 16 illustrates a surgical instrument or tool comprising a plurality of motors which can be activated to perform various functions. In certain instances, a first motor can be activated to perform a first function, a second motor can be activated to perform a second function, a third motor can be activated to perform a third function, a fourth motor can be activated to perform a fourth function, and so on. In certain instances, the plurality of motors of robotic surgical instrument 600 can be individually activated to cause firing, closure, and/or articulation motions in the end effector. The firing, closure, and/or articulation motions can be transmitted to the end effector through a shaft assembly, for example.

In certain instances, the surgical instrument system or tool may include a firing motor 602. The firing motor 602 may be operably coupled to a firing motor drive assembly 604 which can be configured to transmit firing motions, generated by the motor 602 to the end effector, in particular to displace the I-beam element. In certain instances, the firing motions generated by the motor 602 may cause the staples to be deployed from the staple cartridge into tissue captured by the end effector and/or the cutting edge of the I-beam element to be advanced to cut the captured tissue, for example. The I-beam element may be retracted by reversing the direction of the motor 602.

In certain instances, the surgical instrument or tool may include a closure motor 603. The closure motor 603 may be operably coupled to a closure motor drive assembly 605 which can be configured to transmit closure motions, generated by the motor 603 to the end effector, in particular to displace a closure tube to close the anvil and compress tissue between the anvil and the staple cartridge. The closure motions may cause the end effector to transition from an open configuration to an approximated configuration to capture tissue, for example. The end effector may be transitioned to an open position by reversing the direction of the motor 603.

In certain instances, the surgical instrument or tool may include one or more articulation motors 606a, 606b, for example. The motors 606a, 606b may be operably coupled to respective articulation motor drive assemblies 608a, 608b, which can be configured to transmit articulation motions generated by the motors 606a, 606b to the end effector. In certain instances, the articulation motions may cause the end effector to articulate relative to the shaft, for example.

As described above, the surgical instrument or tool may include a plurality of motors which may be configured to perform various independent functions. In certain instances, the plurality of motors of the surgical instrument or tool can be individually or separately activated to perform one or more functions while the other motors remain inactive. For example, the articulation motors 606a, 606b can be activated to cause the end effector to be articulated while the firing motor 602 remains inactive. Alternatively, the firing motor 602 can be activated to fire the plurality of staples, and/or to advance the cutting edge, while the articulation motor 606 remains inactive. Furthermore the closure motor 603 may be activated simultaneously with the firing motor 602 to cause the closure tube and the I-beam element to advance distally as described in more detail hereinbelow.

In certain instances, the surgical instrument or tool may include a common control module 610 which can be employed with a plurality of motors of the surgical instrument or tool. In certain instances, the common control module 610 may accommodate one of the plurality of motors at a time. For example, the common control module 610 can be couplable to and separable from the plurality of motors of the robotic surgical instrument individually. In certain instances, a plurality of the motors of the surgical instrument or tool may share one or more common control modules such as the common control module 610. In certain instances, a plurality of motors of the surgical instrument or tool can be individually and selectively engaged with the common control module 610. In certain instances, the common control module 610 can be selectively switched from interfacing with one of a plurality of motors of the surgical instrument or tool to interfacing with another one of the plurality of motors of the surgical instrument or tool.

In at least one example, the common control module 610 can be selectively switched between operable engagement with the articulation motors 606a, 606b and operable engagement with either the firing motor 602 or the closure motor 603. In at least one example, as illustrated in FIG. 16, a switch 614 can be moved or transitioned between a plurality of positions and/or states. In a first position 616, the switch 614 may electrically couple the common control module 610 to the firing motor 602; in a second position 617, the switch 614 may electrically couple the common control module 610 to the closure motor 603; in a third position 618a, the switch 614 may electrically couple the common control module 610 to the first articulation motor 606a; and in a fourth position 618b, the switch 614 may electrically couple the common control module 610 to the second articulation motor 606b, for example. In certain instances, separate common control modules 610 can be electrically coupled to the firing motor 602, the closure motor 603, and the articulations motor 606a, 606b at the same time. In certain instances, the switch 614 may be a mechanical switch, an electromechanical switch, a solid-state switch, or any suitable switching mechanism.

Each of the motors 602, 603, 606a, 606b may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 16, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described above.

In certain instances, the microcontroller 620 may include a microprocessor 622 (the "processor") and one or more non-transitory computer-readable mediums or memory units 624 (the "memory"). In certain instances, the memory 624 may store various program instructions, which when executed may cause the processor 622 to perform a plurality of functions and/or calculations described herein. In certain instances, one or more of the memory units 624 may be coupled to the processor 622, for example. In certain instances, the microcontroller 620 may be in communication with a display 625.

In certain instances, the power source 628 can be employed to supply power to the microcontroller 620, for example. In certain instances, the power source 628 may comprise a battery (or "battery pack" or "power pack"), such as a lithium-ion battery, for example. In certain instances, the battery pack may be configured to be releasably mounted to a handle for supplying power to the surgical instrument 600. A number of battery cells connected in series may be used as the power source 628. In certain instances, the power source 628 may be replaceable and/or rechargeable, for example.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610. It should be understood that the term "processor" as used herein includes any suitable microprocessor, microcontroller, or other basic computing device that incorporates the functions of a computer's central processing unit (CPU) on an integrated circuit or, at most, a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one instance, the processor 622 may be any single-core or multicore processor such as those known under the trade name ARM Cortex by Texas Instruments. In certain instances, the microcontroller 620 may be an LM 4F230H5QR, available from Texas Instruments, for example. In at least one example, the Texas Instruments LM4F230H5QR is an ARM Cortex-M4F Processor Core comprising an on-chip memory of 256 KB single-cycle flash memory, or other non-volatile memory, up to 40 MHz, a prefetch buffer to improve performance above 40 MHz, a 32 KB single-cycle SRAM, an internal ROM loaded with StellarisWare® software, a 2 KB EEPROM, one or more PWM modules, one or more QEI analogs, one or more 12-bit ADCs with 12 analog input channels, among other features that are readily available for the product datasheet. Other microcontrollers may be readily substituted for use with the module 4410. Accordingly, the present disclosure should not be limited in this context.

In certain instances, the memory 624 may include program instructions for controlling each of the motors of the surgical instrument 600 that are couplable to the common control module 610. For example, the memory 624 may include program instructions for controlling the firing motor 602, the closure motor 603, and the articulation motors 606a, 606b. Such program instructions may cause the processor 622 to control the firing, closure, and articulation functions in accordance with inputs from algorithms or control programs of the surgical instrument or tool.

In certain instances, one or more mechanisms and/or sensors such as, for example, sensors 630 can be employed to alert the processor 622 to the program instructions that should be used in a particular setting. For example, the sensors 630 may alert the processor 622 to use the program instructions associated with firing, closing, and articulating the end effector. In certain instances, the sensors 630 may comprise position sensors which can be employed to sense the position of the switch 614, for example. Accordingly, the processor 622 may use the program instructions associated with firing the I-beam of the end effector upon detecting, through the sensors 630 for example, that the switch 614 is in the first position 616; the processor 622 may use the program instructions associated with closing the anvil upon detecting, through the sensors 630 for example, that the switch 614 is in the second position 617; and the processor 622 may use the program instructions associated with articulating the end effector upon detecting, through the sensors 630 for example, that the switch 614 is in the third or fourth position 618a, 618b.

Figure 17:
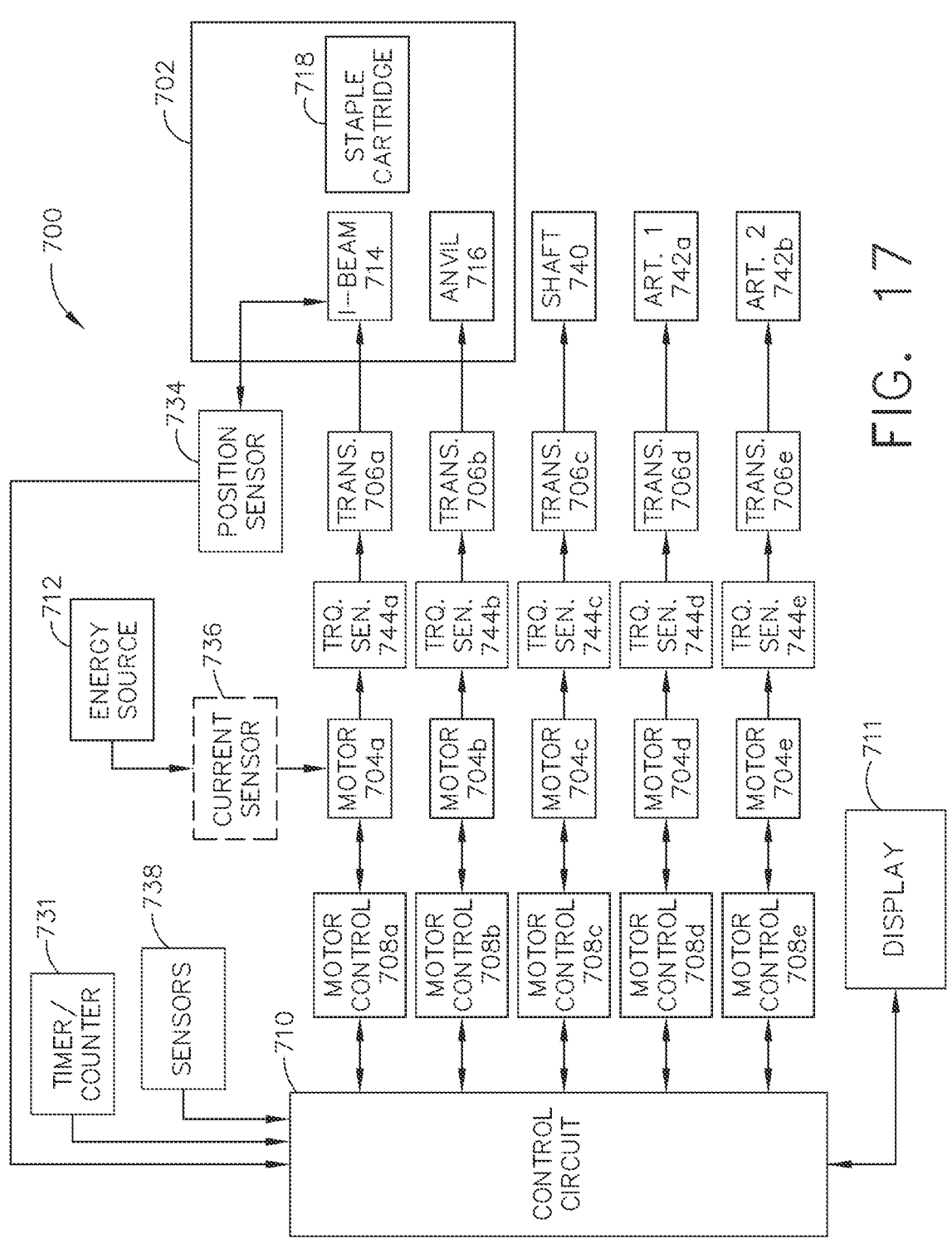
FIG. 17 is a schematic diagram of a robotic surgical instrument configured to operate a surgical tool described herein, in accordance with at least one aspect of the present disclosure.

FIG. 17 is a schematic diagram of a robotic surgical instrument 700 configured to operate a surgical tool described herein according to one aspect of this disclosure. The robotic surgical instrument 700 may be programmed or configured to control distal/proximal translation of a displacement member, distal/proximal displacement of a closure tube, shaft rotation, and articulation, either with single or multiple articulation drive links. In one aspect, the surgical instrument 700 may be programmed or configured to individually control a firing member, a closure member, a shaft member, and/or one or more articulation members. The surgical instrument 700 comprises a display 711 and a control circuit 710 configured to control motor-driven firing members, closure members, shaft members, and/or one or more articulation members.

In one aspect, the robotic surgical instrument 700 comprises a control circuit 710 configured to control an anvil 716 and an I-beam 714 (including a sharp cutting edge) portion of an end effector 702, a removable staple cartridge 718, a shaft 740, and one or more articulation members 742a, 742b via a plurality of motors 704a-704e. A position sensor 734 may be configured to provide position feedback of the I-beam 714 to the control circuit 710. Other sensors 738 may be configured to provide feedback to the control circuit 710. A timer/counter 731 provides timing and counting information to the control circuit 710. An energy source 712 may be provided to operate the motors 704a-704e, and a current sensor 736 provides motor current feedback to the control circuit 710. The motors 704a-704e can be operated individually by the control circuit 710 in a open-loop or closed-loop feedback control.

In one aspect, the control circuit 710 may comprise one or more microcontrollers, microprocessors, or other suitable processors for executing instructions that cause the processor or processors to perform one or more tasks. In one aspect, a timer/counter 731 provides an output signal, such as the elapsed time or a digital count, to the control circuit 710 to correlate the position of the I-beam 714 as determined by the position sensor 734 with the output of the timer/counter 731 such that the control circuit 710 can determine the position of the I-beam 714 at a specific time (t) relative to a starting position or the time (t) when the I-beam 714 is at a specific position relative to a starting position. The timer/counter 731 may be configured to measure elapsed time, count external events, or time external events.

In one aspect, the control circuit 710 may be programmed to control functions of the end effector 702 based on one or more tissue conditions. The control circuit 710 may be programmed to sense tissue conditions, such as thickness, either directly or indirectly, as described herein. The control circuit 710 may be programmed to select a firing control program or closure control program based on tissue conditions. A firing control program may describe the distal motion of the displacement member. Different firing control programs may be selected to better treat different tissue conditions. For example, when thicker tissue is present, the control circuit 710 may be programmed to translate the displacement member at a lower velocity and/or with lower power. When thinner tissue is present, the control circuit 710 may be programmed to translate the displacement member at a higher velocity and/or with higher power. A closure control program may control the closure force applied to the tissue by the anvil 716. Other control programs control the rotation of the shaft 740 and the articulation members 742a, 742b.

In one aspect, the control circuit 710 may generate motor set point signals. The motor set point signals may be provided to various motor controllers 708a-708e. The motor controllers 708a-708e may comprise one or more circuits configured to provide motor drive signals to the motors 704a-704e to drive the motors 704a-704e as described herein. In some examples, the motors 704a-704e may be brushed DC electric motors. For example, the velocity of the motors 704a-704e may be proportional to the respective motor drive signals. In some examples, the motors 704a-704e may be brushless DC electric motors, and the respective motor drive signals may comprise a PWM signal provided to one or more stator windings of the motors 704a-704e. Also, in some examples, the motor controllers 708a-708e may be omitted and the control circuit 710 may generate the motor drive signals directly.

In one aspect, the control circuit 710 may initially operate each of the motors 704a-704e in an open-loop configuration for a first open-loop portion of a stroke of the displacement member. Based on the response of the robotic surgical instrument 700 during the open-loop portion of the stroke, the control circuit 710 may select a firing control program in a closed-loop configuration. The response of the instrument may include a translation distance of the displacement member during the open-loop portion, a time elapsed during the open-loop portion, the energy provided to one of the motors 704a-704e during the open-loop portion, a sum of pulse widths of a motor drive signal, etc. After the open-loop portion, the control circuit 710 may implement the selected firing control program for a second portion of the displacement member stroke. For example, during a closed-loop portion of the stroke, the control circuit 710 may modulate one of the motors 704a-704e based on translation data describing a position of the displacement member in a closed-loop manner to translate the displacement member at a constant velocity.

In one aspect, the motors 704a-704e may receive power from an energy source 712. The energy source 712 may be a DC power supply driven by a main alternating current power source, a battery, a super capacitor, or any other suitable energy source. The motors 704a-704e may be mechanically coupled to individual movable mechanical elements such as the I-beam 714, anvil 716, shaft 740, articulation 742a, and articulation 742b via respective transmissions 706a-706e. The transmissions 706a-706e may include one or more gears or other linkage components to couple the motors 704a-704e to movable mechanical elements. A position sensor 734 may sense a position of the I-beam 714. The position sensor 734 may be or include any type of sensor that is capable of generating position data that indicate a position of the I-beam 714. In some examples, the position sensor 734 may include an encoder configured to provide a series of pulses to the control circuit 710 as the I-beam 714 translates distally and proximally. The control circuit 710 may track the pulses to determine the position of the I-beam 714. Other suitable position sensors may be used, including, for example, a proximity sensor. Other types of position sensors may provide other signals indicating motion of the I-beam 714. Also, in some examples, the position sensor 734 may be omitted. Where any of the motors 704a-704e is a stepper motor, the control circuit 710 may track the position of the I-beam 714 by aggregating the number and direction of steps that the motor 704 has been instructed to execute. The position sensor 734 may be located in the end effector 702 or at any other portion of the instrument. The outputs of each of the motors 704a-704e include a torque sensor 744a-744e to sense force and have an encoder to sense rotation of the drive shaft.

In one aspect, the control circuit 710 is configured to drive a firing member such as the I-beam 714 portion of the end effector 702. The control circuit 710 provides a motor set point to a motor control 708a, which provides a drive signal to the motor 704a. The output shaft of the motor 704a is coupled to a torque sensor 744a. The torque sensor 744a is coupled to a transmission 706a which is coupled to the I-beam 714. The transmission 706a comprises movable mechanical elements such as rotating elements and a firing member to control the movement of the I-beam 714 distally and proximally along a longitudinal axis of the end effector 702. In one aspect, the motor 704a may be coupled to the knife gear assembly, which includes a knife gear reduction set that includes a first knife drive gear and a second knife drive gear. A torque sensor 744a provides a firing force feedback signal to the control circuit 710. The firing force signal represents the force required to fire or displace the I-beam 714. A position sensor 734 may be configured to provide the position of the I-beam 714 along the firing stroke or the position of the firing member as a feedback signal to the control circuit 710. The end effector 702 may include additional sensors 738 configured to provide feedback signals to the control circuit 710. When ready to use, the control circuit 710 may provide a firing signal to the motor control 708a. In response to the firing signal, the motor 704a may drive the firing member distally along the longitudinal axis of the end effector 702 from a proximal stroke start position to a stroke end position distal to the stroke start position. As the firing member translates distally, an I-beam 714, with a cutting element positioned at a distal end, advances distally to cut tissue located between the staple cartridge 718 and the anvil 716.

In one aspect, the control circuit 710 is configured to drive a closure member such as the anvil 716 portion of the end effector 702. The control circuit 710 provides a motor set point to a motor control 708b, which provides a drive signal to the motor 704b. The output shaft of the motor 704b is coupled to a torque sensor 744b. The torque sensor 744b is coupled to a transmission 706b which is coupled to the anvil 716. The transmission 706b comprises movable mechanical elements such as rotating elements and a closure member to control the movement of the anvil 716 from the open and closed positions. In one aspect, the motor 704b is coupled to a closure gear assembly, which includes a closure reduction gear set that is supported in meshing engagement with the closure spur gear. The torque sensor 744b provides a closure force feedback signal to the control circuit 710. The closure force feedback signal represents the closure force applied to the anvil 716. The position sensor 734 may be configured to provide the position of the closure member as a feedback signal to the control circuit 710. Additional sensors 738 in the end effector 702 may provide the closure force feedback signal to the control circuit 710. The pivotable anvil 716 is positioned opposite the staple cartridge 718. When ready to use, the control circuit 710 may provide a closure signal to the motor control 708b. In response to the closure signal, the motor 704b advances a closure member to grasp tissue between the anvil 716 and the staple cartridge 718.

In one aspect, the control circuit 710 is configured to rotate a shaft member such as the shaft 740 to rotate the end effector 702. The control circuit 710 provides a motor set point to a motor control 708c, which provides a drive signal to the motor 704c. The output shaft of the motor 704c is coupled to a torque sensor 744c. The torque sensor 744c is coupled to a transmission 706c which is coupled to the shaft 740. The transmission 706c comprises movable mechanical elements such as rotating elements to control the rotation of the shaft 740 clockwise or counterclockwise up to and over 360°. In one aspect, the motor 704c is coupled to the rotational transmission assembly, which includes a tube gear segment that is formed on (or attached to) the proximal end of the proximal closure tube for operable engagement by a rotational gear assembly that is operably supported on the tool mounting plate. The torque sensor 744c provides a rotation force feedback signal to the control circuit 710. The rotation force feedback signal represents the rotation force applied to the shaft 740. The position sensor 734 may be configured to provide the position of the closure member as a feedback signal to the control circuit 710. Additional sensors 738 such as a shaft encoder may provide the rotational position of the shaft 740 to the control circuit 710.

In one aspect, the control circuit 710 is configured to articulate the end effector 702. The control circuit 710 provides a motor set point to a motor control 708d, which provides a drive signal to the motor 704d. The output shaft of the motor 704d is coupled to a torque sensor 744d. The torque sensor 744d is coupled to a transmission 706d which is coupled to an articulation member 742a. The transmission 706d comprises movable mechanical elements such as articulation elements to control the articulation of the end effector 702 ±65°. In one aspect, the motor 704d is coupled to an articulation nut, which is rotatably journaled on the proximal end portion of the distal spine portion and is rotatably driven thereon by an articulation gear assembly. The torque sensor 744d provides an articulation force feedback signal to the control circuit 710. The articulation force feedback signal represents the articulation force applied to the end effector 702. Sensors 738, such as an articulation encoder, may provide the articulation position of the end effector 702 to the control circuit 710.

In another aspect, the articulation function of the robotic surgical system 700 may comprise two articulation members, or links, 742a, 742b. These articulation members 742a, 742b are driven by separate disks on the robot interface (the rack) which are driven by the two motors 708d, 708e. When the separate firing motor 704a is provided, each of articulation links 742a, 742b can be antagonistically driven with respect to the other link in order to provide a resistive holding motion and a load to the head when it is not moving and to provide an articulation motion as the head is articulated. The articulation members 742a, 742b attach to the head at a fixed radius as the head is rotated. Accordingly, the mechanical advantage of the push-and-pull link changes as the head is rotated. This change in the mechanical advantage may be more pronounced with other articulation link drive systems.

In one aspect, the one or more motors 704a-704e may comprise a brushed DC motor with a gearbox and mechanical links to a firing member, closure member, or articulation member. Another example includes electric motors 704a-704e that operate the movable mechanical elements such as the displacement member, articulation links, closure tube, and shaft. An outside influence is an unmeasured, unpredictable influence of things like tissue, surrounding bodies, and friction on the physical system. Such outside influence can be referred to as drag, which acts in opposition to one of electric motors 704a-704e. The outside influence, such as drag, may cause the operation of the physical system to deviate from a desired operation of the physical system.

In one aspect, the position sensor 734 may be implemented as an absolute positioning system. In one aspect, the position sensor 734 may comprise a magnetic rotary absolute positioning system implemented as an AS5055EQFT single-chip magnetic rotary position sensor available from Austria Microsystems, AG. The position sensor 734 may interface with the control circuit 710 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the control circuit 710 may be in communication with one or more sensors 738. The sensors 738 may be positioned on the end effectors 702 and adapted to operate with the robotic surgical instrument 700 to measure the various derived parameters such as the gap distance versus time, tissue compression versus time, and anvil strain versus time. The sensors 738 may comprise a magnetic sensor, a magnetic field sensor, a strain gauge, a load cell, a pressure sensor, a force sensor, a torque sensor, an inductive sensor such as an eddy current sensor, a resistive sensor, a capacitive sensor, an optical sensor, and/or any other suitable sensor for measuring one or more parameters of the end effector 702. The sensors 738 may include one or more sensors. The sensors 738 may be located on the staple cartridge 718 deck to determine tissue location using segmented electrodes. The torque sensors 744a-744e may be configured to sense force such as firing force, closure force, and/or articulation force, among others. Accordingly, the control circuit 710 can sense (1) the closure load experienced by the distal closure tube and its position, (2) the firing member at the rack and its position, (3) what portion of the staple cartridge 718 has tissue on it, and (4) the load and position on both articulation rods.

In one aspect, the one or more sensors 738 may comprise a strain gauge, such as a micro-strain gauge, configured to measure the magnitude of the strain in the anvil 716 during a clamped condition. The strain gauge provides an electrical signal whose amplitude varies with the magnitude of the strain. The sensors 738 may comprise a pressure sensor configured to detect a pressure generated by the presence of compressed tissue between the anvil 716 and the staple cartridge 718. The sensors 738 may be configured to detect impedance of a tissue section located between the anvil 716 and the staple cartridge 718 that is indicative of the thickness and/or fullness of tissue located therebetween.

In one aspect, the sensors 738 may be implemented as one or more limit switches, electromechanical devices, solid-state switches, Hall-effect devices, magneto-resistive (MR) devices, giant magneto-resistive (GMR) devices, magnetometers, among others. In other implementations, the sensors 738 may be implemented as solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 738 may include electrical conductorless switches, ultrasonic switches, accelerometers, and inertial sensors, among others.

In one aspect, the sensors 738 may be configured to measure forces exerted on the anvil 716 by the closure drive system. For example, one or more sensors 738 can be at an interaction point between the closure tube and the anvil 716 to detect the closure forces applied by the closure tube to the anvil 716. The forces exerted on the anvil 716 can be representative of the tissue compression experienced by the tissue section captured between the anvil 716 and the staple cartridge 718. The one or more sensors 738 can be positioned at various interaction points along the closure drive system to detect the closure forces applied to the anvil 716 by the closure drive system. The one or more sensors 738 may be sampled in real time during a clamping operation by the processor of the control circuit 710. The control circuit 710 receives real-time sample measurements to provide and analyze time-based information and assess, in real time, closure forces applied to the anvil 716.

In one aspect, a current sensor 736 can be employed to measure the current drawn by each of the motors 704a-704e. The force required to advance any of the movable mechanical elements such as the I-beam 714 corresponds to the current drawn by one of the motors 704a-704e. The force is converted to a digital signal and provided to the control circuit 710. The control circuit 710 can be configured to simulate the response of the actual system of the instrument in the software of the controller. A displacement member can be actuated to move an I-beam 714 in the end effector 702 at or near a target velocity. The robotic surgical instrument 700 can include a feedback controller, which can be one of any feedback controllers, including, but not limited to a PID, a state feedback, a linear-quadratic (LQR), and/or an adaptive controller, for example. The robotic surgical instrument 700 can include a power source to convert the signal from the feedback controller into a physical input such as case voltage, PWM voltage, frequency modulated voltage, current, torque, and/or force, for example. Additional details are disclosed in U.S. patent application Ser. No. 15/636,829, titled CLOSED LOOP VELOCITY CONTROL TECHNIQUES FOR ROBOTIC SURGICAL INSTRUMENT, filed Jun. 29, 2017, now U.S. Pat. No. 10,932,772, which is herein incorporated by reference in its entirety.

Figure 18:
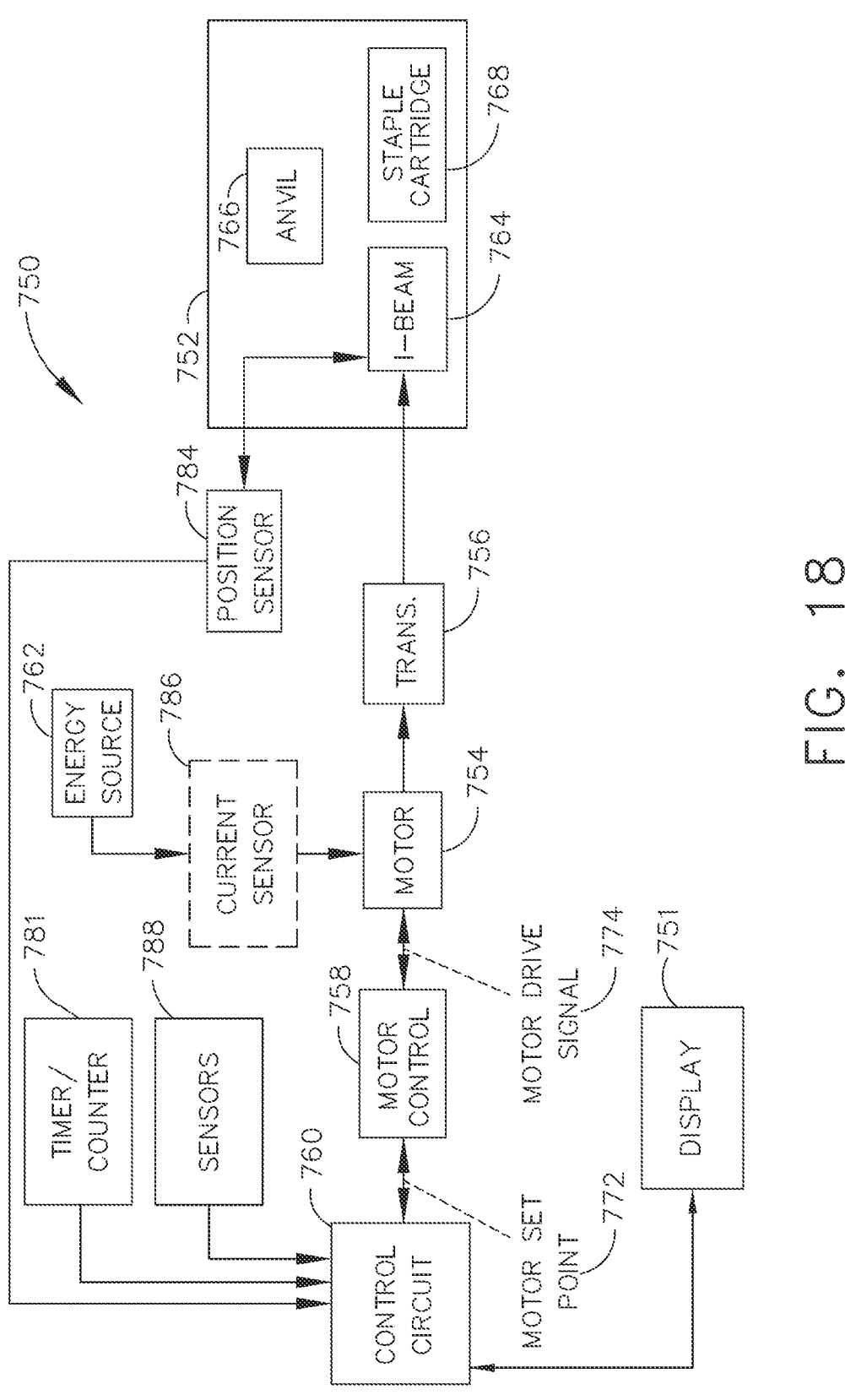
FIG. 18 illustrates a block diagram of a surgical instrument programmed to control the distal translation of a displacement member, in accordance with at least one aspect of the present disclosure.

FIG. 18 illustrates a block diagram of a surgical instrument 750 programmed to control the distal translation of a displacement member according to one aspect of this disclosure. In one aspect, the surgical instrument 750 is programmed to control the distal translation of a displacement member such as the I-beam 764. The surgical instrument 750 comprises an end effector 752 that may comprise an anvil 766, an I-beam 764 (including a sharp cutting edge), and a removable staple cartridge 768. The surgical instrument 750 may further include a display 751.

The position, movement, displacement, and/or translation of a linear displacement member, such as the I-beam 764, can be measured by an absolute positioning system, sensor arrangement, and position sensor 784. Because the I-beam 764 is coupled to a longitudinally movable drive member, the position of the I-beam 764 can be determined by measuring the position of the longitudinally movable drive member employing the position sensor 784. Accordingly, in the following description, the position, displacement, and/or translation of the I-beam 764 can be achieved by the position sensor 784 as described herein. A control circuit 760 may be programmed to control the translation of the displacement member, such as the I-beam 764. The control circuit 760, in some examples, may comprise one or more microcontrollers, microprocessors, or other suitable processors for executing instructions that cause the processor or processors to control the displacement member, e.g., the I-beam 764, in the manner described. In one aspect, a timer/counter 781 provides an output signal, such as the elapsed time or a digital count, to the control circuit 760 to correlate the position of the I-beam 764 as determined by the position sensor 784 with the output of the timer/counter 781 such that the control circuit 760 can determine the position of the I-beam 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the I-beam 764 via a transmission 756. The transmission 756 may include one or more gears or other linkage components to couple the motor 754 to the I-beam 764. A position sensor 784 may sense a position of the I-beam 764. The position sensor 784 may be or include any type of sensor that is capable of generating position data that indicate a position of the I-beam 764. In some examples, the position sensor 784 may include an encoder configured to provide a series of pulses to the control circuit 760 as the I-beam 764 translates distally and proximally. The control circuit 760 may track the pulses to determine the position of the I-beam 764. Other suitable position sensors may be used, including, for example, a proximity sensor. Other types of position sensors may provide other signals indicating motion of the I-beam 764. Also, in some examples, the position sensor 784 may be omitted. Where the motor 754 is a stepper motor, the control circuit 760 may track the position of the I-beam 764 by aggregating the number and direction of steps that the motor 754 has been instructed to execute. The position sensor 784 may be located in the end effector 752 or at any other portion of the instrument.

The control circuit 760 may be in communication with one or more sensors 788. The sensors 788 may be positioned on the end effector 752 and adapted to operate with the surgical instrument 750 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 752. The sensors 788 may include one or more sensors.

The one or more sensors 788 may comprise a strain gauge, such as a micro-strain gauge, configured to measure the magnitude of the strain in the anvil 766 during a clamped condition. The strain gauge provides an electrical signal whose amplitude varies with the magnitude of the strain. The sensors 788 may comprise a pressure sensor configured to detect a pressure generated by the presence of compressed tissue between the anvil 766 and the staple cartridge 768. The sensors 788 may be configured to detect impedance of a tissue section located between the anvil 766 and the staple cartridge 768 that is indicative of the thickness and/or fullness of tissue located therebetween.

The sensors 788 may be is configured to measure forces exerted on the anvil 766 by a closure drive system. For example, one or more sensors 788 can be at an interaction point between a closure tube and the anvil 766 to detect the closure forces applied by a closure tube to the anvil 766. The forces exerted on the anvil 766 can be representative of the tissue compression experienced by the tissue section captured between the anvil 766 and the staple cartridge 768. The one or more sensors 788 can be positioned at various interaction points along the closure drive system to detect the closure forces applied to the anvil 766 by the closure drive system. The one or more sensors 788 may be sampled in real time during a clamping operation by a processor of the control circuit 760. The control circuit 760 receives real-time sample measurements to provide and analyze time-based information and assess, in real time, closure forces applied to the anvil 766.

A current sensor 786 can be employed to measure the current drawn by the motor 754. The force required to advance the I-beam 764 corresponds to the current drawn by the motor 754. The force is converted to a digital signal and provided to the control circuit 760.

The control circuit 760 can be configured to simulate the response of the actual system of the instrument in the software of the controller. A displacement member can be actuated to move an I-beam 764 in the end effector 752 at or near a target velocity. The surgical instrument 750 can include a feedback controller, which can be one of any feedback controllers, including, but not limited to a PID, a state feedback, LQR, and/or an adaptive controller, for example. The surgical instrument 750 can include a power source to convert the signal from the feedback controller into a physical input such as case voltage, PWM voltage, frequency modulated voltage, current, torque, and/or force, for example.

The actual drive system of the surgical instrument 750 is configured to drive the displacement member, cutting member, or I-beam 764, by a brushed DC motor with gearbox and mechanical links to an articulation and/or knife system. Another example is the electric motor 754 that operates the displacement member and the articulation driver, for example, of an interchangeable shaft assembly. An outside influence is an unmeasured, unpredictable influence of things like tissue, surrounding bodies and friction on the physical system. Such outside influence can be referred to as drag which acts in opposition to the electric motor 754. The outside influence, such as drag, may cause the operation of the physical system to deviate from a desired operation of the physical system.

Various example aspects are directed to a surgical instrument 750 comprising an end effector 752 with motor-driven surgical stapling and cutting implements. For example, a motor 754 may drive a displacement member distally and proximally along a longitudinal axis of the end effector 752. The end effector 752 may comprise a pivotable anvil 766 and, when configured for use, a staple cartridge 768 positioned opposite the anvil 766. A clinician may grasp tissue between the anvil 766 and the staple cartridge 768, as described herein. When ready to use the instrument 750, the clinician may provide a firing signal, for example by depressing a trigger of the instrument 750. In response to the firing signal, the motor 754 may drive the displacement member distally along the longitudinal axis of the end effector 752 from a proximal stroke begin position to a stroke end position distal of the stroke begin position. As the displacement member translates distally, an I-beam 764 with a cutting element positioned at a distal end, may cut the tissue between the staple cartridge 768 and the anvil 766.

In various examples, the surgical instrument 750 may comprise a control circuit 760 programmed to control the distal translation of the displacement member, such as the I-beam 764, for example, based on one or more tissue conditions. The control circuit 760 may be programmed to sense tissue conditions, such as thickness, either directly or indirectly, as described herein. The control circuit 760 may be programmed to select a firing control program based on tissue conditions. A firing control program may describe the distal motion of the displacement member. Different firing control programs may be selected to better treat different tissue conditions. For example, when thicker tissue is present, the control circuit 760 may be programmed to translate the displacement member at a lower velocity and/or with lower power. When thinner tissue is present, the control circuit 760 may be programmed to translate the displacement member at a higher velocity and/or with higher power.

In some examples, the control circuit 760 may initially operate the motor 754 in an open loop configuration for a first open loop portion of a stroke of the displacement member. Based on a response of the instrument 750 during the open loop portion of the stroke, the control circuit 760 may select a firing control program. The response of the instrument may include, a translation distance of the displacement member during the open loop portion, a time elapsed during the open loop portion, energy provided to the motor 754 during the open loop portion, a sum of pulse widths of a motor drive signal, etc. After the open loop portion, the control circuit 760 may implement the selected firing control program for a second portion of the displacement member stroke. For example, during the closed loop portion of the stroke, the control circuit 760 may modulate the motor 754 based on translation data describing a position of the displacement member in a closed loop manner to translate the displacement member at a constant velocity. Additional details are disclosed in U.S. patent application Ser. No. 15/720,852, titled SYSTEM AND METHODS FOR CONTROLLING A DISPLAY OF A SURGICAL INSTRUMENT, filed Sep. 29, 2017, now U.S. Pat. No. 10,743,872, which is herein incorporated by reference in its entirety.

Figure 19:
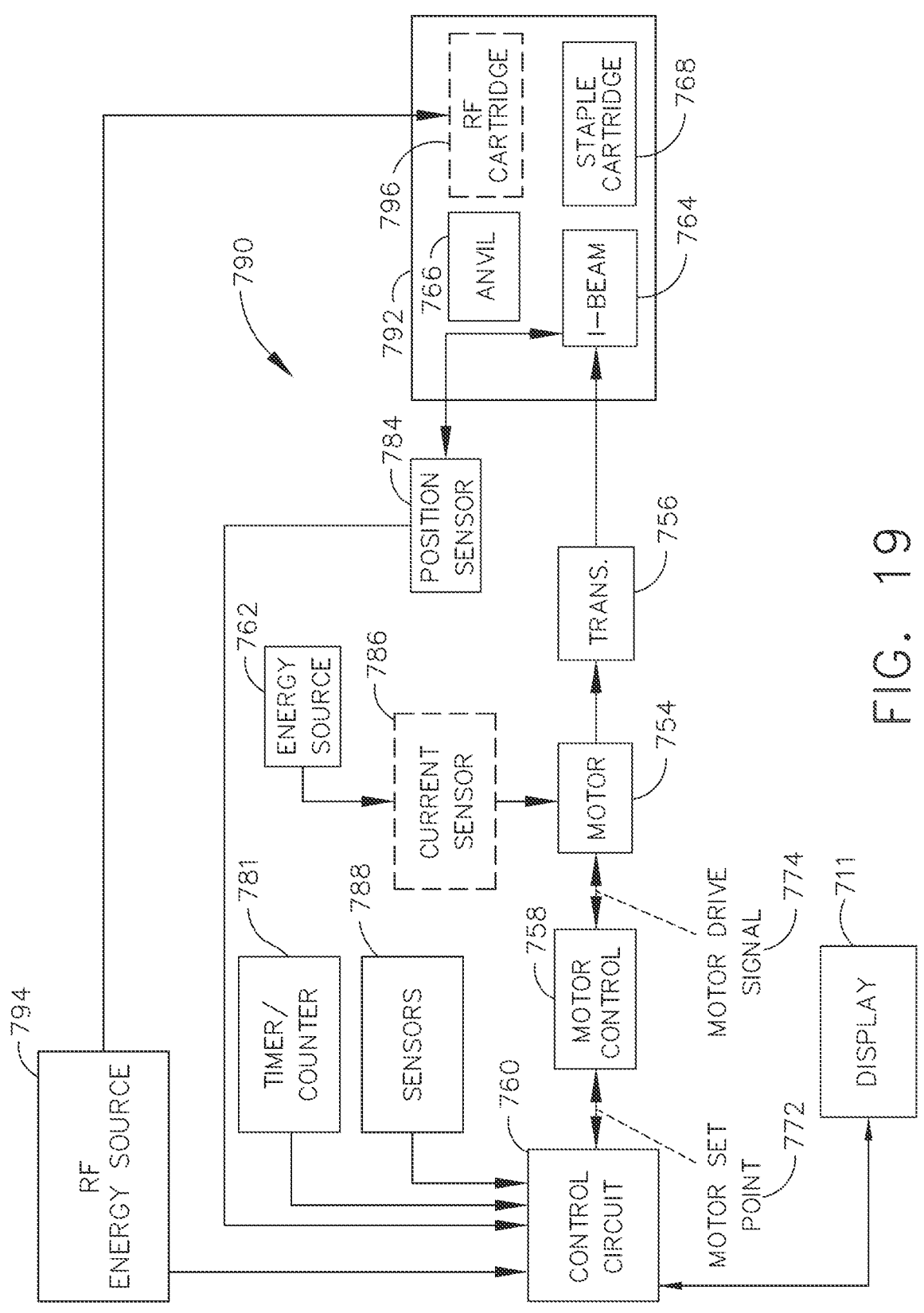
FIG. 19 is a schematic diagram of a surgical instrument configured to control various functions, in accordance with at least one aspect of the present disclosure.

FIG. 19 is a schematic diagram of a surgical instrument 790 configured to control various functions according to one aspect of this disclosure. In one aspect, the surgical instrument 790 is programmed to control distal translation of a displacement member such as the I-beam 764. The surgical instrument 790 comprises an end effector 792 that may comprise an anvil 766, an I-beam 764, and a removable staple cartridge 768 which may be interchanged with an RF cartridge 796 (shown in dashed line). The surgical instrument 790 may include a display 711.

In one aspect, sensors 788 may be implemented as a limit switch, electromechanical device, solid-state switches, Hall-effect devices, MR devices, GMR devices, magnetometers, among others. In other implementations, the sensors 638 may be solid-state switches that operate under the influence of light, such as optical sensors, IR sensors, ultraviolet sensors, among others. Still, the switches may be solid-state devices such as transistors (e.g., FET, junction FET, MOS-FET, bipolar, and the like). In other implementations, the sensors 788 may include electrical conductorless switches, ultrasonic switches, accelerometers, and inertial sensors, among others.

In one aspect, the position sensor 784 may be implemented as an absolute positioning system comprising a magnetic rotary absolute positioning system implemented as an AS5055EQFT single-chip magnetic rotary position sensor available from Austria Microsystems, AG. The position sensor 784 may interface with the control circuit 760 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the I-beam 764 may be implemented as a knife member comprising a knife body that operably supports a tissue cutting blade thereon and may further include anvil engagement tabs or features and channel engagement features or a foot. In one aspect, the staple cartridge 768 may be implemented as a standard (mechanical) surgical fastener cartridge. In one aspect, the RF cartridge 796 may be implemented as an RF cartridge. These and other sensors arrangements are described in commonly owned U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, now U.S. Pat. No. 10,881,399, which is herein incorporated by reference in its entirety.

The position, movement, displacement, and/or translation of a linear displacement member, such as the I-beam 764, can be measured by an absolute positioning system, sensor arrangement, and position sensor represented as position sensor 784. Because the I-beam 764 is coupled to the longitudinally movable drive member, the position of the I-beam 764 can be determined by measuring the position of the longitudinally movable drive member employing the position sensor 784. Accordingly, in the following description, the position, displacement, and/or translation of the I-beam 764 can be achieved by the position sensor 784 as described herein. A control circuit 760 may be programmed to control the translation of the displacement member, such as the I-beam 764, as described herein. The control circuit 760, in some examples, may comprise one or more micro-controllers, microprocessors, or other suitable processors for executing instructions that cause the processor or processors to control the displacement member, e.g., the I-beam 764, in the manner described. In one aspect, a timer/counter 781 provides an output signal, such as the elapsed time or a digital count, to the control circuit 760 to correlate the position of the I-beam 764 as determined by the position sensor 784 with the output of the timer/counter 781 such that the control circuit 760 can determine the position of the I-beam 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the I-beam 764 via a transmission 756. The transmission 756 may include one or more gears or other linkage components to couple the motor 754 to the I-beam 764. A position sensor 784 may sense a position of the I-beam 764. The position sensor 784 may be or include any type of sensor that is capable of generating position data that indicate a position of the I-beam 764. In some examples, the position sensor 784 may include an encoder configured to provide a series of pulses to the control circuit 760 as the I-beam 764 translates distally and proximally. The control circuit 760 may track the pulses to determine the position of the I-beam 764. Other suitable position sensors may be used, including, for example, a proximity sensor. Other types of position sensors may provide other signals indicating motion of the I-beam 764. Also, in some examples, the position sensor 784 may be omitted. Where the motor 754 is a stepper motor, the control circuit 760 may track the position of the I-beam 764 by aggregating the number and direction of steps that the motor has been instructed to execute. The position sensor 784 may be located in the end effector 792 or at any other portion of the instrument.

The control circuit 760 may be in communication with one or more sensors 788. The sensors 788 may be positioned on the end effector 792 and adapted to operate with the surgical instrument 790 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 792. The sensors 788 may include one or more sensors.

The one or more sensors 788 may comprise a strain gauge, such as a micro-strain gauge, configured to measure the magnitude of the strain in the anvil 766 during a clamped condition. The strain gauge provides an electrical signal whose amplitude varies with the magnitude of the strain. The sensors 788 may comprise a pressure sensor configured to detect a pressure generated by the presence of compressed tissue between the anvil 766 and the staple cartridge 768. The sensors 788 may be configured to detect impedance of a tissue section located between the anvil 766 and the staple cartridge 768 that is indicative of the thickness and/or fullness of tissue located therebetween.

The sensors 788 may be is configured to measure forces exerted on the anvil 766 by the closure drive system. For example, one or more sensors 788 can be at an interaction point between a closure tube and the anvil 766 to detect the closure forces applied by a closure tube to the anvil 766. The forces exerted on the anvil 766 can be representative of the tissue compression experienced by the tissue section captured between the anvil 766 and the staple cartridge 768. The one or more sensors 788 can be positioned at various interaction points along the closure drive system to detect the closure forces applied to the anvil 766 by the closure drive system. The one or more sensors 788 may be sampled in real time during a clamping operation by a processor portion of the control circuit 760. The control circuit 760 receives real-time sample measurements to provide and analyze time-based information and assess, in real time, closure forces applied to the anvil 766.

A current sensor 786 can be employed to measure the current drawn by the motor 754. The force required to advance the I-beam 764 corresponds to the current drawn by the motor 754. The force is converted to a digital signal and provided to the control circuit 760.

An RF energy source 794 is coupled to the end effector 792 and is applied to the RF cartridge 796 when the RF cartridge 796 is loaded in the end effector 792 in place of the staple cartridge 768. The control circuit 760 controls the delivery of the RF energy to the RF cartridge 796.

Additional details are disclosed in U.S. patent application Ser. No. 15/636,096, titled SURGICAL SYSTEM COUPLABLE WITH STAPLE CARTRIDGE AND RADIO FREQUENCY CARTRIDGE, AND METHOD OF USING SAME, filed Jun. 28, 2017, now U.S. Patent Application Publication No. 2019/0000478, which is herein incorporated by reference in its entirety.

Generator Hardware

Figure 20:
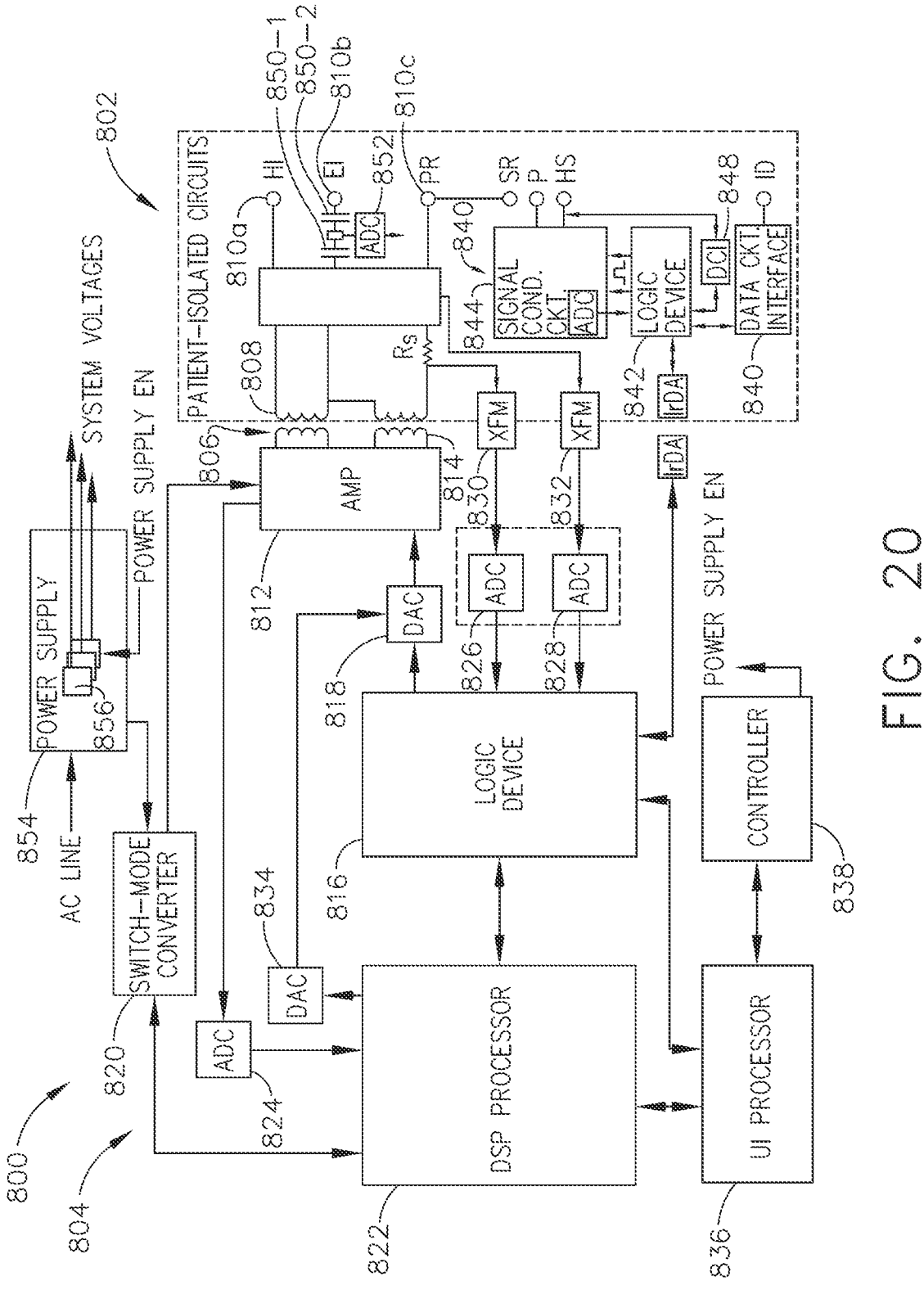
FIG. 20 is a simplified block diagram of a generator configured to provide inductorless tuning, among other benefits, in accordance with at least one aspect of the present disclosure.

FIG. 20 is a simplified block diagram of a generator 800 configured to provide inductorless tuning, among other benefits. Additional details of the generator 800 are described in U.S. Pat. No. 9,060,775, titled SURGICAL GENERATOR FOR ULTRASONIC AND ELECTROSURGICAL DEVICES, which issued on Jun. 23, 2015, which is herein incorporated by reference in its entirety. The generator 800 may comprise a patient isolated stage 802 in communication with a non-isolated stage 804 via a power transformer 806. A secondary winding 808 of the power transformer 806 is contained in the isolated stage 802 and may comprise a tapped configuration (e.g., a center-tapped or a non-center-tapped configuration) to define drive signal outputs 810a, 810b, 810c for delivering drive signals to different surgical instruments, such as, for example, an ultrasonic surgical instrument, an RF electrosurgical instrument, and a multifunction surgical instrument which includes ultrasonic and RF energy modes that can be delivered alone or simultaneously. In particular, drive signal outputs 810a, 810c may output an ultrasonic drive signal (e.g., a 420V root-mean-square (RMS) drive signal) to an ultrasonic surgical instrument, and drive signal outputs 810b, 810c may output an RF electrosurgical drive signal (e.g., a 100V RMS drive signal) to an RF electrosurgical instrument, with the drive signal output 810b corresponding to the center tap of the power transformer 806.

In certain forms, the ultrasonic and electrosurgical drive signals may be provided simultaneously to distinct surgical instruments and/or to a single surgical instrument, such as the multifunction surgical instrument, having the capability to deliver both ultrasonic and electrosurgical energy to tissue. It will be appreciated that the electrosurgical signal, provided either to a dedicated electrosurgical instrument and/or to a combined multifunction ultrasonic/electrosurgical instrument may be either a therapeutic or sub-therapeutic level signal where the sub-therapeutic signal can be used, for example, to monitor tissue or instrument conditions and provide feedback to the generator. For example, the ultrasonic and RF signals can be delivered separately or simultaneously from a generator with a single output port in order to provide the desired output signal to the surgical instrument, as will be discussed in more detail below. Accordingly, the generator can combine the ultrasonic and electrosurgical RF energies and deliver the combined energies to the multifunction ultrasonic/electrosurgical instrument. Bipolar electrodes can be placed on one or both jaws of the end effector. One jaw may be driven by ultrasonic energy in addition to electrosurgical RF energy, working simultaneously. The ultrasonic energy may be employed to dissect tissue, while the electrosurgical RF energy may be employed for vessel sealing.

The non-isolated stage 804 may comprise a power amplifier 812 having an output connected to a primary winding 814 of the power transformer 806. In certain forms, the power amplifier 812 may comprise a push-pull amplifier. For example, the non-isolated stage 804 may further comprise a logic device 816 for supplying a digital output to a digital-to-analog converter (DAC) circuit 818, which in turn supplies a corresponding analog signal to an input of the power amplifier 812. In certain forms, the logic device 816 may comprise a programmable gate array (PGA), a FPGA, programmable logic device (PLD), among other logic circuits, for example. The logic device 816, by virtue of controlling the input of the power amplifier 812 via the DAC circuit 818, may therefore control any of a number of parameters (e.g., frequency, waveform shape, waveform amplitude) of drive signals appearing at the drive signal outputs 810a, 810b, 810c. In certain forms and as discussed below, the logic device 816, in conjunction with a processor (e.g., a DSP discussed below), may implement a number of DSP-based and/or other control algorithms to control parameters of the drive signals output by the generator 800.

Power may be supplied to a power rail of the power amplifier 812 by a switch-mode regulator 820, e.g., a power converter. In certain forms, the switch-mode regulator 820 may comprise an adjustable buck regulator, for example. The non-isolated stage 804 may further comprise a first processor 822, which in one form may comprise a DSP processor such as an Analog Devices ADSP-21469 SHARC DSP, available from Analog Devices, Norwood, MA, for example, although in various forms any suitable processor may be employed. In certain forms the DSP processor 822 may control the operation of the switch-mode regulator 820 responsive to voltage feedback data received from the power amplifier 812 by the DSP processor 822 via an ADC circuit 824. In one form, for example, the DSP processor 822 may receive as input, via the ADC circuit 824, the waveform envelope of a signal (e.g., an RF signal) being amplified by the power amplifier 812. The DSP processor 822 may then control the switch-mode regulator 820 (e.g., via a PWM output) such that the rail voltage supplied to the power amplifier 812 tracks the waveform envelope of the amplified signal. By dynamically modulating the rail voltage of the power amplifier 812 based on the waveform envelope, the efficiency of the power amplifier 812 may be significantly improved relative to a fixed rail voltage amplifier schemes.

In certain forms, the logic device 816, in conjunction with the DSP processor 822, may implement a digital synthesis circuit such as a direct digital synthesizer control scheme to control the waveform shape, frequency, and/or amplitude of drive signals output by the generator 800. In one form, for example, the logic device 816 may implement a DDS control algorithm by recalling waveform samples stored in a dynamically updated lookup table (LUT), such as a RAM LUT, which may be embedded in an FPGA. This control algorithm is particularly useful for ultrasonic applications in which an ultrasonic transducer, such as an ultrasonic transducer, may be driven by a clean sinusoidal current at its resonant frequency. Because other frequencies may excite parasitic resonances, minimizing or reducing the total distortion of the motional branch current may correspondingly minimize or reduce undesirable resonance effects. Because the waveform shape of a drive signal output by the generator 800 is impacted by various sources of distortion present in the output drive circuit (e.g., the power transformer 806, the power amplifier 812), voltage and current feedback data based on the drive signal may be input into an algorithm, such as an error control algorithm implemented by the DSP processor 822, which compensates for distortion by suitably pre-distorting or modifying the waveform samples stored in the LUT on a dynamic, ongoing basis (e.g., in real time). In one form, the amount or degree of pre-distortion applied to the LUT samples may be based on the error between a computed motional branch current and a desired current waveform shape, with the error being determined on a sample-by-sample basis. In this way, the pre-distorted LUT samples, when processed through the drive circuit, may result in a motional branch drive signal having the desired waveform shape (e.g., sinusoidal) for optimally driving the ultrasonic transducer. In such forms, the LUT waveform samples will therefore not represent the desired waveform shape of the drive signal, but rather the waveform shape that is required to ultimately produce the desired waveform shape of the motional branch drive signal when distortion effects are taken into account.

The non-isolated stage 804 may further comprise a first ADC circuit 826 and a second ADC circuit 828 coupled to the output of the power transformer 806 via respective isolation transformers 830, 832 for respectively sampling the voltage and current of drive signals output by the generator 800. In certain forms, the ADC circuits 826, 828 may be configured to sample at high speeds (e.g., 80 mega samples per second (MSPS)) to enable oversampling of the drive signals. In one form, for example, the sampling speed of the ADC circuits 826, 828 may enable approximately 200× (depending on frequency) oversampling of the drive signals. In certain forms, the sampling operations of the ADC circuit 826, 828 may be performed by a single ADC circuit receiving input voltage and current signals via a two-way multiplexer. The use of high-speed sampling in forms of the generator 800 may enable, among other things, calculation of the complex current flowing through the motional branch (which may be used in certain forms to implement DDS-based waveform shape control described above), accurate digital filtering of the sampled signals, and calculation of real power consumption with a high degree of precision. Voltage and current feedback data output by the ADC circuits 826, 828 may be received and processed (e.g., first-in-first-out (FIFO) buffer, multiplexer) by the logic device 816 and stored in data memory for subsequent retrieval by, for example, the DSP processor 822. As noted above, voltage and current feedback data may be used as input to an algorithm for pre-distorting or modifying LUT waveform samples on a dynamic and ongoing basis. In certain forms, this may require each stored voltage and current feedback data pair to be indexed based on, or otherwise associated with, a corresponding LUT sample that was output by the logic device 816 when the voltage and current feedback data pair was acquired. Synchronization of the LUT samples and the voltage and current feedback data in this manner contributes to the correct timing and stability of the pre-distortion algorithm.

In certain forms, the voltage and current feedback data may be used to control the frequency and/or amplitude (e.g., current amplitude) of the drive signals. In one form, for example, voltage and current feedback data may be used to determine impedance phase. The frequency of the drive signal may then be controlled to minimize or reduce the difference between the determined impedance phase and an impedance phase setpoint (e.g., 0°), thereby minimizing or reducing the effects of harmonic distortion and correspondingly enhancing impedance phase measurement accuracy. The determination of phase impedance and a frequency control signal may be implemented in the DSP processor 822, for example, with the frequency control signal being supplied as input to a DDS control algorithm implemented by the logic device 816.

In another form, for example, the current feedback data may be monitored in order to maintain the current amplitude of the drive signal at a current amplitude setpoint. The current amplitude setpoint may be specified directly or determined indirectly based on specified voltage amplitude and power setpoints. In certain forms, control of the current amplitude may be implemented by control algorithm, such as, for example, a proportional-integral-derivative (PID) control algorithm, in the DSP processor 822. Variables controlled by the control algorithm to suitably control the current amplitude of the drive signal may include, for example, the scaling of the LUT waveform samples stored in the logic device 816 and/or the full-scale output voltage of the DAC circuit 818 (which supplies the input to the power amplifier 812) via a DAC circuit 834.

The non-isolated stage 804 may further comprise a second processor 836 for providing, among other things user interface (UI) functionality. In one form, the UI processor 836 may comprise an Atmel AT91SAM9263 processor having an ARM 926EJ-S core, available from Atmel Corporation, San Jose, California, for example. Examples of UI functionality supported by the UI processor 836 may include audible and visual user feedback, communication with peripheral devices (e.g., via a USB interface), communication with a foot switch, communication with an input device (e.g., a touch screen display) and communication with an output device (e.g., a speaker). The UI processor 836 may communicate with the DSP processor 822 and the logic device 816 (e.g., via SPI buses). Although the UI processor 836 may primarily support UI functionality, it may also coordinate with the DSP processor 822 to implement hazard mitigation in certain forms. For example, the UI processor 836 may be programmed to monitor various aspects of user input and/or other inputs (e.g., touch screen inputs, foot switch inputs, temperature sensor inputs) and may disable the drive output of the generator 800 when an erroneous condition is detected.

In certain forms, both the DSP processor 822 and the UI processor 836, for example, may determine and monitor the operating state of the generator 800. For the DSP processor 822, the operating state of the generator 800 may dictate, for example, which control and/or diagnostic processes are implemented by the DSP processor 822. For the UI processor 836, the operating state of the generator 800 may dictate, for example, which elements of a UI (e.g., display screens, sounds) are presented to a user. The respective DSP and UI processors 822, 836 may independently maintain the current operating state of the generator 800 and recognize and evaluate possible transitions out of the current operating state. The DSP processor 822 may function as the master in this relationship and determine when transitions between operating states are to occur. The UI processor 836 may be aware of valid transitions between operating states and may confirm if a particular transition is appropriate. For example, when the DSP processor 822 instructs the UI processor 836 to transition to a specific state, the UI processor 836 may verify that requested transition is valid. In the event that a requested transition between states is determined to be invalid by the UI processor 836, the UI processor 836 may cause the generator 800 to enter a failure mode.

The non-isolated stage 804 may further comprise a controller 838 for monitoring input devices (e.g., a capacitive touch sensor used for turning the generator 800 on and off, a capacitive touch screen). In certain forms, the controller 838 may comprise at least one processor and/or other controller device in communication with the UI processor 836. In one form, for example, the controller 838 may comprise a processor (e.g., a Meg168 8-bit controller available from Atmel) configured to monitor user input provided via one or more capacitive touch sensors. In one form, the controller 838 may comprise a touch screen controller (e.g., a QT5480 touch screen controller available from Atmel) to control and manage the acquisition of touch data from a capacitive touch screen.

In certain forms, when the generator 800 is in a "power off" state, the controller 838 may continue to receive operating power (e.g., via a line from a power supply of the generator 800, such as the power supply 854 discussed below). In this way, the controller 838 may continue to monitor an input device (e.g., a capacitive touch sensor located on a front panel of the generator 800) for turning the generator 800 on and off. When the generator 800 is in the power off state, the controller 838 may wake the power supply (e.g., enable operation of one or more DC/DC voltage converters 856 of the power supply 854) if activation of the "on/off" input device by a user is detected. The controller 838 may therefore initiate a sequence for transitioning the generator 800 to a "power on" state. Conversely, the controller 838 may initiate a sequence for transitioning the generator 800 to the power off state if activation of the "on/off" input device is detected when the generator 800 is in the power on state. In certain forms, for example, the controller 838 may report activation of the "on/off" input device to the UI processor 836, which in turn implements the necessary process sequence for transitioning the generator 800 to the power off state. In such forms, the controller 838 may have no independent ability for causing the removal of power from the generator 800 after its power on state has been established.

In certain forms, the controller 838 may cause the generator 800 to provide audible or other sensory feedback for alerting the user that a power on or power off sequence has been initiated. Such an alert may be provided at the beginning of a power on or power off sequence and prior to the commencement of other processes associated with the sequence.

In certain forms, the isolated stage 802 may comprise an instrument interface circuit 840 to, for example, provide a communication interface between a control circuit of a surgical instrument (e.g., a control circuit comprising handpiece switches) and components of the non-isolated stage 804, such as, for example, the logic device 816, the DSP processor 822, and/or the UI processor 836. The instrument interface circuit 840 may exchange information with components of the non-isolated stage 804 via a communication link that maintains a suitable degree of electrical isolation between the isolated and non-isolated stages 802, 804, such as, for example, an IR-based communication link. Power may be supplied to the instrument interface circuit 840 using, for example, a low-dropout voltage regulator powered by an isolation transformer driven from the non-isolated stage 804.

In one form, the instrument interface circuit 840 may comprise a logic circuit 842 (e.g., logic circuit, programmable logic circuit, PGA, FPGA, PLD) in communication with a signal conditioning circuit 844. The signal conditioning circuit 844 may be configured to receive a periodic signal from the logic circuit 842 (e.g., a 2 kHz square wave) to generate a bipolar interrogation signal having an identical frequency. The interrogation signal may be generated, for example, using a bipolar current source fed by a differential amplifier. The interrogation signal may be communicated to a surgical instrument control circuit (e.g., by using a conductive pair in a cable that connects the generator 800 to the surgical instrument) and monitored to determine a state or configuration of the control circuit. The control circuit may comprise a number of switches, resistors, and/or diodes to modify one or more characteristics (e.g., amplitude, rectification) of the interrogation signal such that a state or configuration of the control circuit is uniquely discernable based on the one or more characteristics. In one form, for example, the signal conditioning circuit 844 may comprise an ADC circuit for generating samples of a voltage signal appearing across inputs of the control circuit resulting from passage of interrogation signal therethrough. The logic circuit 842 (or a component of the non-isolated stage 804) may then determine the state or configuration of the control circuit based on the ADC circuit samples.

In one form, the instrument interface circuit 840 may comprise a first data circuit interface 846 to enable information exchange between the logic circuit 842 (or other element of the instrument interface circuit 840) and a first data circuit disposed in or otherwise associated with a surgical instrument. In certain forms, for example, a first data circuit may be disposed in a cable integrally attached to a surgical instrument handpiece or in an adaptor for interfacing a specific surgical instrument type or model with the generator 800. The first data circuit may be implemented in any suitable manner and may communicate with the generator according to any suitable protocol, including, for example, as described herein with respect to the first data circuit. In certain forms, the first data circuit may comprise a non-volatile storage device, such as an EEPROM device. In certain forms, the first data circuit interface 846 may be implemented separately from the logic circuit 842 and comprise suitable circuitry (e.g., discrete logic devices, a processor) to enable communication between the logic circuit 842 and the first data circuit. In other forms, the first data circuit interface 846 may be integral with the logic circuit 842.

In certain forms, the first data circuit may store information pertaining to the particular surgical instrument with which it is associated. Such information may include, for example, a model number, a serial number, a number of operations in which the surgical instrument has been used, and/or any other type of information. This information may be read by the instrument interface circuit 840 (e.g., by the logic circuit 842), transferred to a component of the non-isolated stage 804 (e.g., to logic device 816, DSP processor 822, and/or UI processor 836) for presentation to a user via an output device and/or for controlling a function or operation of the generator 800. Additionally, any type of information may be communicated to the first data circuit for storage therein via the first data circuit interface 846 (e.g., using the logic circuit 842). Such information may comprise, for example, an updated number of operations in which the surgical instrument has been used and/or dates and/or times of its usage.

As discussed previously, a surgical instrument may be detachable from a handpiece (e.g., the multifunction surgical instrument may be detachable from the handpiece) to promote instrument interchangeability and/or disposability. In such cases, conventional generators may be limited in their ability to recognize particular instrument configurations being used and to optimize control and diagnostic processes accordingly. The addition of readable data circuits to surgical instruments to address this issue is problematic from a compatibility standpoint, however. For example, designing a surgical instrument to remain backwardly compatible with generators that lack the requisite data reading functionality may be impractical due to, for example, differing signal schemes, design complexity, and cost. Forms of instruments discussed herein address these concerns by using data circuits that may be implemented in existing surgical instruments economically and with minimal design changes to preserve compatibility of the surgical instruments with current generator platforms.

Additionally, forms of the generator 800 may enable communication with instrument-based data circuits. For example, the generator 800 may be configured to communicate with a second data circuit contained in an instrument (e.g., the multifunction surgical instrument). In some forms, the second data circuit may be implemented in a many similar to that of the first data circuit described herein. The instrument interface circuit 840 may comprise a second data circuit interface 848 to enable this communication. In one form, the second data circuit interface 848 may comprise a tri-state digital interface, although other interfaces may also be used. In certain forms, the second data circuit may generally be any circuit for transmitting and/or receiving data. In one form, for example, the second data circuit may store information pertaining to the particular surgical instrument with which it is associated. Such information may include, for example, a model number, a serial number, a number of operations in which the surgical instrument has been used, and/or any other type of information.

In some forms, the second data circuit may store information about the electrical and/or ultrasonic properties of an associated ultrasonic transducer, end effector, or ultrasonic drive system. For example, the first data circuit may indicate a burn-in frequency slope, as described herein. Additionally or alternatively, any type of information may be communicated to second data circuit for storage therein via the second data circuit interface 848 (e.g., using the logic circuit 842). Such information may comprise, for example, an updated number of operations in which the instrument has been used and/or dates and/or times of its usage. In certain forms, the second data circuit may transmit data acquired by one or more sensors (e.g., an instrument-based temperature sensor). In certain forms, the second data circuit may receive data from the generator 800 and provide an indication to a user (e.g., a light emitting diode indication or other visible indication) based on the received data.

In certain forms, the second data circuit and the second data circuit interface 848 may be configured such that communication between the logic circuit 842 and the second data circuit can be effected without the need to provide additional conductors for this purpose (e.g., dedicated conductors of a cable connecting a handpiece to the generator 800). In one form, for example, information may be communicated to and from the second data circuit using a one-wire bus communication scheme implemented on existing cabling, such as one of the conductors used transmit interrogation signals from the signal conditioning circuit 844 to a control circuit in a handpiece. In this way, design changes or modifications to the surgical instrument that might otherwise be necessary are minimized or reduced. Moreover, because different types of communications implemented over a common physical channel can be frequency-band separated, the presence of a second data circuit may be "invisible" to generators that do not have the requisite data reading functionality, thus enabling backward compatibility of the surgical instrument.

In certain forms, the isolated stage 802 may comprise at least one blocking capacitor 850-1 connected to the drive signal output 810b to prevent passage of DC current to a patient. A single blocking capacitor may be required to comply with medical regulations or standards, for example. While failure in single-capacitor designs is relatively uncommon, such failure may nonetheless have negative consequences. In one form, a second blocking capacitor 850-2 may be provided in series with the blocking capacitor 850-1, with current leakage from a point between the blocking capacitors 850-1, 850-2 being monitored by, for example, an ADC circuit 852 for sampling a voltage induced by leakage current. The samples may be received by the logic circuit 842, for example. Based changes in the leakage current (as indicated by the voltage samples), the generator 800 may determine when at least one of the blocking capacitors 850-1, 850-2 has failed, thus providing a benefit over single-capacitor designs having a single point of failure.

In certain forms, the non-isolated stage 804 may comprise a power supply 854 for delivering DC power at a suitable voltage and current. The power supply may comprise, for example, a 400 W power supply for delivering a 48 VDC system voltage. The power supply 854 may further comprise one or more DC/DC voltage converters 856 for receiving the output of the power supply to generate DC outputs at the voltages and currents required by the various components of the generator 800. As discussed above in connection with the controller 838, one or more of the DC/DC voltage converters 856 may receive an input from the controller 838 when activation of the "on/off" input device by a user is detected by the controller 838 to enable operation of, or wake, the DC/DC voltage converters 856.

Figure 21:
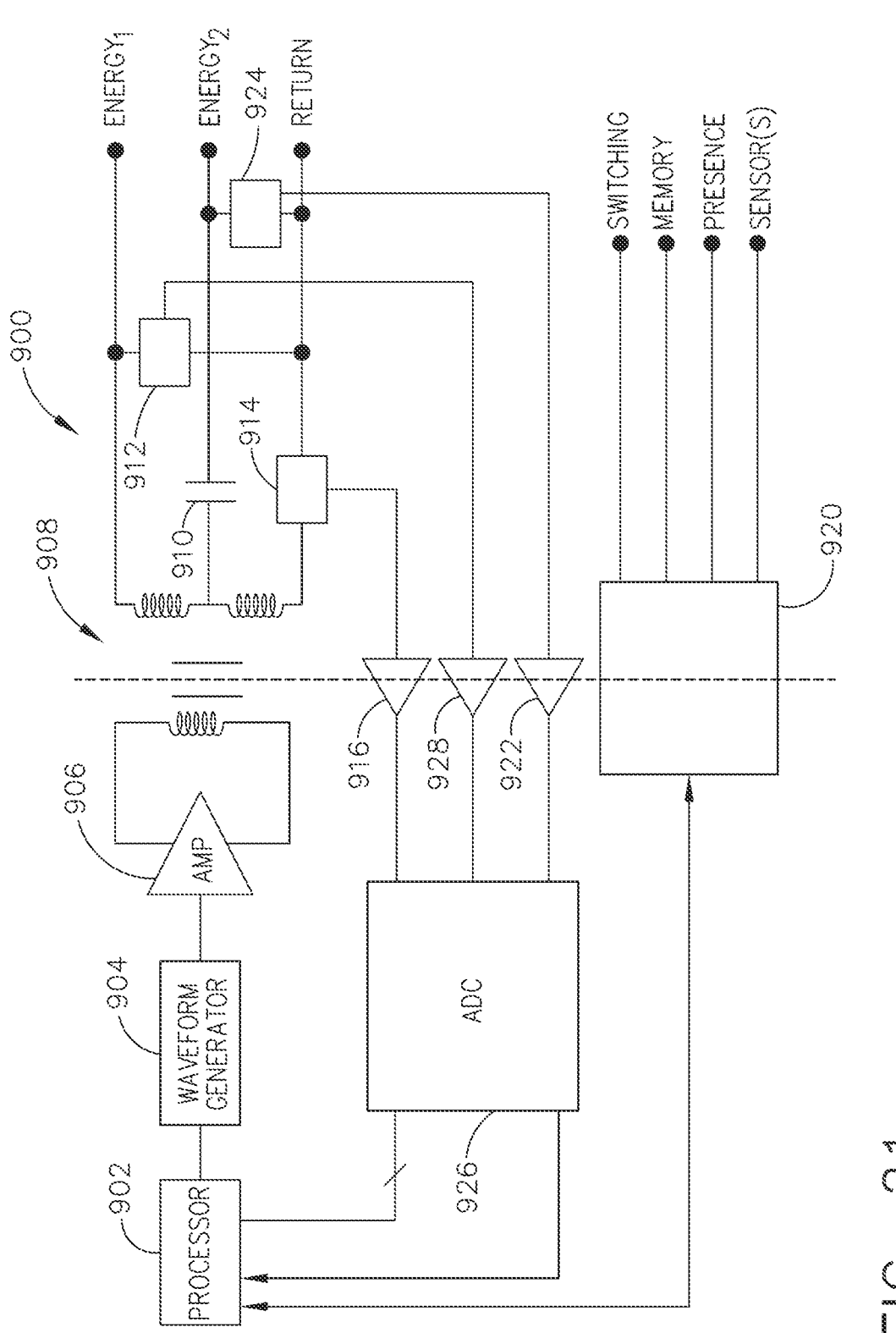
FIG. 21 illustrates an example of a generator, which is one form of the generator of FIG. 20, in accordance with at least one aspect of the present disclosure.

FIG. 21 illustrates an example of a generator 900, which is one form of the generator 800 (FIG. 20). The generator 900 is configured to deliver multiple energy modalities to a surgical instrument. The generator 900 provides RF and ultrasonic signals for delivering energy to a surgical instrument either independently or simultaneously. The RF and ultrasonic signals may be provided alone or in combination and may be provided simultaneously. As noted above, at least one generator output can deliver multiple energy modalities (e.g., ultrasonic, bipolar or monopolar RF, irreversible and/or reversible electroporation, and/or microwave energy, among others) through a single port, and these signals can be delivered separately or simultaneously to the end effector to treat tissue.

The generator 900 comprises a processor 902 coupled to a waveform generator 904. The processor 902 and waveform generator 904 are configured to generate a variety of signal waveforms based on information stored in a memory coupled to the processor 902, not shown for clarity of disclosure. The digital information associated with a waveform is provided to the waveform generator 904 which includes one or more DAC circuits to convert the digital input into an analog output. The analog output is fed to an amplifier 1106 for signal conditioning and amplification. The conditioned and amplified output of the amplifier 906 is coupled to a power transformer 908. The signals are coupled across the power transformer 908 to the secondary side, which is in the patient isolation side. A first signal of a first energy modality is provided to the surgical instrument between the terminals labeled ENERGY1 and RETURN. A second signal of a second energy modality is coupled across a capacitor 910 and is provided to the surgical instrument between the terminals labeled ENERGY2 and RETURN. It will be appreciated that more than two energy modalities may be output and thus the subscript "n" may be used to designate that up to n ENERGYn terminals may be provided, where n is a positive integer greater than 1. It also will be appreciated that up to "n" return paths RETURNn may be provided without departing from the scope of the present disclosure.

A first voltage sensing circuit 912 is coupled across the terminals labeled ENERGY1 and the RETURN path to measure the output voltage therebetween. A second voltage sensing circuit 924 is coupled across the terminals labeled ENERGY2 and the RETURN path to measure the output voltage therebetween. A current sensing circuit 914 is disposed in series with the RETURN leg of the secondary side of the power transformer 908 as shown to measure the output current for either energy modality. If different return paths are provided for each energy modality, then a separate current sensing circuit should be provided in each return leg. The outputs of the first and second voltage sensing circuits 912, 924 are provided to respective isolation transformers 916, 922 and the output of the current sensing circuit 914 is provided to another isolation transformer 918. The outputs of the isolation transformers 916, 928, 922 in the on the primary side of the power transformer 908 (non-patient isolated side) are provided to a one or more ADC circuit 926. The digitized output of the ADC circuit 926 is provided to the processor 902 for further processing and computation. The output voltages and output current feedback information can be employed to adjust the output voltage and current provided to the surgical instrument and to compute output impedance, among other parameters. Input/output communications between the processor 902 and patient isolated circuits is provided through an interface circuit 920. Sensors also may be in electrical communication with the processor 902 by way of the interface circuit 920.

In one aspect, the impedance may be determined by the processor 902 by dividing the output of either the first voltage sensing circuit 912 coupled across the terminals labeled ENERGY1/RETURN or the second voltage sensing circuit 924 coupled across the terminals labeled ENERGY2/RETURN by the output of the current sensing circuit 914 disposed in series with the RETURN leg of the secondary side of the power transformer 908. The outputs of the first and second voltage sensing circuits 912, 924 are provided to separate isolations transformers 916, 922 and the output of the current sensing circuit 914 is provided to another isolation transformer 916. The digitized voltage and current sensing measurements from the ADC circuit 926 are provided the processor 902 for computing impedance. As an example, the first energy modality ENERGY1 may be ultrasonic energy and the second energy modality ENERGY2 may be RF energy. Nevertheless, in addition to ultrasonic and bipolar or monopolar RF energy modalities, other energy modalities include irreversible and/or reversible electroporation and/or microwave energy, among others. Also, although the example illustrated in FIG. 21 shows a single return path RETURN may be provided for two or more energy modalities, in other aspects, multiple return paths RETURNn may be provided for each energy modality ENERGYn. Thus, as described herein, the ultrasonic transducer impedance may be measured by dividing the output of the first voltage sensing circuit 912 by the current sensing circuit 914 and the tissue impedance may be measured by dividing the output of the second voltage sensing circuit 924 by the current sensing circuit 914.

As shown in FIG. 21, the generator 900 comprising at least one output port can include a power transformer 908 with a single output and with multiple taps to provide power in the form of one or more energy modalities, such as ultrasonic, bipolar or monopolar RF, irreversible and/or reversible electroporation, and/or microwave energy, among others, for example, to the end effector depending on the type of treatment of tissue being performed. For example, the generator 900 can deliver energy with higher voltage and lower current to drive an ultrasonic transducer, with lower voltage and higher current to drive RF electrodes for sealing tissue, or with a coagulation waveform for spot coagulation using either monopolar or bipolar RF electrosurgical electrodes. The output waveform from the generator 900 can be steered, switched, or filtered to provide the frequency to the end effector of the surgical instrument. The connection of an ultrasonic transducer to the generator 900 output would be preferably located between the output labeled ENERGY1 and RETURN as shown in FIG. 21. In one example, a connection of RF bipolar electrodes to the generator 900 output would be preferably located between the output labeled ENERGY2 and RETURN. In the case of monopolar output, the preferred connections would be active electrode (e.g., pencil or other probe) to the ENERGY2 output and a suitable return pad connected to the RETURN output.

Additional details are disclosed in U.S. Patent Application Publication No. 2017/0086914, titled TECHNIQUES FOR OPERATING GENERATOR FOR DIGITALLY GENERATING ELECTRICAL SIGNAL WAVEFORMS AND SURGICAL INSTRUMENTS, which published on Mar. 30, 2017, now U.S. Pat. No. 10,624,691, which is herein incorporated by reference in its entirety.

As used throughout this description, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some aspects they might not. The communication module may implement any of a number of wireless or wired communication standards or protocols, including but not limited to Wi-Fi (IEEE 802.11 family), WiMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, Ethernet derivatives thereof, as well as any other wireless and wired protocols that are designated as 3G, 4G, 5G, and beyond. The computing module may include a plurality of communication modules. For instance, a first communication module may be dedicated to shorter range wireless communications such as Wi-Fi and Bluetooth and a second communication module may be dedicated to longer range wireless communications such as GPS, EDGE, GPRS, CDMA, WIMAX, LTE, Ev-DO, and others.

As used herein a processor or processing unit is an electronic circuit which performs operations on some external data source, usually memory or some other data stream. The term is used herein to refer to the central processor (central processing unit) in a system or computer systems (especially systems on a chip (SoCs)) that combine a number of specialized "processors."

As used herein, a system on a chip or system on chip (SoC or SOC) is an integrated circuit (also known as an "IC" or "chip") that integrates all components of a computer or other electronic systems. It may contain digital, analog, mixed-signal, and often radio-frequency functions—all on a single substrate. A SoC integrates a microcontroller (or microprocessor) with advanced peripherals like graphics processing unit (GPU), Wi-Fi module, or coprocessor. A SoC may or may not contain built-in memory.

As used herein, a microcontroller or controller is a system that integrates a microprocessor with peripheral circuits and memory. A microcontroller (or MCU for microcontroller unit) may be implemented as a small computer on a single integrated circuit. It may be similar to a SoC; an SoC may include a microcontroller as one of its components. A microcontroller may contain one or more core processing units (CPUs) along with memory and programmable input/output peripherals. Program memory in the form of Ferroelectric RAM, NOR flash or OTP ROM is also often included on chip, as well as a small amount of RAM. Microcontrollers may be employed for embedded applications, in contrast to the microprocessors used in personal computers or other general purpose applications consisting of various discrete chips.

As used herein, the term controller or microcontroller may be a stand-alone IC or chip device that interfaces with a peripheral device. This may be a link between two parts of a computer or a controller on an external device that manages the operation of (and connection with) that device.

Any of the processors or microcontrollers described herein, may be implemented by any single core or multicore processor such as those known under the trade name ARM Cortex by Texas Instruments. In one aspect, the processor may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHZ, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

In one aspect, the processor may comprise a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

Modular devices include the modules (as described in connection with FIGS. 3 and 9, for example) that are receivable within a surgical hub and the surgical devices or instruments that can be connected to the various modules in order to connect or pair with the corresponding surgical hub. The modular devices include, for example, intelligent surgical instruments, medical imaging devices, suction/irrigation devices, smoke evacuators, energy generators, ventilators, insufflators, and displays. The modular devices described herein can be controlled by control algorithms.

The control algorithms can be executed on the modular device itself, on the surgical hub to which the particular modular device is paired, or on both the modular device and the surgical hub (e.g., via a distributed computing architecture). In some exemplifications, the modular devices' control algorithms control the devices based on data sensed by the modular device itself (i.e., by sensors in, on, or connected to the modular device). This data can be related to the patient being operated on (e.g., tissue properties or insufflation pressure) or the modular device itself (e.g., the rate at which a knife is being advanced, motor current, or energy levels). For example, a control algorithm for a surgical stapling and cutting instrument can control the rate at which the instrument's motor drives its knife through tissue according to resistance encountered by the knife as it advances.

Surgical Hub Situational Awareness

Although an "intelligent" device including control algorithms that respond to sensed data can be an improvement over a "dumb" device that operates without accounting for sensed data, some sensed data can be incomplete or inconclusive when considered in isolation, i.e., without the context of the type of surgical procedure being performed or the type of tissue that is being operated on. Without knowing the procedural context (e.g., knowing the type of tissue being operated on or the type of procedure being performed), the control algorithm may control the modular device incorrectly or suboptimally given the particular context-free sensed data. For example, the optimal manner for a control algorithm to control a surgical instrument in response to a particular sensed parameter can vary according to the particular tissue type being operated on. This is due to the fact that different tissue types have different properties (e.g., resistance to tearing) and thus respond differently to actions taken by surgical instruments. Therefore, it may be desirable for a surgical instrument to take different actions even when the same measurement for a particular parameter is sensed. As one specific example, the optimal manner in which to control a surgical stapling and cutting instrument in response to the instrument sensing an unexpectedly high force to close its end effector will vary depending upon whether the tissue type is susceptible or resistant to tearing. For tissues that are susceptible to tearing, such as lung tissue, the instrument's control algorithm would optimally ramp down the motor in response to an unexpectedly high force to close to avoid tearing the tissue. For tissues that are resistant to tearing, such as stomach tissue, the instrument's control algorithm would optimally ramp up the motor in response to an unexpectedly high force to close to ensure that the end effector is clamped properly on the tissue. Without knowing whether lung or stomach tissue has been clamped, the control algorithm may make a suboptimal decision.

Figure 22:
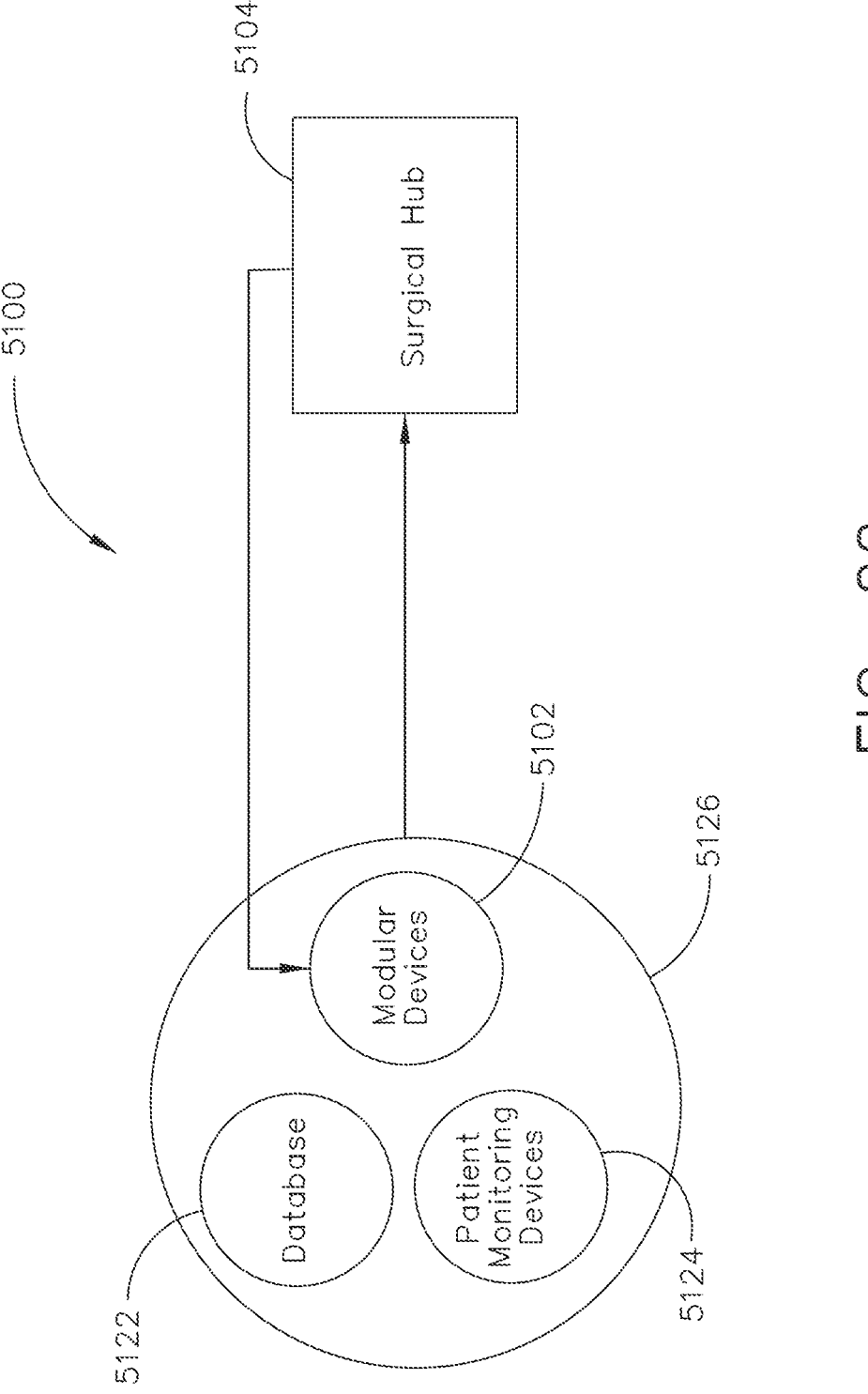
FIG. 22 illustrates a diagram of a situationally aware surgical system, in accordance with at least one aspect of the present disclosure.

One solution utilizes a surgical hub including a system that is configured to derive information about the surgical procedure being performed based on data received from various data sources and then control the paired modular devices accordingly. In other words, the surgical hub is configured to infer information about the surgical procedure from received data and then control the modular devices paired to the surgical hub based upon the inferred context of the surgical procedure. FIG. 22 illustrates a diagram of a situationally aware surgical system 5100, in accordance with at least one aspect of the present disclosure. In some exemplifications, the data sources 5126 include, for example, the modular devices 5102 (which can include sensors configured to detect parameters associated with the patient and/or the modular device itself), databases 5122 (e.g., an EMR database containing patient records), and patient monitoring devices 5124 (e.g., a blood pressure (BP) monitor and an electrocardiography (EKG) monitor). The surgical hub 5104 can be configured to derive the contextual information pertaining to the surgical procedure from the data based upon, for example, the particular combination(s) of received data or the particular order in which the data is received from the data sources 5126. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 5104 to derive or infer information related to the surgical procedure from received data can be referred to as "situational awareness." In one exemplification, the surgical hub 5104 can incorporate a situational awareness system, which is the hardware and/or programming associated with the surgical hub 5104 that derives contextual information pertaining to the surgical procedure from the received data.

The situational awareness system of the surgical hub 5104 can be configured to derive the contextual information from the data received from the data sources 5126 in a variety of different ways. In one exemplification, the situational awareness system includes a pattern recognition system, or machine learning system (e.g., an artificial neural network), that has been trained on training data to correlate various inputs (e.g., data from databases 5122, patient monitoring devices 5124, and/or modular devices 5102) to corresponding contextual information regarding a surgical procedure. In other words, a machine learning system can be trained to accurately derive contextual information regarding a surgical procedure from the provided inputs. In another exemplification, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 5102. In one exemplification, the contextual information received by the situational awareness system of the surgical hub 5104 is associated with a particular control adjustment or set of control adjustments for one or more modular devices 5102. In another exemplification, the situational awareness system includes a further machine learning system, lookup table, or other such system, which generates or retrieves one or more control adjustments for one or more modular devices 5102 when provided the contextual information as input.

A surgical hub 5104 incorporating a situational awareness system provides a number of benefits for the surgical system 5100. One benefit includes improving the interpretation of sensed and collected data, which would in turn improve the processing accuracy and/or the usage of the data during the course of a surgical procedure. To return to a previous example, a situationally aware surgical hub 5104 could determine what type of tissue was being operated on; therefore, when an unexpectedly high force to close the surgical instrument's end effector is detected, the situationally aware surgical hub 5104 could correctly ramp up or ramp down the motor of the surgical instrument for the type of tissue.

As another example, the type of tissue being operated can affect the adjustments that are made to the compression rate and load thresholds of a surgical stapling and cutting instrument for a particular tissue gap measurement. A situationally aware surgical hub 5104 could infer whether a surgical procedure being performed is a thoracic or an abdominal procedure, allowing the surgical hub 5104 to determine whether the tissue clamped by an end effector of the surgical stapling and cutting instrument is lung (for a thoracic procedure) or stomach (for an abdominal procedure) tissue. The surgical hub 5104 could then adjust the compression rate and load thresholds of the surgical stapling and cutting instrument appropriately for the type of tissue.

As yet another example, the type of body cavity being operated in during an insufflation procedure can affect the function of a smoke evacuator. A situationally aware surgical hub 5104 could determine whether the surgical site is under pressure (by determining that the surgical procedure is utilizing insufflation) and determine the procedure type. As a procedure type is generally performed in a specific body cavity, the surgical hub 5104 could then control the motor rate of the smoke evacuator appropriately for the body cavity being operated in. Thus, a situationally aware surgical hub 5104 could provide a consistent amount of smoke evacuation for both thoracic and abdominal procedures.

As yet another example, the type of procedure being performed can affect the optimal energy level for an ultrasonic surgical instrument or radio frequency (RF) electrosurgical instrument to operate at. Arthroscopic procedures, for example, require higher energy levels because the end effector of the ultrasonic surgical instrument or RF electrosurgical instrument is immersed in fluid. A situationally aware surgical hub 5104 could determine whether the surgical procedure is an arthroscopic procedure. The surgical hub 5104 could then adjust the RF power level or the ultrasonic amplitude of the generator (i.e., "energy level") to compensate for the fluid filled environment. Relatedly, the type of tissue being operated on can affect the optimal energy level for an ultrasonic surgical instrument or RF electrosurgical instrument to operate at. A situationally aware surgical hub 5104 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 5104 can be configured to adjust the energy level for the ultrasonic surgical instrument or RF electrosurgical instrument throughout the course of a surgical procedure, rather than just on a procedure-by-procedure basis. A situationally aware surgical hub 5104 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

As yet another example, data can be drawn from additional data sources 5126 to improve the conclusions that the surgical hub 5104 draws from one data source 5126. A situationally aware surgical hub 5104 could augment data that it receives from the modular devices 5102 with contextual information that it has built up regarding the surgical procedure from other data sources 5126. For example, a situationally aware surgical hub 5104 can be configured to determine whether hemostasis has occurred (i.e., whether bleeding at a surgical site has stopped) according to video or image data received from a medical imaging device. However, in some cases the video or image data can be inconclusive. Therefore, in one exemplification, the surgical hub 5104 can be further configured to compare a physiologic measurement (e.g., blood pressure sensed by a BP monitor communicably connected to the surgical hub 5104) with the visual or image data of hemostasis (e.g., from a medical imaging device 124 (FIG. 2) communicably coupled to the surgical hub 5104) to make a determination on the integrity of the staple line or tissue weld. In other words, the situational awareness system of the surgical hub 5104 can consider the physiological measurement data to provide additional context in analyzing the visualization data. The additional context can be useful when the visualization data may be inconclusive or incomplete on its own.

Another benefit includes proactively and automatically controlling the paired modular devices 5102 according to the particular step of the surgical procedure that is being performed to reduce the number of times that medical personnel are required to interact with or control the surgical system 5100 during the course of a surgical procedure. For example, a situationally aware surgical hub 5104 could proactively activate the generator to which an RF electrosurgical instrument is connected if it determines that a subsequent step of the procedure requires the use of the instrument. Proactively activating the energy source allows the instrument to be ready for use a soon as the preceding step of the procedure is completed.

As another example, a situationally aware surgical hub 5104 could determine whether the current or subsequent step of the surgical procedure requires a different view or degree of magnification on the display according to the feature(s) at the surgical site that the surgeon is expected to need to view. The surgical hub 5104 could then proactively change the displayed view (supplied by, e.g., a medical imaging device for the visualization system 108) accordingly so that the display automatically adjusts throughout the surgical procedure.

As yet another example, a situationally aware surgical hub 5104 could determine which step of the surgical procedure is being performed or will subsequently be performed and whether particular data or comparisons between data will be required for that step of the surgical procedure. The surgical hub 5104 can be configured to automatically call up data screens based upon the step of the surgical procedure being performed, without waiting for the surgeon to ask for the particular information.

Another benefit includes checking for errors during the setup of the surgical procedure or during the course of the surgical procedure. For example, a situationally aware surgical hub 5104 could determine whether the operating theater is setup properly or optimally for the surgical procedure to be performed. The surgical hub 5104 can be configured to determine the type of surgical procedure being performed, retrieve the corresponding checklists, product location, or setup needs (e.g., from a memory), and then compare the current operating theater layout to the standard layout for the type of surgical procedure that the surgical hub 5104 determines is being performed. In one exemplification, the surgical hub 5104 can be configured to compare the list of items for the procedure (scanned by the scanner 5132 depicted in FIG. 26B, for example) and/or a list of devices paired with the surgical hub 5104 to a recommended or anticipated manifest of items and/or devices for the given surgical procedure. If there are any discontinuities between the lists, the surgical hub 5104 can be configured to provide an alert indicating that a particular modular device 5102, patient monitoring device 5124, and/or other surgical item is missing. In one exemplification, the surgical hub 5104 can be configured to determine the relative distance or position of the modular devices 5102 and patient monitoring devices 5124 via proximity sensors, for example. The surgical hub 5104 can compare the relative positions of the devices to a recommended or anticipated layout for the particular surgical procedure. If there are any discontinuities between the layouts, the surgical hub 5104 can be configured to provide an alert indicating that the current layout for the surgical procedure deviates from the recommended layout.

As another example, a situationally aware surgical hub 5104 could determine whether the surgeon (or other medical personnel) was making an error or otherwise deviating from the expected course of action during the course of a surgical procedure. For example, the surgical hub 5104 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 5104 determined is being performed. In one exemplification, the surgical hub 5104 can be configured to provide an alert indicating that an unexpected action is being performed or an unexpected device is being utilized at the particular step in the surgical procedure.

Overall, the situational awareness system for the surgical hub 5104 improves surgical procedure outcomes by adjusting the surgical instruments (and other modular devices 5102) for the particular context of each surgical procedure (such as adjusting to different tissue types) and validating actions during a surgical procedure. The situational awareness system also improves surgeons' efficiency in performing surgical procedures by automatically suggesting next steps, providing data, and adjusting displays and other modular devices 5102 in the surgical theater according to the specific context of the procedure.

Figure 23A:
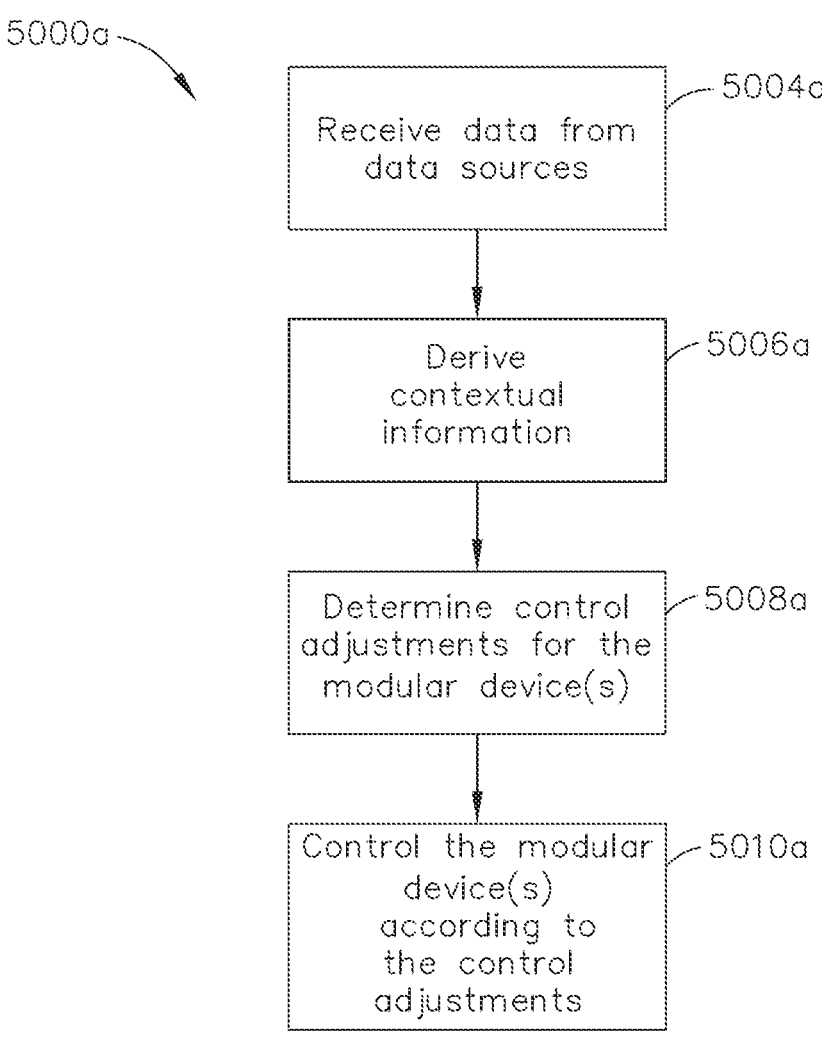
FIG. 23A illustrates a logic flow diagram of a process for controlling a modular device according to contextual information derived from received data, in accordance with at least one aspect of the present disclosure.

FIG. 23A illustrates a logic flow diagram of a process 5000a for controlling a modular device 5102 according to contextual information derived from received data, in accordance with at least one aspect of the present disclosure. In other words, a situationally aware surgical hub 5104 can execute the process 5000a to determine appropriate control adjustments for modular devices 5102 paired with the surgical hub 5104 before, during, or after a surgical procedure as dictated by the context of the surgical procedure. In the following description of the process 5000a, reference should also be made to FIG. 22. In one exemplification, the process 5000a can be executed by a control circuit of a surgical hub 5104, as depicted in FIG. 10 (processor 244). In another exemplification, the process 5000a can be executed by a cloud computing system 104, as depicted in FIG. 1. In yet another exemplification, the process 5000a can be executed by a distributed computing system including at least one of the aforementioned cloud computing system 104 and/or a control circuit of a surgical hub 5104 in combination with a control circuit of a modular device, such as the microcontroller 461 of the surgical instrument depicted in FIG. 12, the microcontroller 620 of the surgical instrument depicted in FIG. 16, the control circuit 710 of the robotic surgical instrument 700 depicted in FIG. 17, the control circuit 760 of the surgical instruments 750, 790 depicted in FIGS. 18 and 19, or the controller 838 of the generator 800 depicted in FIG. 20. For economy, the following description of the process 5000a will be described as being executed by the control circuit of a surgical hub 5104; however, it should be understood that the description of the process 5000a encompasses all of the aforementioned exemplifications.

Figure 26A:
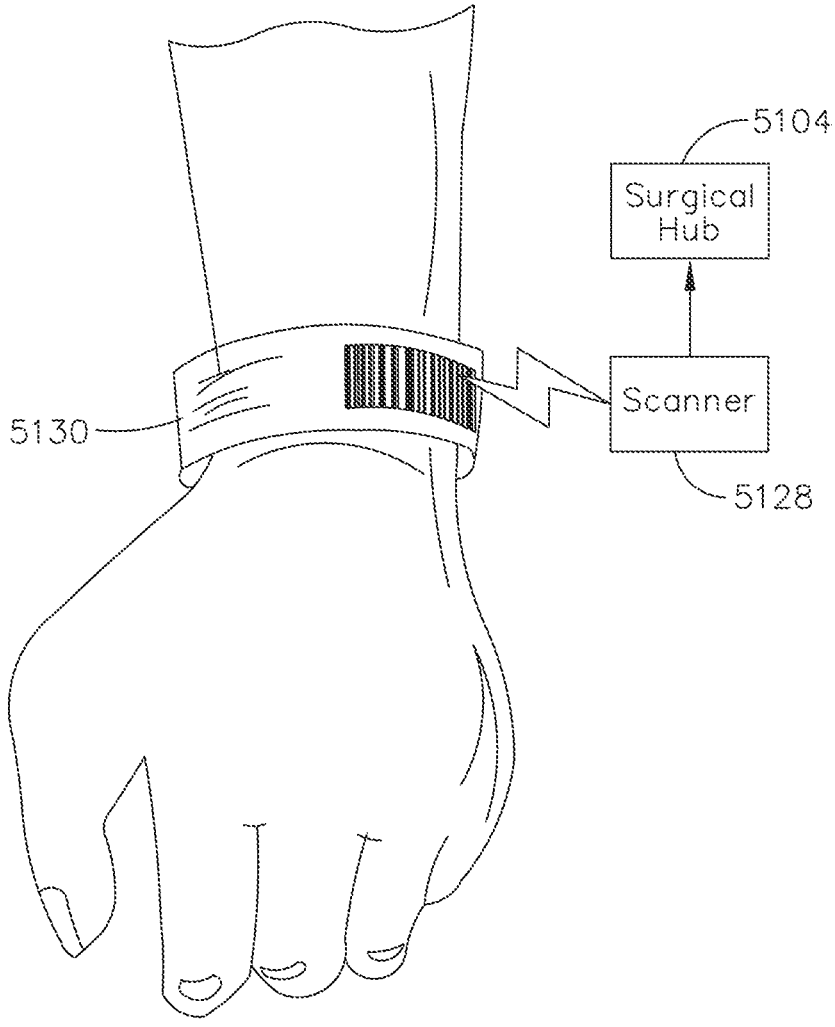
FIG. 26A illustrates a scanner coupled to a surgical hub for scanning a patient wristband, in accordance with at least one aspect of the present disclosure.

The control circuit of the surgical hub 5104 executing the process 5000a receives 5004a data from one or more data sources 5126 to which the surgical hub 5104 is communicably connected. The data sources 5126 include, for example, databases 5122, patient monitoring devices 5124, and modular devices 5102. In one exemplification, the databases 5122 can include a patient EMR database associated with the medical facility at which the surgical procedure is being performed. The data received 5004a from the data sources 5126 can include perioperative data, which includes preoperative data, intraoperative data, and/or postoperative data associated with the given surgical procedure. The data received 5004a from the databases 5122 can include the type of surgical procedure being performed or the patient's medical history (e.g., medical conditions that may or may not be the subject of the present surgical procedure). In one exemplification depicted in FIG. 24A, the control circuit can receive 5004a the patient or surgical procedure data by querying the patient EMR database with a unique identifier associated with the patient. The surgical hub 5104 can receive the unique identifier from, for example, a scanner 5128 for scanning the patient's wristband 5130 encoding the unique identifier associated with the patient when the patient enters the operating theater, as depicted in FIG. 26A. In one exemplification, the patient monitoring devices 5124 include BP monitors, EKG monitors, and other such devices that are configured to monitor one or more parameters associated with a patient. As with the modular devices 5102, the patient monitoring devices 5124 can be paired with the surgical hub 5104 such that the surgical hub 5104 receives 5004a data therefrom. In one exemplification, the data received 5004a from the modular devices 5102 that are paired with (i.e., communicably coupled to) the surgical hub 5104 includes, for example, activation data (i.e., whether the device is powered on or in use), data of the internal state of the modular device 5102 (e.g., force to fire or force to close for a surgical cutting and stapling device, pressure differential for an insufflator or smoke evacuator, or energy level for an RF or ultrasonic surgical instrument), or patient data (e.g., tissue type, tissue thickness, tissue mechanical properties, respiration rate, or airway volume).

As the process 5000a continues, the control circuit of the surgical hub 5104 can derive 5006a contextual information from the data received 5004a from the data sources 5126. The contextual information can include, for example, the type of procedure being performed, the particular step being performed in the surgical procedure, the patient's state (e.g., whether the patient is under anesthesia or whether the patient is in the operating room), or the type of tissue being operated on. The control circuit can derive 5006a contextual information according to data from ether an individual data source 5126 or combinations of data sources 5126. Further, the control circuit can derive 5006a contextual information according to, for example, the type(s) of data that it receives, the order in which the data is received, or particular measurements or values associated with the data. For example, if the control circuit receives data from an RF generator indicating that the RF generator has been activated, the control circuit could thus infer that the RF electrosurgical instrument is now in use and that the surgeon is or will be performing a step of the surgical procedure utilizing the particular instrument. As another example, if the control circuit receives data indicating that a laparoscope imaging device has been activated and an ultrasonic generator is subsequently activated, the control circuit can infer that the surgeon is on a laparoscopic dissection step of the surgical procedure due to the order in which the events occurred. As yet another example, if the control circuit receives data from a ventilator indicating that the patient's respiration is below a particular rate, then the control circuit can determine that the patient is under anesthesia.

The control circuit can then determine 5008a what control adjustments are necessary (if any) for one or more modular devices 5102 according to the derived 5006a contextual information. After determining 5008a the control adjustments, the control circuit of the surgical hub 5104 can then control 5010a the modular devices according to the control adjustments (if the control circuit determined 5008a that any were necessary). For example, if the control circuit determines that an arthroscopic procedure is being performed and that the next step in the procedure utilizes an RF or ultrasonic surgical instrument in a liquid environment, the control circuit can determine 5008a that a control adjustment for the generator of the RF or ultrasonic surgical instrument is necessary to preemptively increase the energy output of the instrument (because such instruments require increased energy in liquid environments to maintain their effectiveness). The control circuit can then control 5010a the generator and/or the RF or ultrasonic surgical instrument accordingly by causing the generator to increase its output and/or causing the RF or ultrasonic surgical instrument to increase the energy drawn from the generator. The control circuit can control 5010a the modular devices 5102 according to the determined 5008a control adjustment by, for example, transmitting the control adjustments to the particular modular device to update the modular device's 5102 programming. In another exemplification wherein the modular device(s) 5102 and the surgical hub 5104 are executing a distributed computing architecture, the control circuit can control 5010a the modular device 5102 according to the determined 5008a control adjustments by updating the distributed program.

Figure 23B:
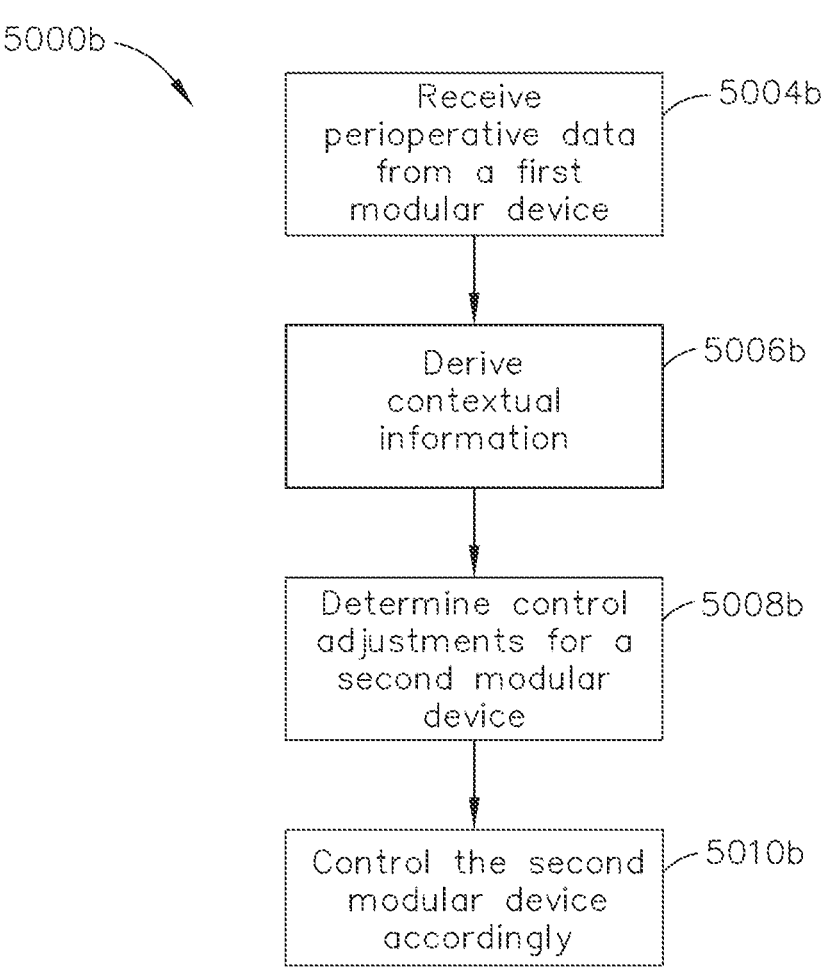
FIG. 23B illustrates a logic flow diagram of a process for controlling a second modular device according to contextual information derived from perioperative data received from a first modular device, in accordance with at least one aspect of the present disclosure.
Figure 23C:
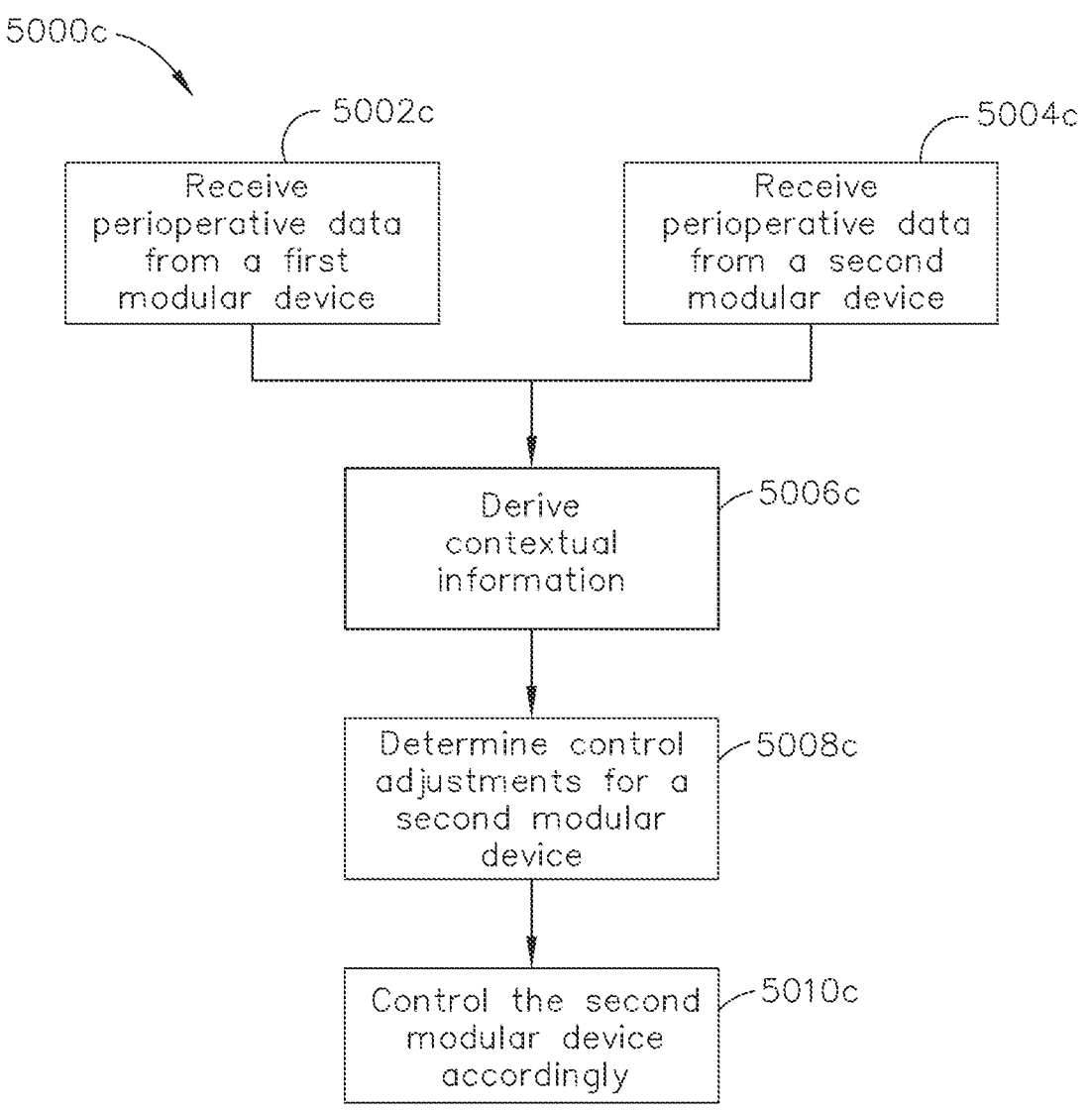
FIG. 23C illustrates a logic flow diagram of a process for controlling a second modular device according to contextual information derived from perioperative data received from a first modular device and the second modular device, in accordance with at least one aspect of the present disclosure.
Figure 23D:
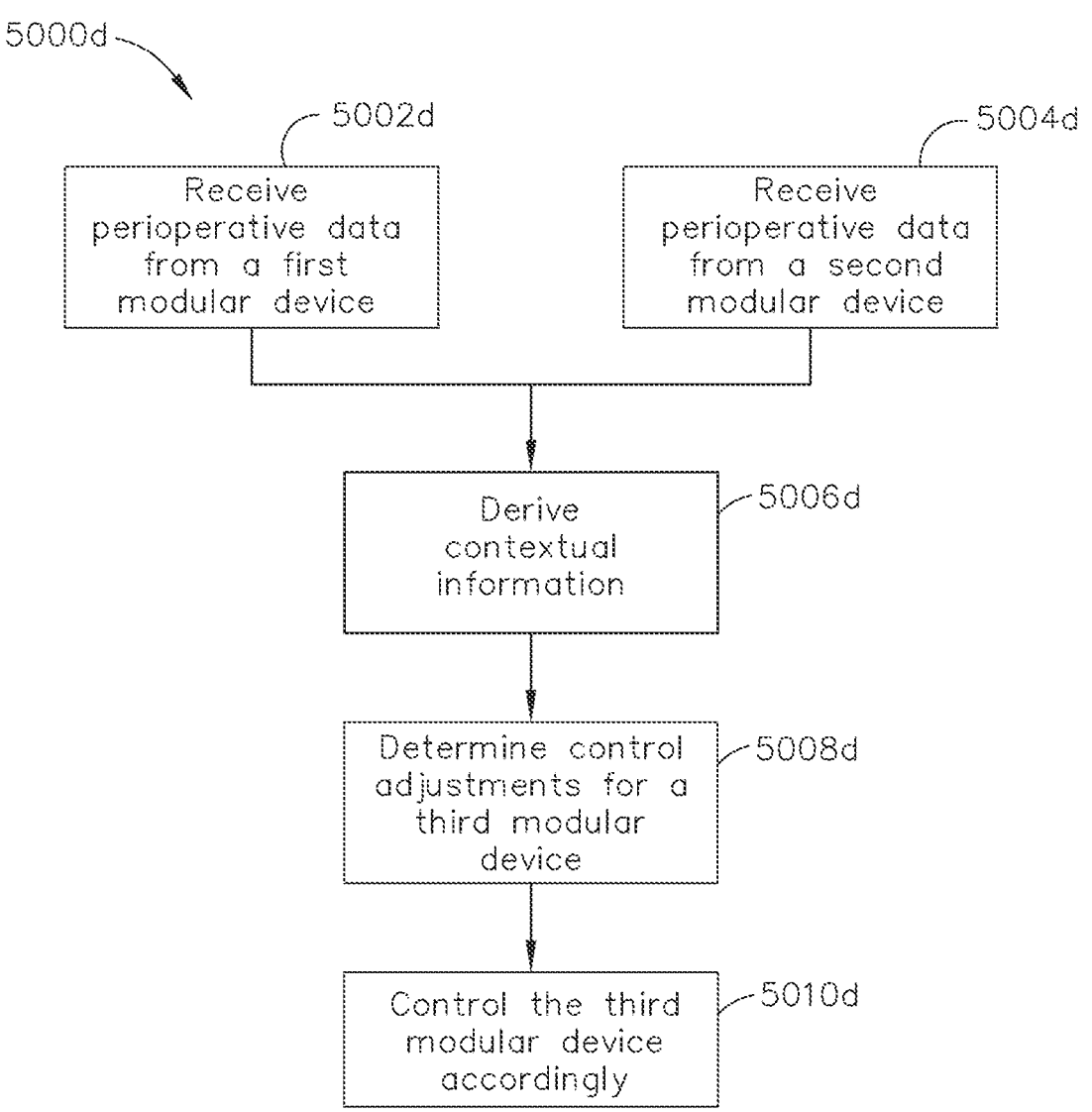
FIG. 23D illustrates a logic flow diagram of a process for controlling a third modular device according to contextual information derived from perioperative data received from a first modular device and a second modular device, in accordance with at least one aspect of the present disclosure.

FIGS. 23B-D illustrate representative implementations of the process 5000a depicted in FIG. 23A. As with the process 5000a depicted in FIG. 23A, the processes illustrated in FIGS. 23B-D can, in one exemplification, be executed by a control circuit of the surgical hub 5104. FIG. 23B illustrates a logic flow diagram of a process 5000b for controlling a second modular device according to contextual information derived from perioperative data received from a first modular device, in accordance with at least one aspect of the present disclosure. In the illustrated exemplification, the control circuit of the surgical hub 5104 receives 5004b perioperative data from a first modular device. The perioperative data can include, for example, data regarding the modular device 5102 itself (e.g., pressure differential, motor current, internal forces, or motor torque) or data regarding the patient with which the modular device 5102 is being utilized (e.g., tissue properties, respiration rate, airway volume, or laparoscopic image data). After receiving 5004b the perioperative data, the control circuit of the surgical hub 5104 derives 5006b contextual information from the perioperative data. The contextual information can include, for example, the procedure type, the step of the procedure being performed, or the status of the patient. The control circuit of the surgical hub 5104 then determines 5008b control adjustments for a second modular device based upon the derived 5006b contextual information and then controls 5010b the second modular device accordingly. For example, the surgical hub 5104 can receive 5004b perioperative data from a ventilator indicating that the patient's lung has been deflated, derive 5006b the contextual information therefrom that the subsequent step in the particular procedure type utilizes a medical imaging device (e.g., a scope), determine 5008b that the medical imaging device should be activated and set to a particular magnification, and then control 5010b the medical imaging device accordingly.

FIG. 23C illustrates a logic flow diagram of a process 5000c for controlling a second modular device according to contextual information derived from perioperative data received from a first modular device and the second modular device. In the illustrated exemplification, the control circuit of the surgical hub 5104 receives 5002c perioperative data from a first modular device and receives 5004c perioperative data from a second modular device. After receiving 5002c, 5004c the perioperative data, the control circuit of the surgical hub 5104 derives 5006c contextual information from the perioperative data. The control circuit of the surgical hub 5104 then determines 5008c control adjustments for the second modular device based upon the derived 5006c contextual information and then controls 5010c the second modular device accordingly. For example, the surgical hub 5104 can receive 5002c perioperative data from a RF electrosurgical instrument indicating that the instrument has been fired, receive 5004c perioperative data from a surgical stapling instrument indicating that the instrument has been fired, derive 5006c the contextual information therefrom that the subsequent step in the particular procedure type requires that the surgical stapling instrument be fired with a particular force (because the optimal force to fire can vary according to the tissue type being operated on), determine 5008c the particular force thresholds that should be applied to the surgical stapling instrument, and then control 5010c the surgical stapling instrument accordingly.

FIG. 23D illustrates a logic flow diagram of a process 5000d for controlling a third modular device according to contextual information derived from perioperative data received from a first modular device and a second modular device. In the illustrated exemplification, the control circuit of the surgical hub 5104 receives 5002d perioperative data from a first modular device and receives 5004d perioperative data from a second modular device. After receiving 5002d, 5004d the perioperative data, the control circuit of the surgical hub 5104 derives 5006d contextual information from the perioperative data. The control circuit of the surgical hub 5104 then determines 5008d control adjustments for a third modular device based upon the derived 5006d contextual information and then controls 5010d the third modular device accordingly. For example, the surgical hub 5104 can receive 5002d, 5004d perioperative data from an insufflator and a medical imaging device indicating that both devices have been activated and paired to the surgical hub 5104, derive 5006d the contextual information therefrom that a video-assisted thoracoscopic surgery (VATS) procedure is being performed, determine 5008d that the displays connected to the surgical hub 5104 should be set to display particular views or information associated with the procedure type, and then control 5010d the displays accordingly.

Figure 24A:
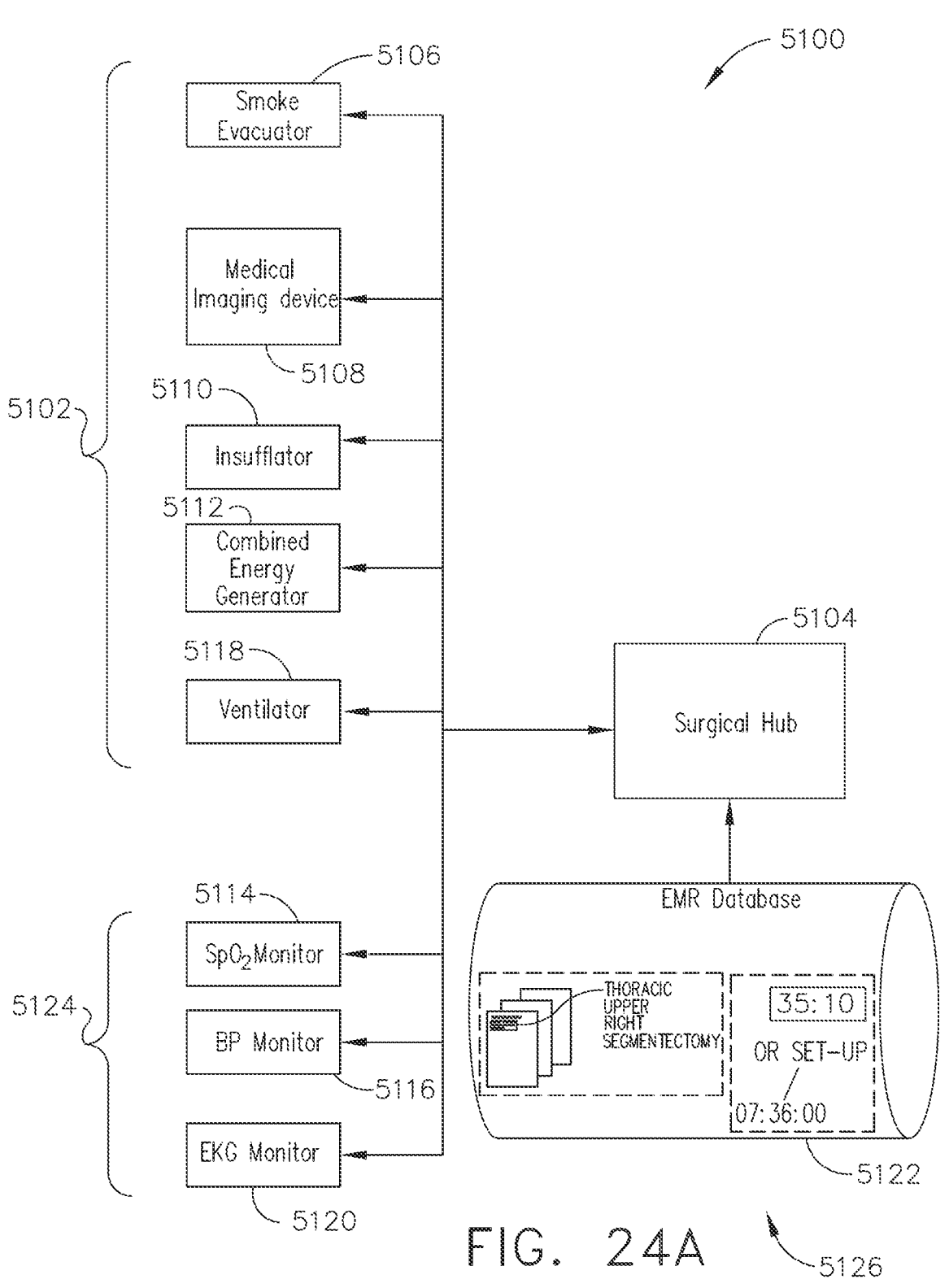
FIG. 24A illustrates a diagram of a surgical hub communicably coupled to a particular set of modular devices and an Electronic Medical Record (EMR) database, in accordance with at least one aspect of the present disclosure.

FIG. 24A illustrates a diagram of a surgical system 5100 including a surgical hub 5104 communicably coupled to a particular set of data sources 5126. A surgical hub 5104 including a situational awareness system can utilize the data received from the data sources 5126 to derive contextual information regarding the surgical procedure that the surgical hub 5104, the modular devices 5102 paired to the surgical hub 5104, and the patient monitoring devices 5124 paired to the surgical hub 5104 are being utilized in connection with. The inferences (i.e., contextual information) that one exemplification of the situational awareness system can derive from the particular set of data sources 5126 are depicted in dashed boxes extending from the data source(s) 5126 from which they are derived. The contextual information derived from the data sources 5126 can include, for example, what step of the surgical procedure is being performed, whether and how a particular modular device 5102 is being used, and the patient's condition.

In the example illustrated in FIG. 24A, the data sources 5126 include a database 5122, a variety of modular devices 5102, and a variety of patient monitoring devices 5124. The surgical hub 5104 can be connected to various databases 5122 to retrieve therefrom data regarding the surgical procedure that is being performed or is to be performed. In one exemplification of the surgical system 5100, the databases 5122 include an EMR database of a hospital. The data that can be received by the situational awareness system of the surgical hub 5104 from the databases 5122 can include, for example, start (or setup) time or operational information regarding the procedure (e.g., a segmentectomy in the upper right portion of the thoracic cavity). The surgical hub 5104 can derive contextual information regarding the surgical procedure from this data alone or from the combination of this data and data from other data sources 5126.

The surgical hub 5104 can also be connected to (i.e., paired with) a variety of patient monitoring devices 5124. In one exemplification of the surgical system 5100, the patient monitoring devices 5124 that can be paired with the surgical hub 5104 can include a pulse oximeter (SpO$_2$ monitor) 5114, a BP monitor 5116, and an EKG monitor 5120. The perioperative data that can be received by the situational awareness system of the surgical hub 5104 from the patient monitoring devices 5124 can include, for example, the patient's oxygen saturation, blood pressure, heart rate, and other physiological parameters. The contextual information that can be derived by the surgical hub 5104 from the perioperative data transmitted by the patient monitoring devices 5124 can include, for example, whether the patient is located in the operating theater or under anesthesia. The surgical hub 5104 can derive these inferences from data from the patient monitoring devices 5124 alone or in combination with data from other data sources 5126 (e.g., the ventilator 5118).

The surgical hub 5104 can also be connected to (i.e., paired with) a variety of modular devices 5102. In one exemplification of the surgical system 5100, the modular devices 5102 that can be paired with the surgical hub 5104 can include a smoke evacuator 5106, a medical imaging device 5108, an insufflator 5110, a combined energy generator 5112 (for powering an ultrasonic surgical instrument and/or an RF electrosurgical instrument), and a ventilator 5118.

The medical imaging device 5108 includes an optical component and an image sensor that generates image data. The optical component includes a lens or a light source, for example. The image sensor includes a charge-coupled device (CCD) or a complementary metal-oxide-semiconductor (CMOS), for example. In various exemplifications, the medical imaging device 5108 includes an endoscope, a laparoscope, a thoracoscope, and other such imaging devices. Various additional components of the medical imaging device 5108 are described above. The perioperative data that can be received by the surgical hub 5104 from the medical imaging device 5108 can include, for example, whether the medical imaging device 5108 is activated and a video or image feed. The contextual information that can be derived by the surgical hub 5104 from the perioperative data transmitted by the medical imaging device 5108 can include, for example, whether the procedure is a VATS procedure (based on whether the medical imaging device 5108 is activated or paired to the surgical hub 5104 at the beginning or during the course of the procedure). Furthermore, the image or video data from the medical imaging device 5108 (or the data stream representing the video for a digital medical imaging device 5108) can processed by a pattern recognition system or a machine learning system to recognize features (e.g., organs or tissue types) in the field of view (FOV) of the medical imaging device 5108, for example. The contextual information that can be derived by the surgical hub 5104 from the recognized features can include, for example, what type of surgical procedure (or step thereof) is being performed, what organ is being operated on, or what body cavity is being operated in.

Figure 24B:
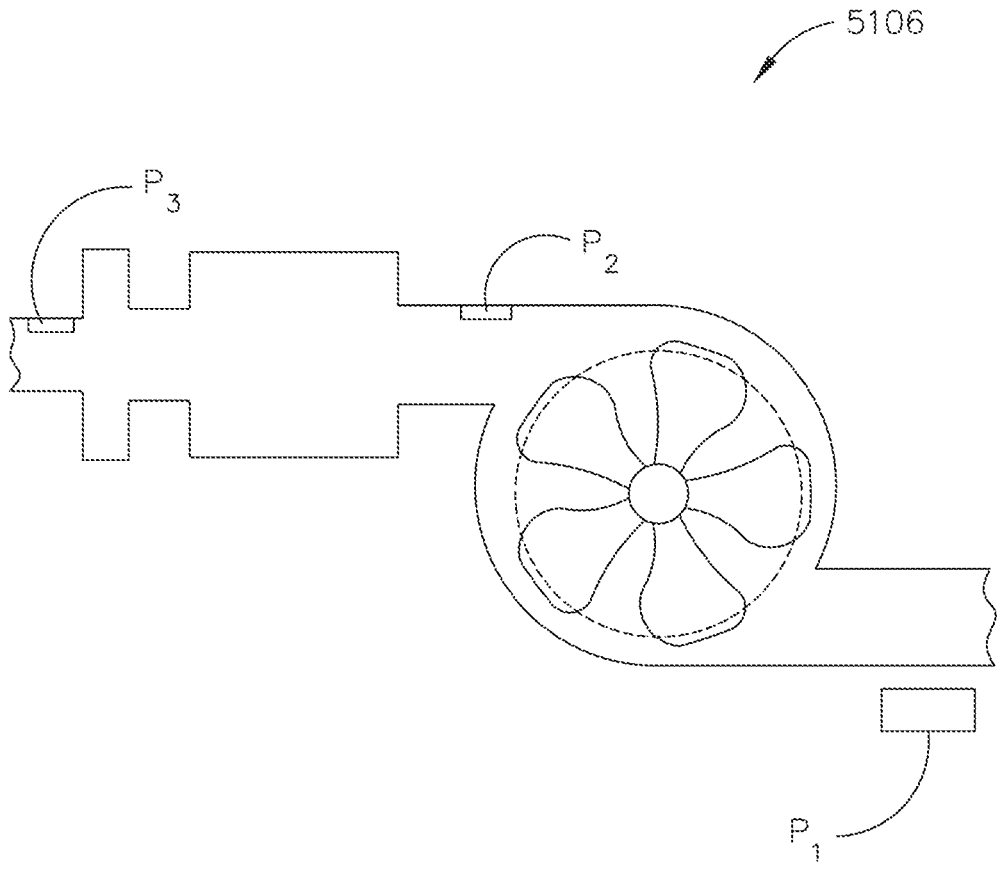
FIG. 24B illustrates a diagram of a smoke evacuator including pressure sensors, in accordance with at least one aspect of the present disclosure.

In one exemplification depicted in FIG. 24B, the smoke evacuator 5106 includes a first pressure sensor $P_1$ configured to detect the ambient pressure in the operating theater, a second pressure sensor $P_2$ configured to detect the internal downstream pressure (i.e., the pressure downstream from the inlet), and a third pressure sensor $P_3$ configured to detect the internal upstream pressure. In one exemplification, the first pressure sensor $P_1$ can be a separate component from the smoke evacuator 5106 or otherwise located externally to the smoke evacuator 5106. The perioperative data that can be received by the surgical hub 5104 from the smoke evacuator 5106 can include, for example, whether the smoke evacuator 5106 is activated, pressure readings from each of the sensors $P_1$, $P_2$, $P_3$, and pressure differentials between pairs of the sensors $P_1$, $P_2$, $P_3$. The perioperative data can also include, for example, the type of tissue being operated on (based upon the chemical composition of the smoke being evacuated) and the amount of tissue being cut. The contextual information that can be derived by the surgical hub 5104 from the perioperative data transmitted by the smoke evacuator 5106 can include, for example, whether the procedure being performed is utilizing insufflation. The smoke evacuator 5106 perioperative data can indicate whether the procedure is utilizing insufflation according to the pressure differential between $P_3$ and $P_1$. If the pressure sensed by $P_3$ is greater than the pressure sensed by $P_1$ (i.e., $P_3–P_1>0$), then the body cavity to which the smoke evacuator 5106 is connected is insufflated. If the pressure sensed by $P_3$ is equal to the pressure sensed by $P_1$ (i.e., $P_3–P_1=0$), then the body cavity is not insufflated. When the body cavity is not insufflated, the procedure may be an open type of procedure.

The insufflator 5110 can include, for example, pressure sensors and current sensors configured to detect internal parameters of the insufflator 5110. The perioperative data that can be received by the surgical hub 5104 from the insufflator can include, for example, whether the insufflator 5110 is activated and the electrical current drawn by the insufflator's 5110 pump. The surgical hub 5104 can determine whether the insufflator 5110 is activated by, for example, directly detecting whether the device is powered on, detecting whether there is a pressure differential between an ambient pressure sensor and a pressure sensor internal to the surgical site, or detecting whether the pressure valves of the insufflator 5110 are pressurized (activated) or non-pressurized (deactivated). The contextual information that can be derived by the surgical hub 5104 from the perioperative data transmitted by the insufflator 5110 can include, for example, the type of procedure being performed (e.g., insufflation is utilized in laparoscopic procedures, but not arthroscopic procedures) and what body cavity is being operated in (e.g., insufflation is utilized in the abdominal cavity, but not in the thoracic cavity). In some exemplifications, the inferences derived from the perioperative data received from different modular devices 5102 can be utilized to confirm and/or increase the confidence of prior inferences. For example, if the surgical hub 5104 determines that the procedure is utilizing insufflation because the insufflator 5110 is activated, the surgical hub 5104 can then confirm that inference by detecting whether the perioperative data from the smoke evacuator 5106 likewise indicates that the body cavity is insufflated.

The combined energy generator 5112 supplies energy to one or more ultrasonic surgical instruments or RF electrosurgical instruments connected thereto. The perioperative data that can be received by the surgical hub 5104 from the combined energy generator 5112 can include, for example, the mode that the combined energy generator 5112 is set to (e.g., a vessel sealing mode or a cutting/coagulation mode). The contextual information that can be derived by the surgical hub 5104 from the perioperative data transmitted by the combined energy generator 5112 can include, for example, the surgical procedural type (based on the number and types of surgical instruments that are connected to the energy generator 5112) and the procedural step that is being performed (because the particular surgical instrument being utilized or the particular order in which the surgical instruments are utilized corresponds to different steps of the surgical procedure). Further, the inferences derived by the surgical hub 5104 can depend upon inferences and/or perioperative data previously received by the surgical hub 5104. Once the surgical hub 5104 has determined the general category or specific type of surgical procedure being performed, the surgical hub 5104 can determine or retrieve an expected sequence of steps for the surgical procedure and then track the surgeon's progression through the surgical procedure by comparing the detected sequence in which the surgical instruments are utilized relative to the expected sequence.

The perioperative data that can be received by the surgical hub 5104 from the ventilator 5118 can include, for example, the respiration rate and airway volume of the patient. The contextual information that can be derived by the surgical hub 5104 from the perioperative data transmitted by the ventilator 5118 can include, for example, whether the patient is under anesthesia and whether the patient's lung is deflated. In some exemplifications, certain contextual information can be inferred by the surgical hub 5104 based on combinations of perioperative data from multiple data sources 5126. For example, the situational awareness system of the surgical hub 5104 can be configured to infer that the patient is under anesthesia when the respiration rate detected by the ventilator 5118, the blood pressure detected by the BP monitor 5116, and the heart rate detected by the EKG monitor 5120 fall below particular thresholds. For certain contextual information, the surgical hub 5104 can be configured to only derive a particular inference when the perioperative data from a certain number or all of the relevant data sources 5126 satisfy the conditions for the inference.

As can be seen from the particular exemplified surgical system 5100, the situational awareness system of a surgical hub 5104 can derive a variety of contextual information regarding the surgical procedure being performed from the data sources 5126. The surgical hub 5104 can utilize the derived contextual information to control the modular devices 5102 and make further inferences about the surgical procedure in combination with data from other data sources

5126. It should be noted that the inferences depicted in FIG. 24A and described in connection with the depicted surgical system 5100 are merely exemplary and should not be interpreted as limiting in any way. Furthermore, the surgical hub 5104 can be configured to derive a variety of other inferences from the same (or different) modular devices 5102 and/or patient monitoring devices 5124. In other exemplifications, a variety of other modular devices 5102 and/or patient monitoring devices 5124 can be paired to the surgical hub 5104 in the operating theater and data received from those additional modular devices 5102 and/or patient monitoring devices 5124 can be utilized by the surgical hub 5104 to derive the same or different contextual information about the particular surgical procedure being performed.

Figure 25A:
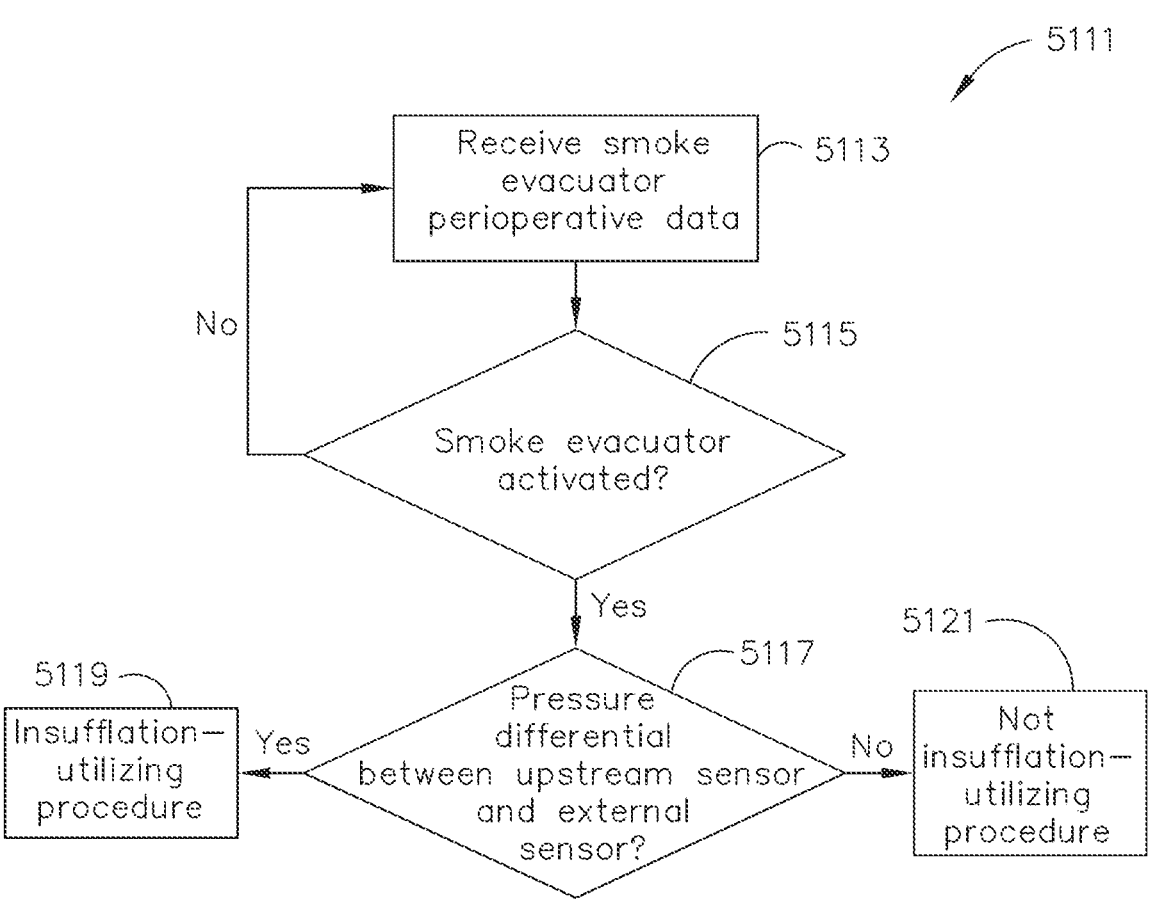
FIG. 25A illustrates a logic flow diagram of a process for determining a procedure type according to smoke evacuator perioperative data, in accordance with at least one aspect of the present disclosure.
Figure 25B:
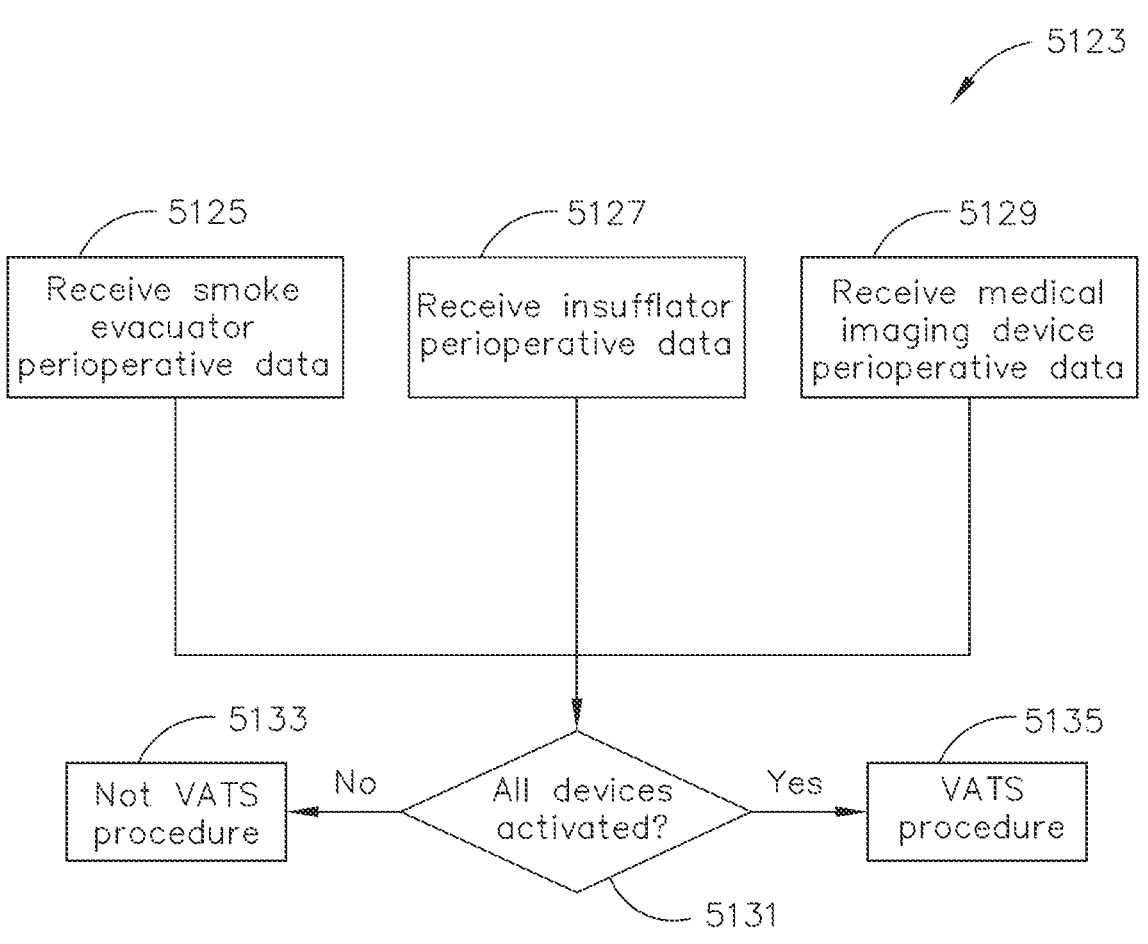
FIG. 25B illustrates a logic flow diagram of a process for determining a procedure type according to smoke evacuator, insufflator, and medical imaging device perioperative data, in accordance with at least one aspect of the present disclosure.
Figure 25C:
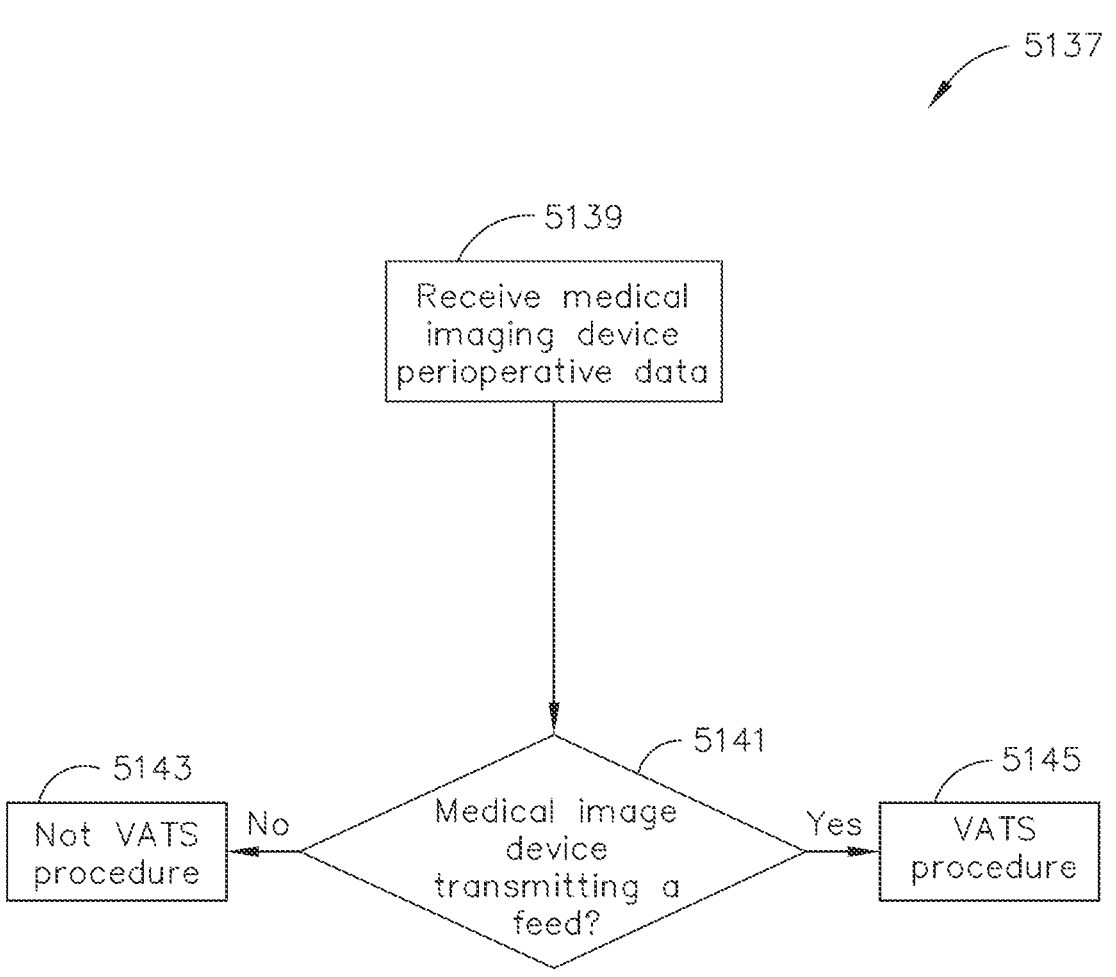
FIG. 25C illustrates a logic flow diagram of a process for determining a procedure type according to medical imaging device perioperative data, in accordance with at least one aspect of the present disclosure.
Figure 25D:
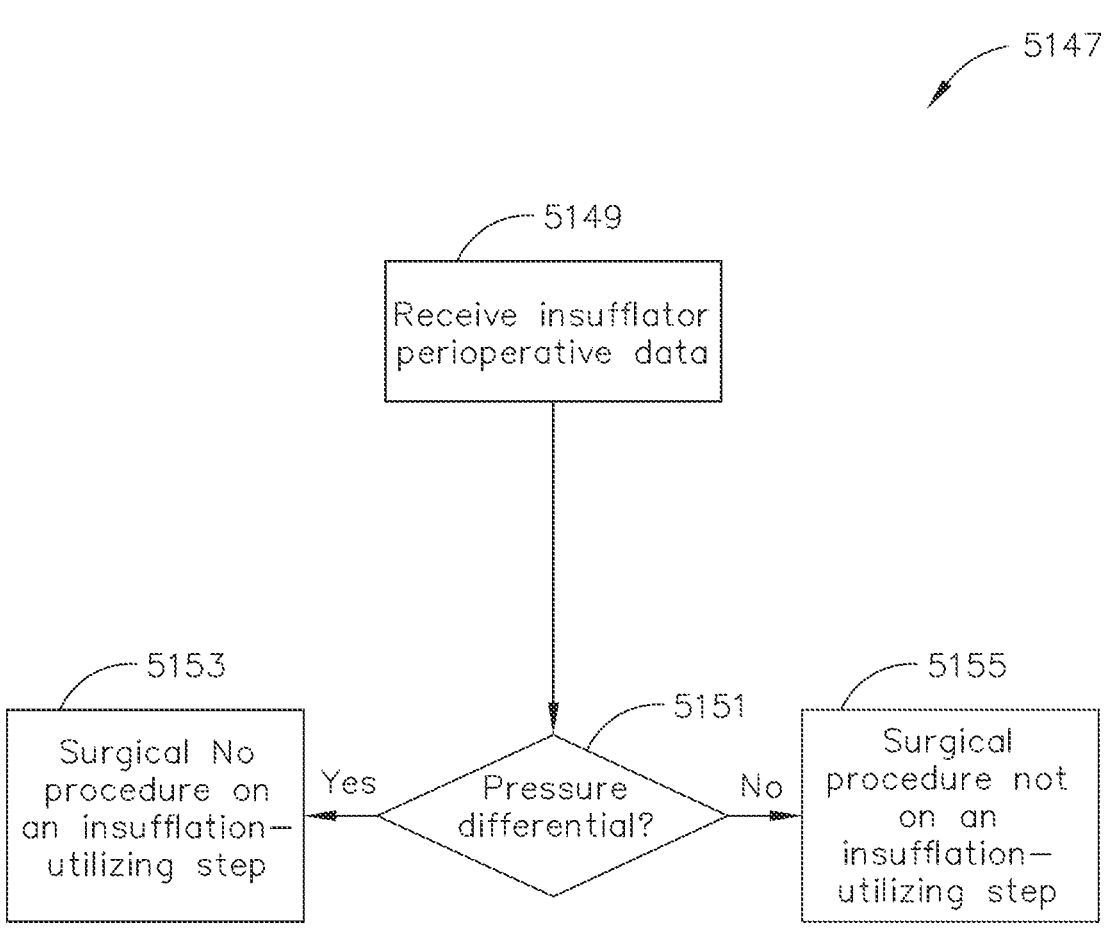
FIG. 25D illustrates a logic flow diagram of a process for determining a procedural step according to insufflator perioperative data, in accordance with at least one aspect of the present disclosure.
Figure 25E:
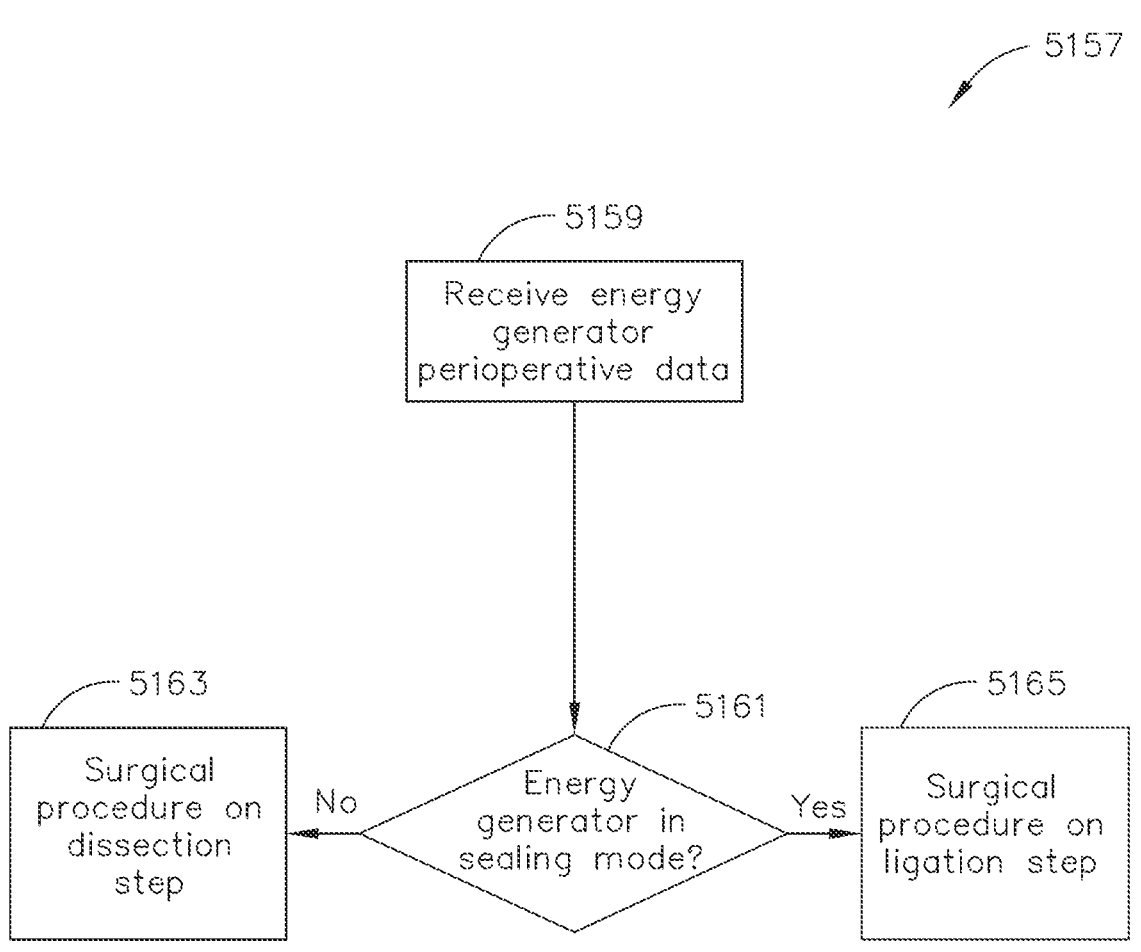
FIG. 25E illustrates a logic flow diagram of a process for determining a procedural step according to energy generator perioperative data, in accordance with at least one aspect of the present disclosure.
Figure 25F:
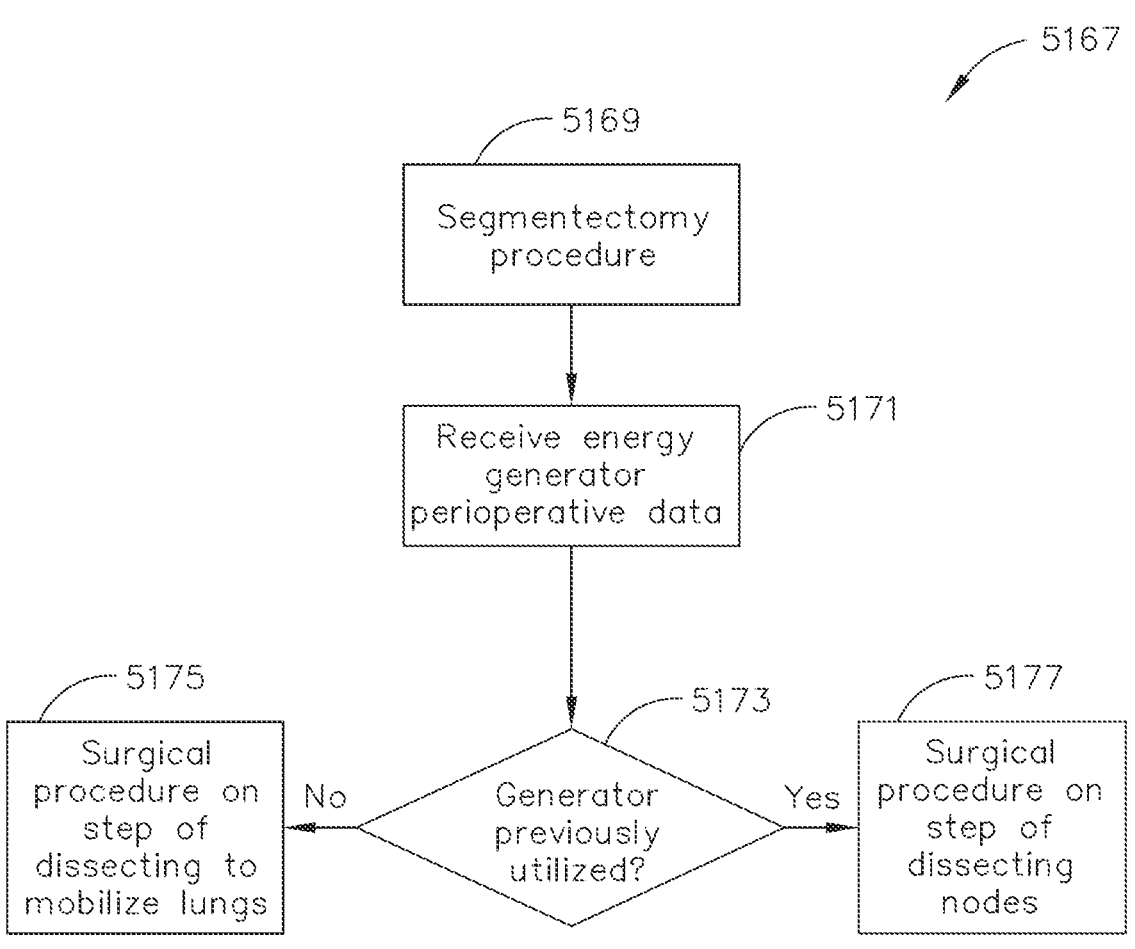
FIG. 25F illustrates a logic flow diagram of a process for determining a procedural step according to energy generator perioperative data, in accordance with at least one aspect of the present disclosure.
Figure 25G:
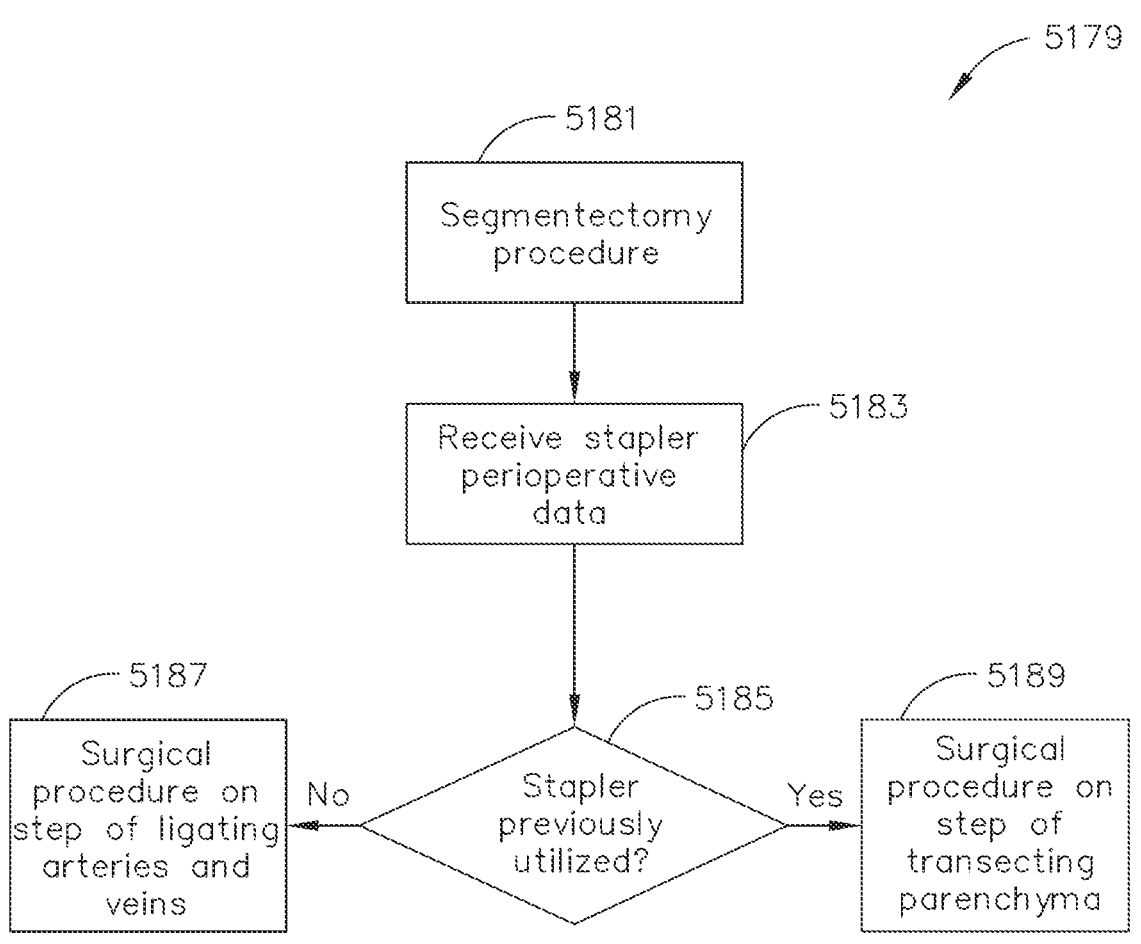
FIG. 25G illustrates a logic flow diagram of a process for determining a procedural step according to stapler perioperative data, in accordance with at least one aspect of the present disclosure.
Figure 25H:
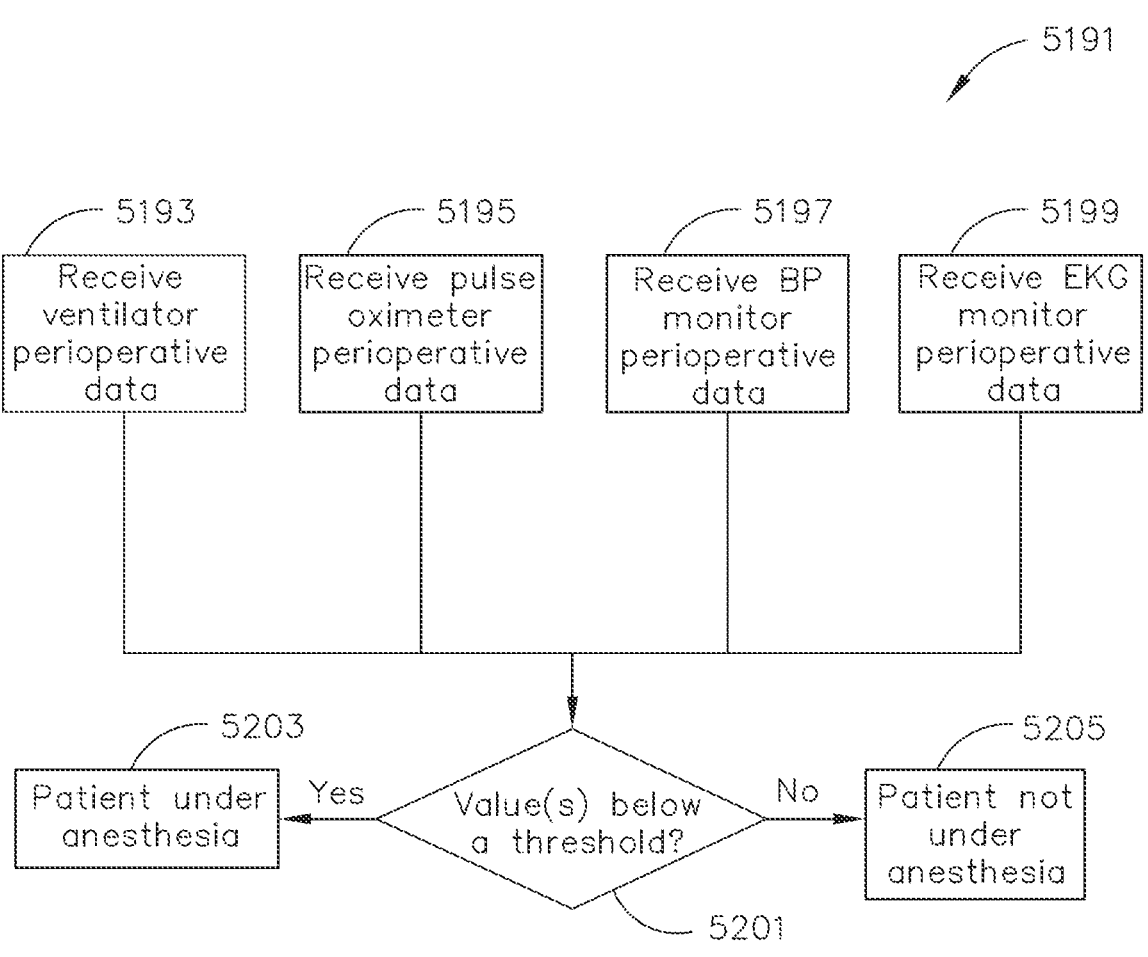
FIG. 25H illustrates a logic flow diagram of a process for determining a patient status according to ventilator, pulse oximeter, blood pressure monitor, and/or EKG monitor perioperative data, in accordance with at least one aspect of the present disclosure.
Figure 25I:
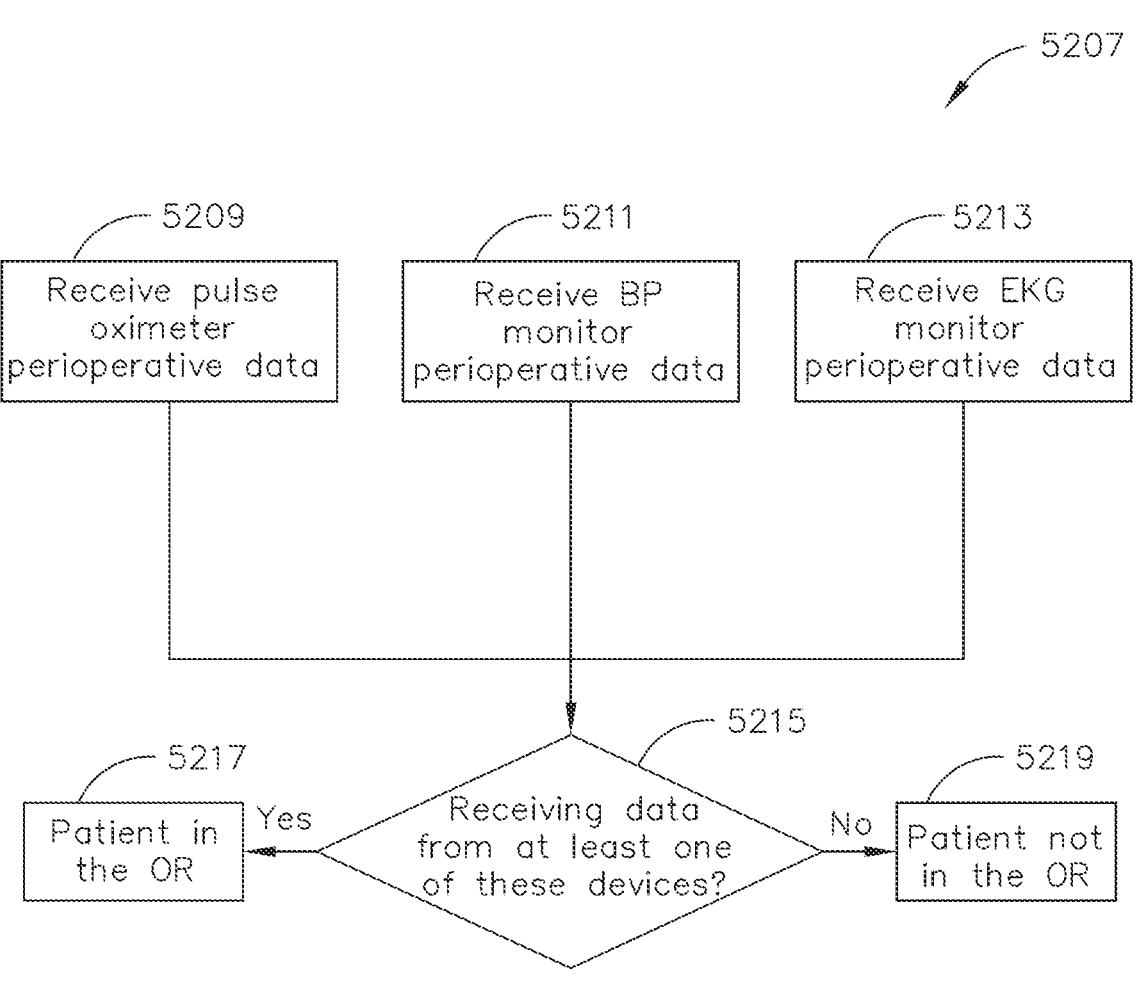
FIG. 25I illustrates a logic flow diagram of a process for determining a patient status according to pulse oximeter, blood pressure monitor, and/or EKG monitor perioperative data, in accordance with at least one aspect of the present disclosure.
Figure 25J:
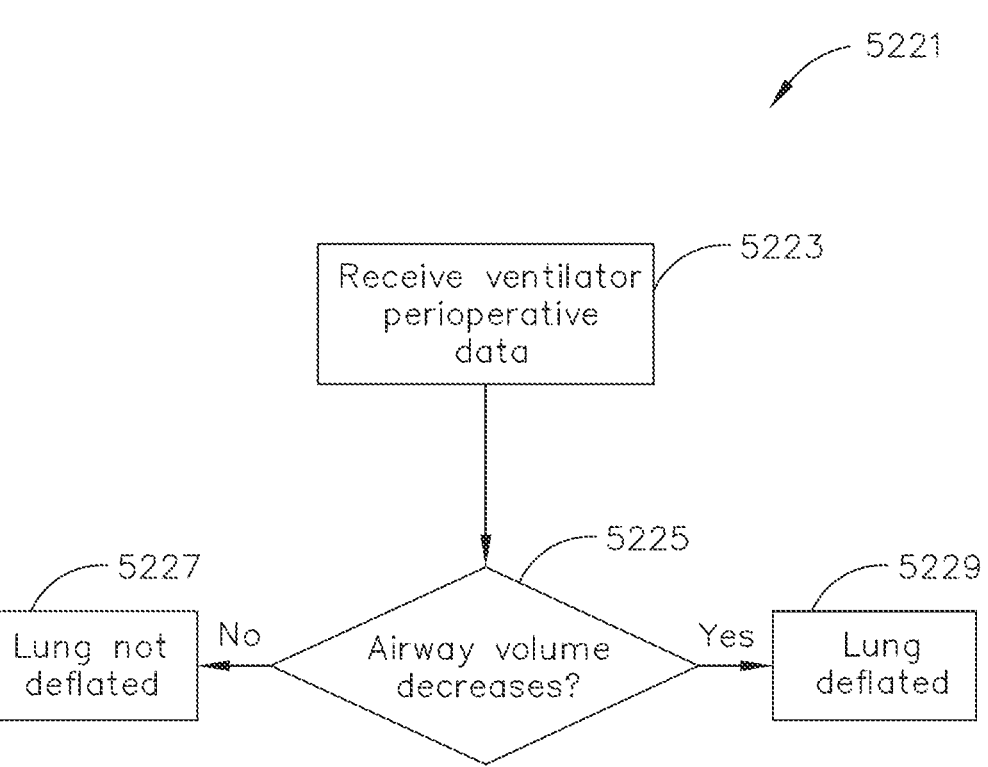
FIG. 25J illustrates a logic flow diagram of a process for determining a patient status according to ventilator perioperative data, in accordance with at least one aspect of the present disclosure.

FIGS. 25A-J depict logic flow diagrams for processes for deriving 5008a, 5008b, 5008c, 5008d contextual information from various modular devices, as discussed above with respect to the processes 5000a, 5000b, 5000c, 5000d depicted in FIGS. 23A-D. The derived contextual information in FIGS. 25A-C is the procedure type. The procedure type can correspond to techniques utilized during the surgical procedure (e.g., a segmentectomy), the category of the surgical procedure (e.g., a laparoscopic procedure), the organ, tissue, or other structure being operated on, and other characteristics to identify the particular surgical procedure (e.g., the procedure utilizes insufflation). The derived contextual information in FIGS. 25D-G is the particular step of the surgical procedure that is being performed. The derived contextual information in FIGS. 25H-J is the patient's status. It can be noted that the patient's status can also correspond to the particular step of the surgical procedure that is being performed (e.g., determining that the patient's status has changed from not being under anesthesia to being under anesthesia can indicate that the step of the surgical procedure of placing the patient under anesthesia was carried out by the surgical staff). As with the process 5000a depicted in FIG. 23A, the processes illustrated in FIGS. 25A-J can, in one exemplification, be executed by a control circuit of the surgical hub 5104. In the following descriptions of the processes illustrated in FIGS. 25A-J, reference should also be made to FIG. 24A.

FIG. 25A illustrates a logic flow diagram of a process 5111 for determining a procedure type according to smoke evacuator 5106 perioperative data. In this exemplification, the control circuit of the surgical hub 5104 executing the process 5111 receives 5113 perioperative data from the smoke evacuator 5106 and then determines 5115 whether the smoke evacuator 5106 is activated based thereon. If the smoke evacuator 5106 is not activated, then the process 5111 continues along the NO branch and the control circuit of the surgical hub 5104 continues monitoring for the receipt of smoke evacuator 5106 perioperative data. If the smoke evacuator 5106 is activated, then the process 5111 continues along the YES branch and the control circuit of the surgical hub 5104 determines 5117 whether there is a pressure differential between an internal upstream pressure sensor $P_3$ (FIG. 24B) and an external or ambient pressure sensor $P_1$ (FIG. 24B). If there is a pressure differential (i.e., the internal upstream pressure of the smoke evacuator 5106 is greater then the ambient pressure of the operating theater), then the process 5111 continues along the YES branch and the control circuit determines 5119 that the surgical procedure is an insufflation-utilizing procedure. If there is not a pressure differential, then the process 5111 continues along the NO branch and the control circuit determines 5121 that the surgical procedure is not an insufflation-utilizing procedure.

FIG. 25B illustrates a logic flow diagram of a process 5123 for determining a procedure type according to smoke evacuator 5106, insufflator 5110, and medical imaging device 5108 perioperative data. In this exemplification, the control circuit of the surgical hub 5104 executing the process 5123 receives 5125, 5127, 5129 perioperative data from the smoke evacuator 5106, insufflator 5110, and medical imaging device 5108 and then determines 5131 whether all of the devices are activated or paired with the surgical hub 5104. If all of these devices are not activated or paired with the surgical hub 5104, then the process 5123 continues along the NO branch and the control circuit determines 5133 that the surgical procedure is not a VATS procedure. If all of the aforementioned devices are activated or paired with the surgical hub 5104, then the process 5123 continues along the YES branch and the control circuit determines 5135 that the surgical procedure is a VATS procedure. The control circuit can make this determination based upon the fact that al of these devices are required for a VATS procedure; therefore, if not all of these devices are being utilized in the surgical procedure, it cannot be a VATS procedure.

FIG. 25C illustrates a logic flow diagram of a process 5137 for determining a procedure type according to medical imaging device 5108 perioperative data. In this exemplification, the control circuit of the surgical hub 5104 executing the process 5137 receives 5139 perioperative data from the medical imaging device 5108 and then determines 5141 whether the medical imaging device 5108 is transmitting an image or video feed. If the medical imaging device 5108 is not transmitting an image or video feed, then the process 5137 continues along the NO branch and the control circuit determines 5143 that the surgical procedure is not a VATS procedure. If the medical imaging device 5108 is not transmitting an image or video feed, then the process 5137 continues along the YES branch and the control circuit determines 5145 that the surgical procedure is a VATS procedure. In one exemplification, the control circuit of the surgical hub 5104 can execute the process 5137 depicted in FIG. 25C in combination with the process 5123 depicted in FIG. 25B in order to confirm or increase the confidence in the contextual information derived by both processes 5123, 5137. If there is a discontinuity between the determinations of the processes 5123, 5137 (e.g., the medical imaging device 5108 is transmitting a feed, but not all of the requisite devices are paired with the surgical hub 5104), then the surgical hub 5104 can execute additional processes to come to a final determination that resolves the discontinuities between the processes 5123, 5137 or display an alert or feedback to the surgical staff as to the discontinuity.

FIG. 25D illustrates a logic flow diagram of a process 5147 for determining a procedural step according to insufflator 5110 perioperative data. In this exemplification, the control circuit of the surgical hub 5104 executing the process 5147 receives 5149 perioperative data from the insufflator 5110 and then determines 5151 whether there is a pressure differential between the surgical site and the ambient environment of the operating theater. In one exemplification, the insufflator 5110 perioperative data can include a surgical site pressure (e.g., the intra-abdominal pressure) sensed by a first pressure sensor associated with the insufflator 5110, which can be compared against a pressure sensed by a second pressure sensor configured to detect the ambient pressure. The first pressure sensor can be configured to detect an intra-abdominal pressure between 0-10 mmHg, for example. If there is a pressure differential, then the process 5147 continues along the YES branch and the control circuit determines 5153 that an insufflation-utilizing step of the surgical procedure is being performed. If there is not a pressure differential, then the process 5147 continues along the NO branch and the control circuit determines 5155 that an insufflation-utilizing step of the surgical procedure is not being performed.

FIG. 25E illustrates a logic flow diagram of a process 5157 for determining a procedural step according to energy generator 5112 perioperative data. In this exemplification, the control circuit of the surgical hub 5104 executing the process 5157 receives 5159 perioperative data from the energy generator 5112 and then determines 5161 whether the energy generator 5112 is in the sealing mode. In various exemplifications, the energy generator 5112 can include two modes: a sealing mode corresponding to a first energy level and a cut/coagulation mode corresponding to a second energy level. If the energy generator 5112 is not in the sealing mode, then the process 5157 proceeds along the NO branch and the control circuit determines 5163 that a dissection step of the surgical procedure is being performed. The control circuit can make this determination 5163 because if the energy generator 5112 is not on the sealing mode, then it must thus be on the cut/coagulation mode for energy generators 5112 having two modes of operation. The cut/coagulation mode of the energy generator 5112 corresponds to a dissection procedural step because it provides an appropriate degree of energy to the ultrasonic surgical instrument or RF electrosurgical instrument to dissect tissue. If the energy generator 5112 is in the sealing mode, then the process 5157 proceeds along the YES branch and the control circuit determines 5165 that a ligation step of the surgical procedure is being performed. The sealing mode of the energy generator 5112 corresponds to a ligation procedural step because it provides an appropriate degree of energy to the ultrasonic surgical instrument or RF electrosurgical instrument to ligate vessels.

FIG. 25F illustrates a logic flow diagram of a process 5167 for determining a procedural step according to energy generator 5112 perioperative data. In various aspects, previously received perioperative data and/or previously derived contextual information can also be considered by processes in deriving subsequent contextual information. This allows the situational awareness system of the surgical hub 5104 to derive additional and/or increasingly detailed contextual information about the surgical procedure as the procedure is performed. In this exemplification, the process 5167 determines 5169 that a segmentectomy procedure is being performed. This contextual information can be derived by this process 5167 or other processes based upon other received perioperative data and/or retrieved from a memory. Subsequently, the control circuit receives 5171 perioperative data from the energy generator 5112 indicating that a surgical instrument is being fired and then determines 5173 whether the energy generator 5112 was utilized in a previous step of the procedure to fire the surgical instrument. The control circuit can determine 5173 whether the energy generator 5112 was previously utilized in a prior step of the procedure by retrieving a list of the steps that have been performed in the current surgical procedure from a memory, for example. In such exemplifications, when the surgical hub 5104 determines that a step of the surgical procedure has been performed or completed by the surgical staff, the surgical hub 5104 can update a list of the procedural steps that have been performed, which can then be subsequently retrieved by the control circuit of the surgical hub 5104. In one exemplification, the surgical hub 5104 can distinguish between sequences of firings of the surgical instrument as corresponding to separate steps of the surgical procedure according to the time delay between the sequences of firings, whether any intervening actions were taken or modular devices 5102 were utilized by the surgical staff, or other factors that the situational awareness system can detect. If the energy generator 5112 has not been previously utilized during the course of the segmentectomy procedure, the process 5167 proceeds along the NO branch and the control circuit determines 5175 that the step of dissecting tissue to mobilize the patient's lungs is being performed by the surgical staff. If the energy generator 5112 has been previously utilized during the course of the segmentectomy procedure, the process 5167 proceeds along the YES branch and the control circuit determines 5177 that the step of dissecting nodes is being performed by the surgical staff. An ultrasonic surgical instrument or RF electrosurgical instrument is utilized twice during the course of an example of a segmentectomy procedure (e.g., FIG. 27); therefore, the situational awareness system of the surgical hub 5104 executing the process 5167 can distinguish between which step the utilization of the energy generator 5112 indicates is currently being performed based upon whether the energy generator 5112 was previously utilized.

FIG. 25G illustrates a logic flow diagram of a process 5179 for determining a procedural step according to stapler perioperative data. As described above with respect to the process 5167 illustrated in FIG. 25F, the process 5179 utilizes previously received perioperative data and/or previously derived contextual information in deriving subsequent contextual information. In this exemplification, the process 5179 determines 5181 that a segmentectomy procedure is being performed. This contextual information can be derived by this process 5179 or other processes based upon other received perioperative data and/or retrieved from a memory. Subsequently, the control circuit receives 5183 perioperative data from the surgical stapling instrument (i.e., stapler) indicating that the surgical stapling instrument is being fired and then determines 5185 whether the surgical stapling instrument was utilized in a previous step of the surgical procedure. As described above, the control circuit can determine 5185 whether the surgical stapling instrument was previously utilized in a prior step of the procedure by retrieving a list of the steps that have been performed in the current surgical procedure from a memory, for example. If the surgical stapling instrument has not been utilized previously, then the process 5179 proceeds along the NO branch and the control circuit determines 5187 that the step of ligating arteries and veins is being performed by the surgical staff. If the surgical stapling instrument has been previously utilized during the course of the segmentectomy procedure, the process 5179 proceeds along the YES branch and the control circuit determines 5189 that the step of transecting parenchyma is being performed by the surgical staff. A surgical stapling instrument is utilized twice during the course of an example of a segmentectomy procedure (e.g., FIG. 27); therefore, the situational awareness system of the surgical hub 5104 executing the process 5179 can distinguish between which step the utilization of the surgical stapling instrument indicates is currently being performed based upon whether the surgical stapling instrument was previously utilized.

FIG. 25H illustrates a logic flow diagram of a process 5191 for determining a patient status according to ventilator 5110, pulse oximeter 5114, BP monitor 5116, and/or EKG monitor 5120 perioperative data. In this exemplification, the control circuit of the surgical hub 5104 executing the process 5191 receives 5193, 5195, 5197, 5199 perioperative data from each of the ventilator 5110, pulse oximeter 5114, BP monitor 5116, and/or EKG monitor 5120 and then determines whether one or more values of the physiological parameters sensed by each of the devices fall below a threshold for each of the physiological parameters. The threshold for each physiological parameter can correspond to a value that corresponds to a patient being under anesthesia. In other words, the control circuit determines 5201 whether the patient's respiration rate, oxygen saturation, blood pressure, and/or heart rate indicate that the patient is under anesthesia according data sensed by the respective modular device 5102 and/or patient monitoring devices 5124. In one exemplification, if the all of the values from the perioperative data are below their respective thresholds, then the process 5191 proceeds along the YES branch and the control circuit determines 5203 that the patient is under anesthesia. In another exemplification, the control circuit can determine 5203 that the patient is under anesthesia if a particular number or ratio of the monitored physiological parameters indicate that the patient is under anesthesia. Otherwise, the process 5191 proceeds along the NO branch and the control circuit determines 5205 that the patient is not under anesthesia.

FIG. 25I illustrates a logic flow diagram of a process 5207 for determining a patient status according to pulse oximeter 5114, BP monitor 5116, and/or EKG monitor 5120 perioperative data. In this exemplification, the control circuit of the surgical hub 5104 executing the process 5207 receives 5209, 5211, 5213 (or attempts to receive) perioperative data the pulse oximeter 5114, BP monitor 5116, and/or EKG monitor 5120 and then determines 5215 whether at least one of the devices is paired with the surgical hub 5104 or the surgical hub 5104 is otherwise receiving data therefrom. If the control circuit is receiving data from at least one of these patient monitoring devices 5124, the process 5207 proceeds along the YES branch and the control circuit determines 5217 that the patient is in the operating theater. The control circuit can make this determination because the patient monitoring devices 5214 connected to the surgical hub 5104 must be in the operating theater and thus the patient must likewise be in the operating theater. If the control circuit is not receiving data from at least one of these patient monitoring devices 5124, the process 5207 proceeds along the NO branch and the control circuit determines 5219 that the patient is not in the operating theater.

FIG. 25J illustrates a logic flow diagram of a process 5221 for determining a patient status according to ventilator 5110 perioperative data. In this exemplification, the control circuit of the surgical hub 5104 executing the process 5221 receives 5223 perioperative data from the ventilator 5110 and then determines 5225 whether the patient's airway volume has decreased or is decreasing. In one exemplification, the control circuit determines 5225 whether the patient's airway volume falls below a particular threshold value indicative of a lung having collapsed or been deflated. In another exemplification, the control circuit determines 5225 whether the patient's airway volume falls below an average or baseline level by a threshold amount. If the patient's airway volume has not decreased sufficiently, the process 5221 proceeds along the NO branch and the control circuit determines 5227 that the patient's lung is not deflated. If the patient's airway volume has decreased sufficiently, the process 5221 proceeds along the YES branch and the control circuit determines 5229 that the patient's lung is not deflated.

Figure 26B:
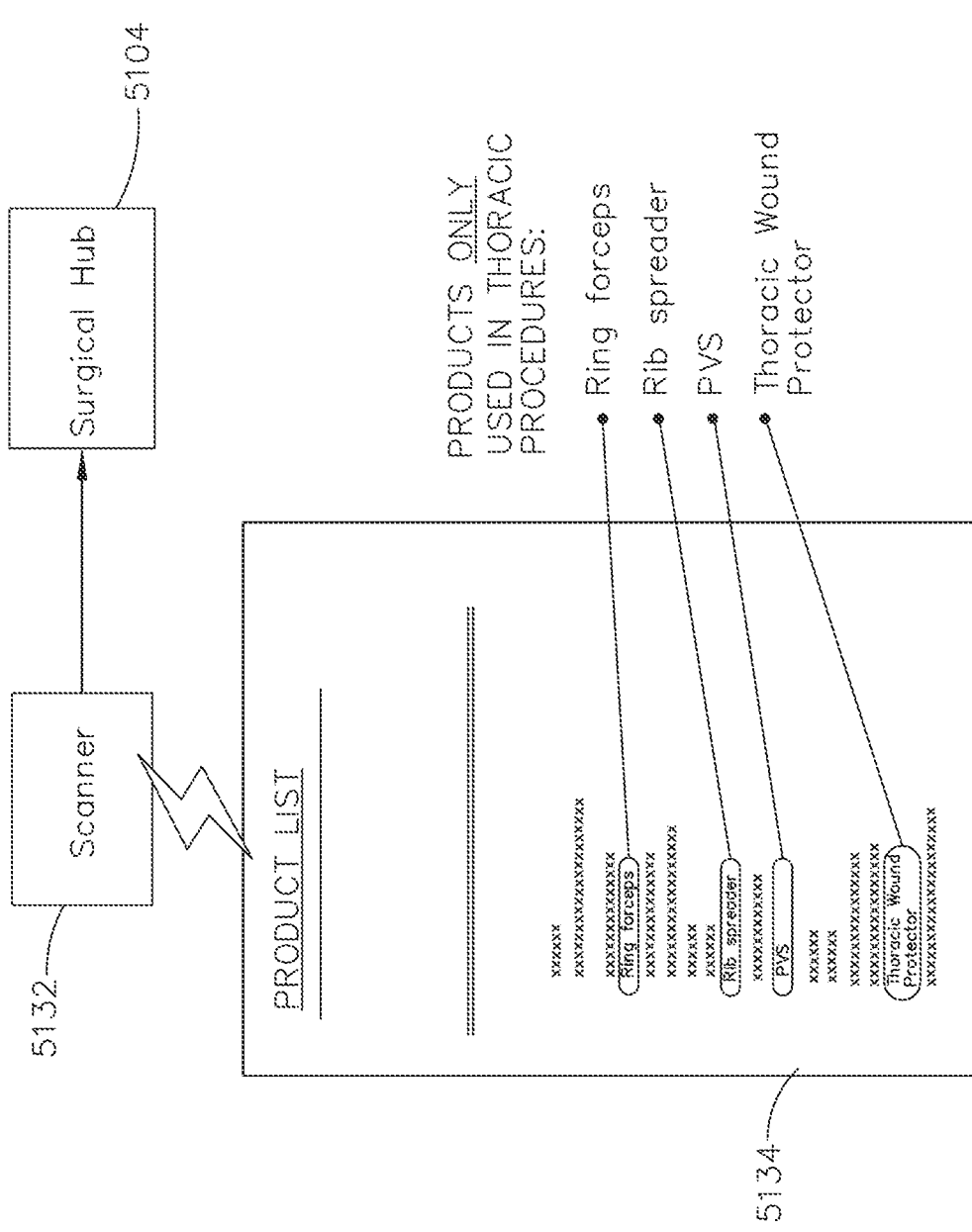
FIG. 26B illustrates a scanner coupled to a surgical hub for scanning a list of surgical items, in accordance with at least one aspect of the present disclosure.

In one exemplification, the surgical system 5100 can further include various scanners that can be paired with the surgical hub 5104 to detect and record objects and individuals that enter and exit the operating theater. FIG. 26A illustrates a scanner 5128 paired with a surgical hub 5104 that is configured to scan a patient wristband 5130. In one aspect, the scanner 5128 includes, for example, a barcode reader or a radio-frequency identification (RFID) reader that is able to read patient information from the patient wristband 5130 and then transmit that information to the surgical hub 5104. The patient information can include the surgical procedure to be performed or identifying information that can be cross-referenced with the hospital's EMR database 5122 by the surgical hub 5104, for example. FIG. 26B illustrates a scanner 5132 paired with a surgical hub 5104 that is configured to scan a product list 5134 for a surgical procedure. The surgical hub 5104 can utilize data from the scanner 5132 regarding the number, type, and mix of items to be used in the surgical procedure to identify the type of surgical procedure being performed. In one exemplification, the scanner 5132 includes a product scanner (e.g., a barcode reader or an RFID reader) that is able to read the product information (e.g., name and quantity) from the product itself or the product packaging as the products are brought into the operating theater and then transmit that information to the surgical hub 5104. In another exemplification, the scanner 5132 includes a camera (or other visualization device) and associated optical character recognition software that is able to read the product information from a product list 5134. The surgical hub 5104 can be configured to cross-reference the list of items indicated by the received data with a lookup table or database of items utilized for various types of surgical procedures in order to infer the particular surgical procedure that is to be (or was) performed. As shown in FIG. 26B, the illustrative product list 5134 includes ring forceps, rib spreaders, a powered vascular stapler (PVS), and a thoracic wound protector. In this example, the surgical hub 5104 can infer that the surgical procedure is a thoracic procedure from this data since these products are only utilized in thoracic procedures. In sum, the scanner(s) 5128, 5132 can provide serial numbers, product lists, and patient information to the surgical hub 5104. Based on this data regarding what devices and instruments are being utilized and the patient's medical information, the surgical hub 5104 can determine additional contextual information regarding the surgical procedure.

In order to assist in the understanding of the process 5000a illustrated in FIG. 23A and the other concepts discussed above, FIG. 27 illustrates a timeline 5200 of an illustrative surgical procedure and the contextual information that a surgical hub 5104 can derive from the data received from the data sources 5126 at each step in the surgical procedure. In the following description of the timeline 5200 illustrated in FIG. 27, reference should also be made to FIG. 22. The timeline 5200 depicts the typical steps that would be taken by the nurses, surgeons, and other medical personnel during the course of a lung segmentectomy procedure, beginning with setting up the operating theater and ending with transferring the patient to a post-operative recovery room. The situationally aware surgical hub 5104 receives data from the data sources 5126 throughout the course of the surgical procedure, including data generated each time medical personnel utilize a modular device 5102 that is paired with the surgical hub 5104. The surgical hub 5104 can receive this data from the paired modular devices 5102 and other data sources 5126 and continually derive inferences (i.e., contextual information) about the ongoing procedure as new data is received, such as which step of the procedure is being performed at any given time. The situational awareness system of the surgical hub 5104 is able to, for example, record data pertaining to the procedure for generating reports (e.g., see FIGS. 31-42), verify the steps being taken by the medical personnel, provide data or prompts (e.g., via a display screen) that may be pertinent for the particular procedural step, adjust modular devices 5102 based on the context (e.g., activate monitors, adjust the FOV of the medical imaging device, or change the energy level of an ultrasonic surgical instrument or RF electrosurgical instrument), and take any other such action described above.

As the first step 5202 in this illustrative procedure, the hospital staff members retrieve the patient's EMR from the hospital's EMR database. Based on select patient data in the EMR, the surgical hub 5104 determines that the procedure to be performed is a thoracic procedure. Second 5204, the staff members scan the incoming medical supplies for the procedure. The surgical hub 5104 cross-references the scanned supplies with a list of supplies that are utilized in various types of procedures and confirms that the mix of supplies corresponds to a thoracic procedure (e.g., as depicted in FIG. 26B). Further, the surgical hub 5104 is also able to determine that the procedure is not a wedge procedure (because the incoming supplies either lack certain supplies that are necessary for a thoracic wedge procedure or do not otherwise correspond to a thoracic wedge procedure). Third 5206, the medical personnel scan the patient band (e.g., as depicted in FIG. 26A) via a scanner 5128 that is communicably connected to the surgical hub 5104. The surgical hub 5104 can then confirm the patient's identity based on the scanned data. Fourth 5208, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices 5102 can automatically pair with the surgical hub 5104 that is located within a particular vicinity of the modular devices 5102 as part of their initialization process. The surgical hub 5104 can then derive contextual information about the surgical procedure by detecting the types of modular devices 5102 that pair with it during this pre-operative or initialization phase. In this particular example, the surgical hub 5104 determines that the surgical procedure is a VATS procedure based on this particular combination of paired modular devices 5102. Based on the combination of the data from the patient's EMR, the list of medical supplies to be used in the procedure, and the type of modular devices 5102 that connect to the hub, the surgical hub 5104 can generally infer the specific procedure that the surgical team will be performing. Once the surgical hub 5104 knows what specific procedure is being performed, the surgical hub 5104 can then retrieve the steps of that procedure from a memory or from the cloud and then cross-reference the data it subsequently receives from the connected data sources 5126 (e.g., modular devices 5102 and patient monitoring devices 5124) to infer what step of the surgical procedure the surgical team is performing. Fifth 5210, the staff members attach the EKG electrodes and other patient monitoring devices 5124 to the patient. The EKG electrodes and other patient monitoring devices 5124 are able to pair with the surgical hub 5104. As the surgical hub 5104 begins receiving data from the patient monitoring devices 5124, the surgical hub 5104 thus confirms that the patient is in the operating theater, as described in the process 5207 depicted in FIG. 25I, for example. Sixth 5212, the medical personnel induce anesthesia in the patient. The surgical hub 5104 can infer that the patient is under anesthesia based on data from the modular devices 5102 and/or patient monitoring devices 5124, including EKG data, blood pressure data, ventilator data, or combinations thereof, as described in the process 5191 depicted in FIG. 25H, for example. Upon completion of the sixth step 5212, the pre-operative portion of the lung segmentectomy procedure is completed and the operative portion begins.

Seventh 5214, the patient's lung that is being operated on is collapsed (while ventilation is switched to the contralateral lung). The surgical hub 5104 can infer from the ventilator data that the patient's lung has been collapsed, as described in the process 5221 depicted in FIG. 25J, for example. The surgical hub 5104 can infer that the operative portion of the procedure has commenced as it can compare the detection of the patient's lung collapsing to the expected steps of the procedure (which can be accessed or retrieved previously) and thereby determine that collapsing the lung is the first operative step in this particular procedure. Eighth 5216, the medical imaging device 5108 (e.g., a scope) is inserted and video from the medical imaging device is initiated. The surgical hub 5104 receives the medical imaging device data (i.e., video or image data) through its connection to the medical imaging device. Upon receipt of the medical imaging device data, the surgical hub 5104 can determine that the laparoscopic portion of the surgical procedure has commenced. Further, the surgical hub 5104 can determine that the particular procedure being performed is a segmentectomy, as opposed to a lobectomy (note that a wedge procedure has already been discounted by the surgical hub 5104 based on data received at the second step 5204 of the procedure). The data from the medical imaging device 124 (FIG. 2) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 5104), and monitoring the types of visualization devices utilized. For example, one technique for performing a VATS lobectomy places the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. As another example, one technique for performing a VATS lobectomy utilizes a single medical imaging device, whereas another technique for performing a VATS segmentectomy utilizes multiple cameras. As yet another example, one technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device 5108, the surgical hub 5104 can thereby determine the specific type of surgical procedure being performed and/or the technique being used for a particular type of surgical procedure.

Ninth 5218, the surgical team begins the dissection step of the procedure. The surgical hub 5104 can infer that the surgeon is in the process of dissecting to mobilize the patient's lung because it receives data from the RF or ultrasonic generator indicating that an energy instrument is being fired. The surgical hub 5104 can cross-reference the received data with the retrieved steps of the surgical procedure to determine that an energy instrument being fired at this point in the process (i.e., after the completion of the previously discussed steps of the procedure) corresponds to the dissection step. Tenth 5220, the surgical team proceeds to the ligation step of the procedure. The surgical hub 5104 can infer that the surgeon is ligating arteries and veins because it receives data from the surgical stapling and cutting instrument indicating that the instrument is being fired. Similarly to the prior step, the surgical hub 5104 can derive this inference by cross-referencing the receipt of data from the surgical stapling and cutting instrument with the retrieved steps in the process. Eleventh 5222, the segmentectomy portion of the procedure is performed. The surgical hub 5104 can infer that the surgeon is transecting the parenchyma based on data from the surgical stapling and cutting instrument, including data from its cartridge. The cartridge data can correspond to the size or type of staple being fired by the instrument, for example. As different types of staples are utilized for different types of tissues, the cartridge data can thus indicate the type of tissue being stapled and/or transected. In this case, the type of staple being fired is utilized for parenchyma (or other similar tissue types), which allows the surgical hub 5104 to infer that the segmentectomy portion of the procedure is being performed. Twelfth 5224, the node dissection step is then performed. The surgical hub 5104 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 5104 to make this inference. It should be noted that surgeons regularly switch back and forth between surgical stapling/cutting instruments and surgical energy (i.e., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Upon completion of the twelfth step 5224, the incisions and closed up and the post-operative portion of the procedure begins.

Thirteenth 5226, the patient's anesthesia is reversed. The surgical hub 5104 can infer that the patient is emerging from the anesthesia based on the ventilator data (i.e., the patient's breathing rate begins increasing), for example. Lastly, the fourteenth step 5228 is that the medical personnel remove the various patient monitoring devices 5124 from the patient. The surgical hub 5104 can thus infer that the patient is being transferred to a recovery room when the hub loses EKG, BP, and other data from the patient monitoring devices 5124. As can be seen from the description of this illustrative procedure, the surgical hub 5104 can determine or infer when each step of a given surgical procedure is taking place according to data received from the various data sources 5126 that are communicably coupled to the surgical hub 5104.

Figure 27:
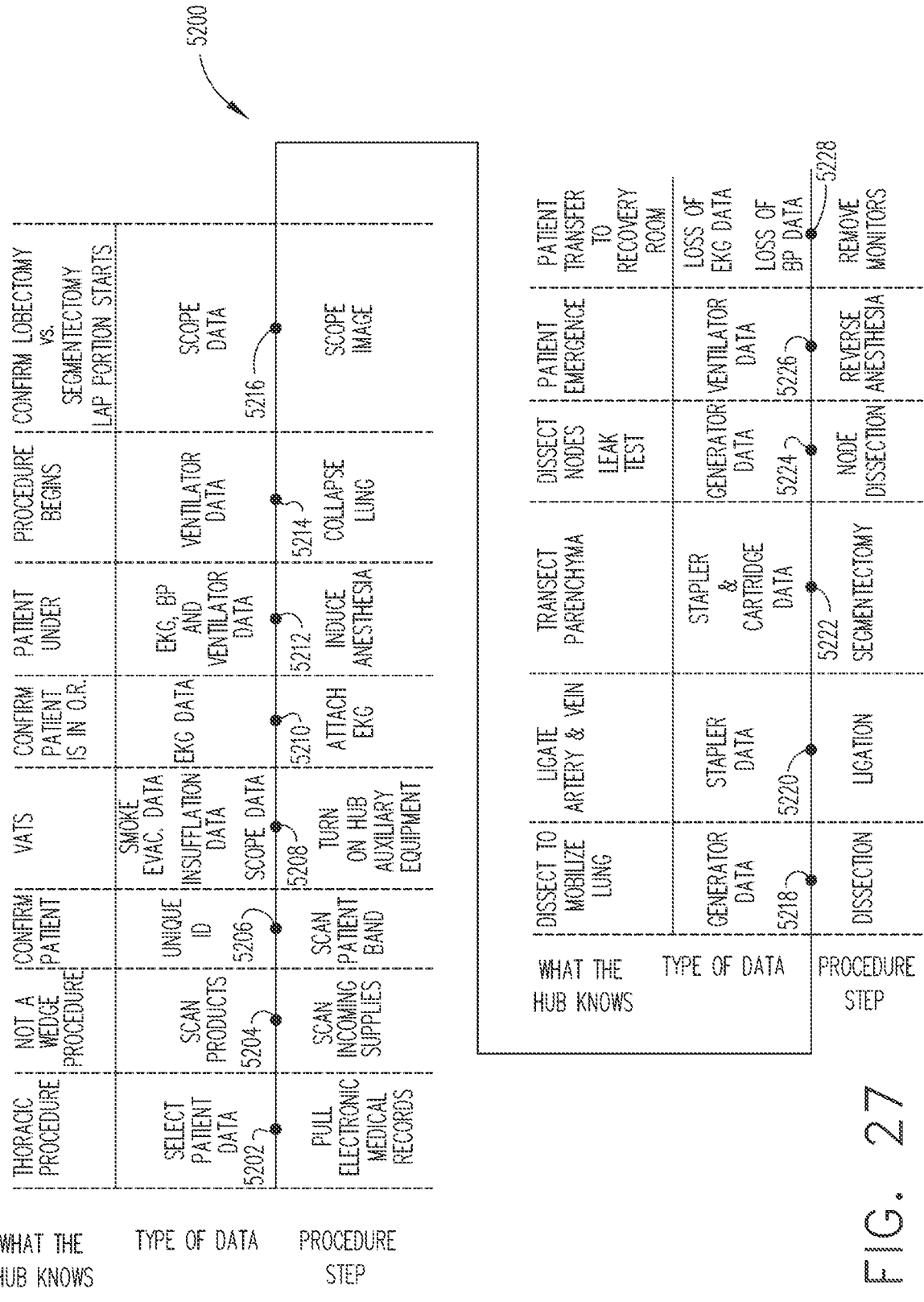
FIG. 27 illustrates a timeline of an illustrative surgical procedure and the inferences that the surgical hub can make from the data detected at each step in the surgical procedure, in accordance with at least one aspect of the present disclosure.
Figure 28A:
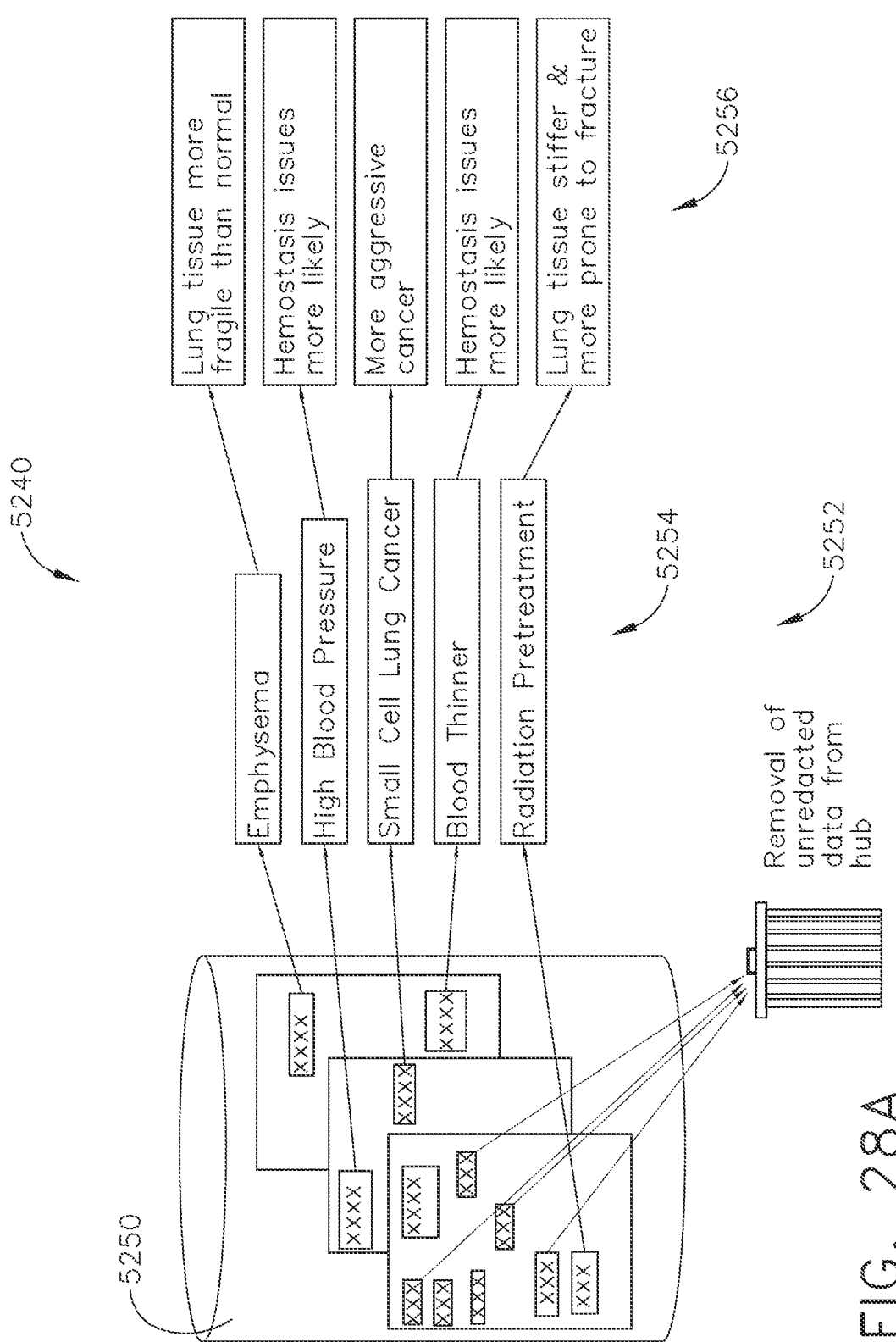
FIG. 28A illustrates a flow diagram depicting the process of importing patient data stored in an EMR database and deriving inferences therefrom, in accordance with at least one aspect of the present disclosure.
Figure 28B:
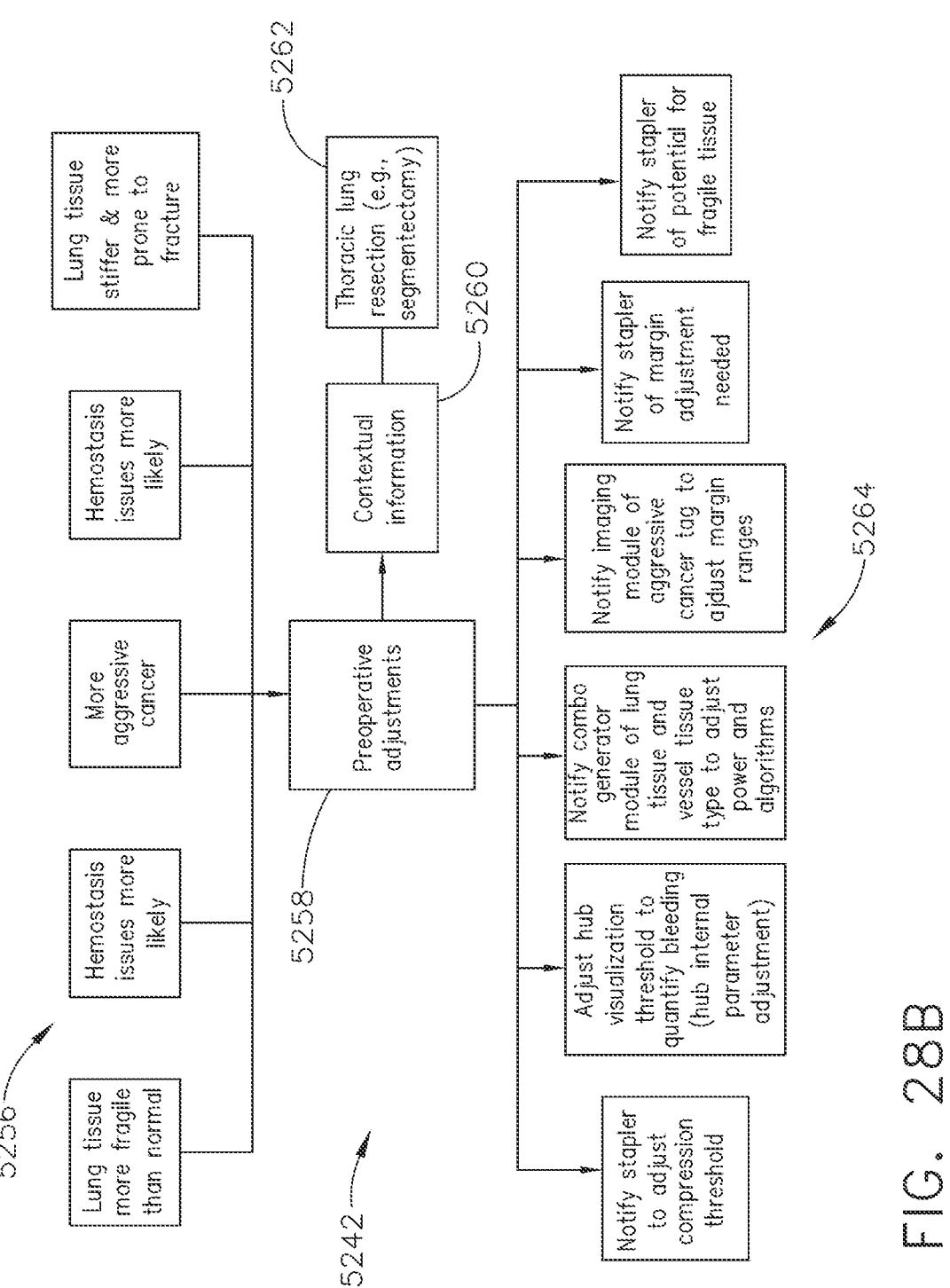
FIG. 28B illustrates a flow diagram depicting the process of determining control adjustments corresponding to the derived inferences from FIG. 28A, in accordance with at least one aspect of the present disclosure.

In addition to utilizing the patient data from EMR database(s) to infer the type of surgical procedure that is to be performed, as illustrated in the first step 5202 of the timeline 5200 depicted in FIG. 27, the patient data can also be utilized by a situationally aware surgical hub 5104 to generate control adjustments for the paired modular devices 5102. FIG. 28A illustrates a flow diagram depicting the process 5240 of importing patient data stored in an EMR database 5250 and deriving inferences 5256 therefrom, in accordance with at least one aspect of the present disclosure. Further, FIG. 28B illustrates a flow diagram depicting the process 5242 of determining control adjustments 5264 corresponding to the derived inferences 5256 from FIG. 28A, in accordance with at least one aspect of the present disclosure. In the following description of the processes 5240, 5242, reference should also be made to FIG. 22.

As shown in FIG. 28A, the surgical hub 5104 retrieves the patient information (e.g., EMR) stored in a database 5250 to which the surgical hub 5104 is communicably connected. The unredacted portion of the patient data is removed 5252 from the surgical hub 5104, leaving anonymized, stripped patient data 5254 related to the patient's condition and/or the surgical procedure to be performed. The unredacted patient data is removed 5252 in order to maintain patient anonymity for the processing of the data (including if the data is uploaded to the cloud for processing and/or data tracking for reports). The stripped patient data 5254 can include any medical conditions that the patient is suffering from, the patient's medical history (including previous treatments or procedures), medication that the patient is taking, and other such medically relevant details. The control circuit of the surgical hub 5104 can then derive various inferences 5256 from the stripped patient data 5254, which can in turn be utilized by the surgical hub 5104 to derive various control adjustments for the paired modular devices 5102. The derived inferences 5256 can be based upon individual pieces of data or combinations of pieces of data. Further, the derived inferences 5256 may, in some cases, be redundant with each other as some data may lead to the same inference. By integrating each patient's stripped patient data 5254 into the situational awareness system, the surgical hub 5104 is thus able to generate pre-procedure adjustments to optimally control each of the modular devices 5102 based on the unique circumstances associated with each individual patient. In the illustrated example, the stripped patient data 5254 includes that (i) the patient is suffering from emphysema, (ii) has high blood pressure, (iii) is suffering from a small cell lung cancer, (iv) is taking warfarin (or another blood thinner), and/or (v) has received radiation pretreatment. In the illustrated example, the inferences 5256 derived from the stripped patient data 5254 include that (i) the lung tissue will be more fragile than normal lung tissue, (ii) hemostasis issues are more likely, (iii) the patient is suffering from a relatively aggressive cancer, (iv) hemostasis issues are more likely, and (v) the lung tissue will be stiffer and more prone to fracture, respectively.

After the control circuit of the surgical hub 5104 receives or identifies the implications 5256 that are derived from anonymized patient data, the control circuit of the surgical hub 5104 is configured to execute a process 5242 to control the modular devices 5102 in a manner consistent with the derived implications 5256. In the example shown in FIG. 28B, the control circuit of the surgical hub 5104 interprets how the derived implications 5256 impacts the modular devices 5102 and then communicates corresponding preoperative adjustments 5258 to each of the modular devices 5102. In the example shown in FIG. 28B, the preoperative adjustments 5258 include (i) adjusting the compression rate threshold parameter of the surgical stapling and cutting instrument, (ii) adjusting the visualization threshold value of the surgical hub 5104 to quantify bleeding via the visualization system 108 (FIG. 2) (this adjustment can apply to the visualization system 108 itself or as an internal parameter of the surgical hub 5104), (iii) adjusts the power and control algorithms of the combo generator module 140 (FIG. 3) for the lung tissue and vessel tissue types, (iv) adjusts the margin ranges of the medical imaging device 124 (FIG. 2) to account for the aggressive cancer type, (v) notifies the surgical stapling and cutting instrument of the margin parameter adjustment needed (the margin parameter corresponds to the distance or amount of tissue around the cancer that will be excised), and (vi) notifies the surgical stapling and cutting instrument that the tissue is potentially fragile, which causes the control algorithm of the surgical stapling and cutting instrument to adjust accordingly. Furthermore, the data regarding the implications 5256 derived from the anonymized patient data 5254 is considered by the situational awareness system to infer contextual information 5260 regarding the surgical procedure being performed. In the example shown in FIG. 28B, the situational awareness system further infers that the procedure is a thoracic lung resection 5262, e.g., segmentectomy.

Determining where inefficiencies or ineffectiveness may reside in a medical facility's practice can be challenging because medical personnel's efficiency in completing a surgical procedure, correlating positive patient outcomes with particular surgical teams or particular techniques in performing a type of surgical procedure, and other performance measures are not easily quantified using legacy systems. As one solution, the surgical hubs can be employed to track and store data pertaining to the surgical procedures that the surgical hubs are being utilized in connection with and generate reports or recommendations related to the tracked data. The tracked data can include, for example, the length of time spent during a particular procedure, the length of time spent on a particular step of a particular procedure, the length of downtime between procedures, modular device(s) (e.g., surgical instruments) utilized during the course of a procedure, and the number and type of surgical items consumed during a procedure (or step thereof). Further, the tracked data can include, for example, the operating theater in which the surgical hub is located, the medical personnel associated with the particular event (e.g., the surgeon or surgical team performing the surgical procedure), the day and time at which the particular event(s) occurred, and patient outcomes. This data can be utilized to create performance metrics, which can be utilized to detect and then ultimately address inefficiencies or ineffectiveness within a medical facility's practice. In one exemplification, the surgical hub includes a situational awareness system, as described above, that is configured to infer or determine information regarding a particular event (e.g., when a particular step of a surgical procedure is being performed and/or how long the step took to complete) based on data received from data sources connected to the surgical hub (e.g., paired modular devices). The surgical hub can then store this tracked data to provide reports or recommendations to users.

Aggregation and Reporting of Surgical Hub Data

Figure 29:
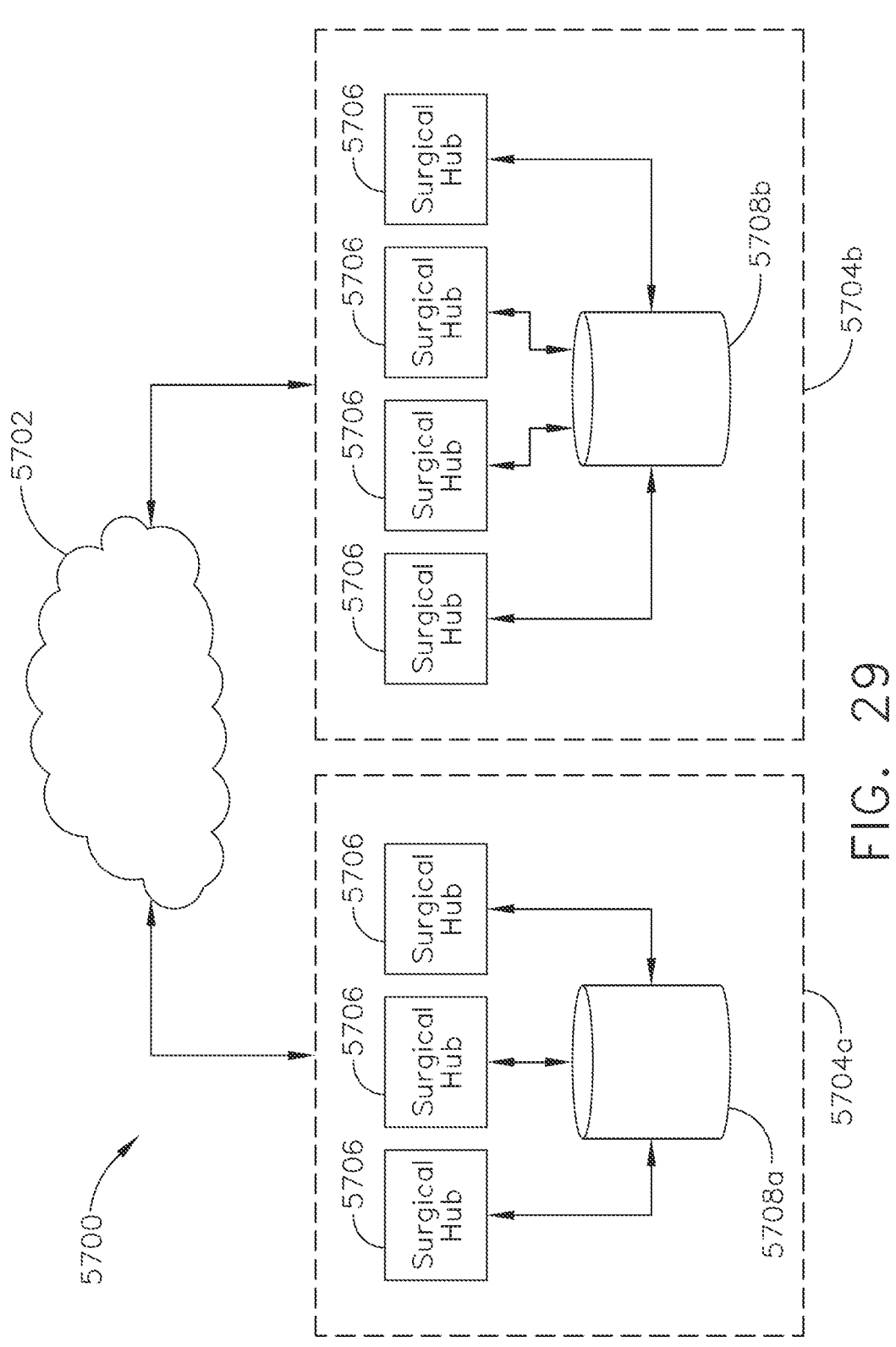
FIG. 29 illustrates a block diagram of a computer-implemented interactive surgical system, in accordance with at least one aspect of the present disclosure.

FIG. 29 illustrates a block diagram of a computer-implemented interactive surgical system 5700, in accordance with at least one aspect of the present disclosure. The system 5700 includes a number of surgical hubs 5706 that, as described above, are able to detect and track data related to surgical procedures that the surgical hubs 5706 (and the modular devices paired to the surgical hubs 5706) are utilized in connection with. In one exemplification, the surgical hubs 5706 are connected to form local networks such that the data being tracked by the surgical hubs 5706 is aggregated together across the network. The networks of surgical hubs 5706 can be associated with a medical facility, for example. The data aggregated from the network of surgical hubs 5706 can be analyzed to provide reports on data trends or recommendations. For example, the surgical hubs 5706 of a first medical facility 5704*a* are communicably connected to a first local database 5708*a* and the surgical hubs 5706 of a second medical facility 5704*b* are communicably connected to a second local database 5708*b*. The network of surgical hubs 5706 associated with the first medical facility 5704*a* can be distinct from the network of surgical hubs 5706 associated with the second medical facility 5704*b*, such that the aggregated data from each network of surgical hubs 5706 corresponds to each medical facility 5704*a*, 5704*b* individually. A surgical hub 5706 or another computer terminal communicably connected to the database 5708*a*, 5708*b* can be configured to provide reports or recommendations based on the aggregated data associated with the respective medical facility 5704*a*, 5704*b*. In this exemplification, the data tracked by the surgical hubs 5706 can be utilized to, for example, report whether a particular incidence of a surgical procedure deviated from the average in-network time to complete the particular procedure type.

In another exemplification, each surgical hub 5706 is configured to upload the tracked data to the cloud 5702, which then processes and aggregates the tracked data across multiple surgical hubs 5706, networks of surgical hubs 5706, and/or medical facilities 5704*a*, 5704*b* that are connected to the cloud 5702. Each surgical hub 5706 can then be utilized to provide reports or recommendations based on the aggregated data. In this exemplification, the data tracked by the surgical hubs 5706 can be utilized to, for example, report whether a particular incidence of a surgical procedure deviated from the average global time to complete the particular procedure type.

In another exemplification, each surgical hub 5706 can further be configured to access the cloud 5702 to compare locally tracked data to global data aggregated from all of the surgical hubs 5706 that are communicably connected to the cloud 5702. Each surgical hub 5706 can be configured to provide reports or recommendations based on the comparison between the tracked local data relative to local (i.e., in-network) or global norms. In this exemplification, the data tracked by the surgical hubs 5706 can be utilized to, for example, report whether a particular incidence of a surgical procedure deviated from either the average in-network time or the average global time to complete the particular procedure type.

In one exemplification, each surgical hub 5706 or another computer system local to the surgical hub 5706 is configured to locally aggregate the data tracked by the surgical hubs 5706, store the tracked data, and generate reports and/or recommendations according to the tracked data in response to queries. In cases where the surgical hub 5706 is connected to a medical facility network (which may include additional surgical hubs 5706), the surgical hub 5706 can be configured to compare the tracked data with the bulk medical facility data. The bulk medical facility data can include EMR data and aggregated data from the local network of surgical hubs 5706. In another exemplification, the cloud 5702 is configured to aggregate the data tracked by the surgical hubs 5706, store the tracked data, and generate reports and/or recommendations according to the tracked data in response to queries.

Each surgical hub 5706 can provide reports regarding trends in the data and/or provide recommendations on improving the efficiency or effectiveness of the surgical procedures being performed. In various exemplifications, the data trends and recommendations can be based on data tracked by the surgical hub 5706 itself, data tracked across a local medical facility network containing multiple surgical hubs 5706, or data tracked across a number of surgical hubs 5706 communicably connected to a cloud 5702. The recommendations provided by the surgical hub 5706 can describe, for example, particular surgical instruments or product mixes to utilize for particular surgical procedures based on correlations between the surgical instruments/product mixes and patient outcomes and procedural efficiency. The reports provided by the surgical hub 5706 can describe, for example, whether a particular surgical procedure was performed efficiently relative to local or global norms, whether a particular type of surgical procedure being performed at the medical facility is being performed efficiently relative to global norms, and the average time taken to complete a particular surgical procedure or step of a surgical procedure for a particular surgical team.

Figure 31:
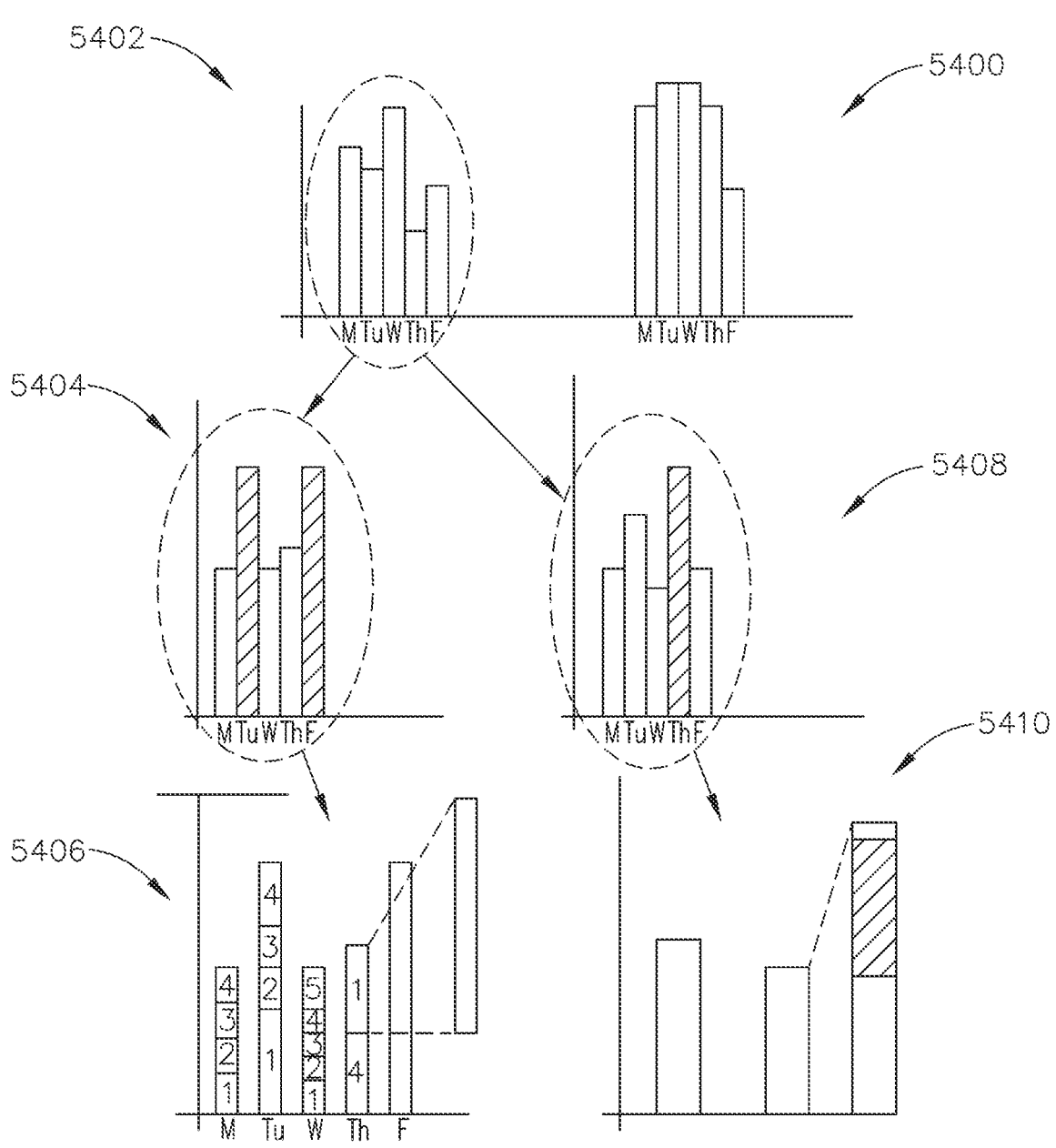
FIG. 31 illustrates a diagram depicting how the data tracked by the surgical hub can be parsed to provide increasingly detailed metrics, in accordance with at least one aspect of the present disclosure.

In one exemplification, each surgical hub 5706 is configured to determine when operating theater events occur (e.g., via a situational awareness system) and then track the length of time spent on each event. An operating theater event is an event that a surgical hub 5706 can detect or infer the occurrence of. An operating theater event can include, for example, a particular surgical procedure, a step or portion of a surgical procedure, or downtime between surgical procedures. The operating theater events can be categorized according to an event type, such as a type of surgical procedure being performed, so that the data from individual procedures can be aggregated together to form searchable data sets. FIG. 31 illustrates an example of a diagram 5400 depicting the data tracked by the surgical hubs 5706 being parsed to provide increasingly detailed metrics related to surgical procedures or the use of the surgical hub 5706 (as depicted further in FIGS. 32-36) for an illustrative data set. In one exemplification, the surgical hub 5706 is configured to determine whether a surgical procedure is being performed and then track both the length of time spent between procedures (i.e., downtime) and the time spent on the procedures themselves. The surgical hub 5706 can further be configured to determine and track the time spent on each of the individual steps taken by the medical personnel (e.g., surgeons, nurses, orderlies) either between or during the surgical procedures. The surgical hub can determine when surgical procedures or different steps of surgical procedures are being performed via a situational awareness system, which is described in further detail above.

Figure 30:
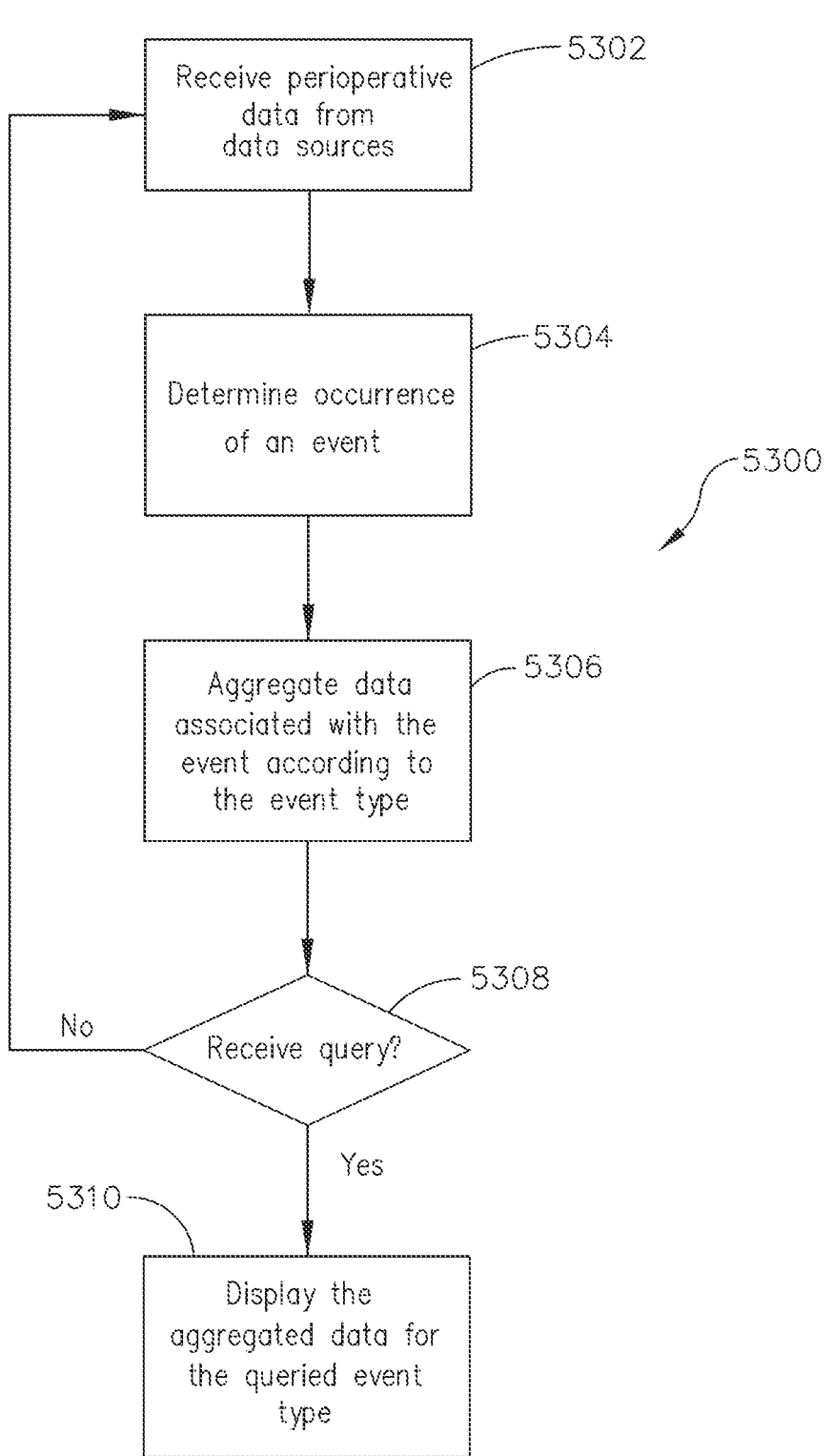
FIG. 30 illustrates a logic flow diagram of tracking data associated with an operating theater event, in accordance with at least one aspect of the present disclosure.

FIG. 30 illustrates a logic flow diagram of a process 5300 for tracking data associated with an operating theater event. In the following description, description of the process 5300, reference should also be made to FIG. 29. In one exemplification, the process 5300 can be executed by a control circuit of a surgical hub 206, as depicted in FIG. 10 (processor 244). In yet another exemplification, the process 5300 can be executed by a distributed computing system including a control circuit of a surgical hub 206 in combination with a control circuit of a modular device, such as the microcontroller 461 of the surgical instrument depicted FIG. 12, the microcontroller 620 of the surgical instrument depicted in FIG. 16, the control circuit 710 of the robotic surgical instrument 700 depicted in FIG. 17, the control circuit 760 of the surgical instruments 750, 790 depicted in FIGS. 18 and 19, or the controller 838 of the generator 800 depicted in FIG. 20. For economy, the following description of the process 5300 will be described as being executed by the control circuit of a surgical hub 5706; however, it should be understood that the description of the process 5300 encompasses all of the aforementioned exemplifications.

The control circuit of the surgical hub 5706 executing the process 5300 receives 5302 perioperative data from the modular devices and other data sources (e.g., databases and patient monitoring devices) that are communicably coupled to the surgical hub 5706. The control circuit then determines 5304 whether an event has occurred via, for example, a situational awareness system that derives contextual information from the received 5302 data. The event can be associated with an operating theater in which the surgical hub 5706 in being used. The event can include, for example, a surgical procedure, a step or portion of a surgical procedure, or downtime between surgical procedures or steps of a surgical procedure. Furthermore, the control circuit tracks data associated with the particular event, such as the length of time of the event, the surgical instruments and/or other medical products utilized during the course of the event, and the medical personnel associated with the event. The surgical hub 5706 can further determine this information regarding the event via, for example, the situational awareness system.

For example, the control circuit of a situationally aware surgical hub 5706 could determine that anesthesia is being induced in a patient through data received from one or more modular devices 5102 (FIG. 22) and/or patient monitoring devices 5124 (FIG. 22). The control circuit could then determine that the operative portion of the surgical procedure has begun upon detecting that an ultrasonic surgical instrument or RF electrosurgical instrument has been activated. The control circuit could thus determine the length of time for the anesthesia inducement step according to the difference in time between the beginning of that particular step and the beginning of the first step in the operative portion of the surgical procedure. Likewise, the control circuit could determine how long the particular operative step in the surgical procedure took according to when the control circuit detects the subsequent step in the procedure begins. Further, the control circuit could determine how long the overall operative portion of the surgical procedure took according to when the control circuit detects that the final operative step in the procedure ends. The control circuit can also determine what surgical instruments (and other modular devices 5102) are being utilized during the course of each step in the surgical procedure by tracking the activation and/or use of the instruments during each of the steps. The control circuit can also detect the completion of the surgical procedure by, for example, detecting when the patient monitoring devices 5124 have been removed from the patient (as in step fourteen 5228 of FIG. 27). The control circuit can then track the downtime between procedures according to when the control circuit infers that the subsequent surgical procedure has begun.

The control circuit executing the process 5300 then aggregates 5306 the data associated with the event according to the event type. In one exemplification, the aggregated 5306 data can be stored in a memory 249 (FIG. 10) of the surgical hub 5706. In another exemplification, the control circuit is configured to upload the data associated with the event to the cloud 5702, whereupon the data is aggregated 5306 according to the event type for all of the data uploaded by each of the surgical hubs 5706 connected to the cloud 5702. In yet another exemplification, the control circuit is configured to upload the data associated with the event to a database associated with a local network of the surgical hubs 5706, whereupon the data is aggregated 5306 according to the event type for all of the data uploaded across the local network of surgical hubs 5706.

In one exemplification, the control circuit is further configured to compare the data associated with the event type to baseline data associated with the event type. The baseline data can correspond to, for example, average values associated with the particular event type for a particular hospital, network of hospitals, or across the entirety of the cloud 5702. The baseline data can be stored on the surgical hub 5706 or retrieved by the surgical 5706 as the perioperative data is received 5302 thereby.

Aggregating 5306 the data from each of the events according to the event type allows individual incidents of the event type to thereafter be compared against the historical or aggregated data to determine when deviations from the norm for an event type occur. The control circuit further determines 5308 whether it has received a query. If the control circuit does not receive a query, then the process 5300 continues along the NO branch and loops back to continue receiving 5302 data from the data sources. If the control circuit does receive a query for a particular event type, the process 5300 continues along the YES branch and the control circuit then retrieves the aggregated data for the particular event type and displays 5310 the appropriate aggregated data corresponding to the query. In various exemplifications, the control circuit can retrieve the appropriate aggregated data from the memory of the surgical hub 5706, the cloud 5702, or a local database 5708*a*, 5708*b*.

In one example, the surgical hub 5706 is configured to determine a length of time for a particular procedure via the aforementioned situational awareness system according to data received from one or more modular devices utilized in the performance of the surgical procedure (and other data sources). Each time a surgical procedure is completed, the surgical hub 5706 uploads or stores the length of time required to complete the particular type of surgical procedure, which is then aggregated with the data from every other instance of the type of procedure. In some aspects, the surgical hub 5706, cloud 5702, and/or local database 5708*a*, 5708*b* can then determine an average or expected procedure length for the particular type of procedure from the aggregated data. When the surgical hub 5706 receives a query as to the particular type of procedure thereafter, the surgical hub 5706 can then provide feedback as to the average (or expected) procedure length or compare an individual incidence of the procedure type to the average procedure length to determine whether the particular incidence deviates therefrom.

In some aspects, the surgical hub 5706 can be configured to automatically compare each incidence of an event type to average or expected norms for the event type and then provide feedback (e.g., display a report) when a particular incidence of the event type deviates from the norm. For example, the surgical hub 5706 can be configured to provide feedback whenever a surgical procedure (or a step of the surgical procedure) deviates from the expected length of time to complete the surgical procedure (or the step of the surgical procedure) by more than a set amount.

Referring back to FIG. 31, the surgical hub 5706 could be configured to track, store, and display data regarding the number of patients operated on (or procedures completed) per day per operating theater (bar graph 5402 depicted further in FIG. 32), for example. The surgical hub 5706 could be configured to further parse the number of patients operated on (or procedures completed) per day per operating theater and can be further parsed according to the downtime between the procedures on a given day (bar graph 5404 depicted further in FIG. 33) or the average procedure length on a given day (bar graph 5408 depicted further in FIG. 35).

Figure 33:
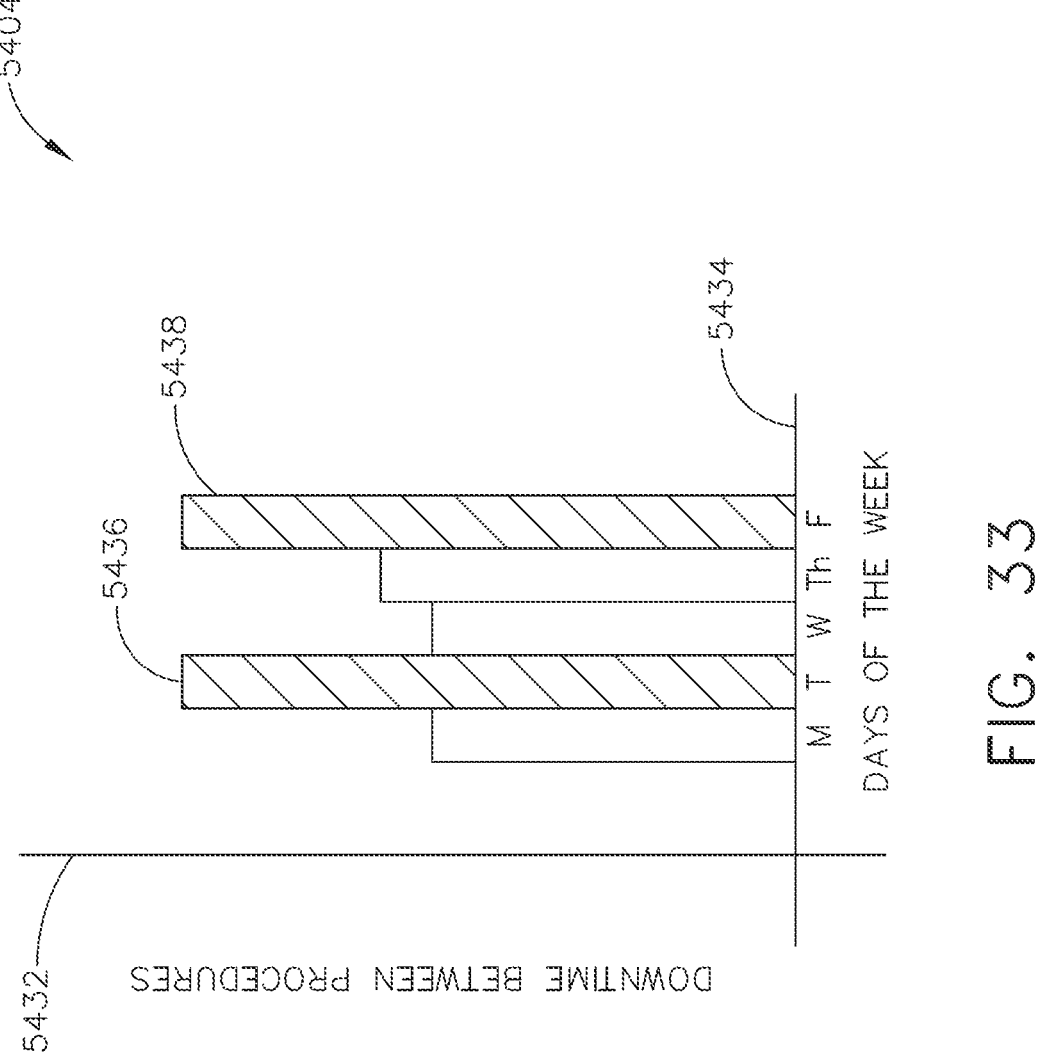
FIG. 33 illustrates a bar graph depicting the total downtime between procedures relative to the days of a week for a particular operating room, in accordance with at least one aspect of the present disclosure.
Figure 34:
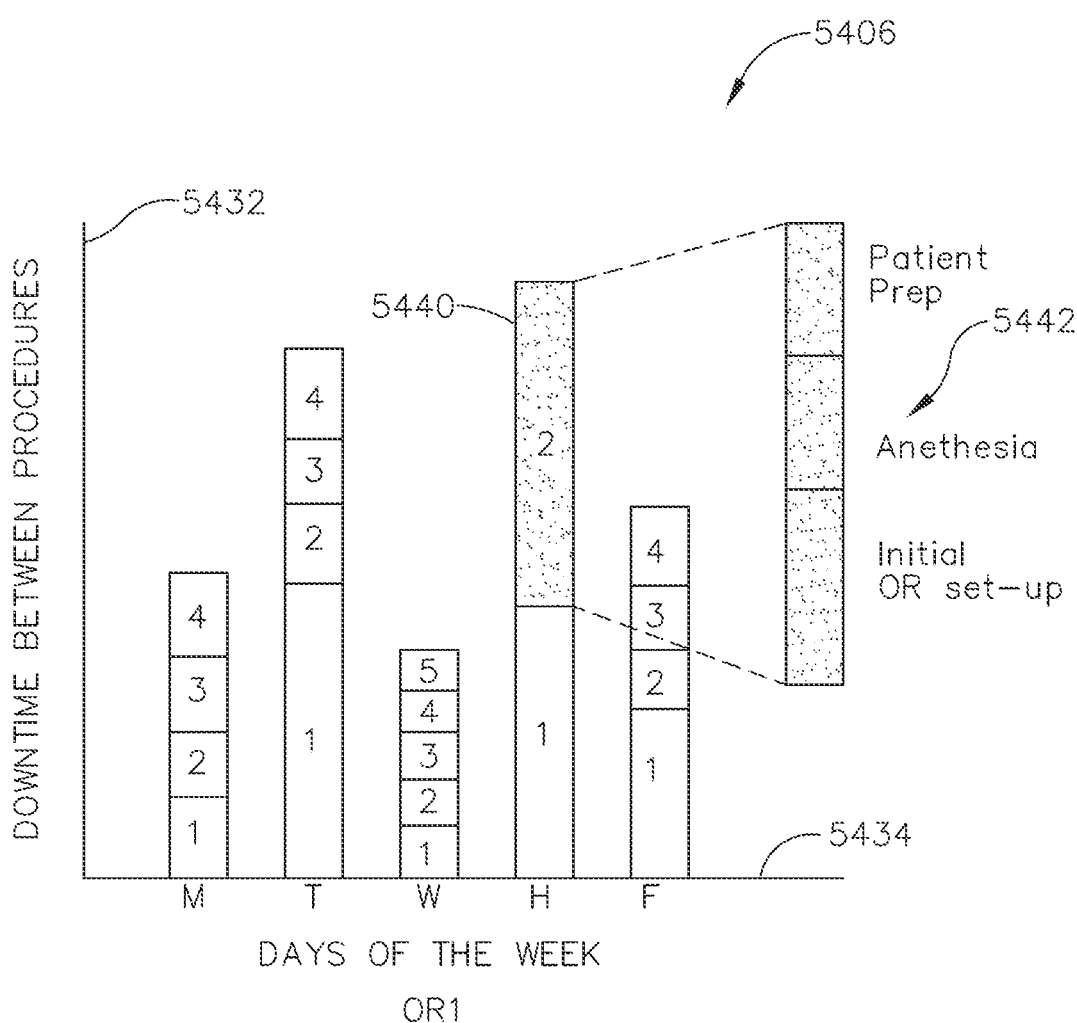
FIG. 34 illustrates a bar graph depicting the total downtime per day of the week depicted in FIG. 33 broken down according to each individual downtime instance, in accordance with at least one aspect of the present disclosure.

The surgical hub 5706 can be further configured to provide a detailed breakdown of the downtime between procedures according to, for example, the number and length of the downtime time periods and the subcategories of the actions or steps during each time period (bar graph 5406 depicted further in FIG. 34). The surgical hub 5706 can be further configured to provide a detailed breakdown of the average procedure length on a given day according to each individual procedure and the subcategory of actions or steps during each procedure (bar graph 5410 depicted further in FIG. 36). The various graphs shown in FIGS. 31-36 can represent data tracked by the surgical hub 5706 and can further be generated automatically or displayed by the surgical hub 5706 in response to queries submitted by users.

Figure 32:
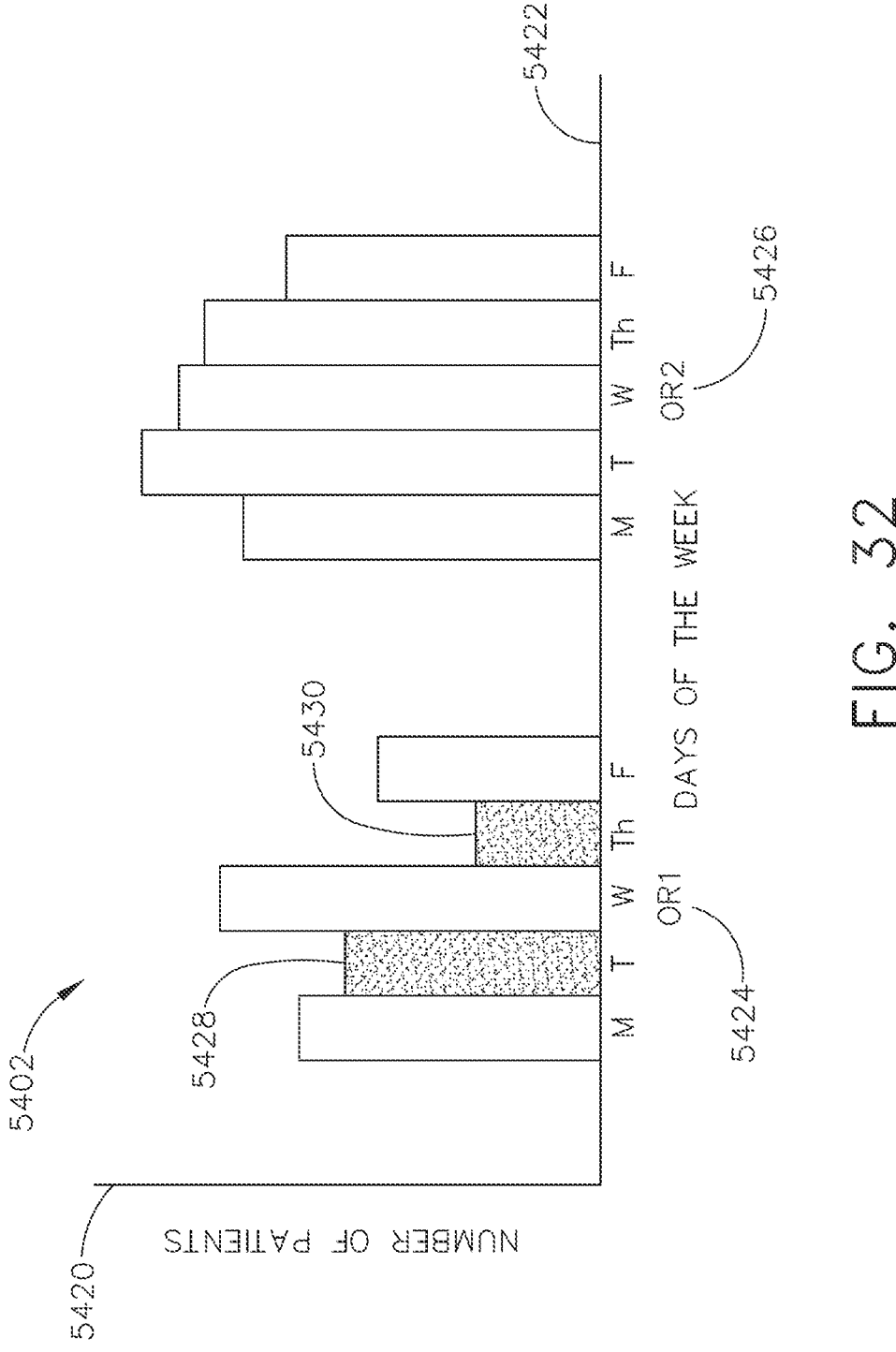
FIG. 32 illustrates a bar graph depicting the number of patients operated on relative to the days of a week for different operating rooms, in accordance with at least one aspect of the present disclosure.

FIG. 32 illustrates an example bar graph 5402 depicting the number of patients 5420 operated on relative to the days of the week 5422 for different operating rooms 5424, 5426. The surgical hub 5706 can be configured to provide (e.g., via a display) the number of patients 5420 operated on or procedures that are completed in connection with each surgical hub 5706, which can be tracked through a situational awareness system or accessing the hospital's EMR database, for example. In one exemplification, the surgical hub 5706 can further be configured to collate this data from different surgical hubs 5706 within the medical facility that are communicably connected together, which allows each individual surgical hub to present the aggregated data of the medical facility on a hub-by-hub or operating theater-by-theater basis. In one exemplification, the surgical hub 5706 can be configured to compare one or more tracked metrics to a threshold value (which may be unique to each tracked metric). When at least one of the tracked metrics exceeds the threshold value (i.e., either increases above or drops below the threshold value, as appropriate for the particular tracked metric), then the surgical hub 5706 provides a visual, audible, or tactile alert to notify a user of such. For example, the surgical hub 5706 can be configured to indicate when the number of patients or procedures deviates from an expected, average, or threshold value. For example, FIG. 32 depicts the number of patients on Tuesday 5428 and Thursday 5430 for a first operating theater 5424 as being highlighted for being below expectation. Conversely, no days are highlighted for a second operating theater 5426 for this particular week, which means in this context that the number of patients for each day falls within expectations.

FIG. 33 illustrates a bar graph 5404 depicting the total downtime between procedures 5432 relative to the days of a week 5434 for a particular operating room. The surgical hub 5706 can be configured to track the length of downtime between surgical procedures through a situational awareness system, for example. The situational awareness system can detect or infer when each particular downtime instance is occurring and then track the length of time for each instance of downtime. The surgical hub 5706 can thereby determine the total downtime 5432 for each day of the week 5434 by summing the downtime instances for each particular day. In one exemplification, the surgical hub 5706 can be configured to provide an alert when the total length of downtime on a given day (or another unit of time) deviates from an expected, average, or threshold value. For example, FIG. 33 depicts the total downtime 5432 on Tuesday 5436 and Friday 5438 as being highlighted for deviating from an expected length of time.

FIG. 34 illustrates a bar graph 5406 depicting the total downtime 5432 per day of the week 5434 as depicted in FIG. 33 broken down according to each individual downtime instance. The number of downtime instances and the length of time for each downtime instance can be represented within each day's total downtime. For example, on Tuesday in the first operating theater (OR1) there were four instances of downtime between procedures and the magnitude of the first downtime instance indicates that it was longer than the other three instances. In one exemplification, the surgical hub 5706 is configured to further indicate the particular actions or steps taken during a selected downtime instance. For example, in FIG. 34, Thursday's second downtime instance 5440 has been selected, which then causes a callout 5442 to be displayed indicating that this particular downtime instance consisted of performing the initial set-up of the operating theater, administering anesthesia, and prepping the patient. As with the downtime instances themselves, the relative size or length of the actions or steps within the callout 5442 can correspond to the length of time for each particular action or step. The detail views for the downtime instances can be displayed when a user selects the particular instance, for example.

Figure 35:
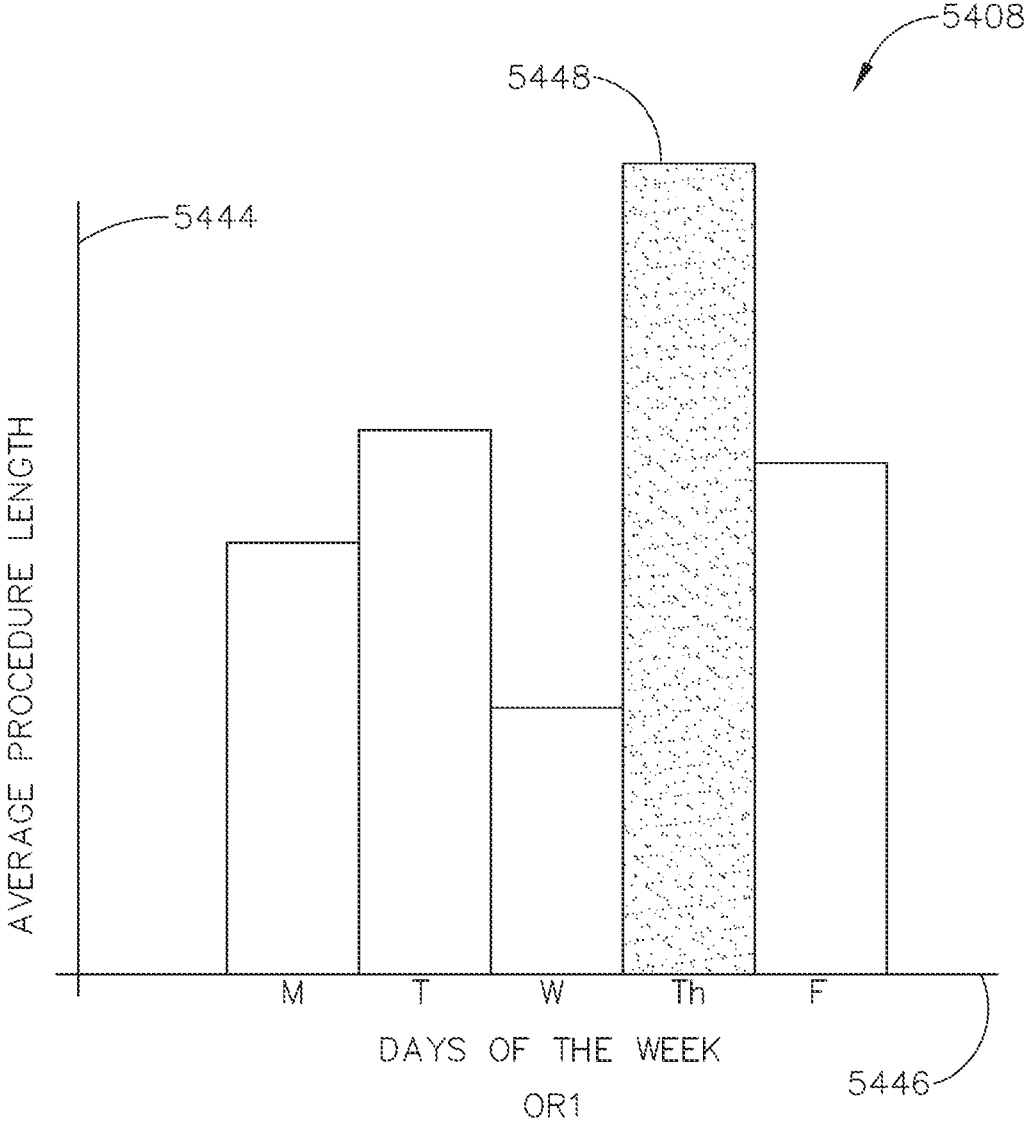
FIG. 35 illustrates a bar graph depicting the average procedure length relative to the days of a week for a particular operating room, in accordance with at least one aspect of the present disclosure.

FIG. 35 illustrates a bar graph 5408 depicting the average procedure length 5444 relative to the days of a week 5446 for a particular operating theater. The surgical hub 5706 can be configured to track the average procedure length through a situational awareness system, for example. The situational awareness system can detect or infer when each particular step of a surgical procedure is occurring (see FIG. 27, for example) and then track the length of time for each of the steps. The surgical hub 5706 can thereby determine the total downtime 5432 for each day of the week 5434 by summing the lengths of the downtime instances for the particular day. In one exemplification, the surgical hub 5706 can be configured to indicate when the average procedure length deviates from an expected value. For example, FIG. 35 depicts Thursday's average procedure length 5448 for the first operating room (OR1) as being highlighted for deviating from an expected length of time.

Figure 36:
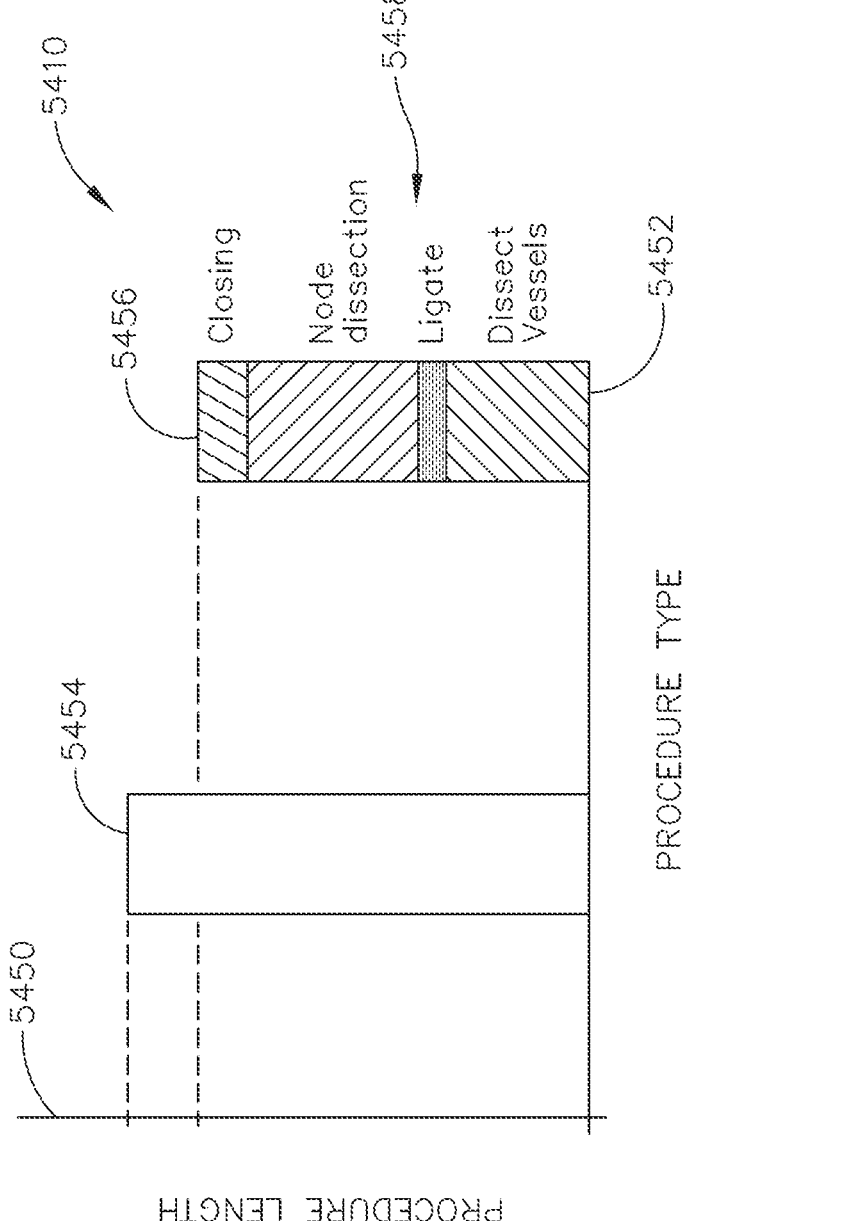
FIG. 36 illustrates a bar graph depicting procedure length relative to procedure type, in accordance with at least one aspect of the present disclosure.

FIG. 36 illustrates a bar graph 5410 depicting the procedure lengths 5450 relative to procedure types 5452. The depicted procedure lengths 5450 can either represent the average procedure lengths for particular types of procedures or the procedure lengths for each individual procedure performed on a given day in a given operating theater. The procedure lengths 5450 for different procedure types 5452 can then be compared. Further, the average lengths for the steps in a procedure type 5452 or the length for each particular step in a particular procedure can be displayed when a procedure is selected. Further, the procedure types 5452 can be tagged with various identifiers for parsing and comparing different data sets. For example, in FIG. 36 the first procedure 5454 corresponds to a colorectal procedure (specifically, a low anterior resection) where there was a preoperative identification of abdominal adhesions. The second procedure 5456 corresponds to a thoracic procedure (specifically, a segmentectomy). It should be noted again that the procedures depicted in FIG. 36 can represent the lengths of time for individual procedures or the average lengths of time for all of the procedures for the given procedure types. Each of the procedures can further be broken down according to the length of time for each step in the procedure. For example, FIG. 36 depicts the second procedure 5456 (a thoracic segmentectomy) as including an icon or graphical representation 5458 of the length of time spent on the dissect vessels, ligate (the vessels), nodal dissection, and closing steps of the surgical procedure. As with the procedure lengths themselves, the relative size or length of the steps within the graphical representation 5442 can correspond to the length of time for each particular step of the surgical procedure. The detail views for the steps of the surgical procedures can be displayed when a user selects the particular procedure, for example. In one exemplification, the surgical hub 5706 can be configured to identify when a length of time to complete a given step in the procedure deviates from an expected length of time. For example, FIG. 36 depicts the nodal dissection step as being highlighted for deviating from an expected length of time.

In one exemplification, an analytics package of the surgical hub 5706 can be configured to provide the user with usage data and results correlations related to the surgical procedures (or downtime between procedures). For example, the surgical hub 5706 can be configured to display methods or suggestions to improve the efficiency or effectiveness of a surgical procedure. As another example, the surgical hub 5706 can be configured to display methods to improve cost allocation. FIGS. 37-42 depict examples of various metrics that can be tracked by the surgical hub 5706, which can then be utilized to provide medical facility personnel suggestions for inventory utilization or technique outcomes. For example, a surgical hub 5706 could provide a surgeon with a suggestion pertaining to a particular technique outcome prior to or at the beginning of a surgical procedure based on the metrics tracked by the surgical hub 5706.

Figure 37:
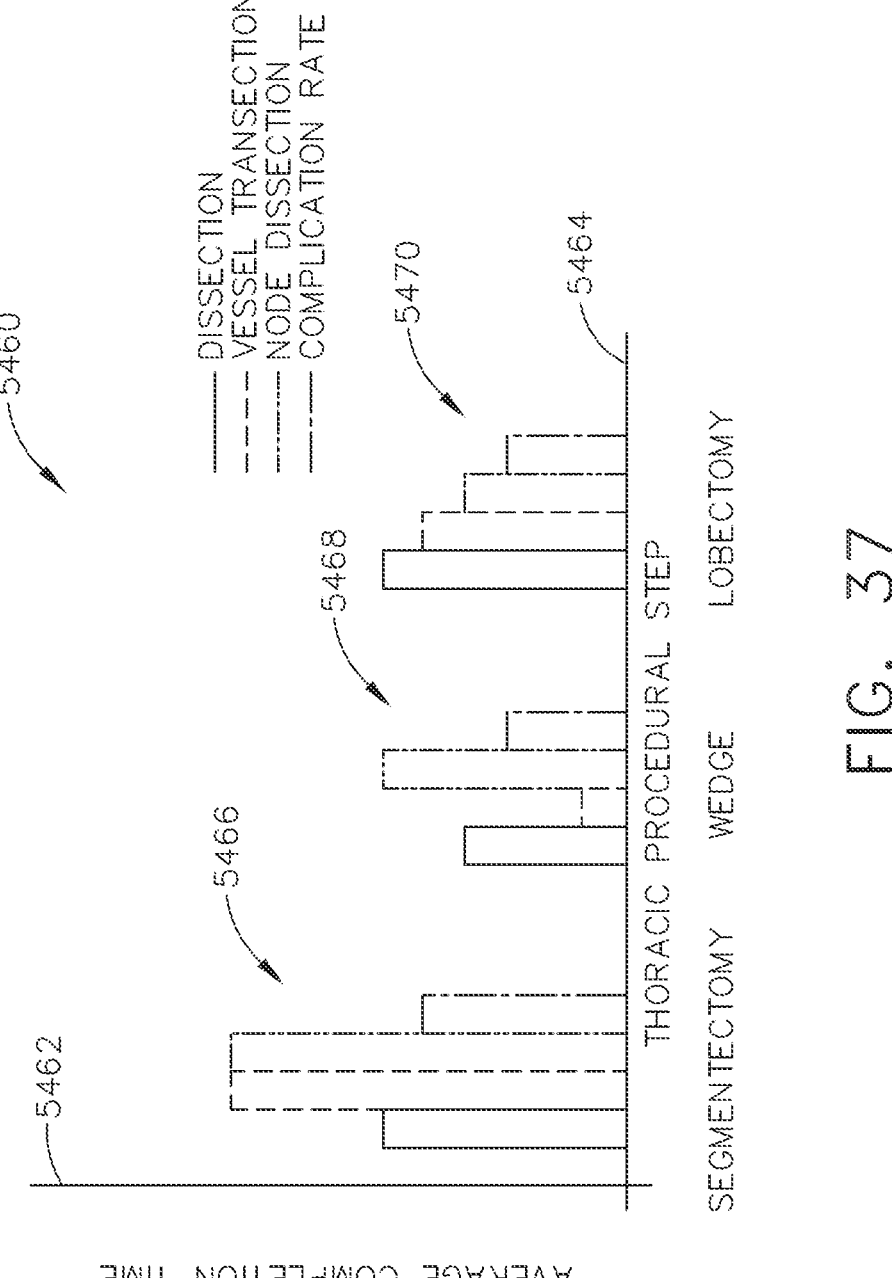
FIG. 37 illustrates a bar graph depicting the average completion time for particular procedural steps for different types of thoracic procedures, in accordance with at least one aspect of the present disclosure.

FIG. 37 illustrates a bar graph 5460 depicting the average completion time 5462 for particular procedural steps 5464 for different types of thoracic procedures. The surgical hub 5706 can be configured to track and store historical data for different types of procedures and calculate the average time to complete the procedure (or an individual step thereof). For example, FIG. 37 depicts the average completion time 5462 for thoracic segmentectomy 5466, wedge 5468, and lobectomy 5470 procedures. For each type of procedure, the surgical hub 5706 can track the average time to complete each step thereof. In this particular example, the dissection, vessel transection, and node dissection steps are indicated for each type of procedure. In addition to tracking and providing the average time for the steps of the procedure types, the surgical hub 5706 can additionally track other metrics or historical data, such as the complication rate for each procedure type (i.e., the rate of procedures having at least one complication as defined by the surgical hub 5706 or the surgeon). Additional tracked metrics for each procedure type, such as the complication rate, can also be depicted for comparison between the different procedure types.

Figure 38:
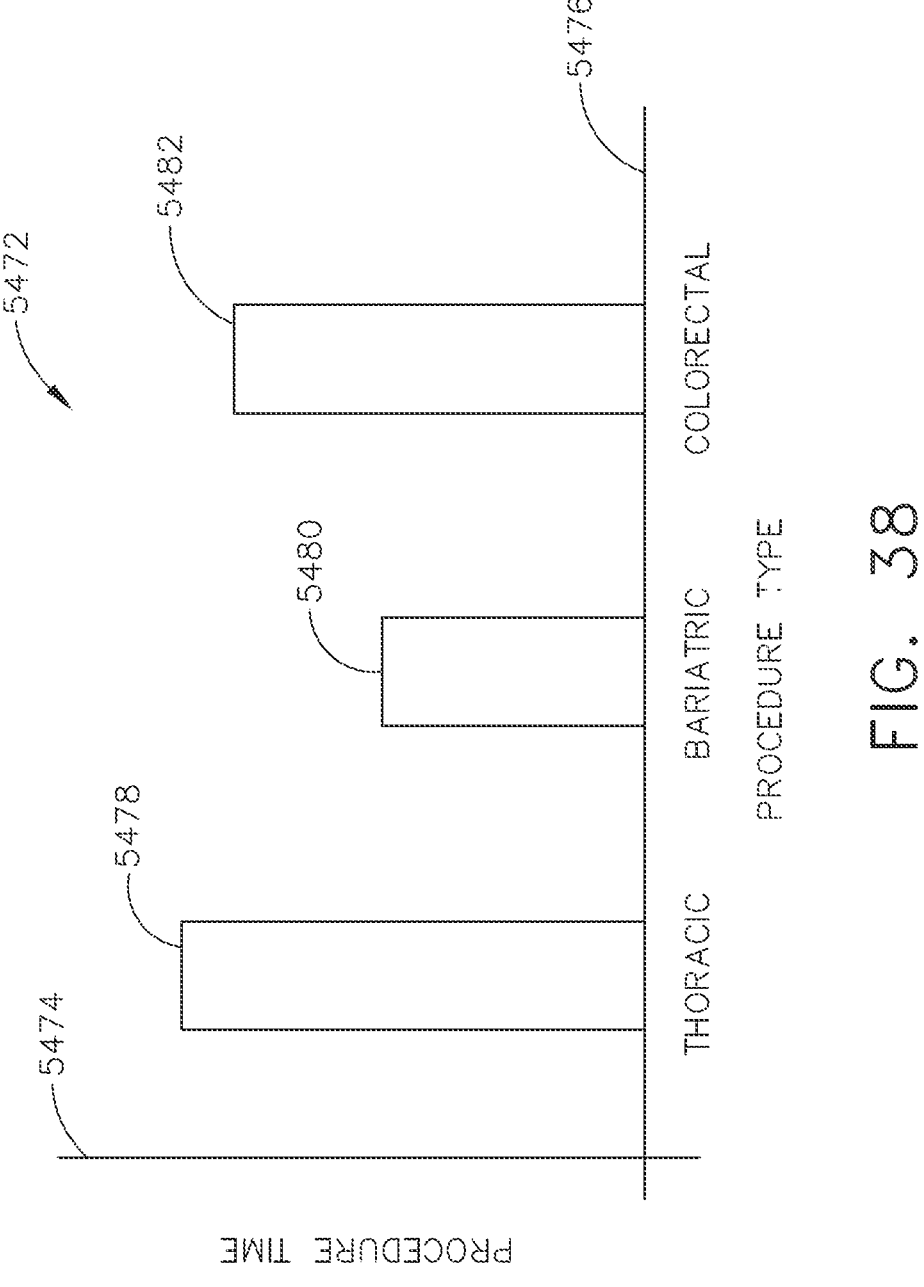
FIG. 38 illustrates a bar graph depicting procedure time relative to procedure types, in accordance with at least one aspect of the present disclosure.

FIG. 38 illustrates a bar graph 5472 depicting the procedure time 5474 relative to procedure types 5476. The surgical hub 5706 can be configured to track and store historical data or metrics for different procedure types 5476 or classes, which can encompass multiple subtypes of procedures. For example, FIG. 38 depicts the procedure time 5474 for surgical procedures classified as a thoracic 5478, bariatric 5480, or colorectal 5482 procedure. In various exemplifications, the surgical hub 5706 can output the procedure time 5474 for the procedure classifications expressed in terms of either the total length of time or the average time spent on the given procedure types 5476. The analytics package of the surgical hub 5706 can, for example, provide this data to the surgeons, hospital officials, or medical personnel to track the efficiency of the queried procedures. For example, FIG. 38 depicts bariatric procedures 5480 as taking a lower average time (i.e., being more time efficient) than either thoracic procedures 5478 or colorectal procedures 5482.

Figure 39:
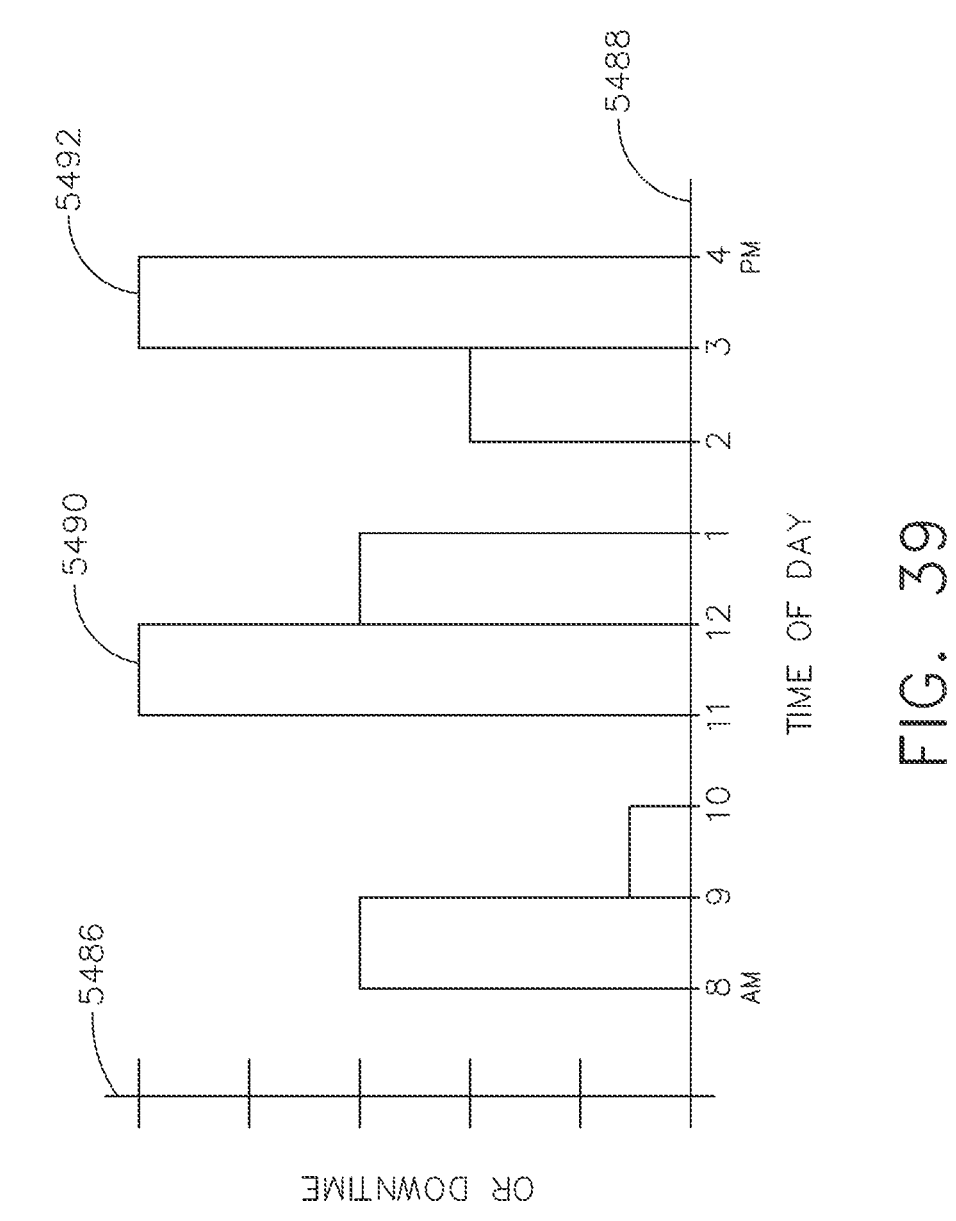
FIG. 39 illustrates a bar graph depicting operating room downtime relative to the time of day, in accordance with at least one aspect of the present disclosure.

FIG. 39 illustrates a bar graph 5484 depicting operating room downtime 5486 relative to the time of day 5488.

Figure 40:
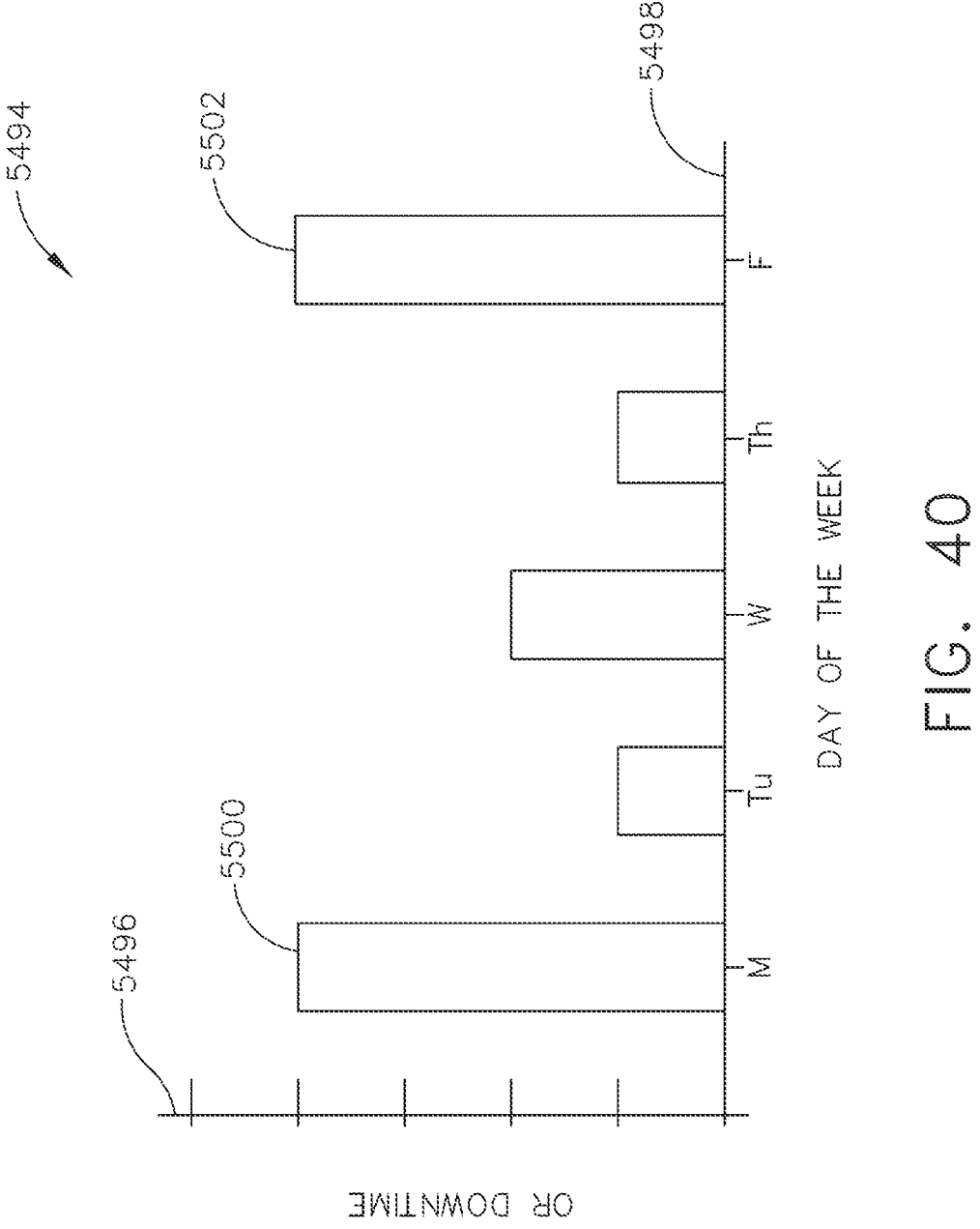
FIG. 40 illustrates a bar graph depicting operating room downtime relative to the day of the week, in accordance with at least one aspect of the present disclosure.

Relatedly, FIG. 40 illustrates a bar graph 5494 depicting operating room downtime 5496 relative to the day of the week 5498. Operating room downtime 5486, 5496 can be expressed in, for example, a length of a unit of time or relative utilization (i.e., percentage of time that the operating room is in use). The operating room downtime data can encompass an individual operating room or an aggregation of multiple operating rooms at a medical facility. As discussed above, a surgical hub 5706 can be configured to track whether a surgical procedure is being performed in the operating theater associated with the surgical hub 5706 (including the length of time that a surgical procedure is or is not being performed) utilizing a situational awareness system, for example. As shown in FIGS. 39 and 40, the surgical hub 5706 can provide an output (e.g., bar graphs 5484, 5494 or other graphical representations of data) depicting the tracked data pertaining to when the operating room is being utilized (i.e., when a surgical procedure is being performed) and/or when there is downtime between procedures. Such data can be utilized to identify ineffectiveness or inefficiencies in performing surgical procedures, cleaning or preparing operating theaters for surgery, scheduling, and other metrics associated with operating theater use. For example, FIG. 39 depicts a comparative increase in operating room downtime 5486 at a first instance 5490 from 11:00 a.m.-12:00 p.m. and a second instance 5492 from 3:00-4:00 p.m. As another example, FIG. 40 depicts a comparative increase in operating room downtime 5496 on Mondays 5500 and Fridays 5502. In various exemplifications, the surgical hub 5706 can provide operating theater downtime data for a particular instance (i.e., a specific time, day, week, etc.) or an average operating theater downtime data for a category of instances (i.e., aggregated data for a day, time, week, etc.). Hospital officials or other medical personnel thus could use this data to identify specific instances where an inefficiency may have occurred or identify trends in particular days and/or times of day where there may be inefficiencies. From such data, the hospital officials or other medical personnel could then investigate to identify the specific reasons for these increased downtimes and take corrective action to address the identified reason.

Figure 41:
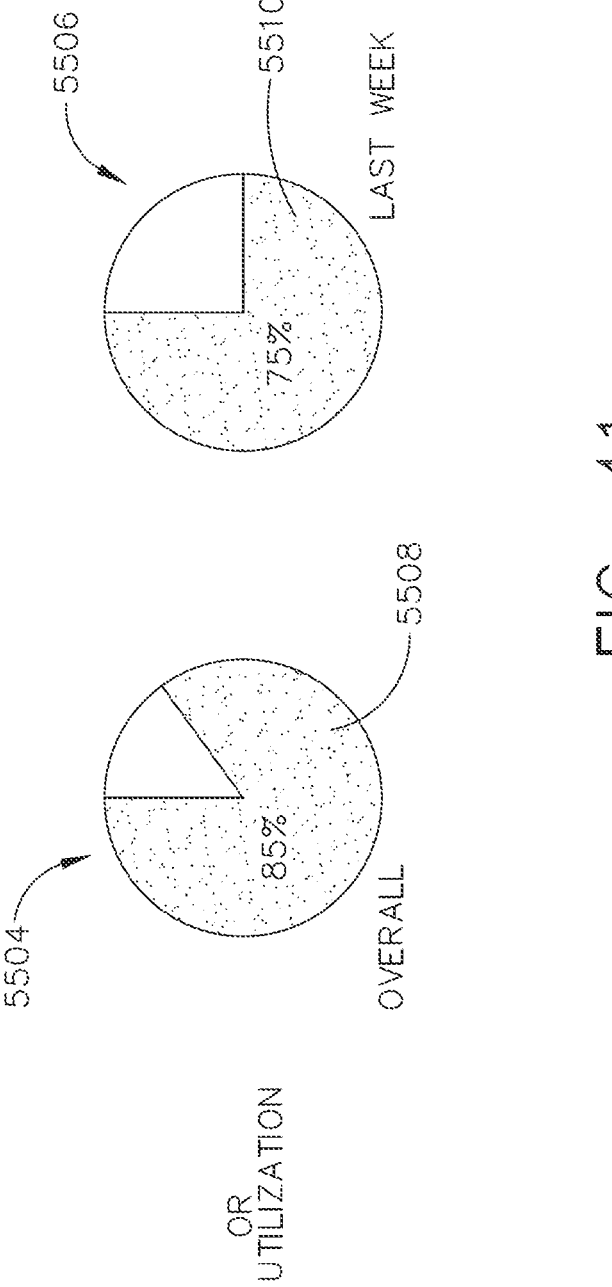
FIG. 41 illustrates a pair of pie charts depicting the percentage of time that the operating theater is utilized, in accordance with at least one aspect of the present disclosure.

In various exemplifications, the surgical hub 5706 can be configured to display data in response to queries in a variety of different formats (e.g., bar graphs, pie graphs, infographics). FIG. 41 illustrates a pair of pie charts depicting the percentage of time that the operating theater is utilized. The operating theater utilization percentage can encompass an individual operating theater or an aggregation of multiple operating theaters (e.g., the operating rooms at a medical facility or every operating room for all medical facilities having surgical hubs 5706 connected to the cloud 5702). As discussed above, a surgical hub 5706 can be configured to determine when a surgical procedure is or is not being performed (i.e., whether the operating theater associated with the surgical hub 5706 is being utilized) using a situational awareness system, for example. In addition to expressing operating theater utilization in terms of an average or absolute amount for different time periods (as depicted in FIGS. 39-40), the surgical hub 5706 can additionally express operating theater utilization in terms of a percentage or relative amount compared to a maximum possible utilization. As above, the operating theater utilization can be parsed for particular time periods, including the overall utilization (i.e., the total historical percentage of time in use) for the particular operating theater (or groups of operating theaters) or the utilization over the span of a particular time period. As shown in FIG. 41, a first pie chart

5504 depicts the overall operating theater utilization 5508 (85%) and a second pie chart 5506 depicts the operating theater utilization for the prior week 5510 (75%). Hospital officials and other medical personnel could use this data to identify that there may have been some inefficiency that occurred in the prior week that caused the particular operating theater (or group of operating theaters) to be utilized less efficiently compared to the historical average so that further investigations can be carried out to identify the specific reasons for this decreased utilization.

Figure 42:
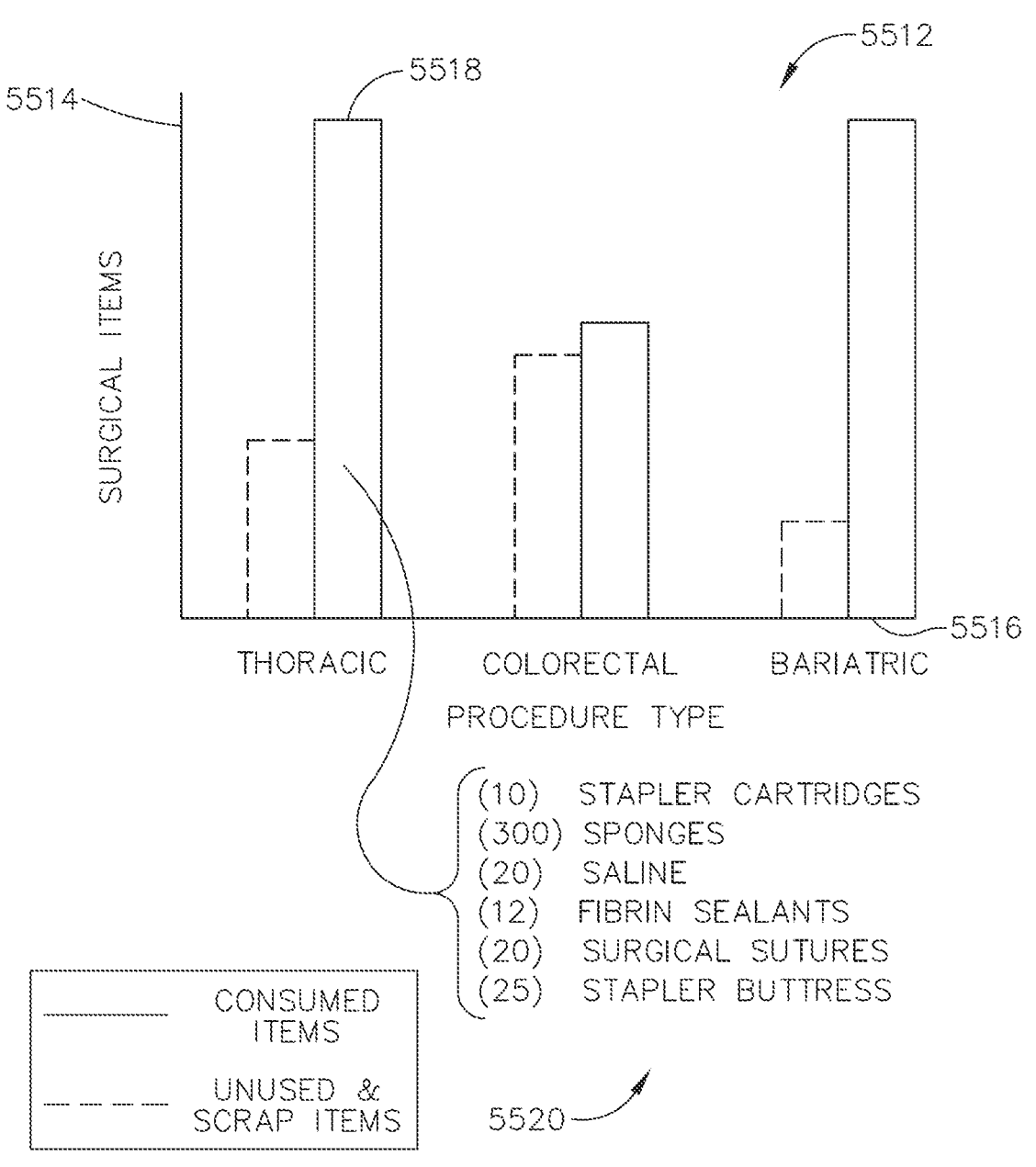
FIG. 42 illustrates a bar graph depicting consumed and unused surgical items relative to procedure type, in accordance with at least one aspect of the present disclosure.

In some exemplifications, the surgical hub 5706 is configured to track detect and track the number of surgical items that are utilized during the course of a surgical procedure. This data can then be aggregated and displayed (either automatically or in response to a query) according to, for example, a particular time period (e.g., per day or per week) or for a particular surgical procedure type (e.g., thoracic procedures or abdominal procedures). FIG. 42 illustrates a bar graph 5512 depicting consumed and unused surgical items 5514 relative to procedure type 5516. The surgical hub 5706 can be configured to determine or infer what surgical items are being consumed during the course of each surgical procedure via a situational awareness system. The situational awareness system can determine or receive the list of surgical items to be used in a procedure (e.g., see FIG. 26B), determine or infer when each procedure (and steps thereof) begins and ends, and determine when a particular surgical item is being utilized according to the procedural step being performed. The inventory of surgical items that are consumed or unused during the course of a surgical procedure can be represented in terms of the total number of surgical items or the average number of surgical items per procedure type 5516, for example. The consumed surgical items can include non-reusable items that are utilized during the course of a surgical procedure. The unused surgical items can include additional items that are not utilized during the procedure(s) or scrap items. The procedure type can correspond to broad classifications of procedures or a specific procedure type or technique for performing a procedure type. For example, in FIG. 42 the procedure types 5516 being compared are thoracic, colorectal, and bariatric procedures. For each of these procedure types 5516, the average number of consumed and unused surgical items 5514 are both provided. In one aspect, the surgical hub 5706 can be configured to further parse the consumed and/or unused surgical items 5514 by the specific item type. In one exemplification, the surgical hub 5706 can provide a detailed breakdown of the surgical items 5514 making up each item category for each surgical procedure type 5516 and graphically represent the different categories of surgical items 5514. For example, in FIG. 42, the unused surgical items are depicted in dashed lines and the consumed surgical items are depicted in solid lines. In one exemplification, the surgical hub 5706 is configured to further indicate the specific within a category for a particular procedure type 5516. For example, in FIG. 42, the consumed items category for the thoracic procedure type has been selected at 5518, which then causes a callout 5520 to be displayed listing the particular surgical items in the category: stapler cartridges, sponges, saline, fibrin sealants, surgical sutures, and stapler buttress material. Furthermore, the callout 5520 can be configured to provide the quantities of the listed items in the category, which may be the average or absolute quantities of the items (either consumed or unused) for the particular procedure type.

In one exemplification, the surgical hub 5706 can be configured to aggregate tracked data in a redacted format (i.e., with any patient-identifying information stripped out). Such bulk data can be utilized for academic or business analysis purposes. Further, the surgical hub 5706 can be configured to upload the redacted or anonymized data to a local database of the medical facility in which the surgical hub 5706 is located, an external database system, or the cloud 5702, whereupon the anonymized data can be accessed by user/client applications on demand. The anonymized data can be utilized to compare outcomes and efficiencies within a hospital or between geographic regions, for example.

The process 5300 depicted in FIG. 30 improves scheduling efficiency by allowing the surgical hubs 5706 to automatically store and provide granular detail on correlations between lengths of time required for various procedures according to particular days, particular types of procedures, particular hospital staff members, and other such metrics. This process 5300 also reduces surgical item waste by allowing the surgical hubs 5706 to provide alerts when the amount of surgical items being consumed, either on a per-procedure basis or as a category, are deviating from the expected amounts. Such alerts can be provided either automatically or in response to receiving a query.

Figure 43:
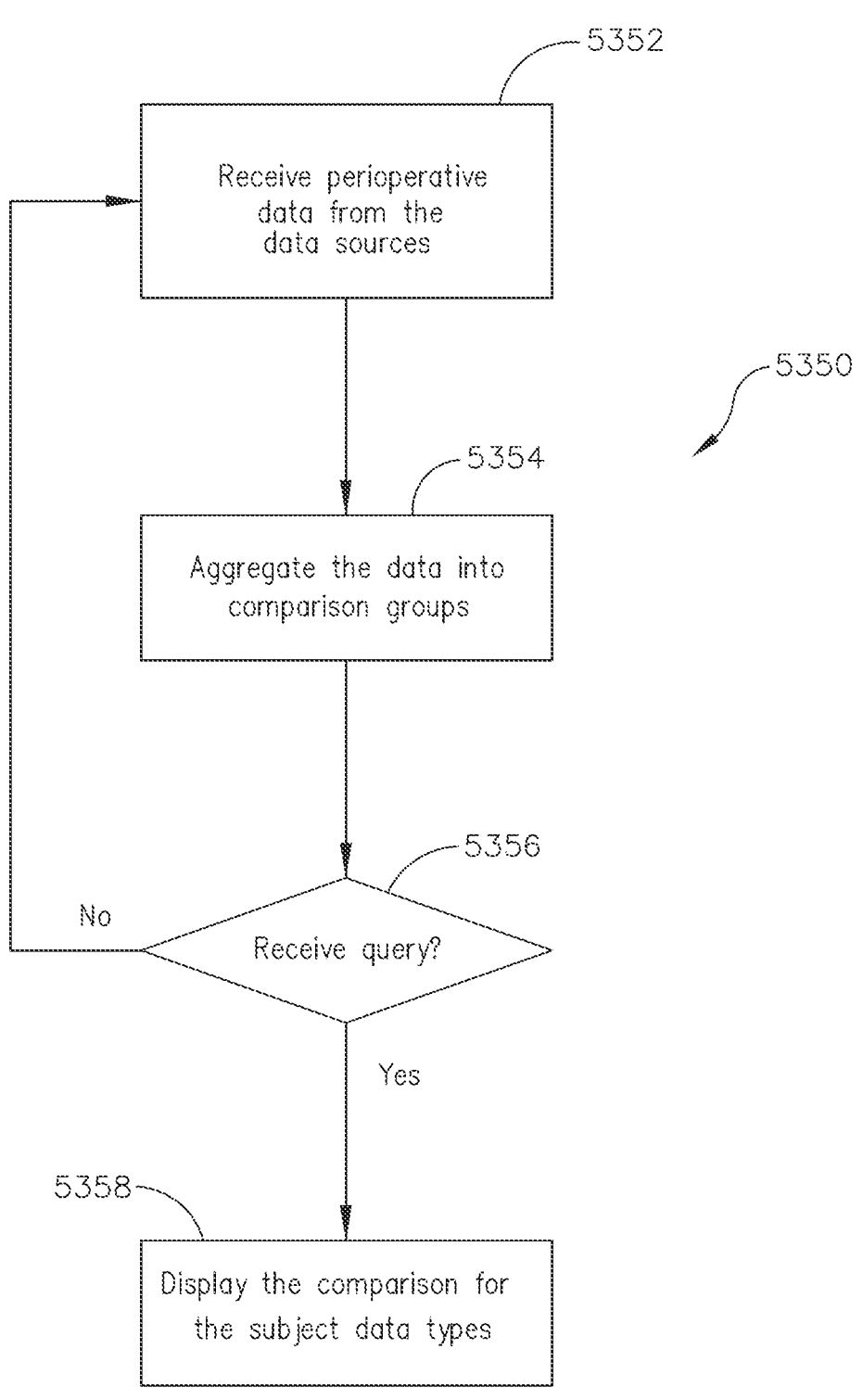
FIG. 43 illustrates a logic flow diagram of a process for storing data from the modular devices and patient information database for comparison, in accordance with at least one aspect of the present disclosure.

FIG. 43 illustrates a logic flow diagram of a process 5350 for storing data from the modular devices and patient information database for comparison. In the following description, description of the process 5350, reference should also be made to FIG. 29. In one exemplification, the process 5350 can be executed by a control circuit of a surgical hub 206, as depicted in FIG. 10 (processor 244). In yet another exemplification, the process 5350 can be executed by a distributed computing system including a control circuit of a surgical hub 206 in combination with a control circuit of a modular device, such as the microcontroller 461 of the surgical instrument depicted FIG. 12, the microcontroller 620 of the surgical instrument depicted in FIG. 16, the control circuit 710 of the robotic surgical instrument 700 depicted in FIG. 17, the control circuit 760 of the surgical instruments 750, 790 depicted in FIGS. 18 and 19, or the controller 838 of the generator 800 depicted in FIG. 20. For economy, the following description of the process 5350 will be described as being executed by the control circuit of a surgical hub 5706; however, it should be understood that the description of the process 5350 encompasses all of the aforementioned exemplifications.

The control circuit executing the process 5350 receives data from the data sources, such as the modular device(s) and the patient information database(s) (e.g., EMR databases) that are communicably coupled to the surgical hub 5706. The data from the modular devices can include, for example, usage data (e.g., data pertaining to how often the modular device has been utilized, what procedures the modular device has been utilized in connection with, and who utilized the modular devices) and performance data (e.g., data pertaining to the internal state of the modular device and the tissue being operated on). The data from the patient information databases can include, for example, patient data (e.g., data pertaining to the patient's age, sex, and medical history) and patient outcome data (e.g., data pertaining to the outcomes from the surgical procedure). In some exemplifications, the control circuit can continuously receive 5352 data from the data sources before, during, or after a surgical procedure.

As the data is received 5352, the control circuit aggregates 5354 the data in comparison groups of types of data. In other words, the control circuit causes a first type of data to be stored in association with a second type of data. However, more than two different types of data can be aggregated 5354 together into a comparison group. For example, the control circuit could store a particular type of performance data for a particular type of modular device (e.g., the force to fire for a surgical cutting and stapling instrument or the characterization of the energy expended by an RF or ultrasonic surgical instrument) in association with patient data, such as sex, age (or age range), a condition (e.g., emphysema) associated with the patient. In one exemplification, when the data is aggregated 5354 into comparison groups, the data is anonymized such that all patient-identifying information is removed from the data. This allows the data aggregated 5354 into comparison groups to be utilized for studies, without compromising confidential patient information. The various types of data can be aggregated 5354 and stored in association with each other in lookup tables, arrays, and other such formats. In one exemplification, the received 5352 data is automatically aggregated 5354 into comparison groups. Automatically aggregating 5354 and storing the data allows the surgical hub 5706 to quickly return results for queries and the groups of data to be exported for analysis according to specifically desired data types.

When the control circuit receives 5356 a query for a comparison between two or more of the tracked data types, the process 5350 proceeds along the YES branch. The control circuit then retrieves the particular combination of the data types stored in association with each other and then displays 5358 a comparison (e.g., a graph or other graphical representation of the data) between the subject data types. If the control circuit does not receive 5356 a query, the process 5350 continues along the NO branch and the control circuit continues receiving 5352 data from the data sources.

In one exemplification, the control circuit can be configured to automatically quantify a correlation between the received 5352 data types. In such aspects, the control circuit can calculate a correlation coefficient (e.g., the Pearson's coefficient) between pairs of data types. In one aspect, the control circuit can be configured to automatically display a report providing suggestions or other feedback if the quantified correlation exceeds a particular threshold value. In one aspect, the control circuit of the surgical hub 5706 can be configured to display a report on quantified correlations exceeding a particular threshold value upon receiving a query or request from a user.

In one exemplification, a surgical hub 5706 can compile information on procedures that the surgical hub 5706 was utilized in the performance of, communicate with other surgical hubs 5706 within its network (e.g., a local network of a medical facility or a number of surgical hubs 5706 connected by the cloud 5702), and compare results between type of surgical procedures or particular operating theaters, doctors, or departments. Each surgical hub 5706 can calculate and analyze utilization, efficiency, and comparative results (relative to all surgical hubs 5706 across a hospital network, a region, etc.). For example, the surgical hub 5706 can display efficiency and comparative data, including operating theater downtime, operating theater clean-up and recycle time, step-by-step completion timing for procedures (including highlighting which procedural steps take the longest, for example), average times for surgeons to complete procedures (including parsing the completion times on a procedure-by-procedure basis), historical completion times (e.g., for completing classes of procedures, specific procedures, or specific steps within a procedure), and/or operating theater utilization efficiency (i.e., the time efficiency from a procedure to a subsequent procedure). The data that is accessed and shared across networks by the surgical hubs 5706 can include the anonymized data aggregated into comparison groups, as discussed above.

For example, the surgical hub 5706 can be utilized to perform studies of performance by instrument type or cartridge type for various procedures. As another example, the surgical hub 5706 can be utilized to perform studies on the performance of individual surgeons. As yet another example, the surgical hub 5706 can be utilized to perform studies on the effectiveness of different surgical procedures according to patients' characteristics or disease states.

In another exemplification, a surgical hub 5706 can provide suggestions on streamlining processes based on tracked data. For example, the surgical hub 5706 can suggest different product mixes according to the length of certain procedures or steps within a procedure (e.g., suggest a particular item that is more appropriate for long procedure steps), suggest more cost effective product mixes based on the utilization of items, and/or suggest kitting or pre-grouping certain items to lower set-up time. In another exemplification, a surgical hub 5706 can compare operating theater utilization across different surgical groups in order to better balance high volume surgical groups with surgical groups that have more flexible bandwidth. In yet another aspect, the surgical hub 5706 could be put in a forecasting mode that would allow the surgical hub 5706 to monitor upcoming procedure preparation and scheduling, then notify the administration or department of upcoming bottlenecks or allow them to plan for scalable staffing. The forecasting mode can be based on, for example, the anticipated future steps of the current surgical procedure that is being performed using the surgical hub 5706, which can be determined by a situational awareness system.

In another exemplification, a surgical hub 5706 can be utilized as a training tool to allow users to compare their procedure timing to other types of individuals or specific individuals within their department (e.g., a resident could compare his or her timing to a particular specialist or the average time for a specialist within the hospital) or the department average times. For example, users could identify what steps of a surgical procedure they are spending an inordinate amount of time on and, thus, what steps of the surgical procedure that they need to improve upon.

In one exemplification, all processing of stored data is performed locally on each surgical hub 5706. In another exemplification, each surgical hub 5706 is part of a distributed computing network, wherein each individual surgical hub 5706 compiles and analyzes its stored data and then communicates the data to the requesting surgical hub 5706. A distributed computing network could permit fast parallel processing. In another exemplification, each surgical hub 5706 is communicably connected to a cloud 5702, which can be configured to receive the data from each surgical hub 5706 and then perform the necessary processing (data aggregation, calculations, and so on) on the data.

The process 5350 depicted in FIG. 43 improves the ability to determine when procedures are being performed inefficiently by allowing the surgical hubs 5706 to provide alerts when particular procedures, either on a per-procedure basis or as category, are deviating from the expected times to complete the procedures. Such alerts can be provided either automatically or in response to receiving a query. This process 5350 also improves the ability to perform studies on what surgical instruments and surgical procedure techniques provide the best patient outcomes by automatically tracking and indexing such data in easily-retrievable and reportable formats.

Some systems described herein offload the data processing that controls the modular devices (e.g., surgical instruments) from the modular devices themselves to an external computing system (e.g., a surgical hub) and/or a cloud. However in some exemplifications, some modular devices can sample data (e.g., from the sensors of the surgical instruments) at a faster rate that the rate at which the data can be transmitted to and processed by a surgical hub. As one solution, the surgical hub and the surgical instruments (or other modular devices) can utilize a distributed computing system where at least a portion of the data processing is performed locally on the surgical instrument. This can avoid data or communication bottlenecks between the instrument and the surgical hub by allowing the onboard processor of the surgical instrument to handle at least some of the data processing when the data sampling rate is exceeding the rate at which the data can be transmitted to the surgical hub. In some exemplifications, the distributed computing system can cease distributing the processing between the surgical hub and the surgical instrument and instead have the processing be executed solely onboard the surgical instrument. The processing can be executed solely by the surgical instrument in situations where, for example, the surgical hub needs to allocate its processing capabilities to other tasks or the surgical instrument is sampling data at a very high rate and it has the capabilities to execute all of the data processing itself.

Similarly, the data processing for controlling the modular devices, such as surgical instruments, can be taxing for an individual surgical hub to perform. If the surgical hub's processing of the control algorithms for the modular devices cannot keep pace with the use of the modular devices, then the modular devices will not perform adequately because their control algorithms will either not be updated as needed or the updates to the control algorithms will lag behind the actual use of the instrument. As one solution, the surgical hubs can be configured to utilize a distributed computing system where at least a portion of the processing is performed across multiple separate surgical hubs. This can avoid data or communication bottlenecks between the modular devices and the surgical hub by allowing each surgical hub to utilize the networked processing power of multiple surgical hubs, which can increase the rate at which the data is processed and thus the rate at which the control algorithm adjustments can be transmitted by the surgical hub to the paired modular devices. In addition to distributing the computing associated with controlling the various modular devices connected to the surgical hubs, a distributed computing system can also dynamically shift computing resources between multiple surgical hubs in order to analyze tracked data in response to queries from users and perform other such functions. The distributed computing system for the surgical hubs can further be configured to dynamically shift data processing resources between the surgical hubs when any particular surgical hub becomes overtaxed.

The modular devices that are communicably connectable to the surgical hub can include sensors, memories, and processors that are coupled to the memories and configured to receive and analyze data sensed by the sensors. The surgical hub can further include a processor coupled to a memory that is configured to receive (through the connection between the modular device and the surgical hub) and analyze the data sensed by the sensors of the modular device. In one exemplification, the data sensed by the modular device is processed externally to the modular device (e.g., external to a handle assembly of a surgical instrument) by a computer that is communicably coupled to the modular device. For example, the advanced energy algorithms for controlling the operation of a surgical instrument can be processed by an external computing system, rather than on a controller embedded in the surgical instrument (such as instrument using an Advanced RISC Machine (ARM) processor). The external computer system processing the data sensed by the modular devices can include the surgical hub to which the modular devices are paired and/or a cloud computing system. In one exemplification, data sampled at a particular rate (e.g., 20 Ms/sec) and a particular resolution (e.g., 12 bits resolution) by a surgical instrument is decimated and then transmitted over a link to the surgical hub to which the surgical instrument is paired. Based on this received data, the control circuit of the surgical hub then determines the appropriate control adjustments for the surgical instrument, such as controlling power for an ultrasonic surgical instrument or RF electrosurgical instrument, setting motor termination points for a motor-driven surgical instrument, and so on. The control adjustments are then transmitted to the surgical instrument for application thereon.

Distributed Processing

Figure 44:
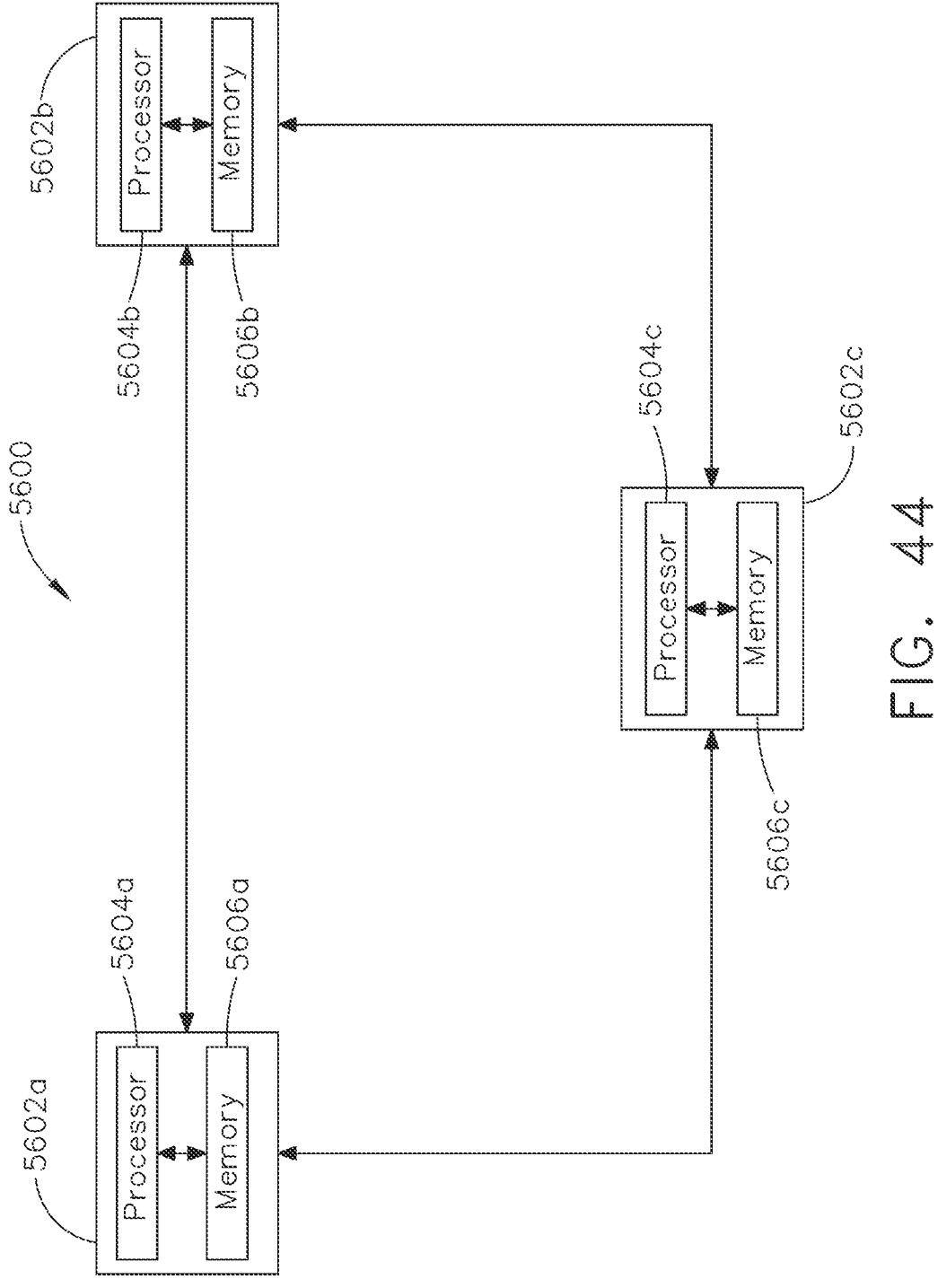
FIG. 44 illustrates a diagram of a distributed computing system, in accordance with at least one aspect of the present disclosure.

FIG. 44 illustrates a diagram of a distributed computing system 5600. The distributed computing system 5600 includes a set of nodes 5602a, 5602b, 5602c that are communicably coupled by a distributed multi-party communication protocol such that they execute a shared or distributed computer program by passing messages therebetween. Although three nodes 5602a, 5602b, 5602c are depicted, the distributed computing system 5600 can include any number of nodes 5602a, 5602b, 5602c that are communicably connected together. Each of the nodes 5602a, 5602b, 5602c comprises a respective memory 5606a, 5606b, 5606c and processor 5604a, 5604b, 5604c coupled thereto. The processors 5604a, 5604b, 5604c execute the distributed multi-party communication protocol, which is stored at least partially in the memories 5606a, 5606b, 5606c. Each node 5602a, 5602b, 5602c can represent either a modular device or a surgical hub. Therefore, the depicted diagram represents aspects wherein various combinations of surgical hubs and/or modular devices are communicably coupled. In various exemplifications, the distributed computing system 5600 can be configured to distribute the computing associated with controlling the modular device(s) (e.g., advanced energy algorithms) over the modular device(s) and/or the surgical hub(s) to which the modular device(s) are connected. In other words, the distributed computing system 5600 embodies a distributed control system for controlling the modular device(s) and/or surgical hub(s).

In some exemplifications, the modular device(s) and surgical hub(s) utilize data compression for their communication protocols. Wireless data transmission over sensor networks can consume a significant amount of energy and/or processing resources compared to data computation on the device itself. Thus data compression can be utilized to reduce the data size at the cost of extra processing time on the device. In one exemplification, the distributed computing system 5600 utilizes temporal correlation for sensing data, data transformation from one dimension to two dimension, and data separation (e.g., upper 8 bit and lower 8 bit data). In another exemplification, the distributed computing system 5600 utilizes a collection tree protocol for data collection from different nodes 5602a, 5602b, 5602c having sensors (e.g., modular devices) to a root node. In yet another aspect, the distributed computing system 5600 utilizes first-order prediction coding to compress the data collected by the nodes 5602a, 5602b, 5602c having sensors (e.g., modular devices), which can minimize the amount of redundant information and greatly reduce the amount of data transmission between the nodes 5602a, 5602b, 5602c of the network. In yet another exemplification, the distributed computing system 5600 is configured to transmit only the electroencephalogram (EEG) features. In still yet another exemplification, the distributed computing system 5600 can be configured to transmit only the complex data features that are pertinent to the surgical instrument detection, which can save significant power in wireless transmission. Various other exemplifications can utilize combinations of the aforementioned data compression techniques and/or additional techniques of data compression.

Figure 45:
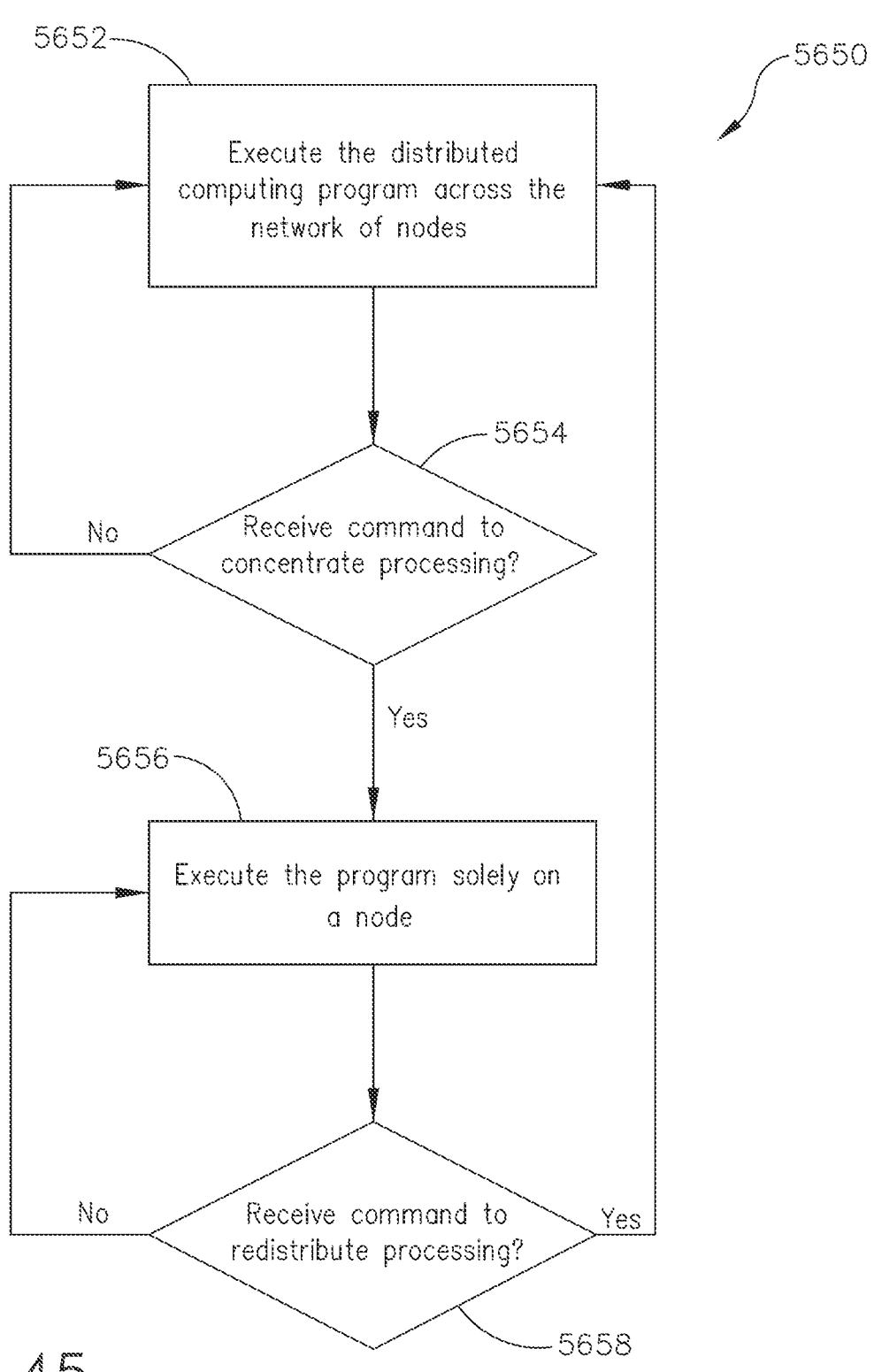
FIG. 45 illustrates a logic flow diagram of a process for shifting distributed computing resources, in accordance with at least one aspect of the present disclosure.

FIG. 45 illustrates a logic flow diagram of a process 5650 for shifting distributed computing resources. In the following description of the 5650, reference should also be made to FIG. 44. In one exemplification, the process 5650 can be executed by a distributed computing system including a control circuit of a surgical hub 206, as depicted in FIG. 10 (processor 244), in combination with a control circuit of a second surgical hub 206 and/or a control circuit of a modular device, such as the microcontroller 461 of the surgical instrument depicted FIG. 12, the microcontroller 620 of the surgical instrument depicted in FIG. 16, the control circuit 710 of the robotic surgical instrument 700 depicted in FIG. 17, the control circuit 760 of the surgical instruments 750, 790 depicted in FIGS. 18 and 19, or the controller 838 of the generator 800 depicted in FIG. 20. For economy, the following description of the process 5650 will be described as being executed by the control circuits of one or more nodes; however, it should be understood that the description of the process 5650 encompasses all of the aforementioned exemplifications.

The control circuits of each node execute 5652 a distributed control program in synchrony. As the distributed control program is being executed across the network of nodes, at least one of the control circuits monitors for a command instructing the distributed computing system to shift from a first mode, wherein the distributed computing program is executed across the network of nodes, to a second mode, wherein the control program is executed by a single node. In one exemplification, the command can be transmitted by a surgical hub in response to the surgical hub's resources being needed for an alternative computing task. In another exemplification, the command can be transmitted by a modular device in response to the rate at which the data is sampled by the modular device outpacing the rate at which the sampled data can be communicated to the other nodes in the network. If a control circuit determines that an appropriate command has been received 5654, the process 5650 continues along the YES branch and the distributed computing system 5600 shifts to a single node executing 5656 the program. For example, the distributed computing system 5600 shifts the distributed computing program from being executed by both a modular device and a surgical hub to being executed solely by the modular device. As another example, the distributed computing system 5600 shifts the distributed computing program from being executed by both a first surgical hub and a second surgical hub to being executed solely by the first surgical hub. If no control circuit determines that an appropriate command has been received 5654, the process continues along the NO branch and the control circuits of the network of nodes continues executing 5652 the distributed computing program across the network of nodes.

In the event that the program has been shifted to being executed 5656 by a single node, the control circuit of the particular node solely executing the distributed program and/or a control circuit of another node within the network (which previously was executing the distributed program) monitors for a command instructing the node to re-distribute the processing of the program across the distributed computing system. In other words, the node monitors for a command to re-initiate the distributed computing system. In one exemplification, the command to re-distribute the processing across the network can be generated when the sampling rate of the sensor is less than the data communication rate between the modular device and the surgical hub. If a control circuit receives 5658 an appropriate command to re-distribute the processing, then the process 5650 proceeds along the YES branch and the program is once again executed 5652 across the node network. If a control circuit has not received 5658 an appropriate command, then the node continues singularly executing 5656 the program.

The process 5650 depicted in FIG. 45 eliminates data or communication bottlenecks in controlling modular devices by utilizing a distributed computing architecture that can shift computing resources either between the modular devices and surgical hubs or between the surgical hubs as needed. This process 5650 also improves the modular devices' data processing speed by allowing the processing of the modular devices' control adjustments to be executed at least in part by the modular devices themselves. This process 5650 also improves the surgical hubs' data processing speed by allowing the surgical hubs to shift computing resources between themselves as necessary.

It can be difficult during video-assisted surgical procedures, such as laparoscopic procedures, to accurately measure sizes or dimensions of features being viewed through a medical imaging device due to distortive effects caused by the device's lens. Being able to accurately measure sizes and dimensions during video-assisted procedures could assist a situational awareness system for a surgical hub by allowing the surgical hub to accurately identify organs and other structures during video-assisted surgical procedures. As one solution, a surgical hub could be configured to automatically calculate sizes or dimensions of structures (or distances between structures) during a surgical procedure by comparing the structures to markings affixed to devices that are intended to be placed within the FOV of the medical imaging device during a surgical procedure. The markings can represent a known scale, which can then be utilized to make measurements by comparing the unknown measured length to the known scale.

In one exemplification, the surgical hub is configured to receive image or video data from a medical imaging device paired with the surgical hub. When a surgical instrument bearing a calibration scale is within the FOV of the medical imaging device, the surgical hub is able to measure organs and other structures that are likewise within the medical imaging device's FOV by comparing the structures to the calibration scale. The calibration scale can be positioned on, for example, the distal end of a surgical instrument.

Figure 46:
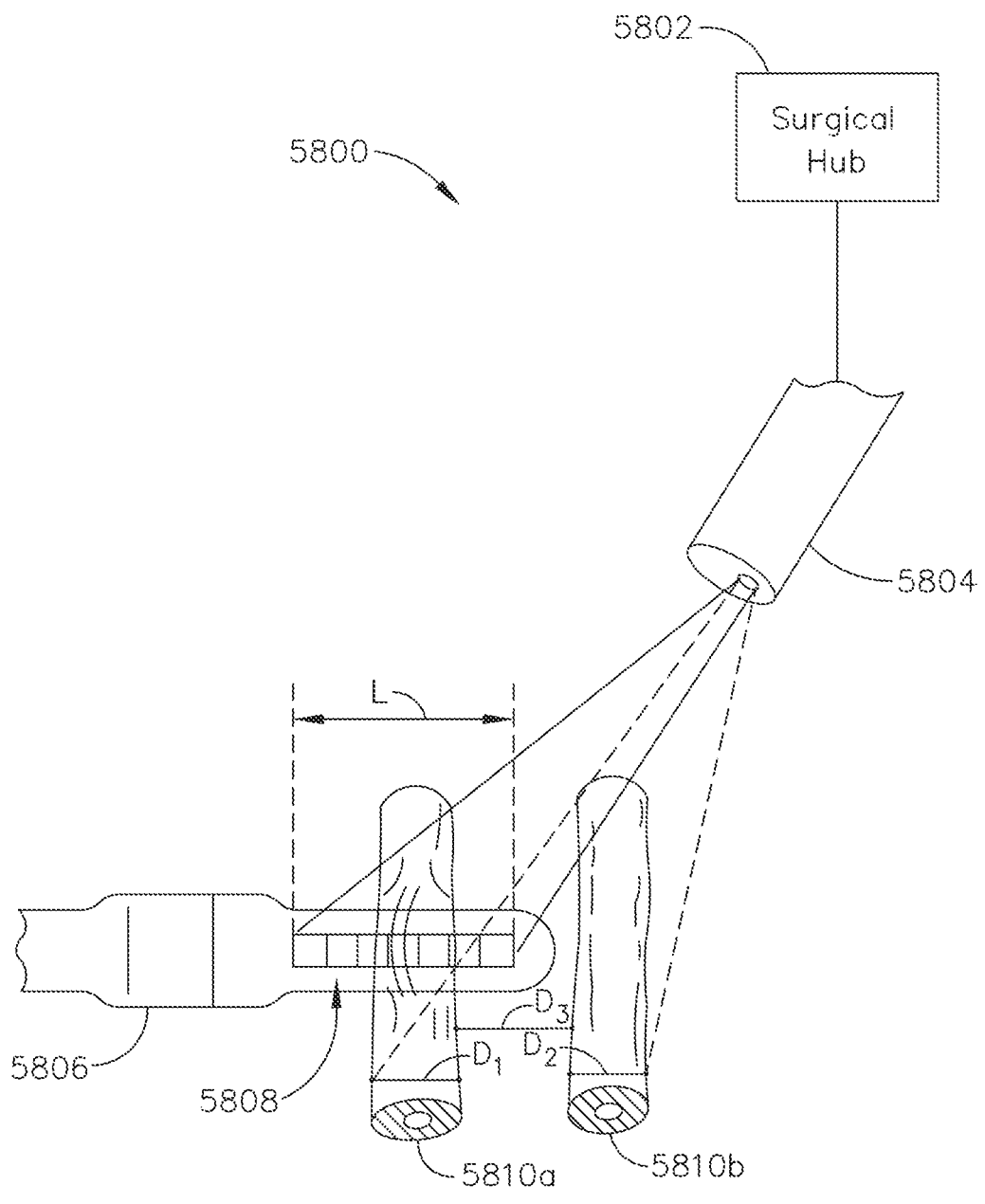
FIG. 46 illustrates a diagram of an imaging system and a surgical instrument bearing a calibration scale, in accordance with at least one aspect of the present disclosure.

FIG. 46 illustrates a diagram of an imaging system 5800 and a surgical instrument 5806 bearing a calibration scale 5808. The imaging system 5800 includes a medical imaging device 5804 that is paired with a surgical hub 5802. The surgical hub 5802 can include a pattern recognition system or a machine learning system configured to recognize features in the FOV from image or video data received from the medical imaging device 5804. In one exemplification, a surgical instrument 5806 (e.g., a surgical cutting and stapling instrument) that is intended to enter the FOV of the medical imaging device 5804 during a surgical procedure includes a calibration scale 5808 affixed thereon. The calibration scale 5808 can be positioned on the exterior surface of the surgical instrument 5806, for example. In aspects wherein the surgical instrument 5806 is a surgical cutting and stapling instrument, the calibration scale 5808 can be positioned along the exterior surface of the anvil. The calibration scale 5808 can include a series of graphical markings separated at fixed and/or known intervals. The distance between the end or terminal markings of the calibration scale 5808 can likewise be a set distance L (e.g., 35 mm). In one exemplification, the end markings (e.g., the most proximal marking and the most distal marking) of the calibration scale 5808 are differentiated from the intermediate markings in size, shape, color, or another such fashion. This allows the image recognition system of the surgical hub 5802 to identify the end markings separately from the intermediate markings. The distance(s) between the markings can be stored in a memory or otherwise retrieved by the surgical hub 5802. The surgical hub 5802 can thus measure lengths or sizes of structures relative to the provided calibration scale 5808. In FIG. 46, for example, the surgical hub 5802 can calculate that the artery 5810a has a diameter or width of D1 (e.g., 17.0 mm), the vein 5810b has a diameter or width of D2 (e.g., 17.5 mm), and the distance between the vessels is D3 (e.g., 20 mm) by comparing the visualizations of these distances D1, D2, D3 to the known length L of the calibration scale 5808 positioned on the surgical instrument 5806 within the FOV of the medical imaging device 5804. The surgical hub 5802 can recognize the presence of the vessels 5810a, 5810b via an image recognition system. In some exemplifications, the surgical hub 5802 can be configured to automatically measure and display the size or dimension of detected features within the FOV of the medical imaging device 5804. In some exemplifications, the surgical hub 5802 can be configured to calculate the distance between various points selected by a user on an interactive display that is paired with the surgical hub 5802.

The imaging system 5800 configured to detect and measure sizes according to a calibration scale 5808 affixed to surgical instruments 5806 provides the ability to accurately measure sizes and distances during video-assisted procedures. This can make it easier for surgeons to precisely perform video-assisted procedures by compensating for the optically distortive effects inherent in such procedures.

Various aspects of the subject matter described herein are set out in the following numbered examples.

Example 1. A system comprising a surgical hub configured to communicably couple to a modular device comprising a sensor configured to detect data associated with the modular device and a device processor, the surgical hub comprising: a hub processor; and a hub memory coupled to the hub processor; and a distributed control system executable at least in part by each of the device processor and the hub processor, the distributed control system configured to: receive the data detected by the sensor; determine control adjustments for the modular device according to the data; and control the modular device according to the control adjustments; wherein in a first mode the distributed control system is executed by both the hub processor and the device processor, and in a second mode the distributed control system is executed solely by the device processor.

Example 2. The system of any one of Examples 1, wherein the distributed control system is configured to shift from the first mode to the second mode when a sampling rate of the sensor is greater than a data transmission rate from the modular device to the surgical hub.

Example 3. The system of any one of Examples 1-2, wherein the distributed control system is configured to shift from the second mode to the first mode when a sampling rate of the sensor is less than a data transmission rate from the modular device to the surgical hub.

Example 4. The system of any one of Examples 1-3, wherein the modular device comprises a radiofrequency (RF) electrosurgical instrument and the distributed control system is configured to control an energy level of the RF electrosurgical instrument.

Example 5. The system of any one of Examples 1-4, wherein the modular device comprises a surgical cutting and stapling instrument and the distributed control system is configured to control a rate at which a motor of the surgical cutting and stapling instrument drives a knife.

Example 6. A system comprising: a modular device configured to communicably couple to a surgical hub comprising a hub processor, the modular device comprising: a sensor configured to detect data associated with the modular device; a device memory; and a device processor coupled to the device memory and the sensor; and a distributed control system executable at least in part by each of the device processor and the hub processor, the distributed control system configured to: receive the data detected by the sensor; determine control adjustments for the modular device according to the data; and control the modular device according to the control adjustments; wherein in a first mode the distributed control system is executed by both the hub processor and the device processor, and in a second mode the distributed control system is executed solely by the device processor.

Example 7. The system of any one of Examples 6, wherein the distributed control system is configured to shift from the first mode to the second mode when a sampling rate of the sensor is greater than a data transmission rate from the modular device to the surgical hub.

Example 8. The system of any one of Examples 6-7, wherein the distributed control system is configured to shift from the second mode to the first mode when a sampling rate of the sensor is less than a data transmission rate from the modular device to the surgical hub.

Example 9. The system of any one of Examples 6-8, wherein the modular device comprises a radiofrequency (RF) electrosurgical instrument and the distributed control system is configured to control an energy level of the RF electrosurgical instrument.

Example 10. The system of any one of Examples 6-9, wherein the modular device comprises a surgical cutting and stapling instrument and the distributed control system is configured to control a rate at which a motor of the surgical cutting and stapling instrument drives a knife.

Example 11. A system configured to control a modular device comprising a sensor configured to detect data associated with the modular device, the system comprising: a first surgical hub configured to communicably couple to the modular device and to a second surgical hub comprising a second processor, the first surgical hub comprising: a memory; and a first processor coupled to the memory; and a distributed control system executable at least in part by each of the first processor and the second processor, the distributed control system configured to: receive the data detected by the sensor; determine control adjustments for the modular device according to the data; and control the modular device according to the control adjustments.

Example 12. The system of any one of Examples 11, wherein the distributed control system is transitionable between a first mode, where the distributed control system is executed by both the first processor and the second processor, and a second mode, where the distributed control system is executed solely by the first processor.

Example 13. The system of any one of Examples 11-12, wherein the distributed control system is configured to shift between the first mode and the second mode upon receiving a command.

Example 14. The system of any one of Examples 11-13, wherein the modular device comprises a radiofrequency (RF) electrosurgical instrument and the distributed control system is configured to control an energy level of the RF electrosurgical instrument.

Example 15. The system of any one of Examples 11-14, wherein the modular device comprises a surgical cutting and stapling instrument and the distributed control system is configured to control a rate at which a motor of the surgical cutting and stapling instrument drives a knife.

While several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor comprising one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:
1. A surgical hub for use with a surgical system in a surgical procedure performed in an operating room, the surgical hub comprising:
a control circuit configured to:
communicably couple to a surgical device in the operating room;
communicably couple to a remote server;
receive real-time usage data from the surgical device during a surgical procedure, wherein the real-time usage data is sensed by at least one sensor of the surgical device during the surgical procedure associated with real-time operations of the surgical device;
anonymize the real-time usage data, wherein anonymizing the real-time usage data comprises:
removing an unredacted portion of the real-time usage data; and

generating anonymized, stripped real-time usage data;
transmit a real-time data stream comprising the anonymized, stripped real-time usage data to the remote server, wherein the remote server remotely monitors the real-time operations of the surgical device based on the real-time data stream;
derive contextual information based on the anonymized, stripped real-time usage data; and
control the surgical device,
wherein controlling the surgical device comprises:
communicating control adjustments to the surgical device based on the contextual information; and
adjusting the surgical device based on the communicated control adjustments.
2. The surgical hub of claim 1, wherein the control circuit is further configured to query grouped anonymized usage data from the remote server.
3. The surgical hub of claim 2, wherein the control circuit is further configured to send a result of a comparison of the real-time usage data to the grouped anonymized usage data to a display screen.
4. The surgical hub of claim 1, wherein the real-time usage data comprises how often the surgical device has been used.
5. The surgical hub of claim 1, wherein the real-time usage data comprises what procedures the surgical device has been used during.
6. The surgical hub of claim 1, wherein the real-time usage data comprises who used the surgical device.
7. The surgical hub of claim 1, wherein the real-time usage data comprises an internal state of the surgical device and a tissue being operated on.
8. The surgical hub of claim 1, wherein the control circuit is further configured to continuously receive real-time usage data from the surgical device before, during, and after the surgical procedure.
9. The surgical hub of claim 1, wherein real-time usage data can be queried from the remote server before, during, or after a procedure.
10. A remote server connected to a plurality of surgical hubs that are used with surgical systems in surgical procedures performed in operating rooms, the remote server comprising:
a control circuit configured to:
communicably couple to at least one surgical hub;
receive a real-time data stream comprising anonymized, stripped real-time usage data from the at least one surgical hub, wherein real-time usage data is sensed by at least one sensor of a surgical device during a surgical procedure associated with real-time operations of the surgical device, wherein the real-time usage data is anonymized by removing an unredacted portion of the real-time usage data and generating the anonymized, stripped real-time usage data;
remotely monitor the real-time operations of the surgical device based on the real-time data stream;
store the anonymized, stripped real-time usage data into types of data;
receive a query on a type of data from the at least one surgical hub;
transmit a group of anonymized, stripped real-time usage data based on the query to the at least one surgical hub; and
control the surgical device, wherein controlling the surgical device comprises:

communicating a control adjustment to the surgical device based on the group of anonymized, stripped real-time usage data; and adjusting the surgical device based on the communicated control adjustment.

11. The remote server of claim 10, wherein the real-time usage data comprises any one or more of how often a surgical device has been utilized, what procedures the surgical device has been utilized in connection with, who utilized the surgical device, an internal state of the surgical device, and a tissue being operated on.

12. The remote server of claim 10, wherein the control circuit causes a first type of data to be stored in association with a second type of data.

13. The remote server of claim 10, wherein a query can be received from the at least one surgical hub before, during, or after a procedure.

14. The remote server of claim 10, wherein types of data can be queried based on a time frame.

15. A surgical device, comprising:

a control circuit configured to:

communicably couple to a surgical hub;

store anonymized, stripped real-time usage data, wherein the anonymized, stripped real-time usage data is generated by removing an unredacted portion of real-time usage data sensed by at least one sensor of the surgical device during a surgical procedure associated with real-time operations of the surgical device;

send a real-time data stream comprising the anonymized, stripped real-time usage data to the surgical hub; and control the surgical device via:

receiving control adjustments from the surgical hub based on the anonymized, stripped real-time usage data; and adjusting the surgical device based on the received control adjustments.

16. The surgical device of claim 15, wherein the real-time usage data comprises any one or more of how often the surgical device has been utilized, what procedures the surgical device has been utilized in connection with, who utilized the surgical device, an internal state of the surgical device, and a tissue being operated on.

17. The surgical device of claim 15, wherein the control circuit is further configured to continuously send real-time usage data before, during, and after the surgical procedure.

18. The surgical device of claim 15, wherein the control adjustments are based on real-time usage data from multiple surgical instruments.

*     *     *     *     *